US012064557B2

(12) United States Patent
Baigent et al.

(10) Patent No.: US 12,064,557 B2
(45) Date of Patent: Aug. 20, 2024

(54) TEXTILE PATIENT INTERFACE

(71) Applicant: ResMed Pty Ltd, Bella Vista (AU)

(72) Inventors: Hollie Elizabeth Baigent, Copenhagen (DK); Jessica Lea Dunn, Sydney (AU); Justin John Formica, Sydney (AU); Joel Edward Gibson, Sydney (AU); Kirrily Michele Haskard, Sydney (AU); Rachel Herman, Sydney (AU); Michiel Kooij, Sydney (AU); Jose Ignacio Romagnoli, Sydney (AU); Gerard Michael Rummery, Woodford (AU); Rupert Christian Scheiner, Sydney (AU); Sandeep Kumar Tiwari, Singapore (SG); Lochlan Von Moger, Sydney (AU); Hadley White, Sydney (AU); Tzu-Chin Yu, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 679 days.

(21) Appl. No.: 17/098,551

(22) Filed: Nov. 16, 2020

(65) Prior Publication Data

US 2021/0069442 A1 Mar. 11, 2021

Related U.S. Application Data

(63) Continuation of application No. 15/529,691, filed as application No. PCT/AU2015/050745 on Nov. 26, 2015, now Pat. No. 10,888,681.

(30) Foreign Application Priority Data

Nov. 26, 2014 (AU) .................................. 2014904796
Jun. 11, 2015 (AU) .................................. 2015902204
Sep. 15, 2015 (WO) ................. PCT/AU2015/050546

(51) Int. Cl.
*A61M 16/06* (2006.01)
*A61M 16/00* (2006.01)
(Continued)

(52) U.S. Cl.
CPC .... *A61M 16/0616* (2014.02); *A61M 16/0683* (2013.01); *A61M 2016/0027* (2013.01); (Continued)

(58) Field of Classification Search
CPC .......... A61M 16/0616; A61M 16/0622; A61M 16/06; A61M 16/0661; A61M 16/0605
See application file for complete search history.

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

AU 2013257426 B2 11/2013
CN 1681553 A 10/2005
(Continued)

OTHER PUBLICATIONS

Final Rejection dated Jun. 8, 2020 issued in Japanese Application No. 2017-528141 with translation (14 pages).
(Continued)

*Primary Examiner* — Margaret M Luarca
(74) *Attorney, Agent, or Firm* — Nixon & Vanderhye P.C.

(57) ABSTRACT

A patient interface for sealed delivery of a flow of air at a continuously positive pressure with respect to ambient air pressure to an entrance to the patient's airways including at least entrance of a patient's nares to ameliorate sleep disordered breathing may include a seal-forming structure comprising a foam undercushion and a textile membrane for contact with the patient's face; a positioning and stabilising
(Continued)

structure to maintain the seal-forming structure in sealing contact with an area surrounding an entrance to the patient's airways while maintaining a therapeutic pressure at the entrance to the patient's airways; and a plenum chamber pressurised at a pressure above ambient pressure in use.

20 Claims, 122 Drawing Sheets

(51) Int. Cl.
A61M 16/10 (2006.01)
A61M 16/16 (2006.01)
A61M 16/20 (2006.01)

(52) U.S. Cl.
CPC . *A61M 2016/0036* (2013.01); *A61M 16/1055* (2013.01); *A61M 16/107* (2014.02); *A61M 16/1075* (2013.01); *A61M 16/16* (2013.01); *A61M 16/161* (2014.02); *A61M 16/208* (2013.01); *A61M 2205/3368* (2013.01); *A61M 2210/0618* (2013.01)

(56) References Cited

U.S. PATENT DOCUMENTS

| | | |
|---|---|---|
| 6,532,959 B1 | 3/2003 | Berthon-Jones |
| 6,581,594 B1 | 6/2003 | Drew et al. |
| 7,302,950 B2 | 12/2007 | Berthon-Jones et al. |
| 7,866,944 B2 | 1/2011 | Kenyon et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,950,404 B2 | 2/2015 | Formica et al. |
| 9,119,929 B2 | 9/2015 | Mcauley et al. |
| 9,526,857 B2 | 12/2016 | Rummery et al. |
| 9,682,207 B2 | 6/2017 | Kwok et al. |
| 9,724,488 B2 | 8/2017 | Guney |
| 2003/0196655 A1 | 10/2003 | Ging et al. |
| 2003/0196656 A1 | 10/2003 | Moore et al. |
| 2005/0076913 A1 | 4/2005 | Ho et al. |
| 2007/0186931 A1 | 8/2007 | Zollinger et al. |
| 2008/0047560 A1 | 2/2008 | Veliss et al. |
| 2008/0060649 A1 | 3/2008 | Veliss |
| 2008/0184994 A1 | 8/2008 | Schnaars et al. |
| 2009/0044808 A1 | 2/2009 | Guney et al. |
| 2009/0050156 A1 | 2/2009 | Ng et al. |
| 2009/0145444 A1 | 6/2009 | Edwards et al. |
| 2010/0000534 A1 | 1/2010 | Kooij et al. |
| 2010/0258136 A1 | 10/2010 | Doherty et al. |
| 2010/0319700 A1 | 12/2010 | Ng et al. |
| 2011/0197341 A1 | 8/2011 | Formica et al. |
| 2012/0138058 A1 | 6/2012 | Fu et al. |
| 2012/0138061 A1 | 6/2012 | Dravitzki |
| 2012/0204878 A1 | 8/2012 | Smith et al. |
| 2012/0204879 A1 | 8/2012 | Cariola et al. |
| 2012/0222680 A1 | 9/2012 | Eves et al. |
| 2013/0139822 A1 | 6/2013 | Gibson et al. |
| 2013/0213400 A1 | 8/2013 | Barlow et al. |
| 2013/0220327 A1 | 8/2013 | Barlow et al. |
| 2013/0263860 A1 | 10/2013 | Sofranko et al. |
| 2014/0007881 A1 | 1/2014 | Rummery et al. |
| 2014/0158136 A1 | 6/2014 | Romagnoli et al. |
| 2014/0190486 A1 | 6/2014 | Dunn et al. |
| 2014/0209098 A1 | 7/2014 | Dunn et al. |
| 2015/0182719 A1 | 7/2015 | Grashow et al. |
| 2017/0326320 A1 | 11/2017 | Baigent et al. |
| 2021/0085908 A1 | 3/2021 | Dunn et al. |
| 2021/0252245 A1 | 8/2021 | Formica et al. |

FOREIGN PATENT DOCUMENTS

| | | |
|---|---|---|
| CN | 101450239 A | 6/2009 |
| CN | 101455871 A | 6/2009 |
| CN | 101861180 A | 10/2010 |
| CN | 101954139 A | 1/2011 |
| CN | 102245250 A | 11/2011 |
| CN | 2012-511341 A | 5/2012 |
| CN | 102921086 A | 2/2013 |
| CN | 103068431 A | 4/2013 |
| CN | 103153378 A | 6/2013 |
| CN | 103260684 A | 8/2013 |
| CN | 103442763 A | 12/2013 |
| CN | 103796700 A | 5/2014 |
| DE | 202013005712 U1 | 9/2013 |
| EP | 1356841 A2 | 10/2003 |
| JP | 2008-543383 A | 12/2008 |
| JP | 2011-500229 A | 1/2011 |
| JP | 2014-524801 | 9/2014 |
| JP | 2014-205066 | 10/2014 |
| JP | 2014-529432 A | 11/2014 |
| JP | 2021-000557 | 1/2021 |
| WO | WO 98/04310 A1 | 2/1998 |
| WO | WO 98/34665 A1 | 8/1998 |
| WO | WO 00/78381 A1 | 12/2000 |
| WO | 2004/007010 A1 | 1/2004 |
| WO | 2004/022146 | 3/2004 |
| WO | WO 2004/041342 A1 | 5/2004 |
| WO | WO 2004/073778 A1 | 9/2004 |
| WO | WO 2005/063328 A1 | 7/2005 |
| WO | 2005/086943 | 9/2005 |
| WO | WO 2006/074513 A1 | 7/2006 |
| WO | WO 2006/130903 A1 | 12/2006 |
| WO | WO 2008/011683 A1 | 1/2008 |
| WO | WO 2008/070929 A1 | 6/2008 |
| WO | WO 2009/052560 A1 | 4/2009 |
| WO | 2009/062265 A1 | 5/2009 |
| WO | WO 2009/062265 A1 | 5/2009 |
| WO | WO 2009/109004 A1 | 9/2009 |
| WO | WO 2010/028425 A1 | 3/2010 |
| WO | 2010/073142 A1 | 7/2010 |
| WO | WO 2010/073138 A1 | 7/2010 |
| WO | WO 2010/135785 A1 | 12/2010 |
| WO | WO 2010/148453 A1 | 12/2010 |
| WO | WO 2012/027792 A1 | 3/2012 |
| WO | 2012/040792 A1 | 4/2012 |
| WO | 2012/122601 A1 | 9/2012 |
| WO | WO 2012/171072 A1 | 12/2012 |
| WO | WO 2013/006913 A1 | 1/2013 |
| WO | WO 2013/020167 A1 | 2/2013 |
| WO | WO 2013/026091 A1 | 2/2013 |
| WO | WO 2013/068950 A1 | 5/2013 |
| WO | 2014/013371 | 1/2014 |
| WO | 2014/013371 A1 | 1/2014 |
| WO | 2014/015382 A1 | 1/2014 |
| WO | 2014/035261 A1 | 3/2014 |
| WO | WO 2014/110622 A1 | 7/2014 |
| WO | WO 2016/041008 A1 | 3/2016 |
| WO | WO 2016/193859 A1 | 12/2016 |

OTHER PUBLICATIONS

Office Action dated Nov. 4, 2019 issued in Chinese Application No. 201580073551.3 with English translation (26 pages).
Office Action dated Sep. 30, 2019 issued in Japanese Application No. 2017-528141 with English translation (13 pages).
PCT International Preliminary Report on Patentability issued in related PCT Application No. PCT/AU2015/050745, dated May 30, 2017, 7 pages.
International Search Report for PCT/AU2015/050745 mailed Mar. 10, 2016, 17 pages.
Written Opinion of the ISA for PCT/AU2015/050745 mailed Mar. 10, 2016, 6 pages.
West, John B., "Respiratory Physiology", Lippincott Williams & Wilkins, 9th edition published 2012, 8 pages.
Circadiance® SleepWeaver® Élan, https://circadiance.com/sleepweaver-elan/#mg, May 19, 2017, 3 pages.
Warp knitting, Wikipedia, https://en.wikipedia.org/wiki/Warp_knitting, May 19, 2017, 5 pages.
Office Action dated Sep. 27, 2021 issued in Japanese Application No. 2020-169774 with English translation (15 pages).

(56) References Cited

OTHER PUBLICATIONS

Extended European Search Report dated Jul. 12, 2021 issued in European Application No. 20215252.6 (7 pages).
Pre-Appeal Examination Report dated Nov. 13, 2020 issued in Japanese Application No. 2017-528141 with English translation (11 pages).
Office Action dated Jan. 19, 2021 issued in Chinese Application No. 201580073551.3 with English translation (6 pages).
Examination Report dated Jun. 20, 2022 issued in New Zealand Application No. 770257 (5 pages).
Examination Report dated Jun. 20, 2022 issued in New Zealand Application No. 770085 (3 pages).
Examination Report dated Jun. 20, 2022 issued in New Zealand Application No. 770091 (3 pages).
Examination Report dated Jun. 20, 2022 issued in New Zealand Application No. 770095 (3 pages).
Examination Report dated Jun. 20, 2022 issued in New Zealand Application No. 770098 (4 pages).
Examination Report dated Jun. 20, 2022 issued in New Zealand Application No. 770108 (6 pages).
Examination Report dated Jun. 20, 2022 issued in New Zealand Application No. 770109 (3 pages).
Examination Report dated Jun. 20, 2022 issued in New Zealand Application No. 770112 (3 pages).
Examination Report dated Nov. 16, 2022 issued in New Zealand Application No. 770091 (5 pages).
Examination Report dated Nov. 21, 2022 issued in New Zealand Application No. 770095 (5 pages).
Examination Report dated Dec. 12, 2022 issued in New Zealand Application No. 770257 (3 pages).
Office Action dated Mar. 6, 2023 issued in Japanese Application No. 2022-062855 with English translation (8 pages).
Notice of Allowance dated Mar. 7, 2022 issued in Japanese Application No. 2020-169774 (3 pages).
First Examination Report dated Apr. 8, 2022 issued in New Zealand Application No. 732522 (3 pages).
Examination Report dated Aug. 11, 2023 issued in New Zealand Application No. 770109 (5 pages).
Notice of Allowance dated Sep. 25, 2023 issued in Japanese Application No. 2022-062855 (3 pages).
Office Action dated Oct. 26, 2023 issued in Chinese Application No. 202110884983.X with English translation (10 pages).
Notice of Grant dated Nov. 20, 2023 issued in Chinese Application No. 202110884983.X (4 pages).

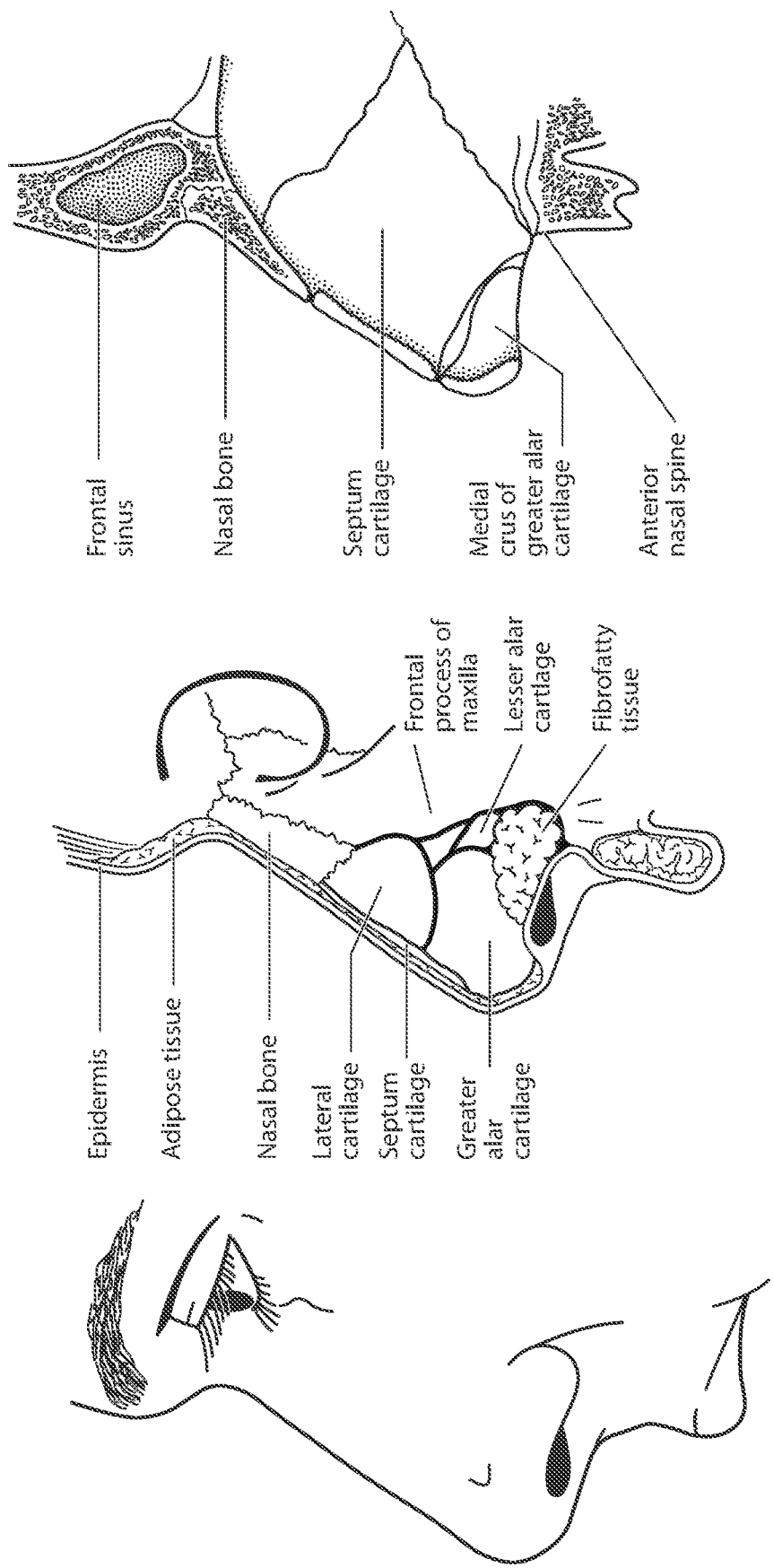

Relatively Large Positive Curvature

Relatively Small Positive Curvature

Zero Curvature

Relatively Small Negative Curvature

Relatively Large Negative Curvature

Copyright 2015 ResMed Limited

Left-hand rule

Right-hand rule

Left ear helix

Right-hand helix
Right-hand positive

Right ear helix

Copyright 2015 ResMed Limited

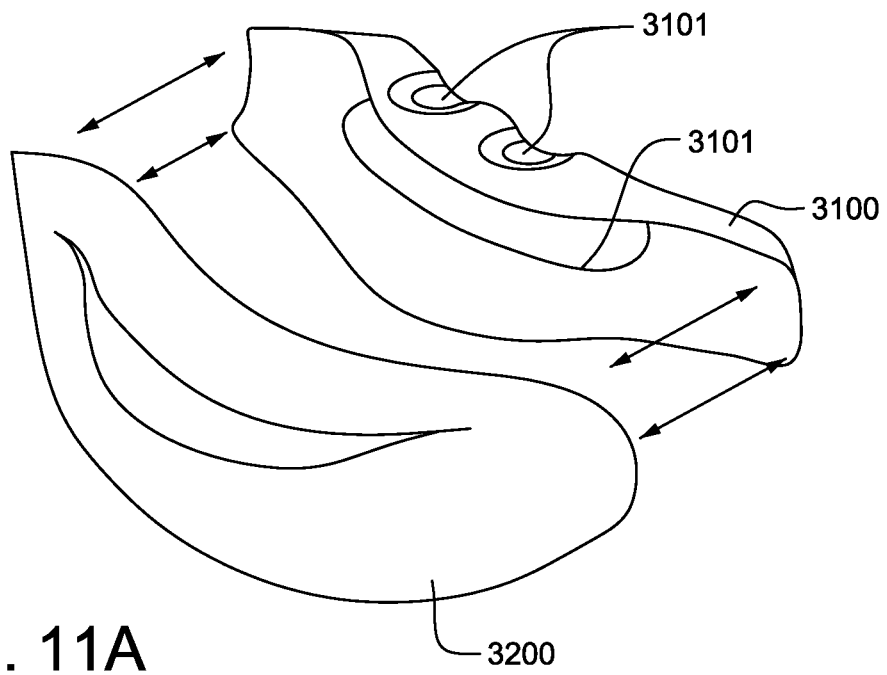
FIG. 11A
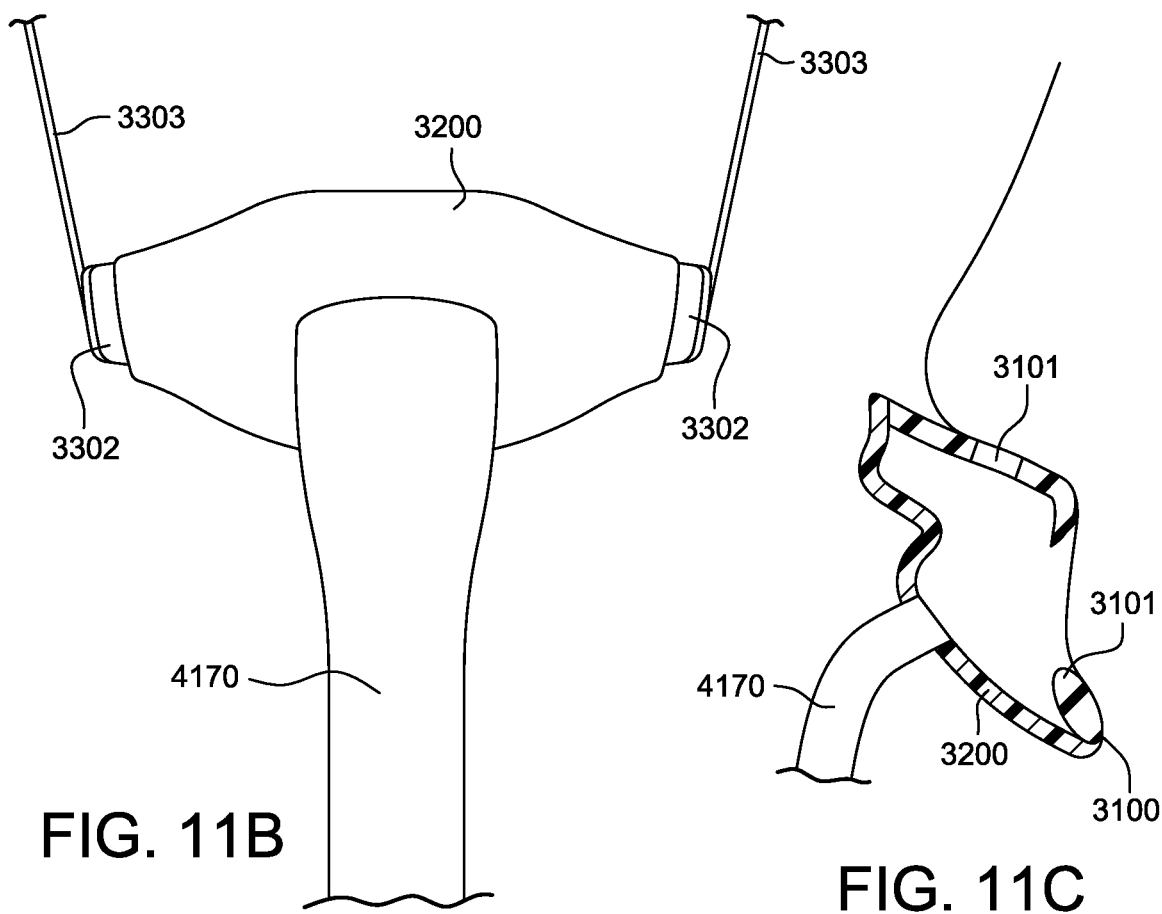
FIG. 11B
FIG. 11C

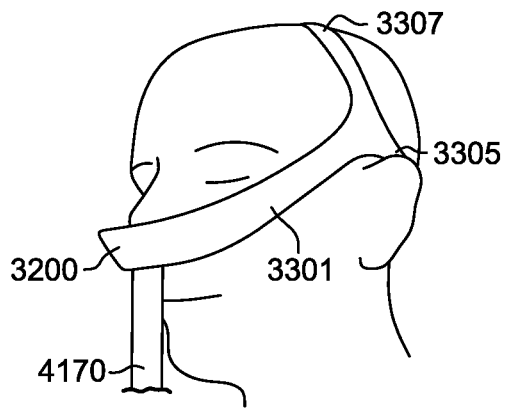
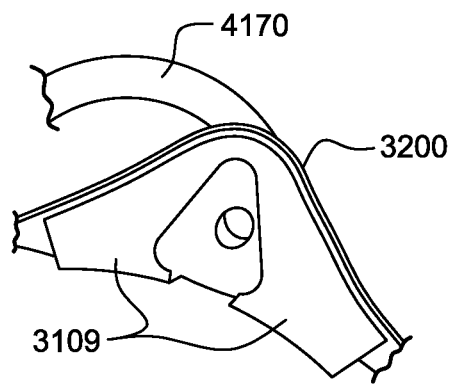
FIG. 32A　　　FIG. 32B
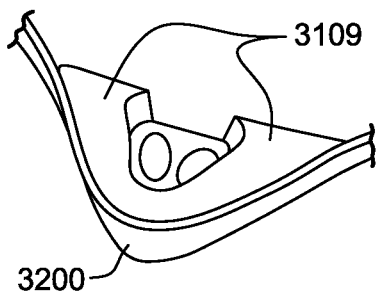
FIG. 32C
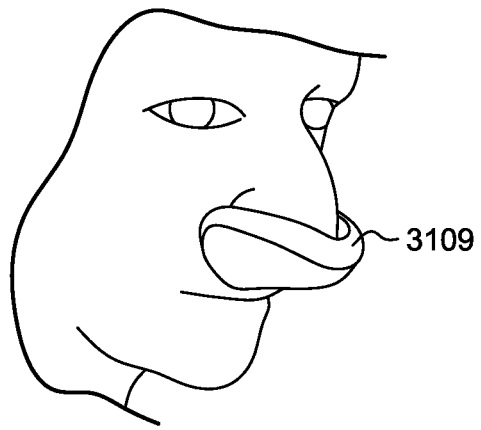
FIG. 32D
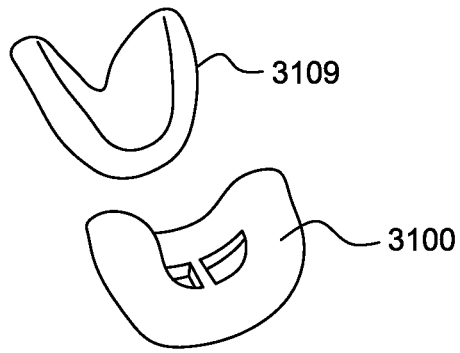
FIG. 32E

TEXTILE PATIENT INTERFACE

1 CROSS-REFERENCE TO RELATED APPLICATIONS

This application is a continuation of U.S. application Ser. No. 15/529,691, filed May 25, 2017, now U.S. Pat. No. 10,888,681, which is the U.S. national phase of International Application No. PCT/AU2015/050745 filed Nov. 26, 2015 which designated the U.S. and claims the benefit of U.S. Provisional Patent Application No. 62/196,329, filed Jul. 24, 2015, International Patent Application No. PCT/AU2015/050546, filed Sep. 15, 2015, Australian Provisional Patent Application No. AU2014904796, filed Nov. 26, 2014, and Australian Provisional Patent Application No. 2015902204, filed Jun. 11, 2015, the entire contents of each of which is incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchairbound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ | nasal | 29 (3) | 22 (3) | 2008 |

-continued

| Mask name | Mask type | A-weighted sound power level dB(A) (uncertainty) | A-weighted sound pressure dB(A) (uncertainty) | Year (approx.) |
|---|---|---|---|---|
| SoftGel | | | | |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH$_2$O)Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology is directed to a patient interface for sealed delivery of a flow of air at a continuously positive pressure with respect to ambient air pressure to an entrance to the patient's airways including at least a patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The patient interface may include: a seal-forming structure comprising a foam undercushion and an air-impermeable textile membrane for contact with the patient's face, an outer periphery of the air-impermeable textile membrane joined to the foam undercushion with an airtight bond such that a remainder of the air-impermeable textile membrane is separable from the foam undercushion by the flow of air, a positioning and stabilising structure to maintain the seal-forming structure in sealing contact with an area surrounding an entrance to the patient's airways while maintaining a therapeutic pressure at the entrance to the patient's airways; and a plenum chamber pressurised at a pressure above ambient pressure in use.

In examples, (a) the textile membrane may be a flocked foam, (b) the flocked foam may be 3D shaped, (c) the textile membrane may be coated to be air impermeable, (d) the seal-forming structure may comprise any one from the group consisting of: silicone and TPE, (e) the seal-forming structure may be integrally formed with the positioning and stabilising structure, and/or (f) the patient interface may comprise an air delivery tube substantially made from a textile and that is air impermeable.

An aspect of the present technology is directed to a patient interface that may include: a plenum chamber; and a seal forming structure including a foam material structured to releasably engage with the plenum chamber and an air-impermeable textile membrane for contact with the patient's face, an outer periphery of the air-impermeable textile membrane joined to the foam undercushion with an airtight bond such that a remainder of the air-impermeable textile membrane is separable from the foam undercushion by the flow of air; wherein the plenum chamber imparts a predetermined shape to the foam material.

In examples, (a) the predetermined shape of the foam material may be V-shaped, (b) the foam material may comprise alar sealing regions to compress against the corners of a patient's nose, (c) the textile material may be coated to be air impermeable, (d) the textile material is laminated may be coated to be air impermeable, (e) the foam material may be air impermeable, (f) the foam material may be die cut, (f) the foam material may have a substantially uniform predetermined thickness, (g) the foam material may have a variable thickness, (h) the foam material may be compression cut, (h) the foam material may have at least one opening to permit pressurised air to enter the patient's nares, (i) the at least one opening may be tapered at a peripheral edge to reduce distortion of the shape of the at least one opening in use, (j) the plenum chamber may be connected to a tube, (k) the tube may be releasably connected to the plenum chamber at a connection port, (l) the patient interface may comprise a textile positioning and stabilising structure operatively connected to the plenum chamber, (m) the plenum chamber may comprise a vent, and/or (n) the textile material may be inflatable in use to engage with the underside of a patient's nose.

An aspect of the patient interface is directed to a patient interface for sealed delivery of a flow of air at a continuously positive pressure with respect to ambient air pressure to an entrance to the patient's airways including at least a patient's nares, wherein the patient interface is configured to maintain a therapy pressure in a range of about 4 cmH₂O to about 30 cmH₂O above ambient air pressure in use, throughout the patient's respiratory cycle, while the patient is sleeping, to ameliorate sleep disordered breathing. The patient interface may include: a seal-forming structure comprising a textile membrane for contact with the patient's face and a foam undercushion to support the textile membrane, the textile membrane configured to form a seal with the entrance to the patient's airways including at least the patient's nares below the bridge of the patient's nose; a positioning and stabilising structure to maintain the seal-forming structure in sealing contact with an area surrounding an entrance to the patient's airways while maintaining a therapeutic pressure at the entrance to the patient's airways; and a plenum chamber pressurised at a pressure above ambient pressure in use.

In examples, (a) the textile membrane may be configured to form a seal with the entrance to the patient's airways including at least the patient's nares below the tip of the patient's nose, (b) the textile membrane may be air-impermeable, (c) the textile membrane may be coated to be air-impermeable, (d) the foam undercushion may be air-impermeable, (e) the textile membrane may be a flocked foam, (f) the flocked foam may be 3D shaped, (g) the seal-forming structure may comprise any one from the group consisting of: silicone and TPE, (h) the seal-forming structure may be integrally formed with the positioning and stabilising structure, and/or (i) the patient interface may comprise an air delivery tube substantially made from a textile and that is air impermeable.

An aspect of the present technology is directed to a patient interface comprising: a plenum chamber, a seal forming structure made from a foam material to permanently engaged with the plenum chamber; and a tube releasably engageable with the plenum chamber, wherein the plenum chamber imparts a predetermined shape to the seal forming structure.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods/systems/devices/apparatus described herein can provide improved functioning in a processor, such as of a processor of a specific purpose computer, respiratory monitor and/or a respiratory therapy apparatus. Moreover, the methods/devices/apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

Figure 1A:
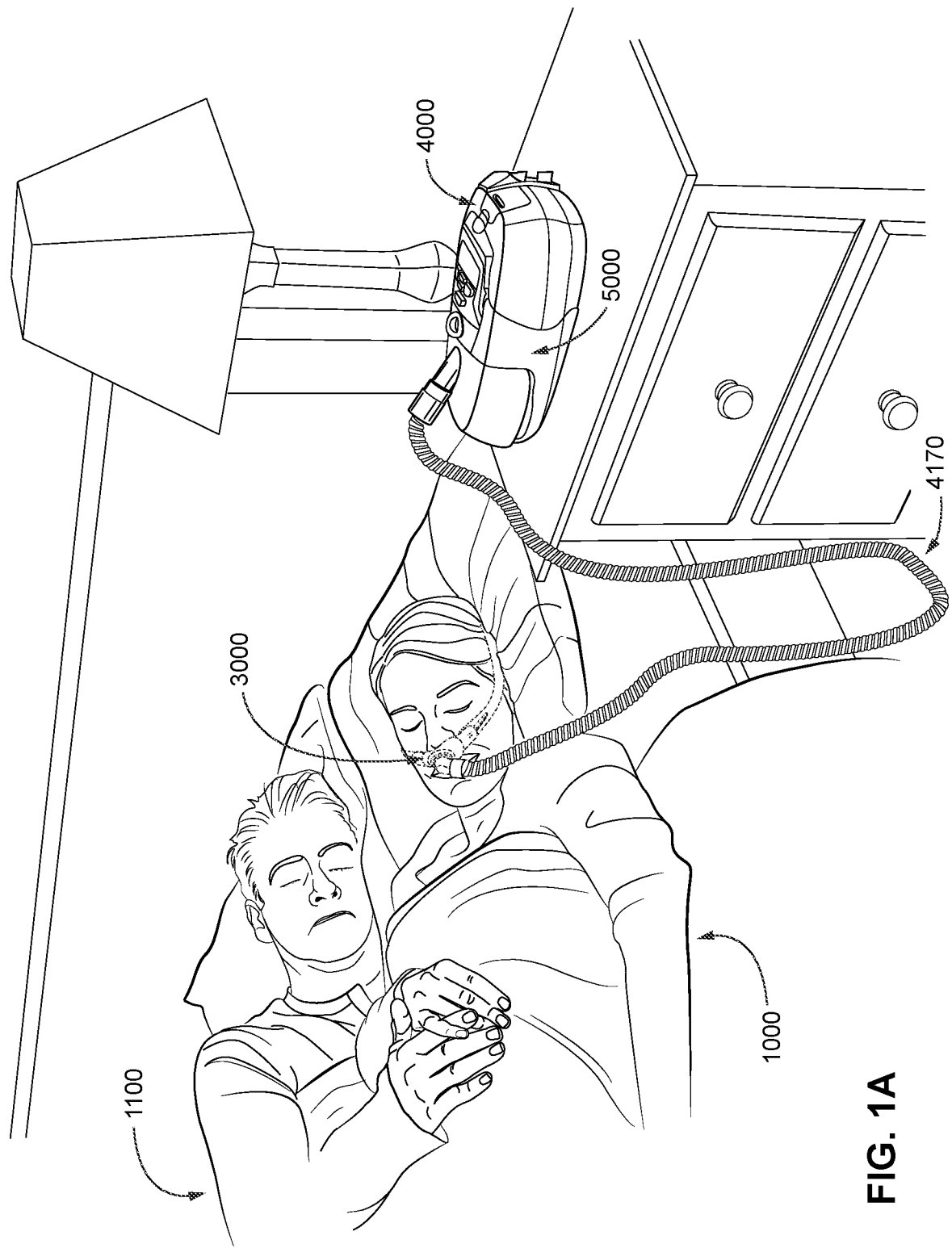
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
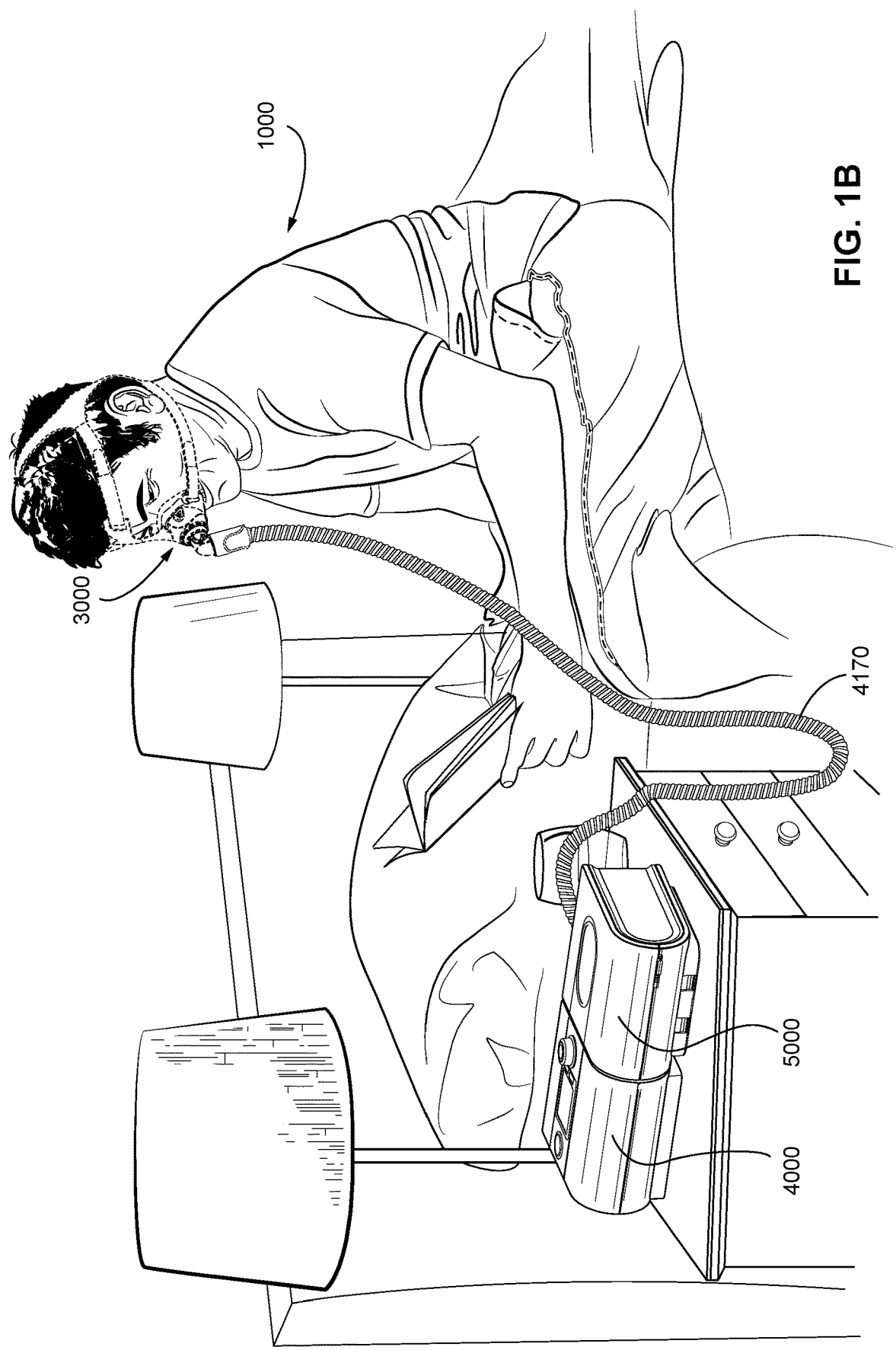
Figure 1C:
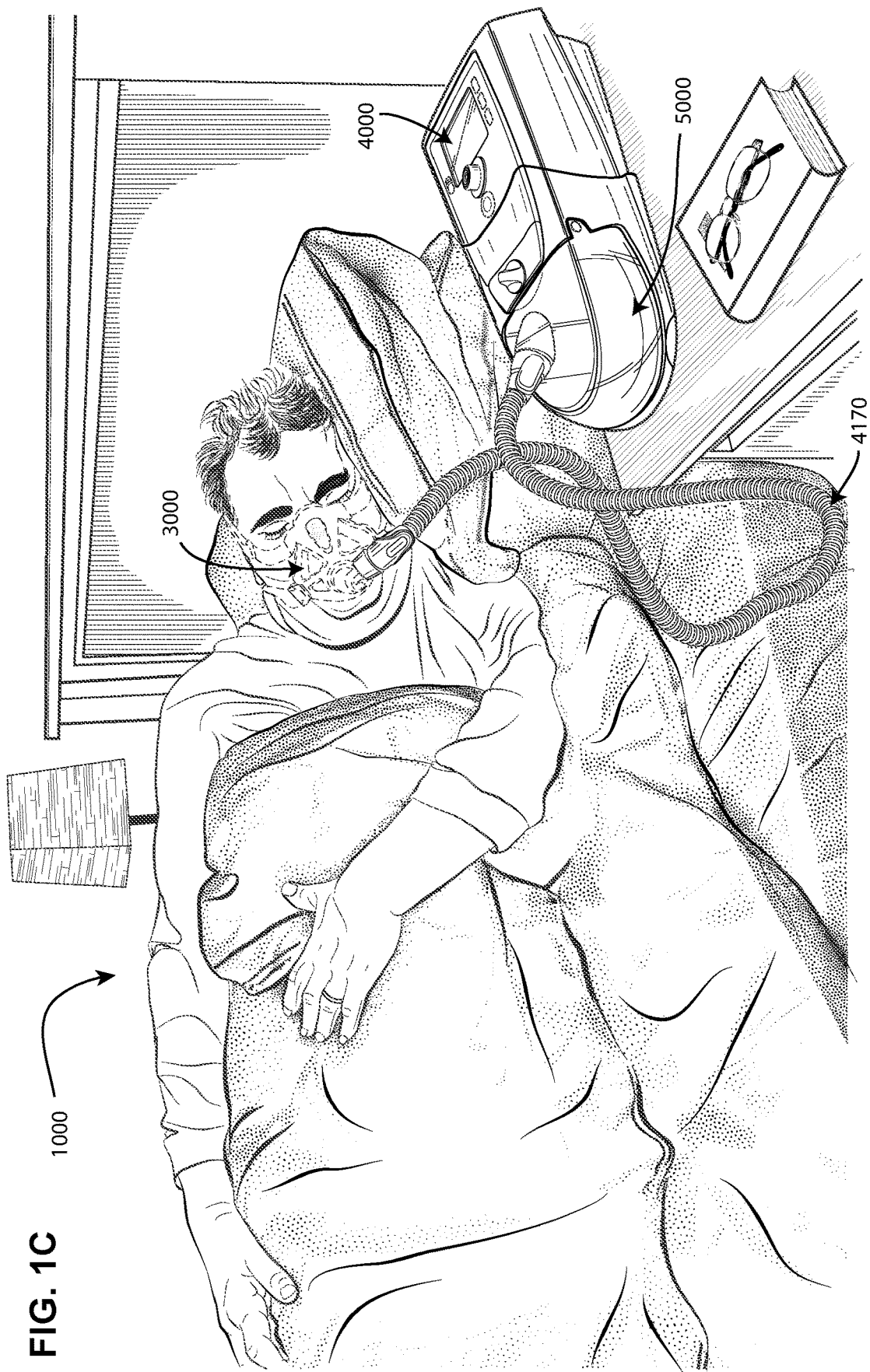
Figure 2A:
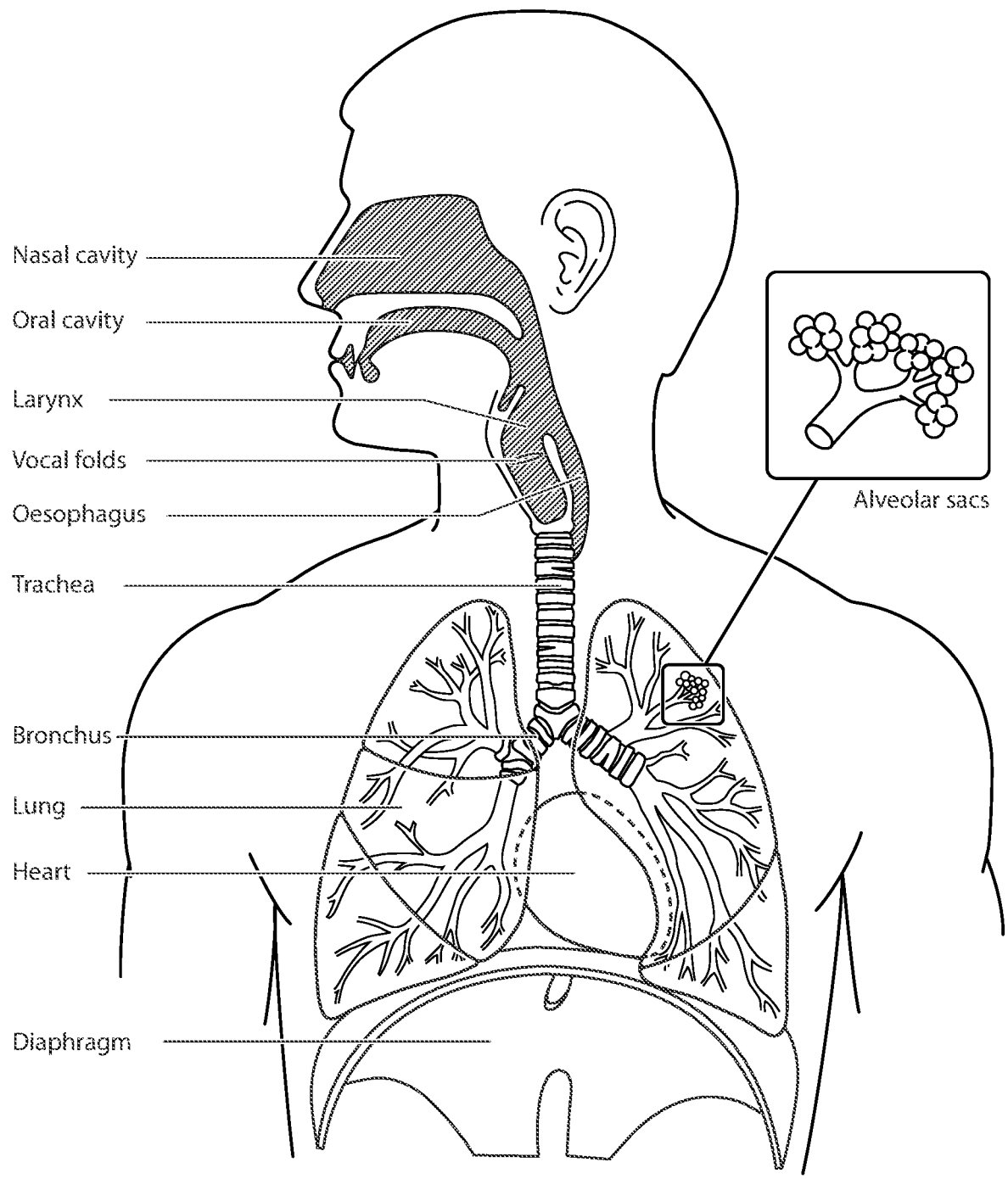

FIG. 2A shows an overview of a human respiratory system including the nasal and oral cavities, the larynx, vocal folds, oesophagus, trachea, bronchus, lung, alveolar sacs, heart and diaphragm.

Figure 2B:
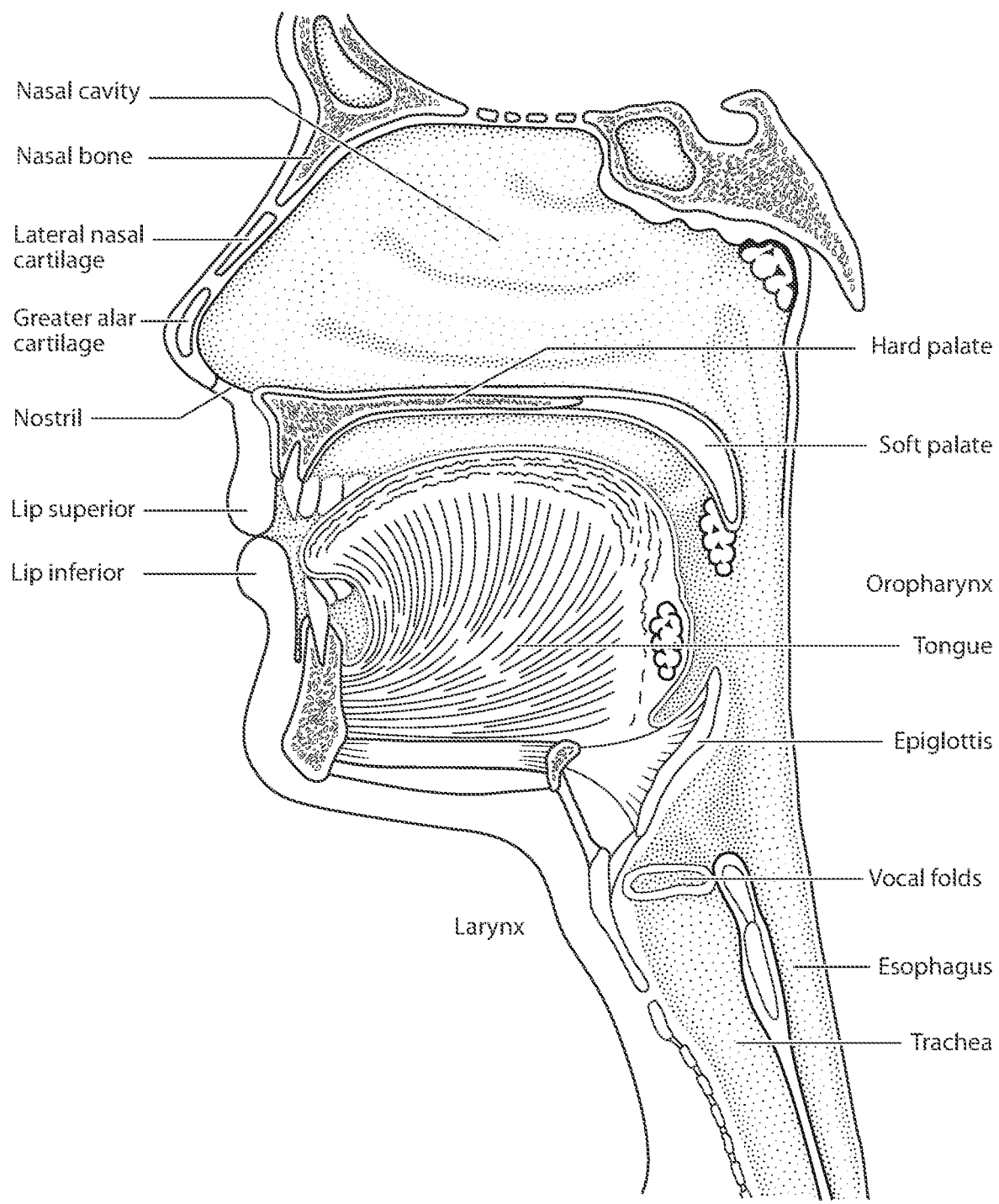

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
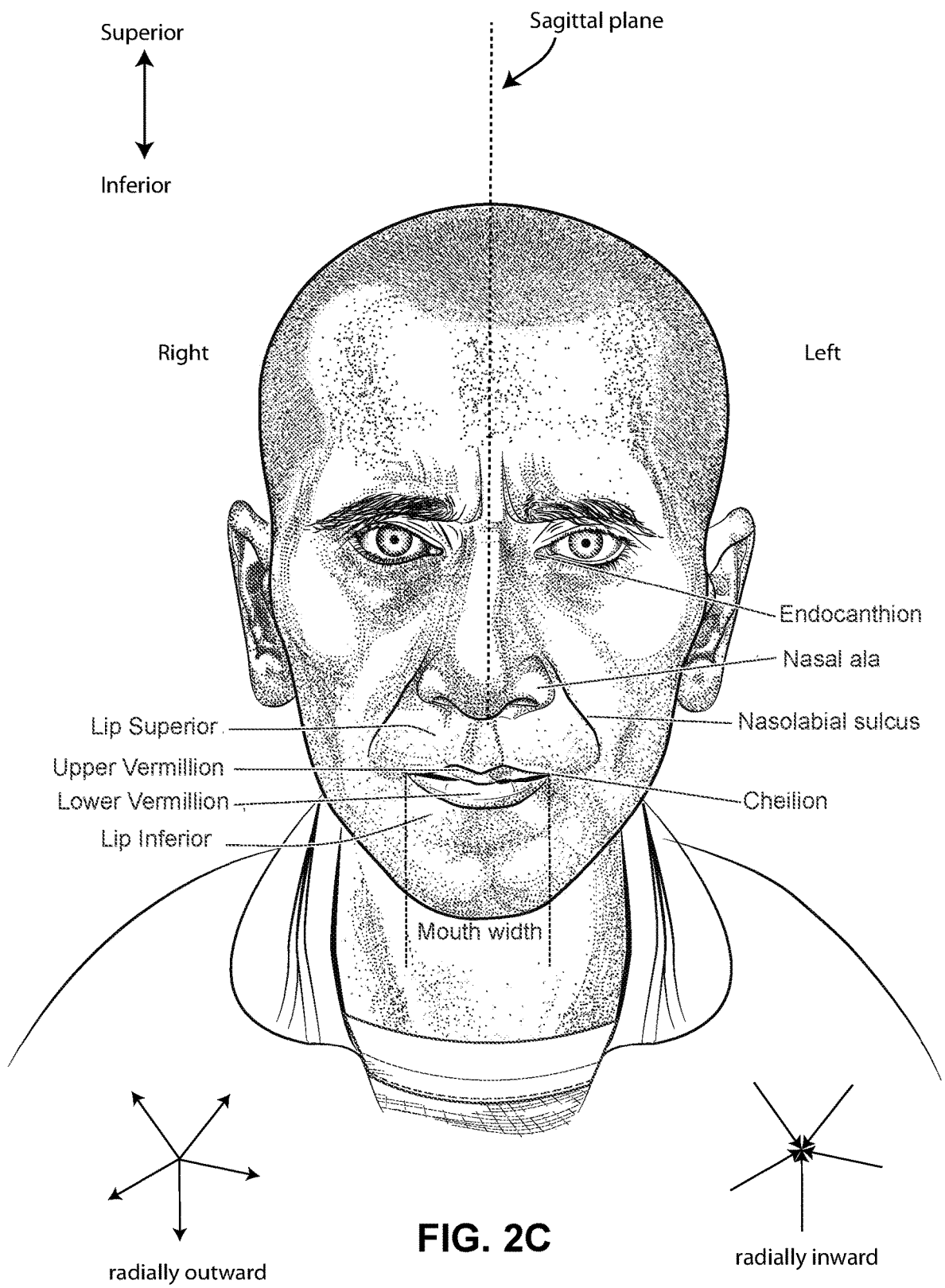

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
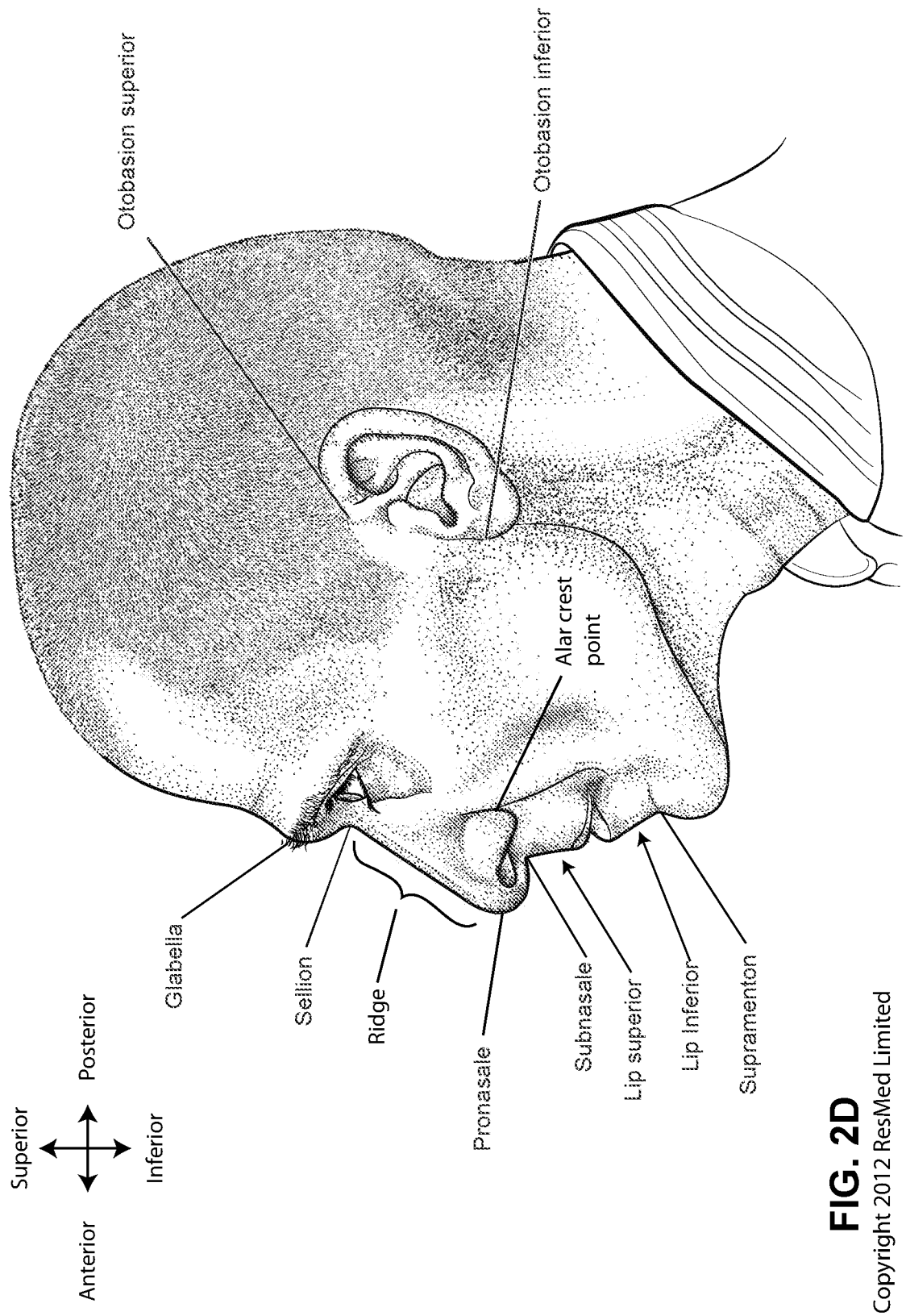

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
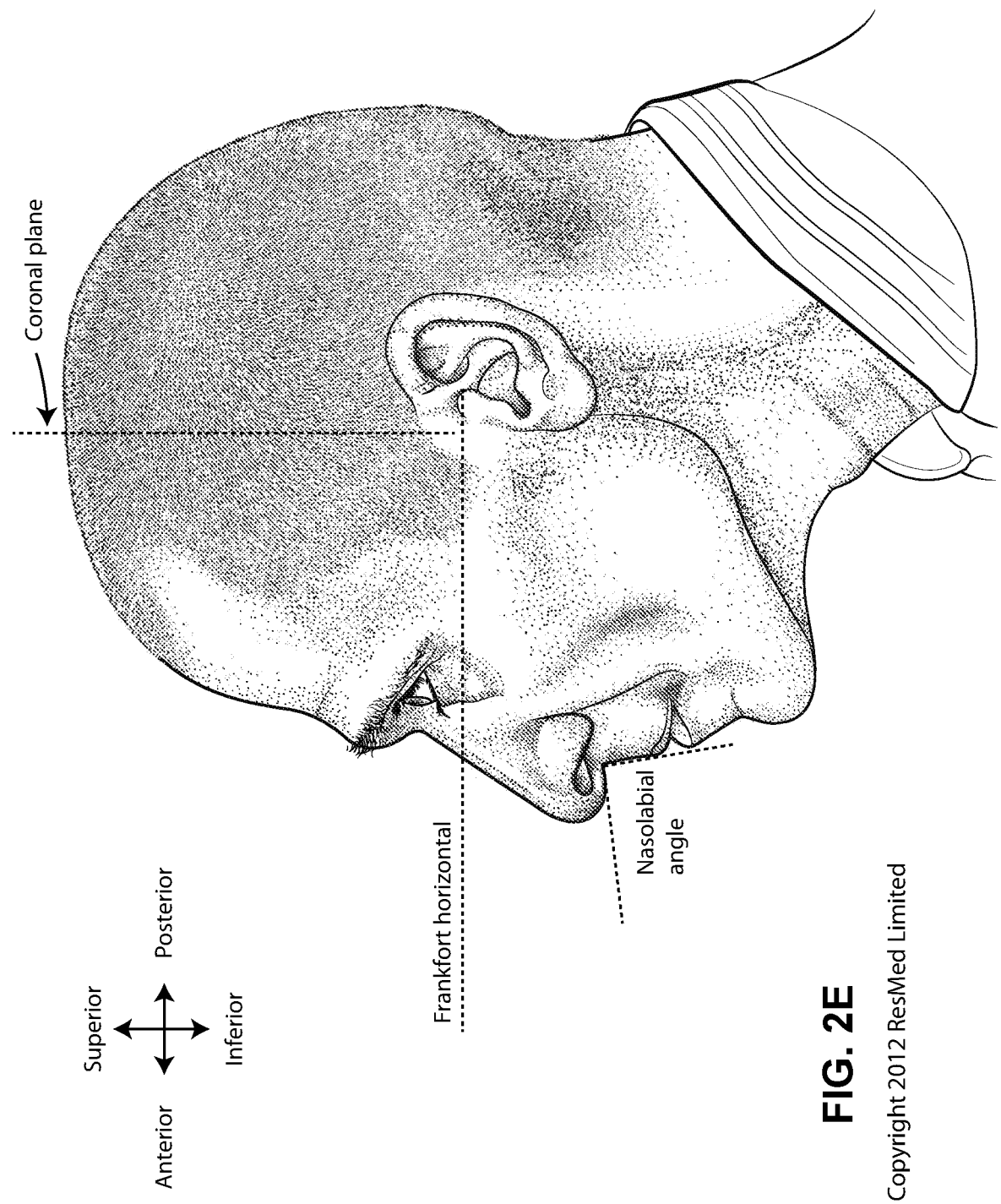

FIG. 2E is a further side view of a head. The approximate locations of the Frankfort horizontal and nasolabial angle are indicated. The coronal plane is also indicated.

Figure 2F:
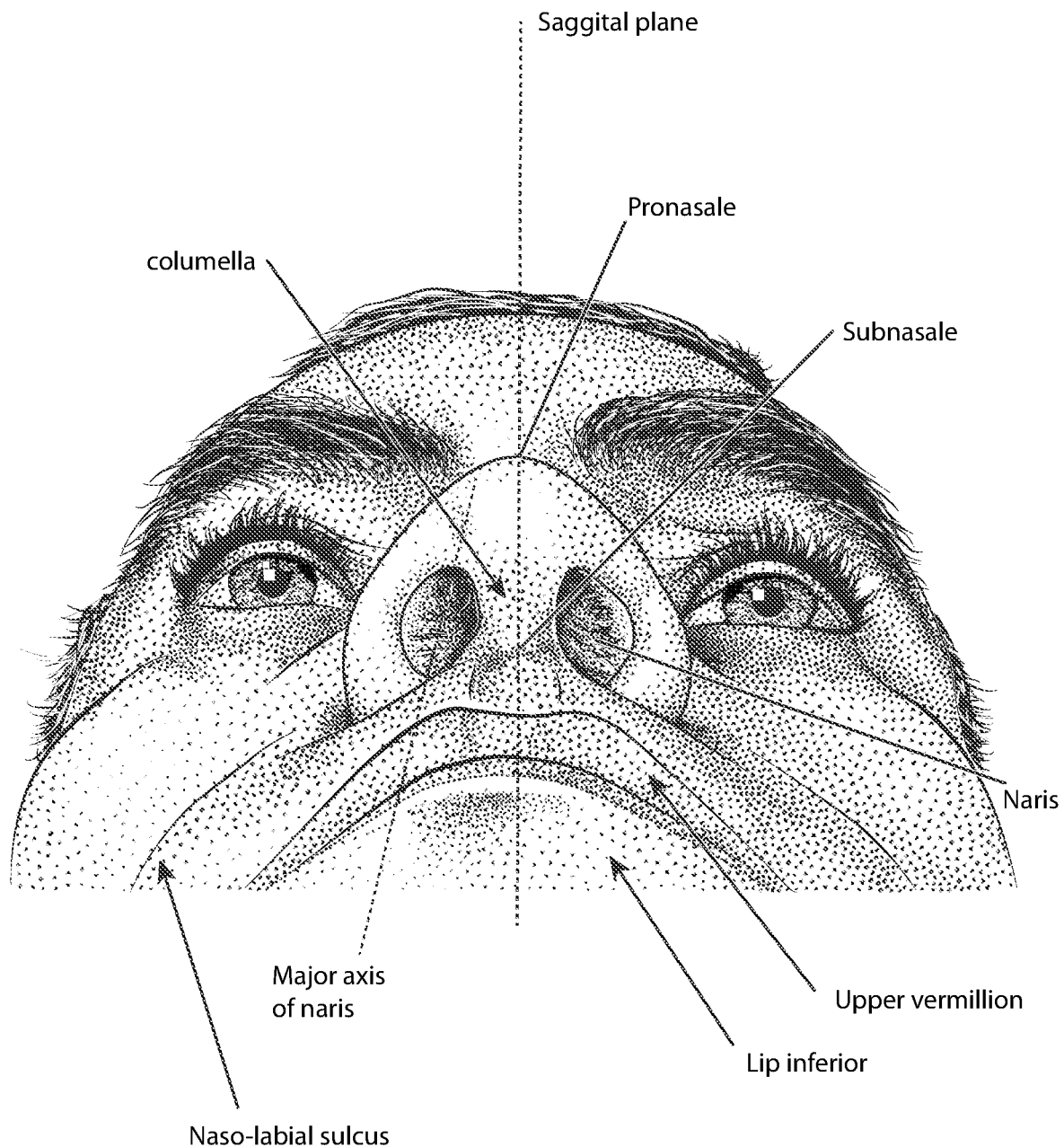

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
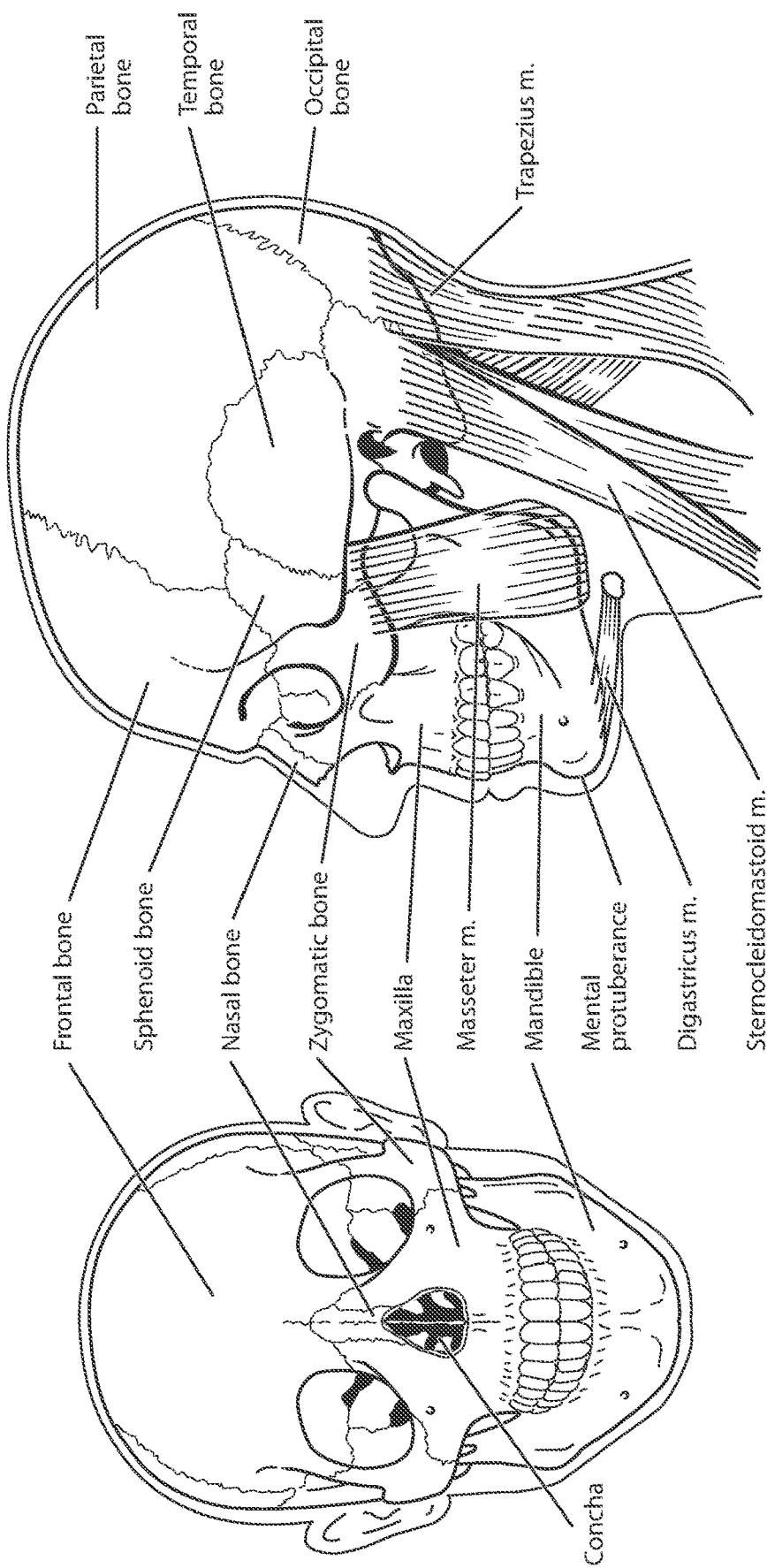

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
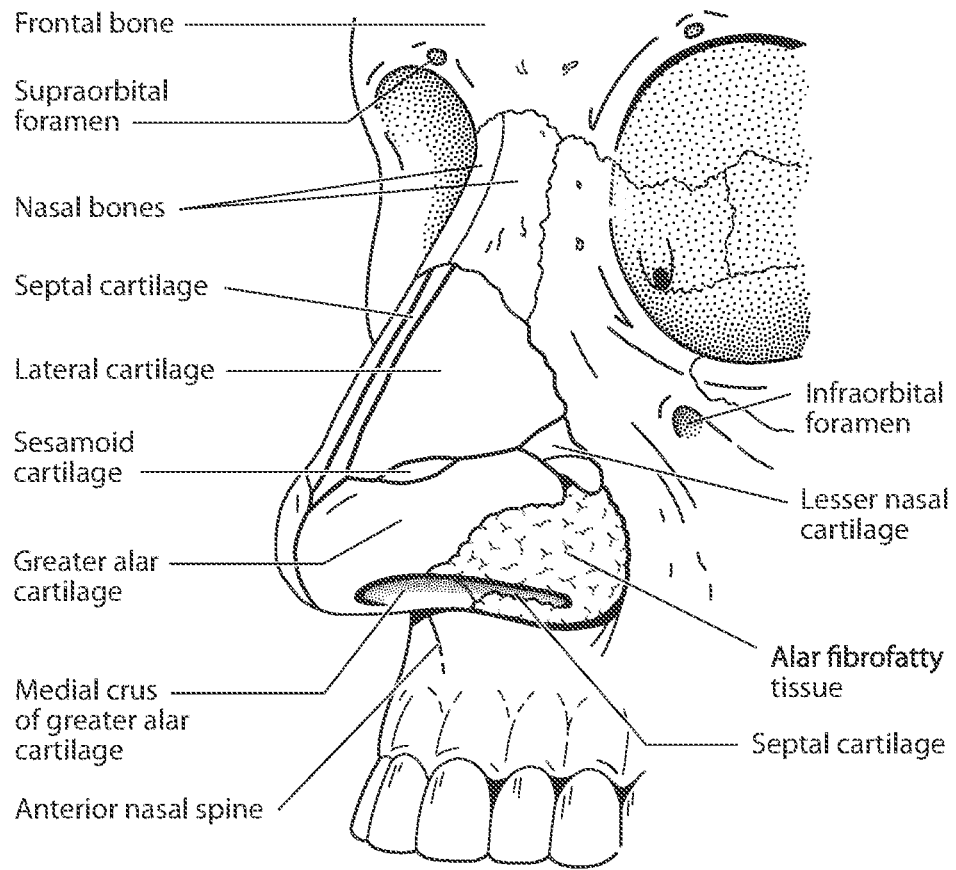

FIG. 2L shows an anterolateral view of a nose.

4.3 Patient Interface

Figure 3A:
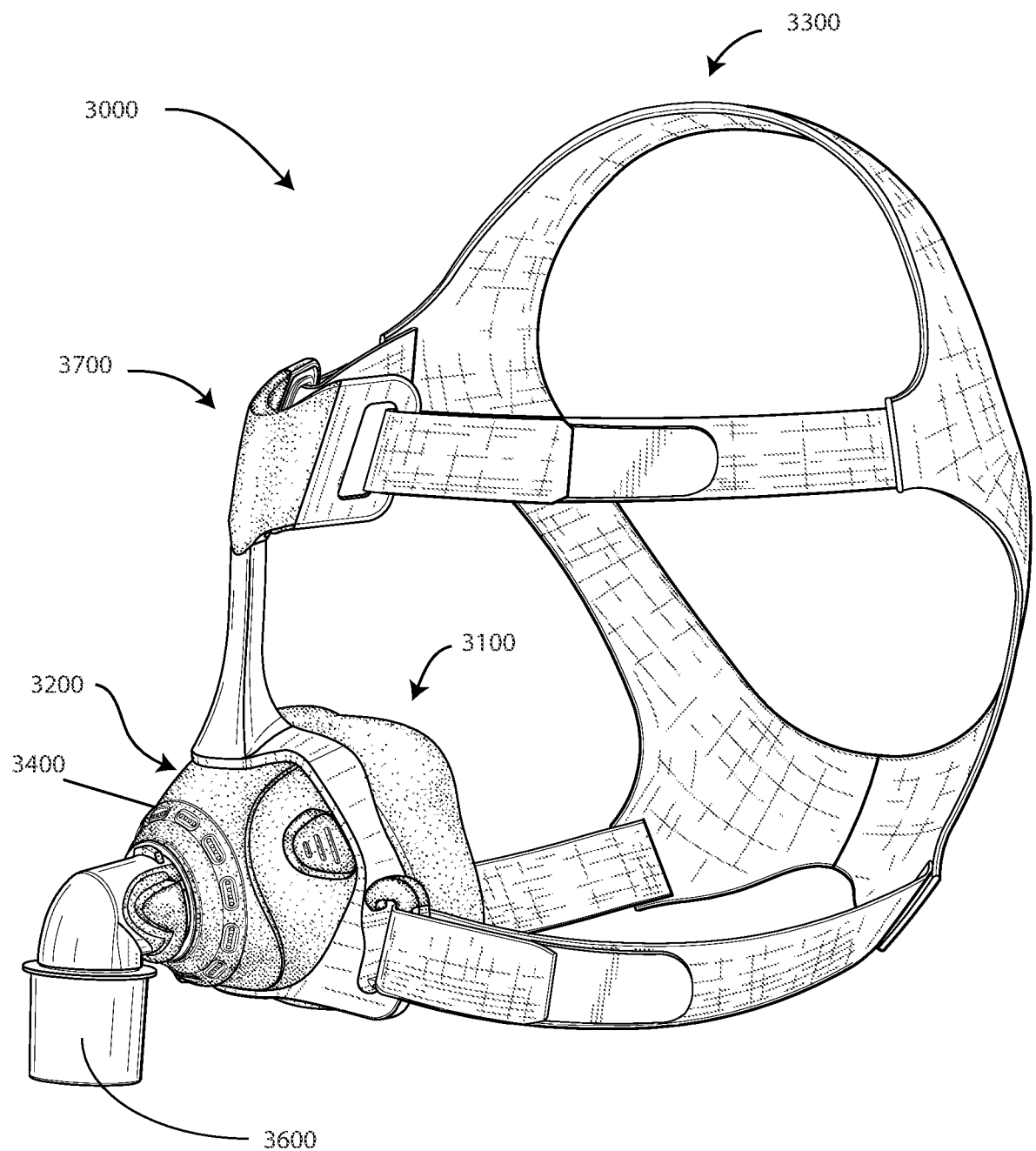

FIG. 3A shows a patient interface in the form of a nasal mask in accordance with one form of the present technology.

Figure 3B:
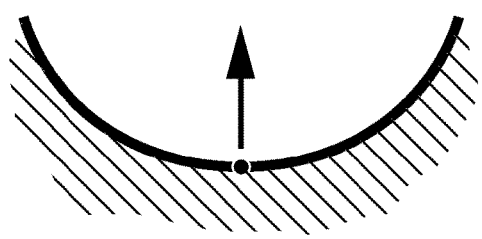

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
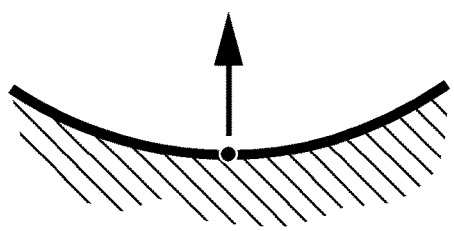

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
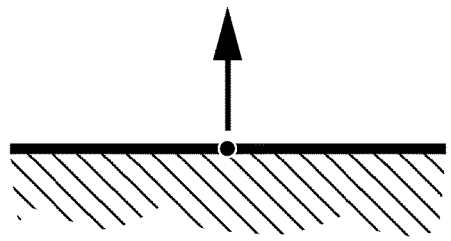

FIG. 3D shows a schematic of a cross-section through a structure at a point. An outward normal at the point is indicated. The curvature at the point has a value of zero.

Figure 3E:
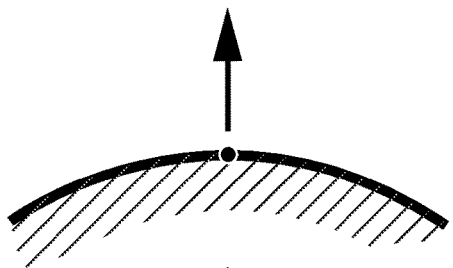

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
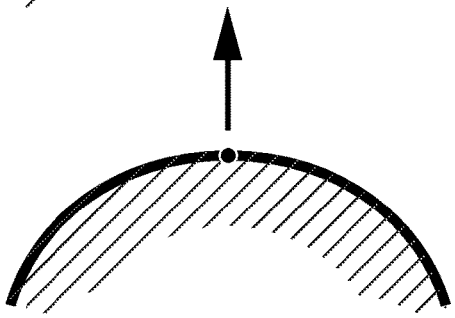

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
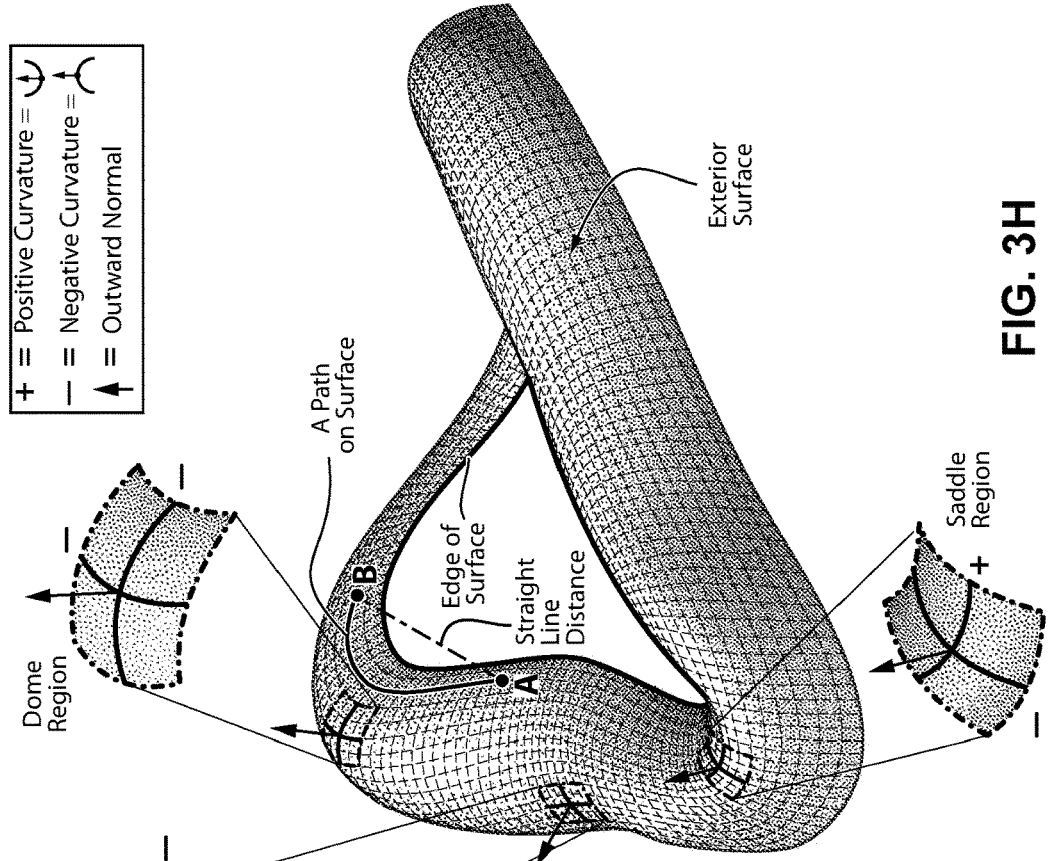
Figure 3G:
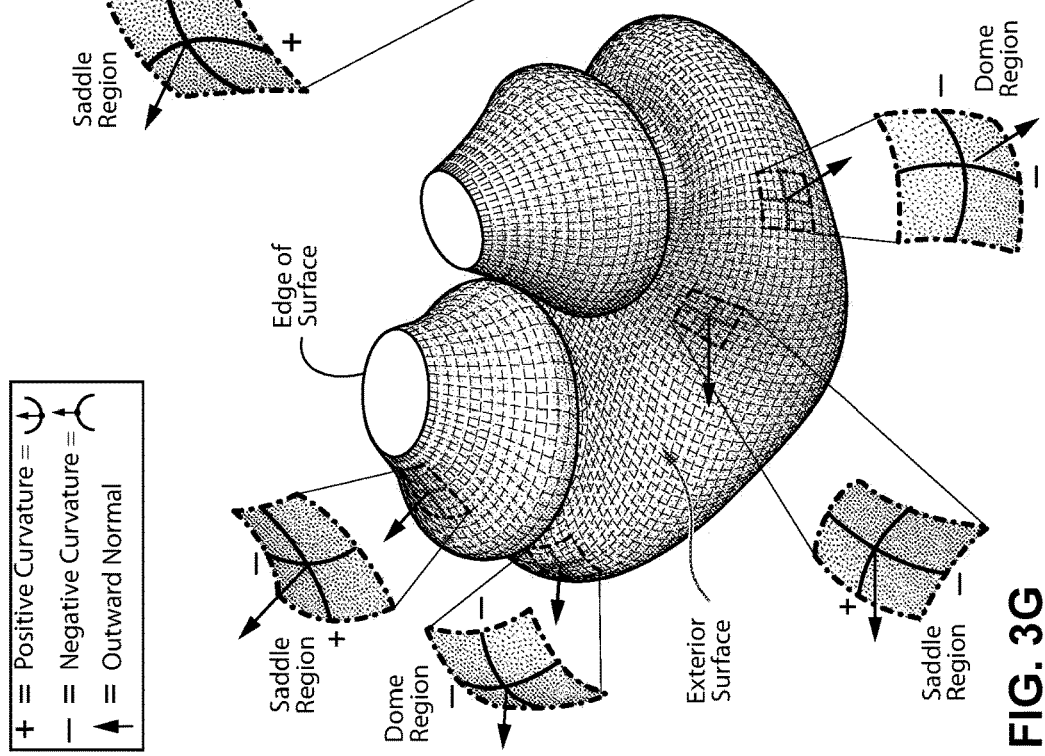

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
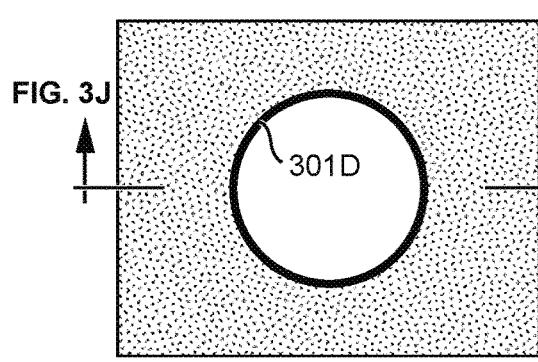

FIG. 3I shows the surface of a structure, with a one dimensional hole in the surface. Plane curve 301D forms the boundary of a one dimensional hole.

Figure 3K:
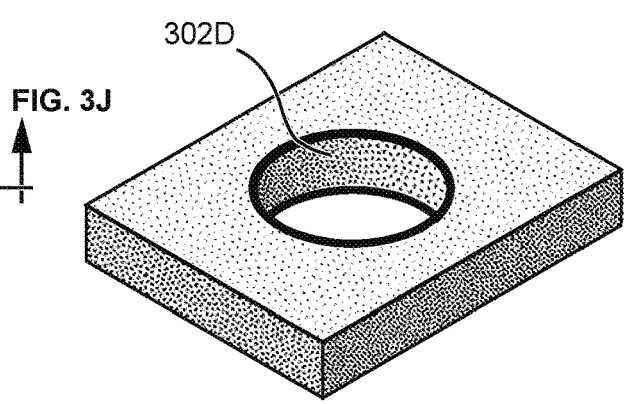
Figure 3J:

FIG. 3J shows a cross-section through the structure of FIG. 3I. Surface 302D that bounds a two dimensional hole in the structure of FIG. 3 is indicated.

FIG. 3K shows a perspective view of the structure of FIG. 3, including the two dimensional hole and the one dimensional hole. Surface 302D that bounds a two dimensional hole in the structure of FIG. 3I is indicated.

Figure 3L:
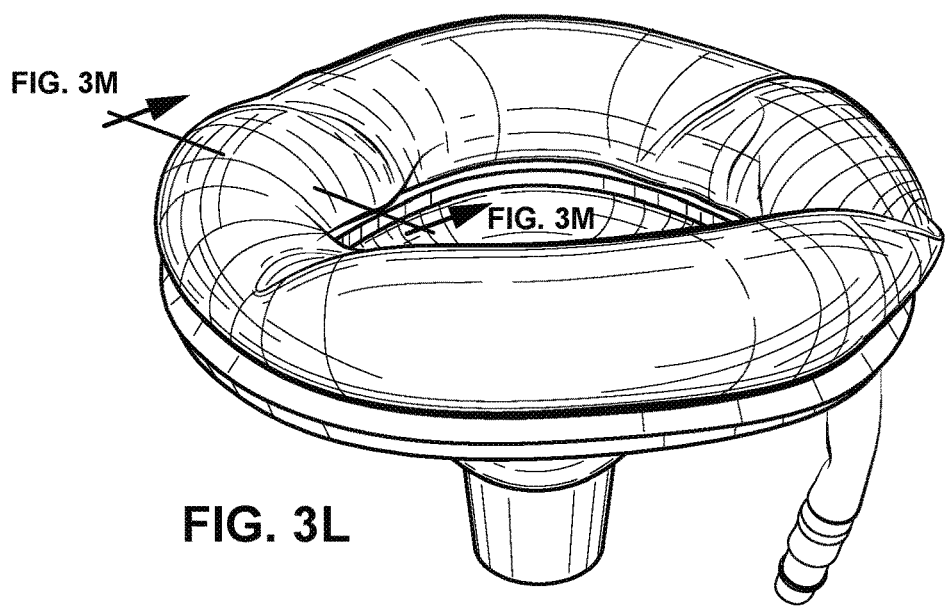

FIG. 3L shows a mask having an inflatable bladder as a cushion.

Figure 3M:
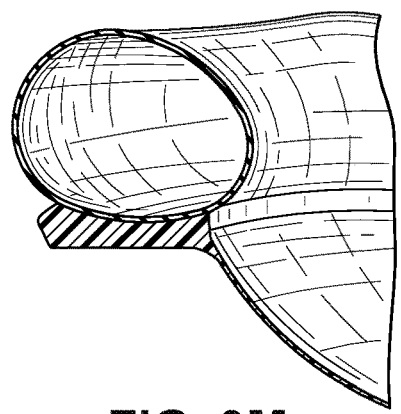

FIG. 3M shows a cross-section through the mask of FIG. 3L, and shows the inside surface of the bladder.

Figure 3N:
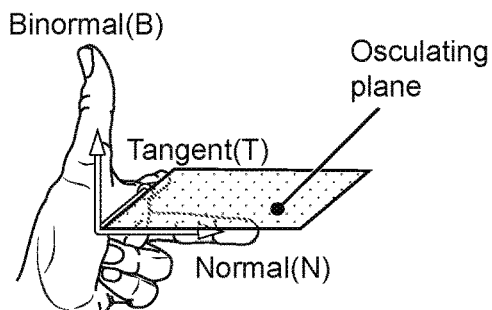

FIG. 3N illustrates a left-hand rule.

Figure 3O:
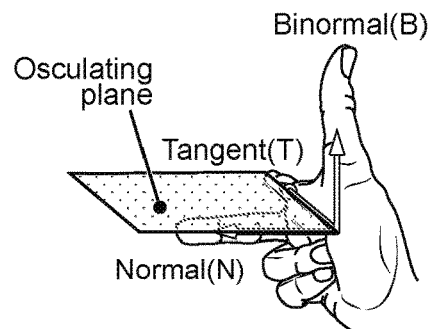

FIG. 3O illustrates a right-hand rule.

Figure 3P:
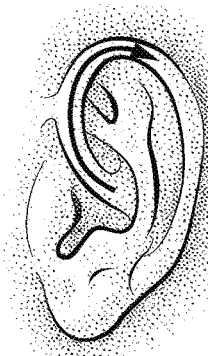

FIG. 3P shows a left ear, including a left ear helix.

Figure 3R:
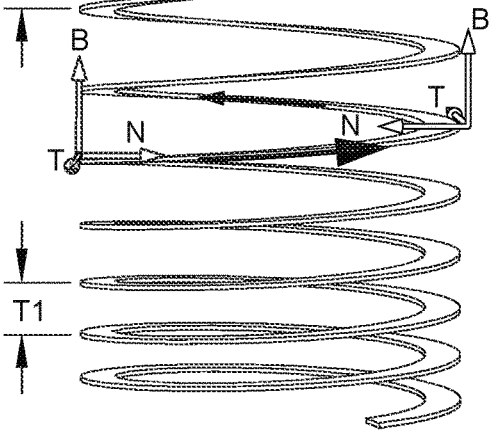
Figure 3Q:
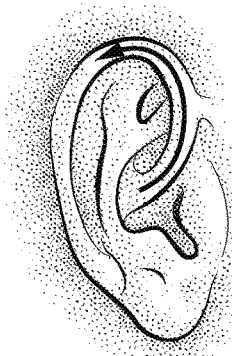

FIG. 3Q shows a right ear, including a right ear helix.

FIG. 3R shows a right-hand helix.

Figure 3S:
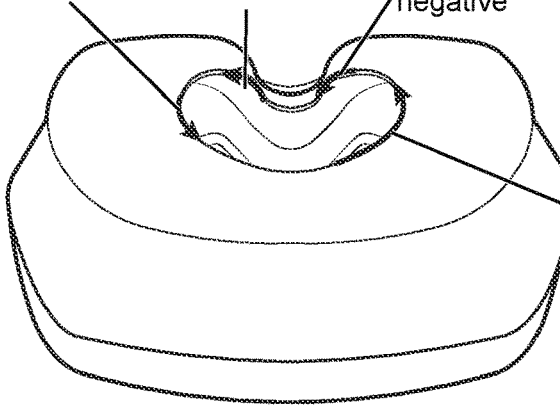

FIG. 3S shows a view of a mask, including the sign of the torsion of the space curve defined by the edge of the sealing membrane in different regions of the mask.

4.4 RPT Device

Figure 4A:
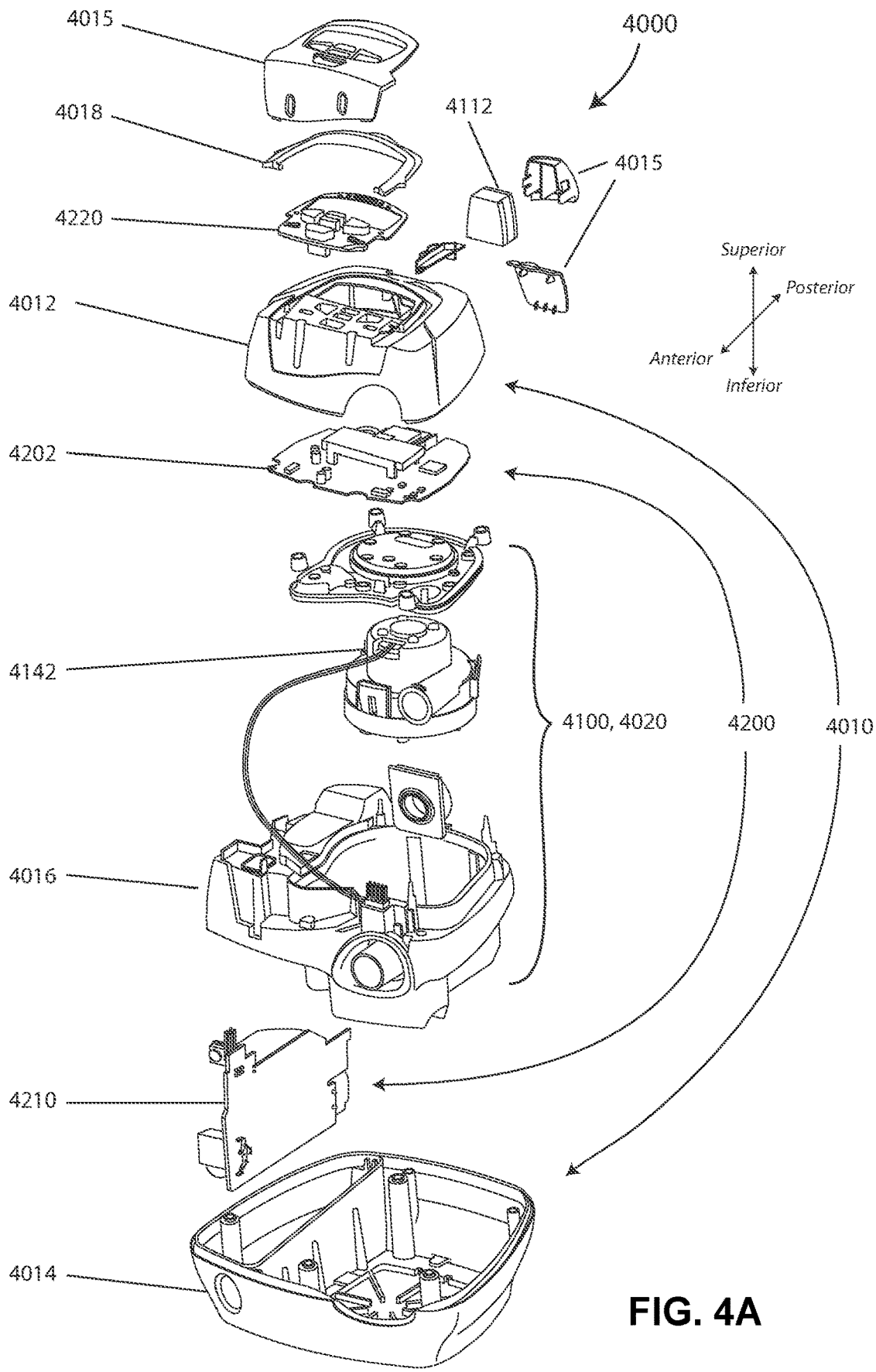

FIG. 4A shows an RPT device in accordance with one form of the present technology.

Figure 4B:
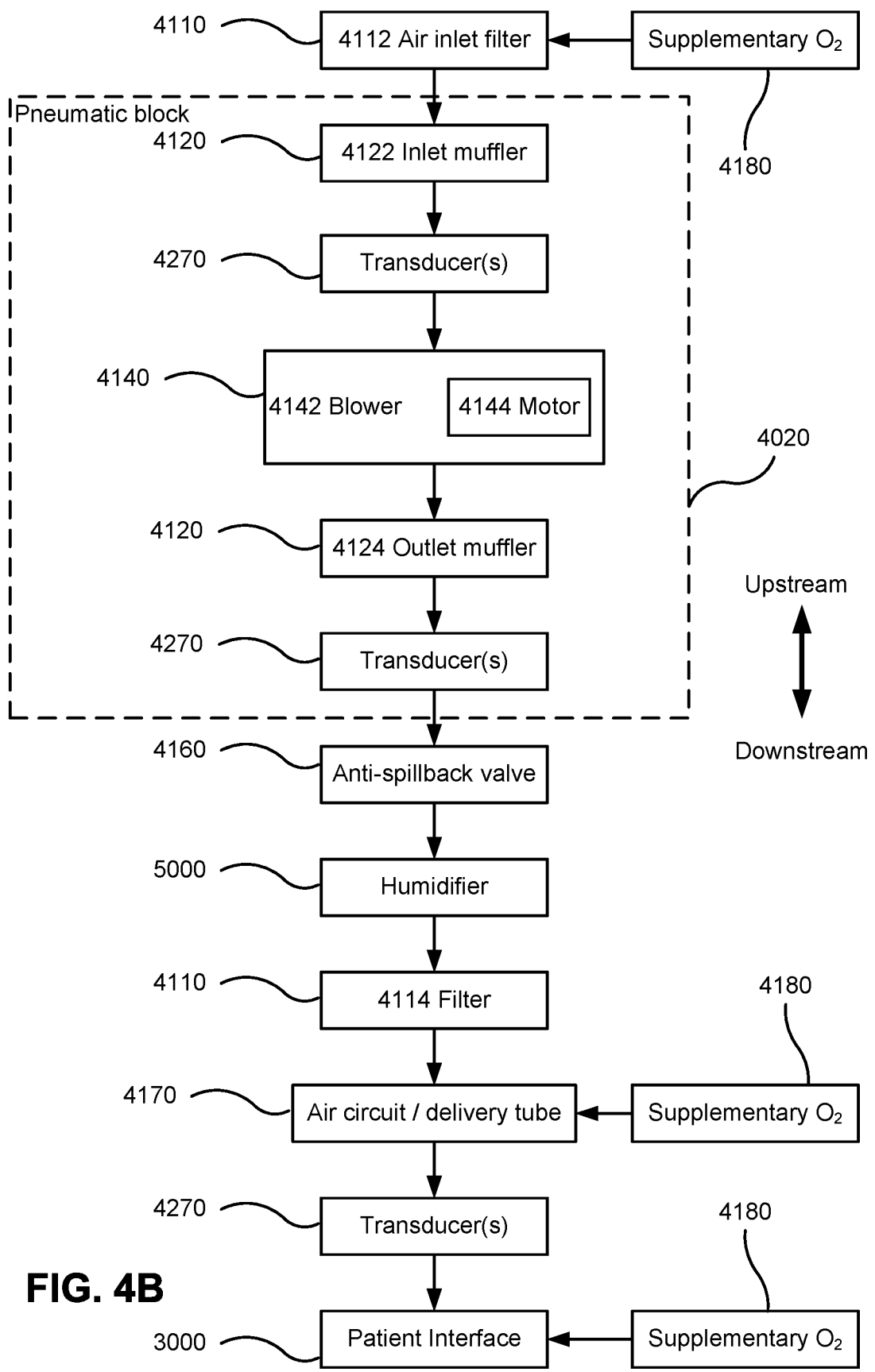

FIG. 4B is a schematic diagram of the pneumatic path of an RPT device in accordance with one form of the present technology. The directions of upstream and downstream are indicated.

Figure 4C:
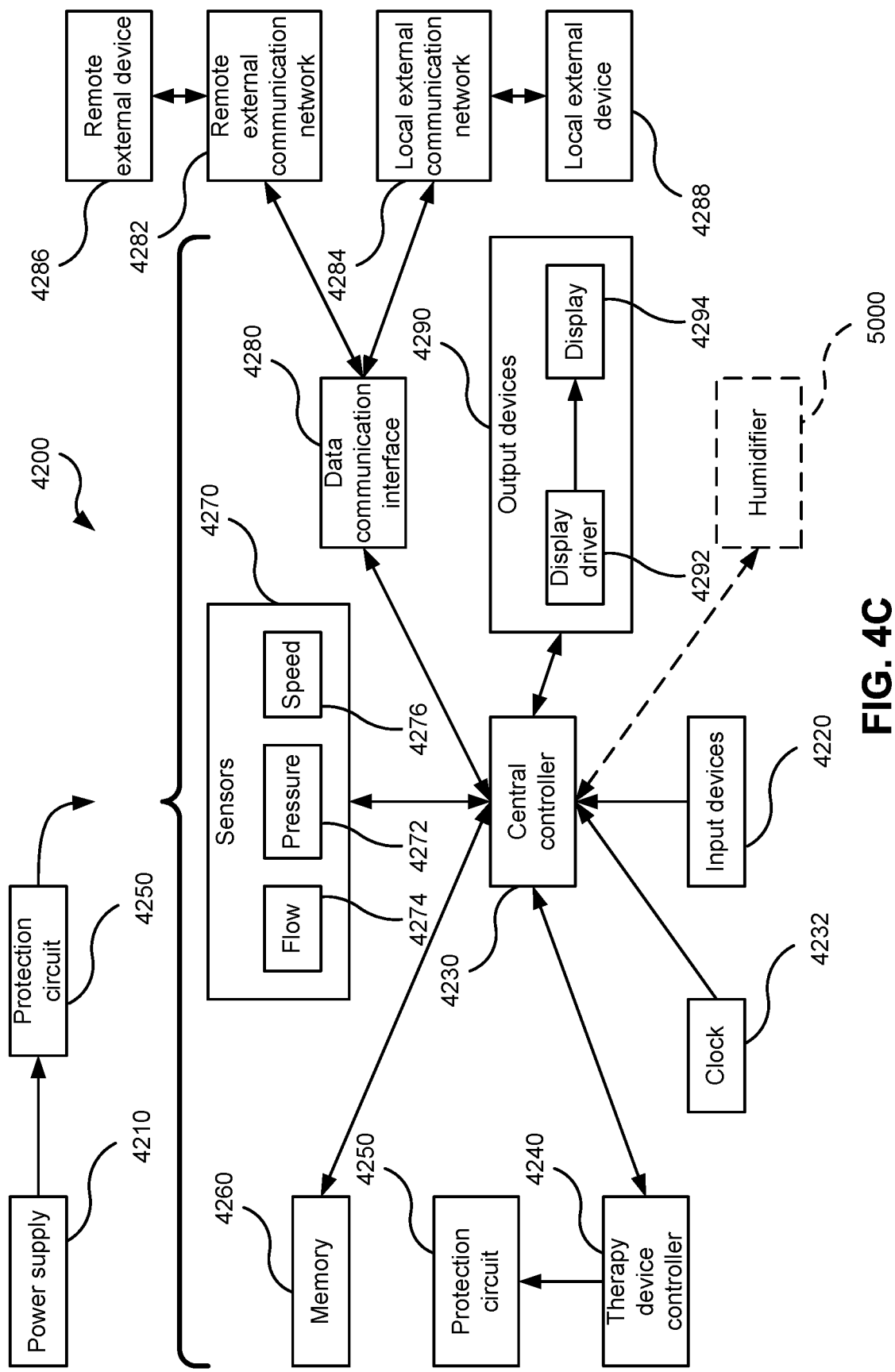

FIG. 4C is a schematic diagram of the electrical components of an RPT device in accordance with one form of the present technology.

4.5 Humidifier

Figure 5A:
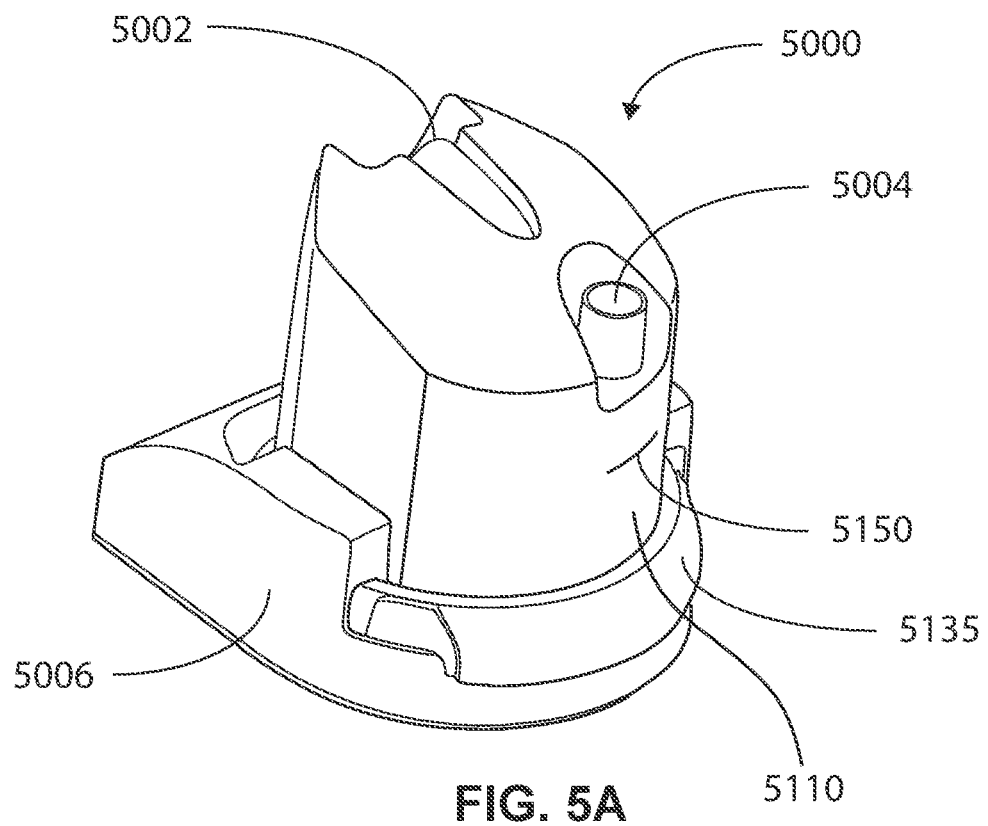

FIG. 5A shows an isometric view of a humidifier in accordance with one form of the present technology.

Figure 5B:
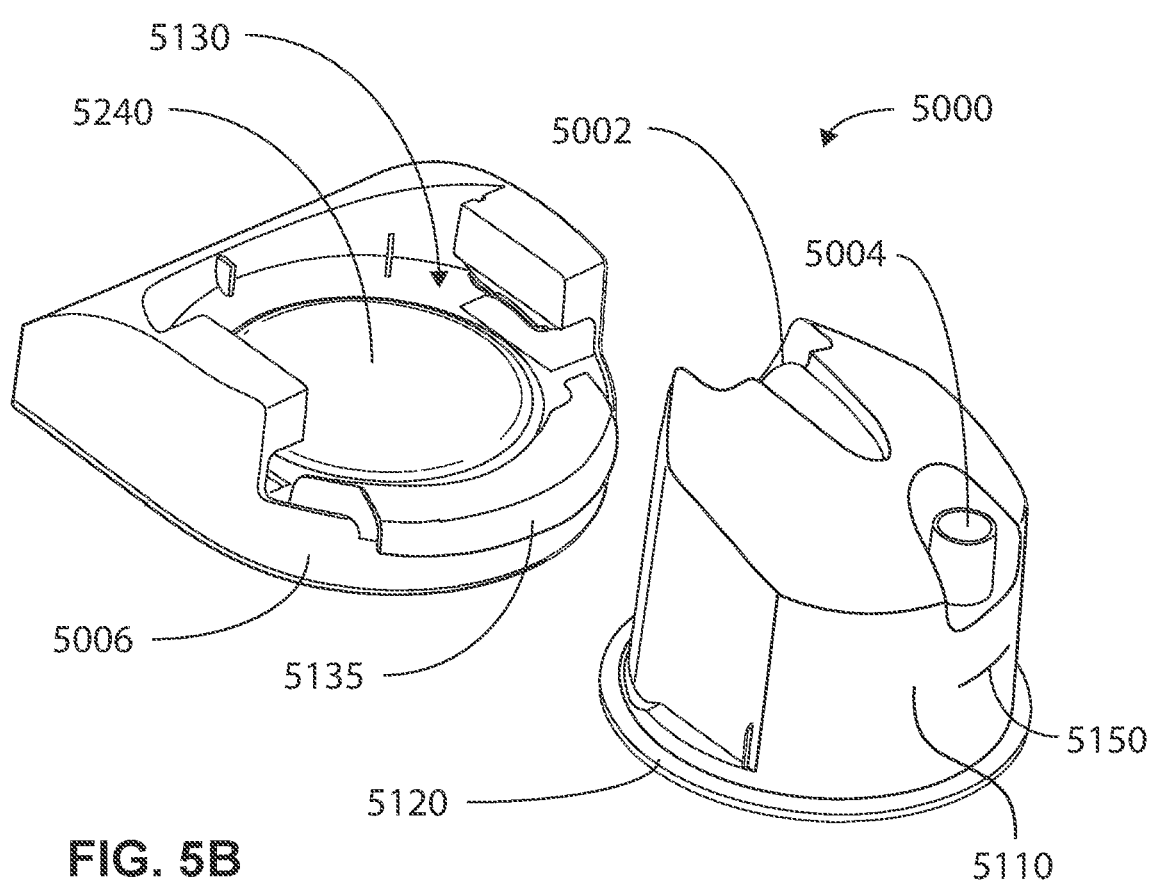

FIG. 5B shows an isometric view of a humidifier in accordance with one form of the present technology, showing a humidifier reservoir 5110 removed from the humidifier reservoir dock 5130.

Figure 5C:
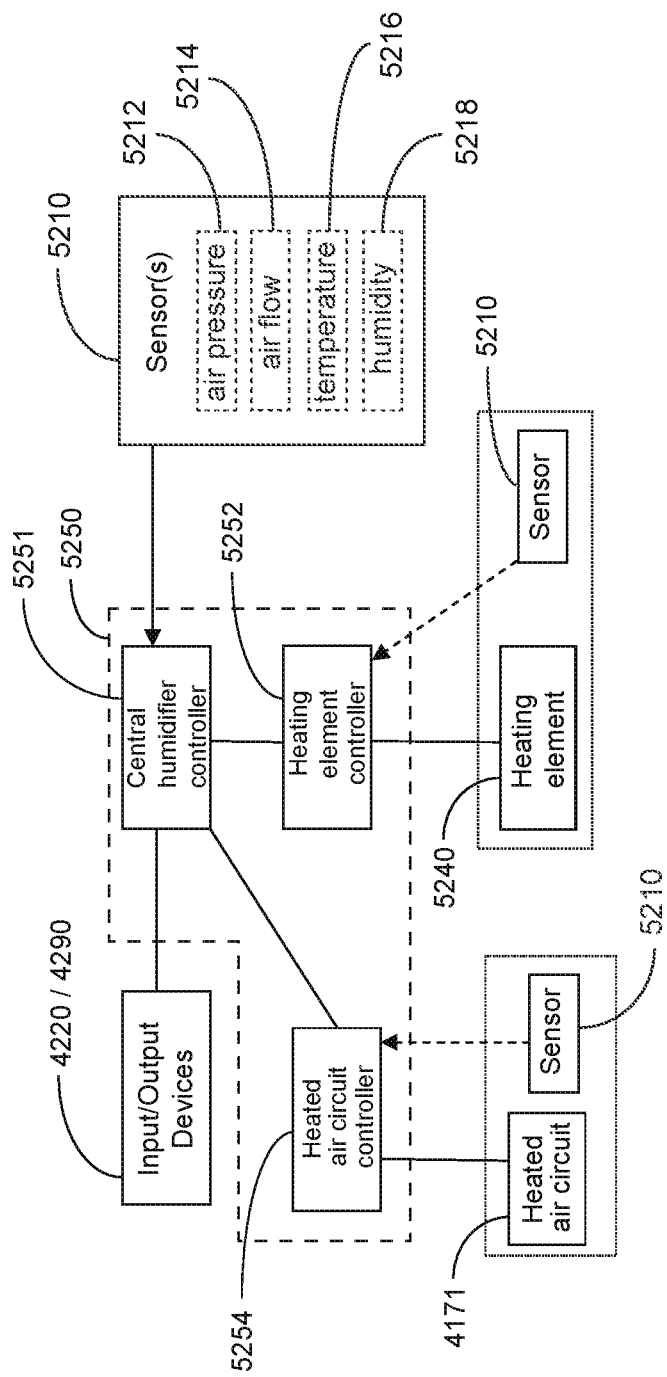

FIG. 5C shows a schematic of a humidifier in accordance with one form of the present technology.

4.6 Patient Interface

Figure 6A:
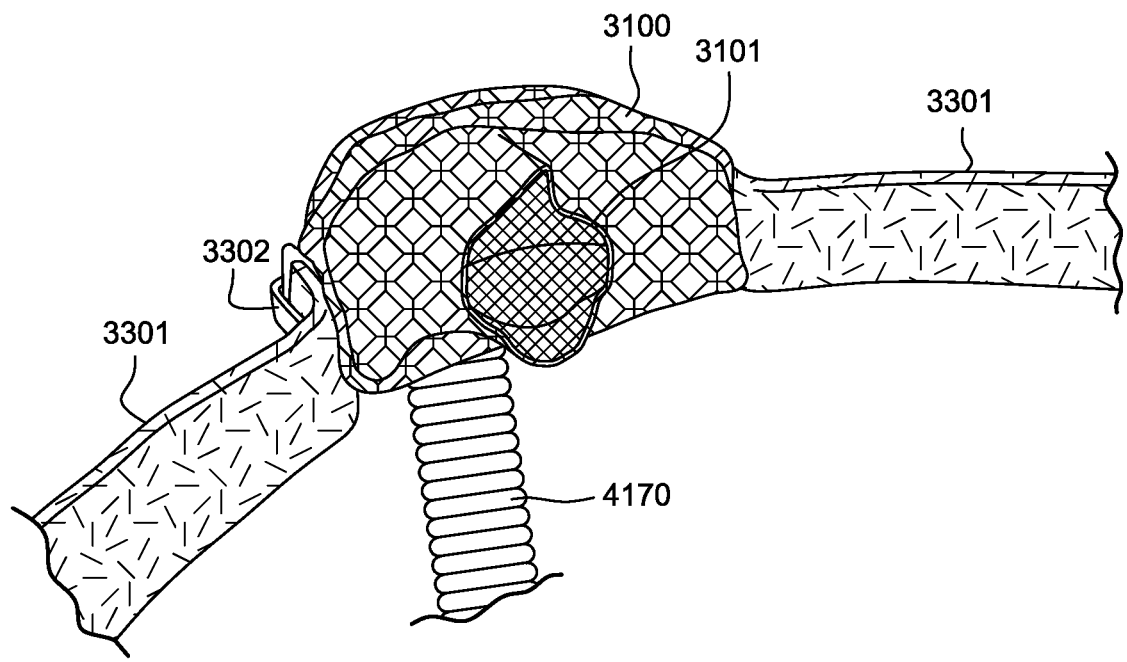

FIG. 6A shows a rear view of a patient interface according to an example of the present technology.

Figure 6B:
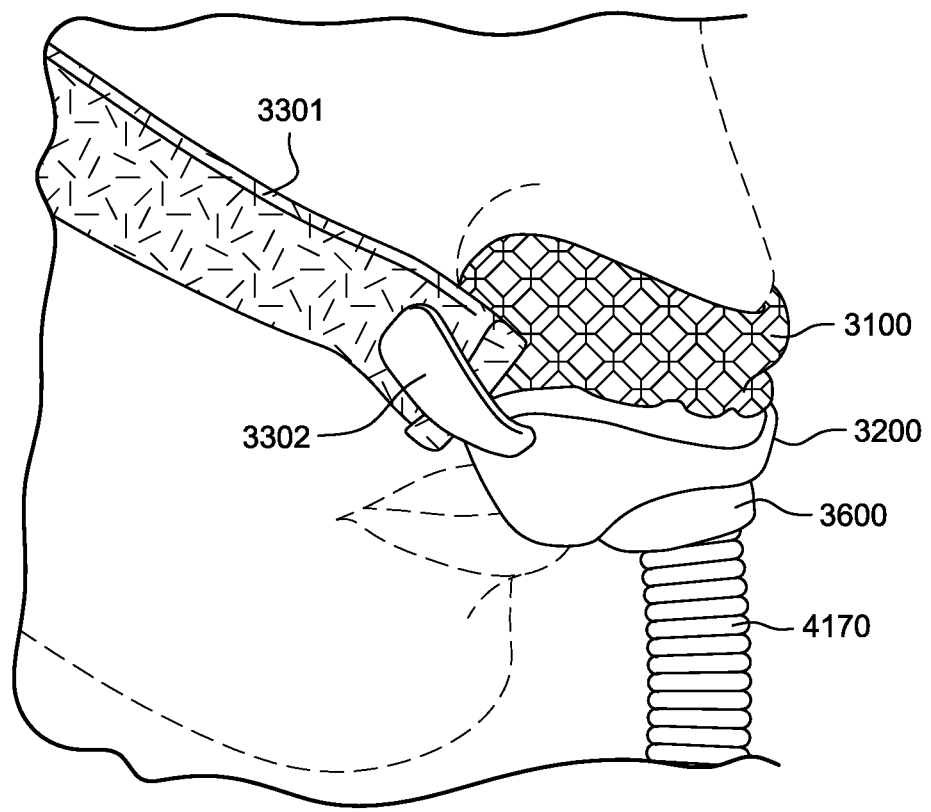

FIG. 6B shows a detailed perspective view of a patient interface according to an example of the present technology worn by a patient.

Figure 6C:
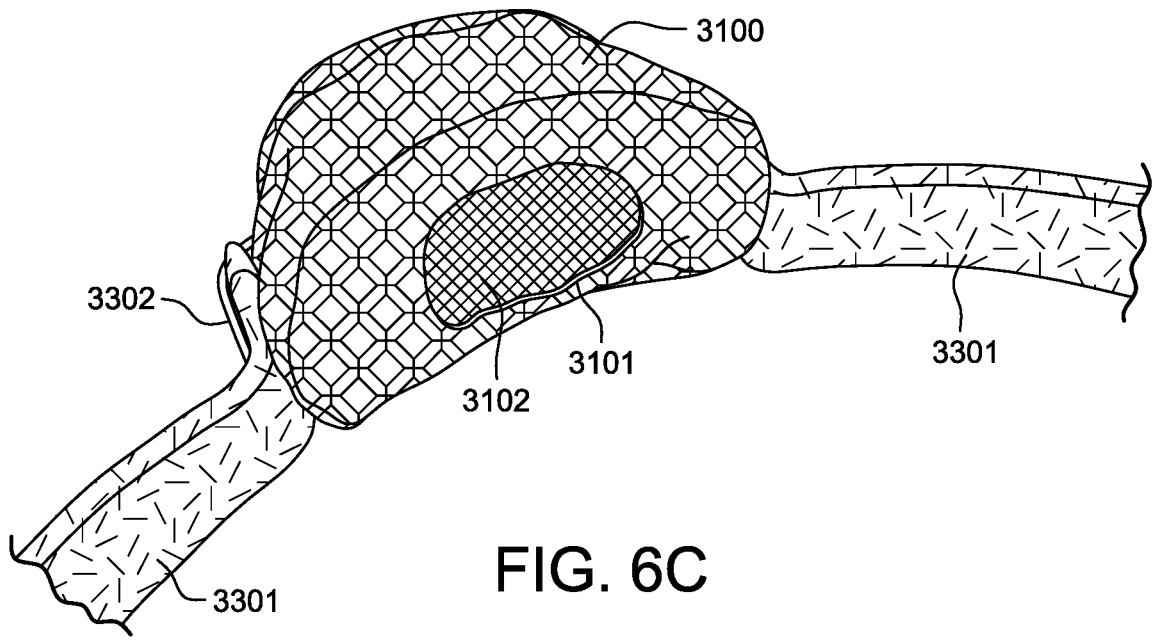

FIG. 6C shows a rear view of a patient interface according to an example of the present technology.

Figure 7A:
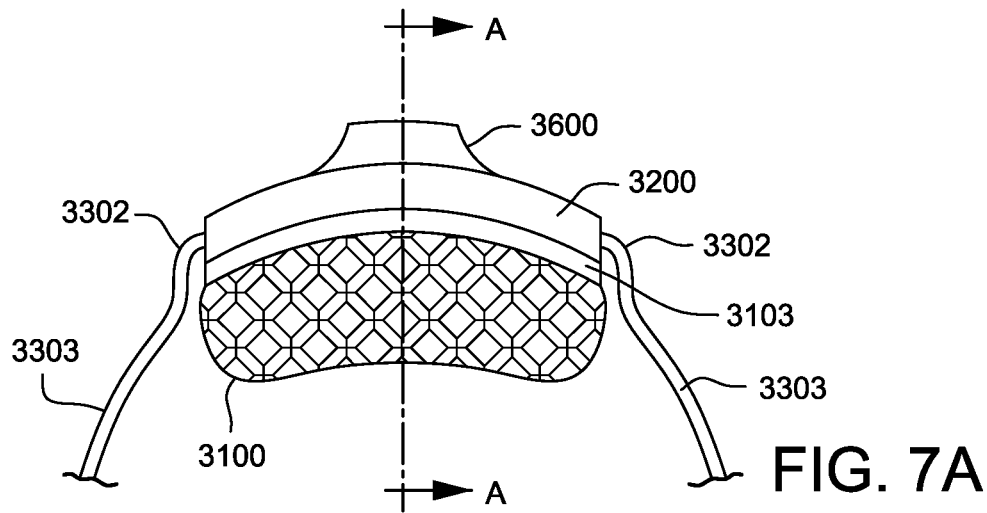

FIG. 7A shows a top view of a patient interface according to an example of the present technology.

Figure 7B:
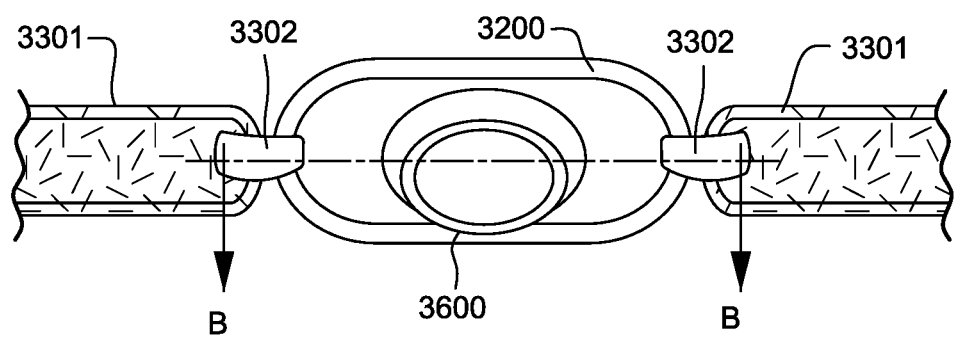

FIG. 7B shows a front view of a patient interface according to an example of the present technology.

Figure 7C:
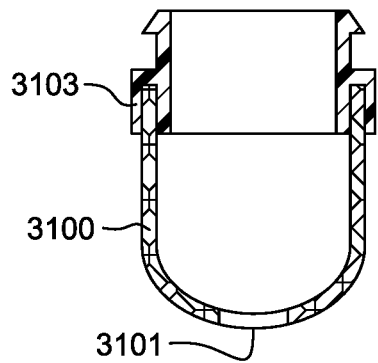

FIG. 7C shows a cross-sectional view of a patient interface according to an example of the present technology taken through line A-A of FIG. 7A.

Figure 7D:
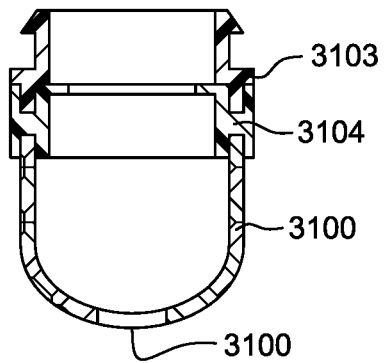

FIG. 7D shows a cross-sectional view of a patient interface according to another example of the present technology taken through line A-A of FIG. 7A.

Figure 7E:
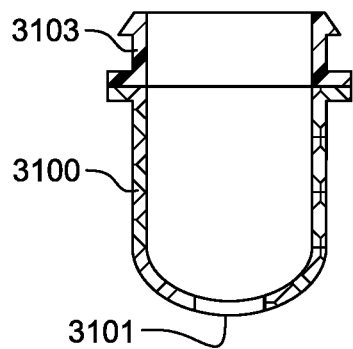

FIG. 7E shows a cross-sectional view of a patient interface according to another example of the present technology taken through line A-A of FIG. 7A.

Figure 7F:
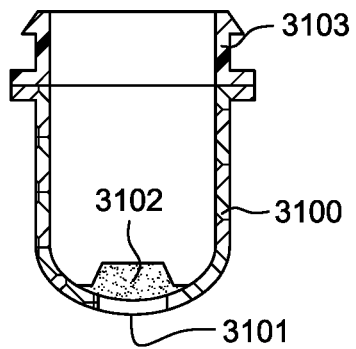

FIG. 7F shows a cross-sectional view of a patient interface according to another example of the present technology taken through line A-A of FIG. 7A.

Figure 7G:
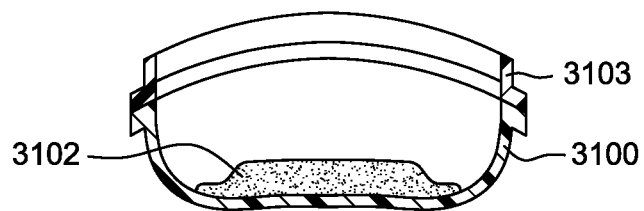

FIG. 7G shows a cross-sectional view of a patient interface according to an example of the present technology taken through line B-B of FIG. 7B.

Figure 8A:
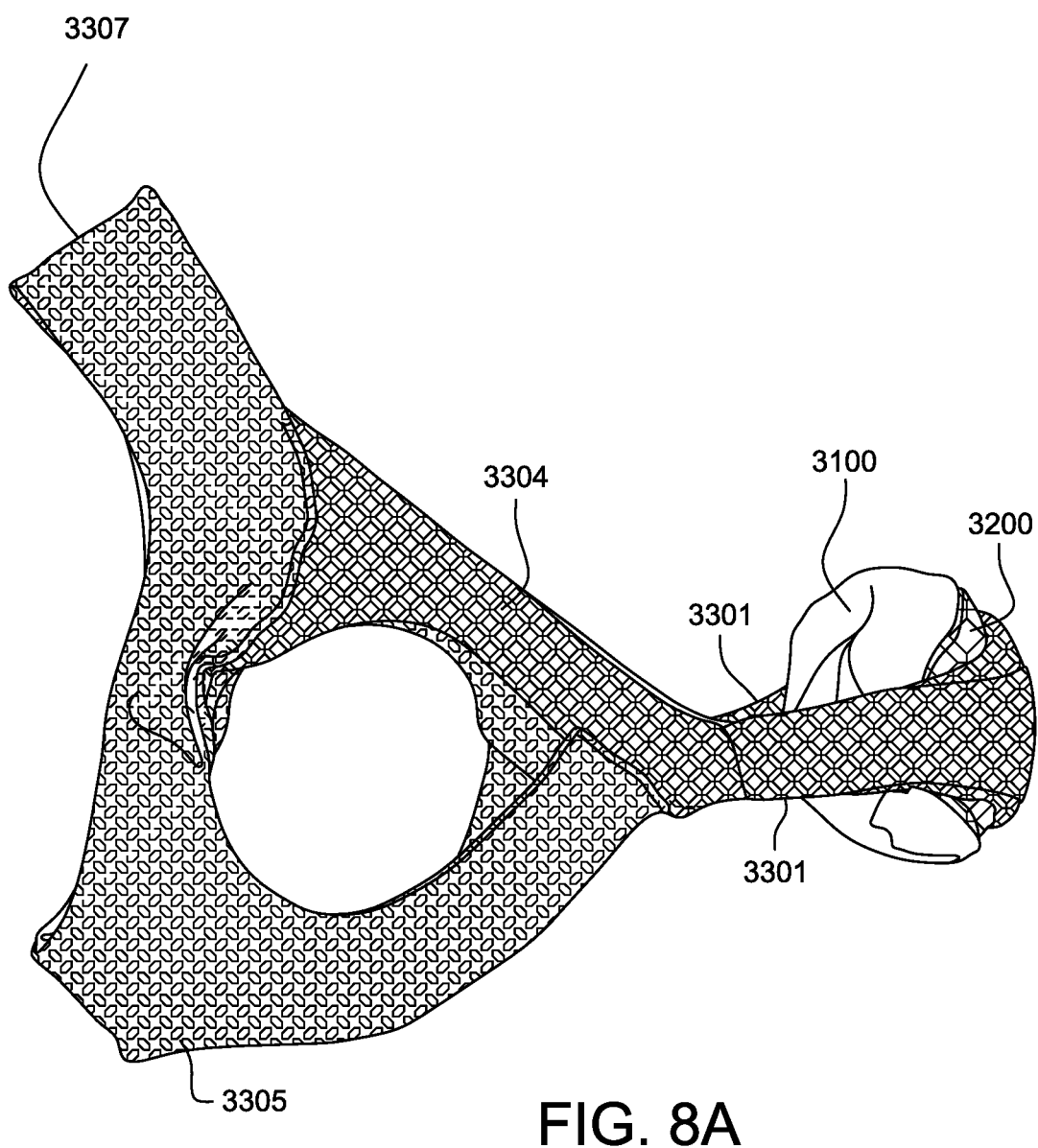

FIG. 8A shows a side view of a patient interface according to an example of the present technology.

Figure 8B:
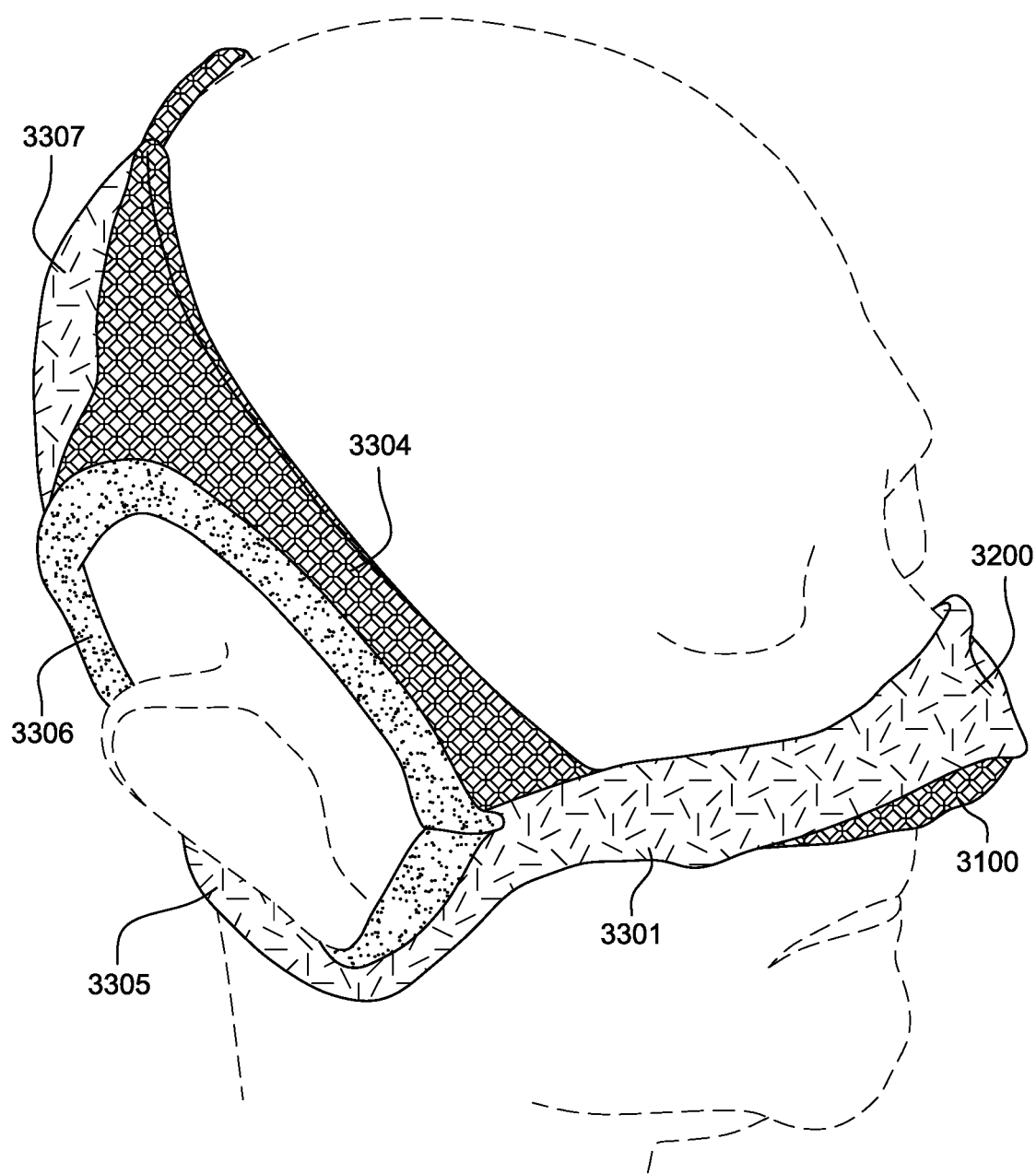

FIG. 8B shows a front perspective view of a patient interface according to an example of the present technology worn by a patient.

Figure 8C:
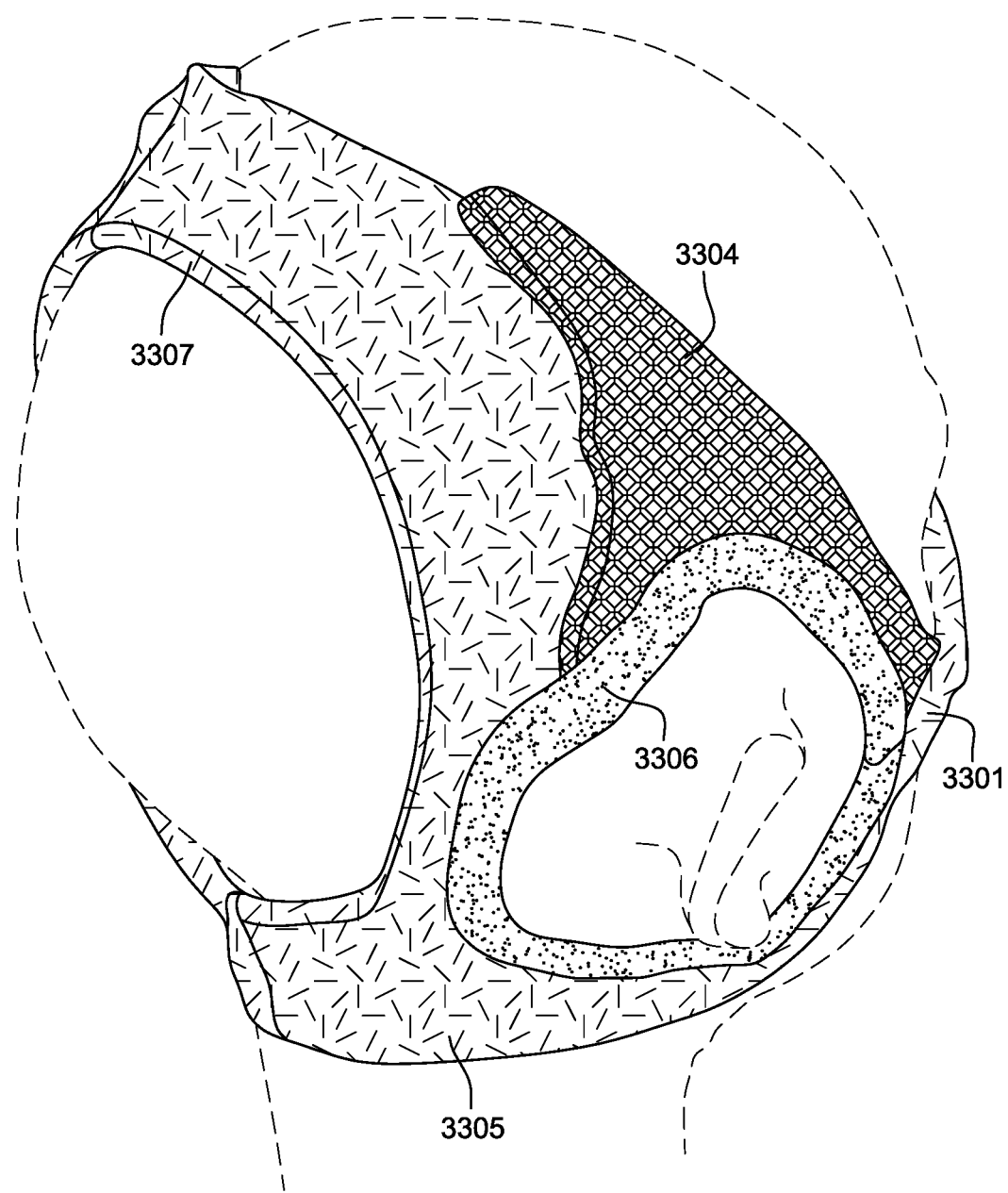

FIG. 8C shows a rear perspective view of a patient interface according to an example of the present technology worn by a patient.

Figure 8D:
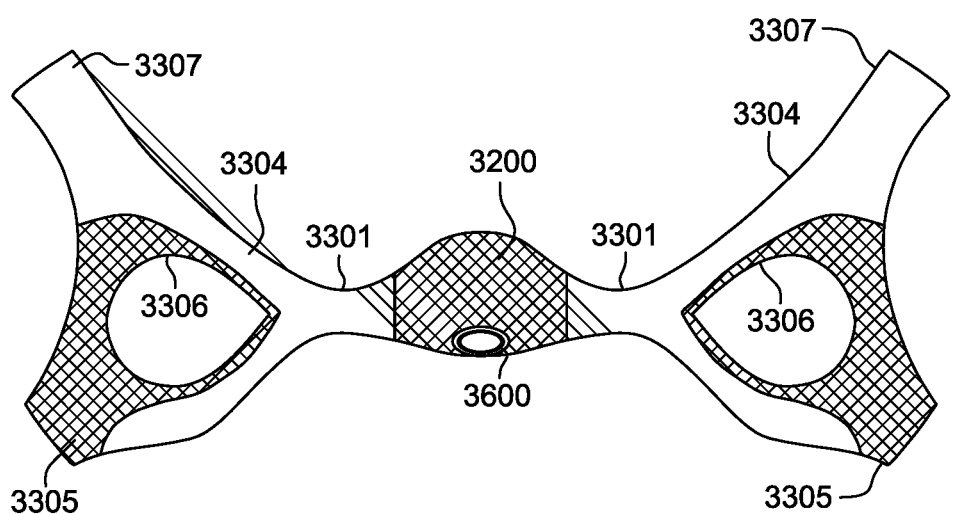

FIG. 8D shows a front view of patient interface according to an example of the present technology in a partially disassembled state.

Figure 9A:
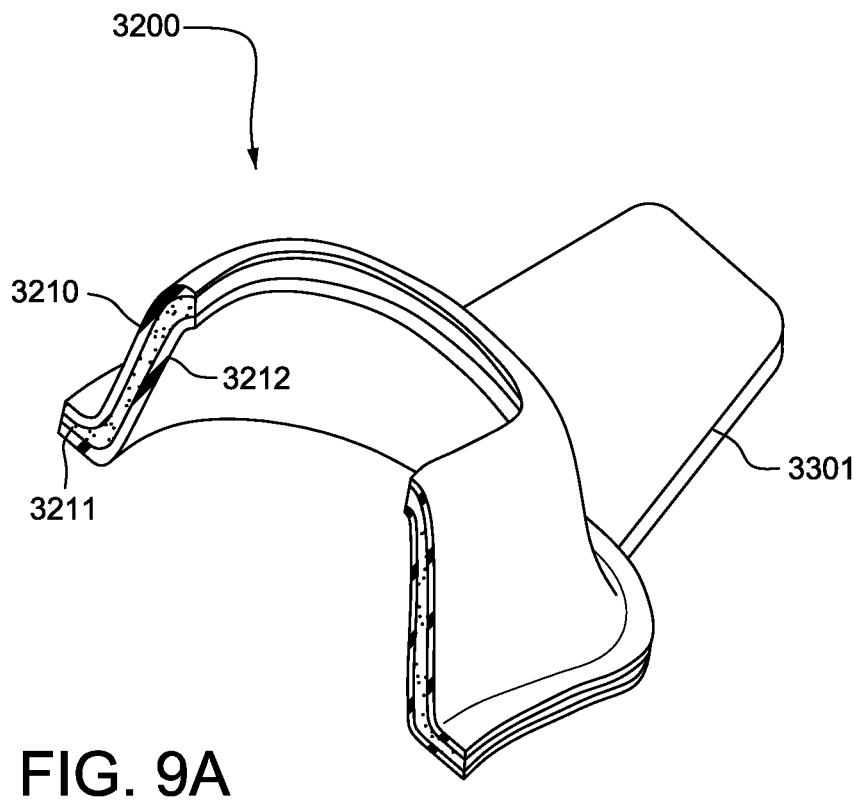

FIG. 9A shows a cross-sectional view of a plenum chamber for a patient interface according to an example of the present technology.

Figure 9B:
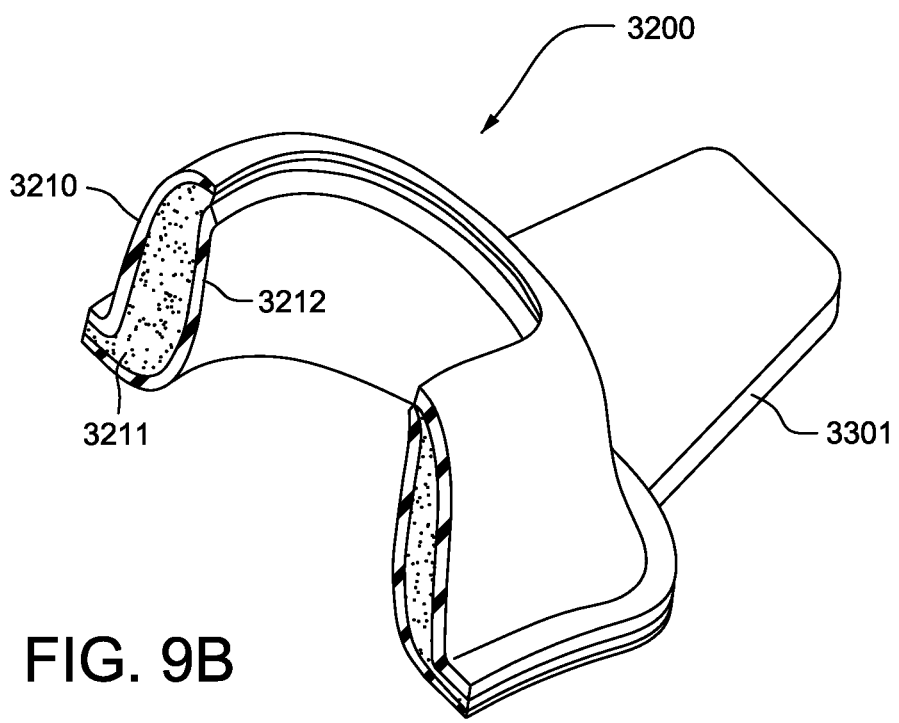

FIG. 9B shows a cross-sectional view of a plenum chamber for a patient interface according to another example of the present technology.

Figure 9C:
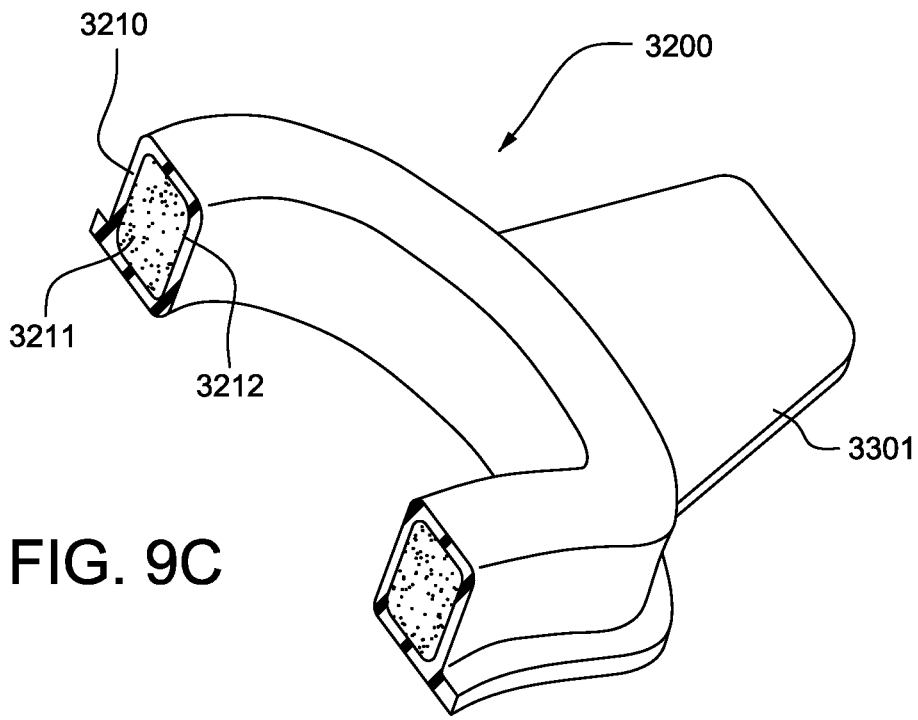

FIG. 9C shows a cross-sectional view of a plenum chamber for a patient interface according to another example of the present technology.

Figure 9D:
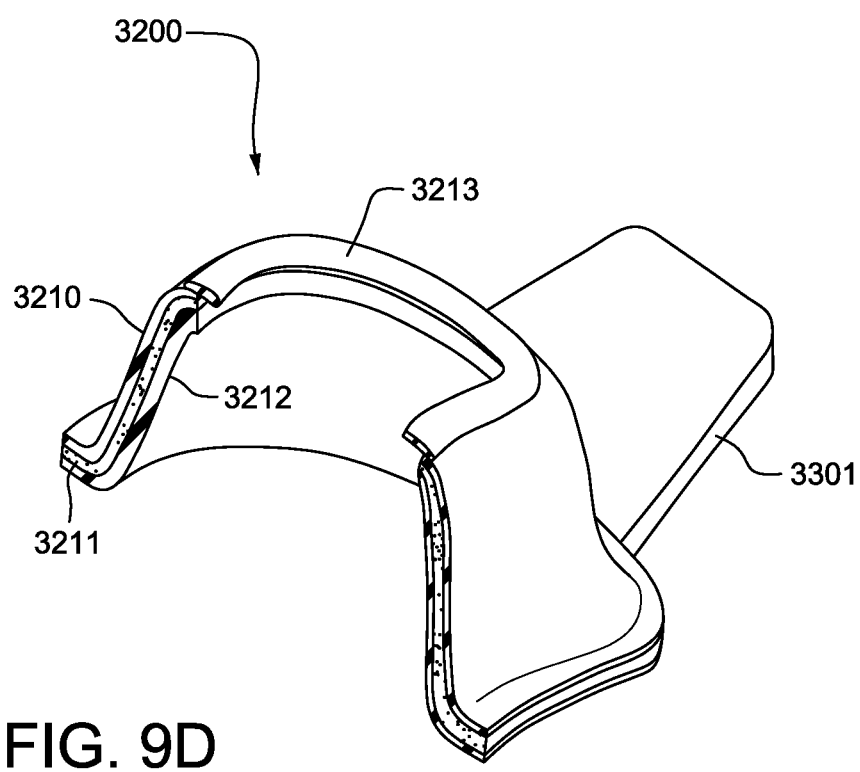

FIG. 9D shows a cross-sectional view of a plenum chamber for a patient interface according to another example of the present technology.

Figure 9E:
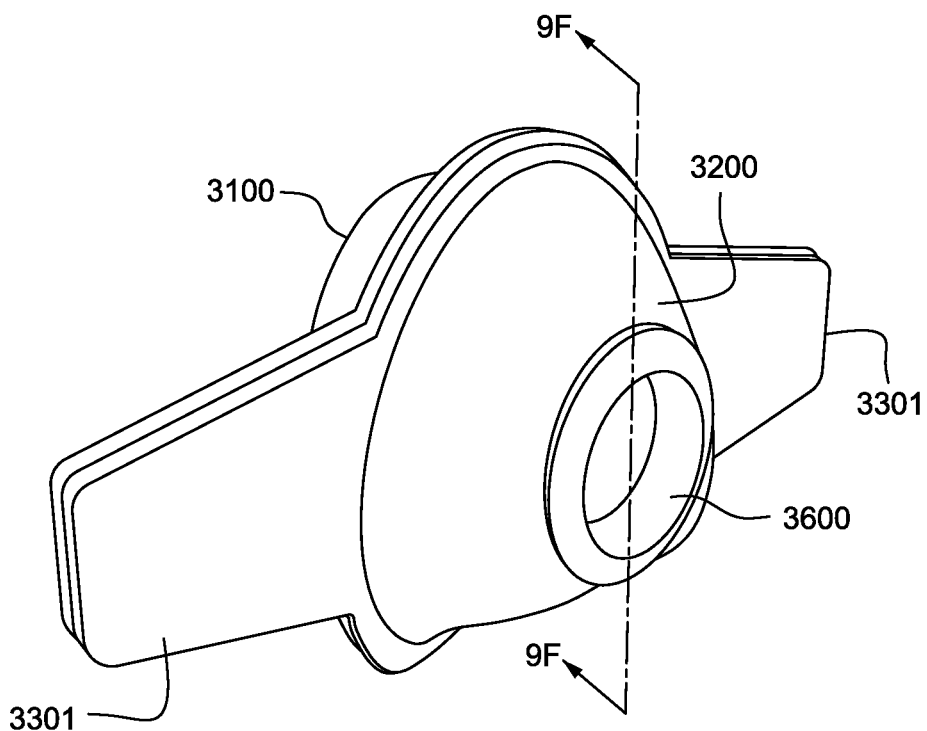

FIG. 9E shows a perspective view of a plenum chamber and seal forming structure for a patient interface according to another example of the present technology.

Figure 9F:
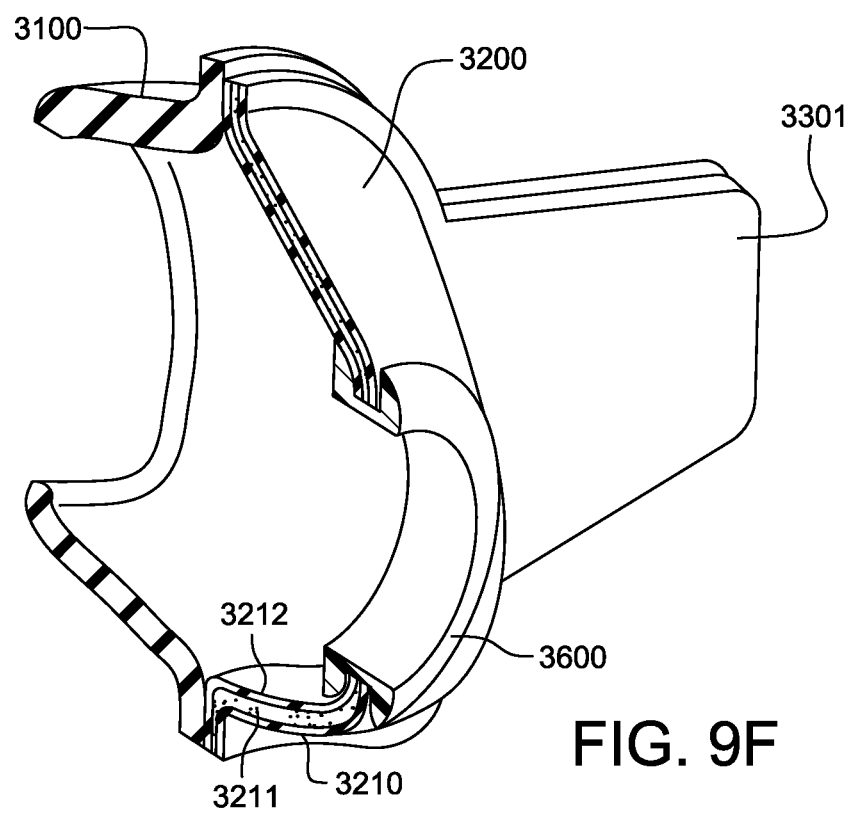

FIG. 9F shows a cross-sectional view of a plenum chamber for a patient interface according to another example of the present technology taken through line 9F-9F of FIG. 9E.

Figure 10A:
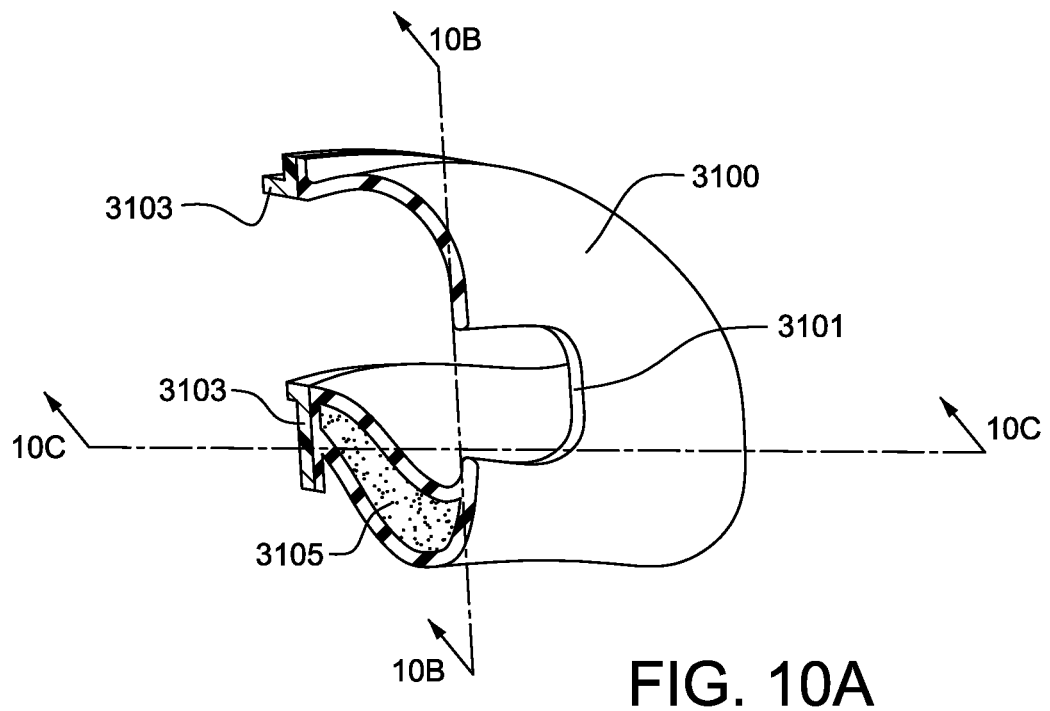

FIG. 10A shows a partial cross-sectional view of a seal forming structure of a patient interface according to an example of the present technology.

Figure 10B:
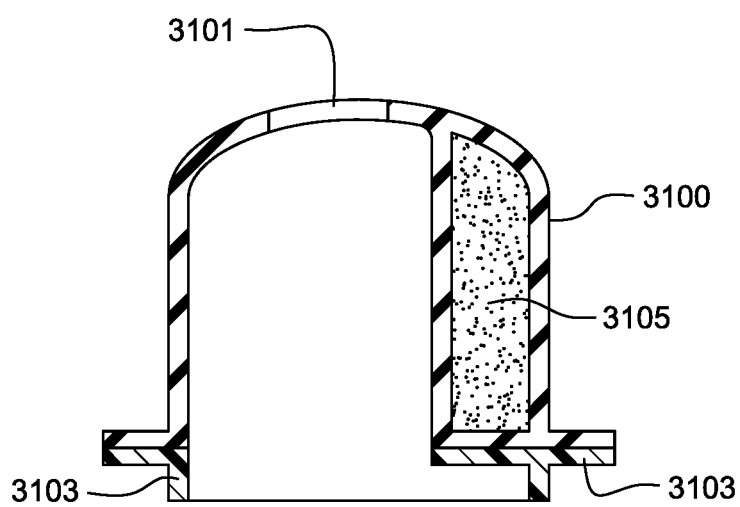

FIG. 10B shows a cross-sectional view of a seal forming structure of a patient interface according to an example of the present technology taken through line 10B-10B of FIG. 10A.

Figure 10C:
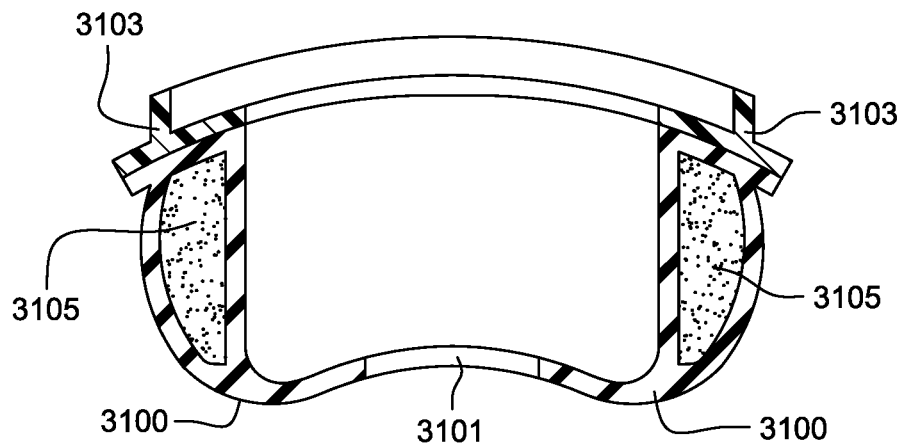

FIG. 10C shows a cross-sectional view of a seal forming structure of a patient interface according to an example of the present technology taken through line 10C-10C of FIG. 10A.

Figure 10D:
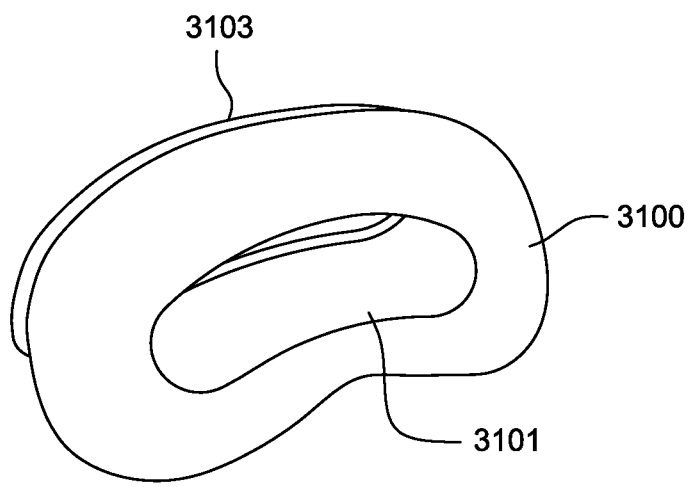

FIG. 10D shows a perspective view of a seal forming structure of a patient interface according to an example of the present technology.

FIG. 11A shows an exploded view of a plenum chamber and a seal forming structure of a patient interface according to an example of the present technology.

FIG. 11B shows a front view of a patient interface according to an example of the present technology.

FIG. 11C shows a cross-sectional view of a patient interface according to an example of the present technology worn by a patient.

Figure 12A:
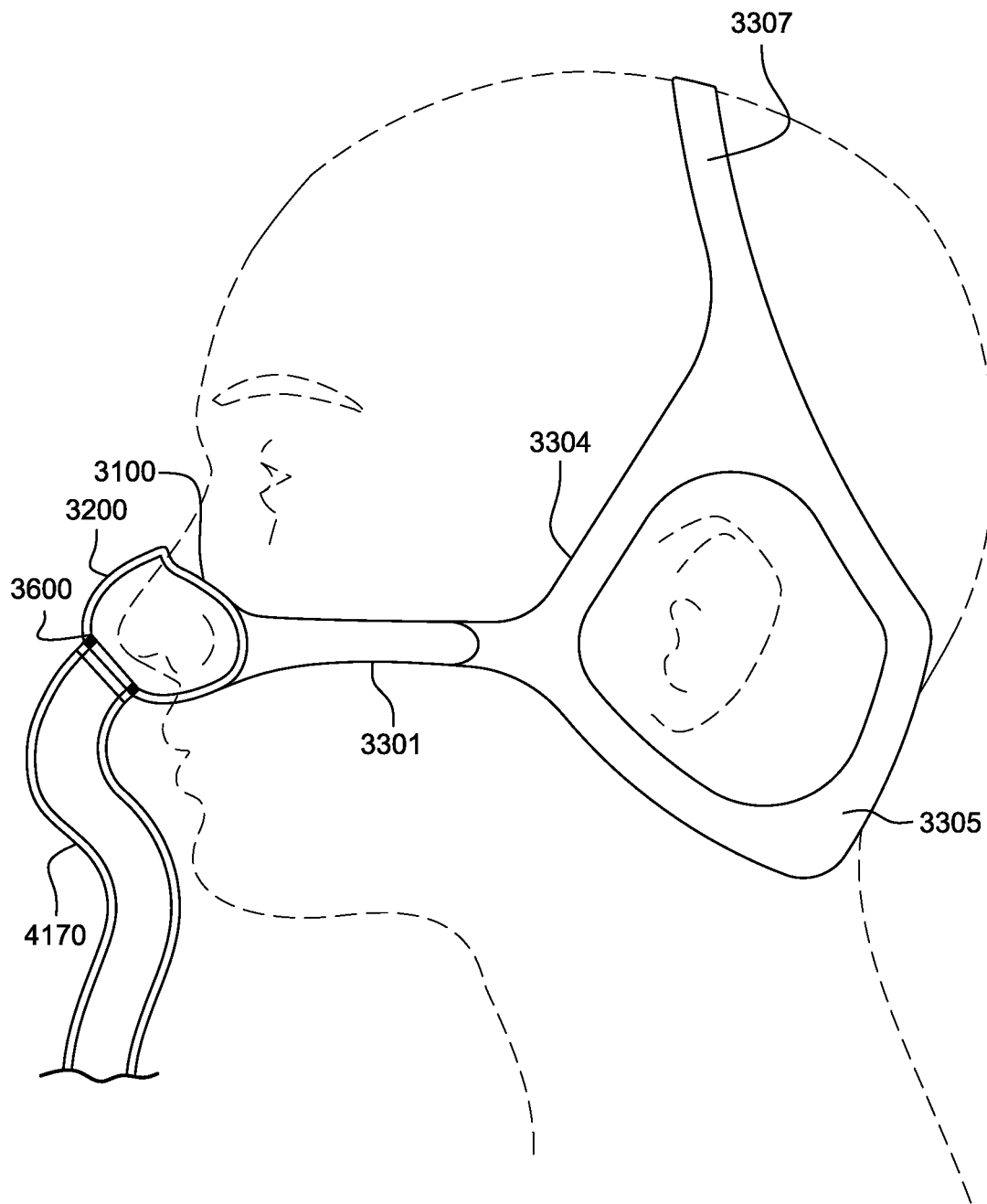

FIG. 12A shows a partial cross-sectional view of a patient interface according to an example of the present technology worn by a patient.

Figure 12B:
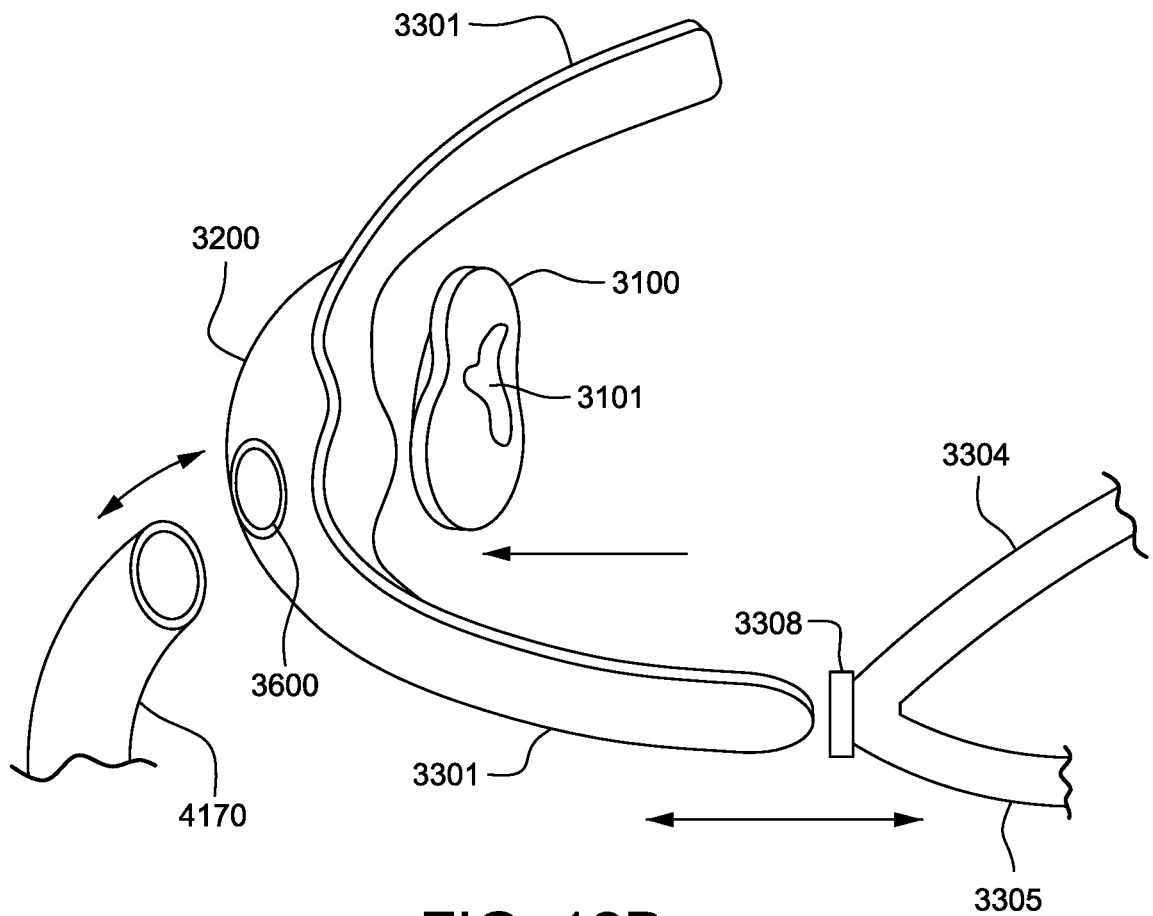

FIG. 12B shows an exploded view of a patient interface according to an example of the present technology.

Figure 12C:
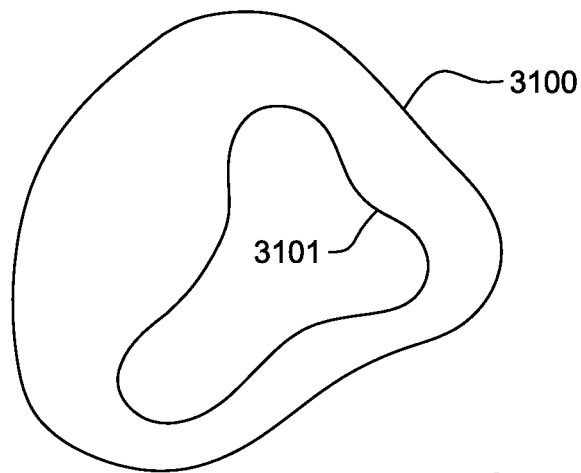

FIG. 12C shows a perspective view of a seal forming structure for a patient interface according to an example of the present technology.

Figure 12D:
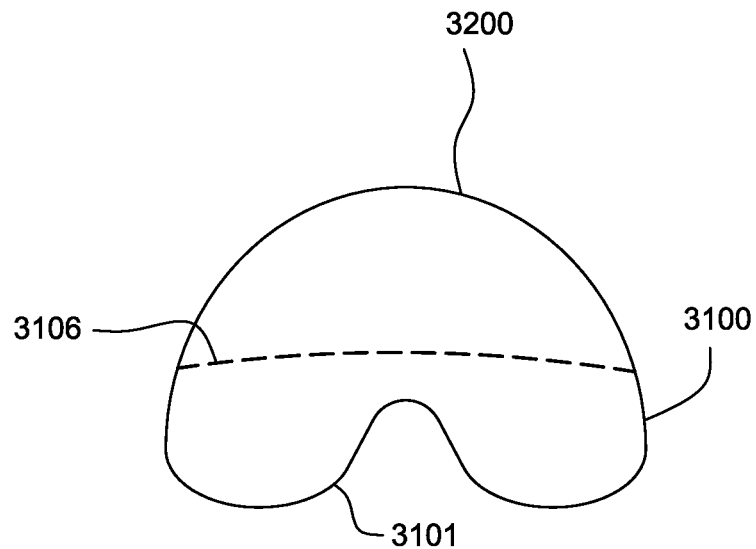

FIG. 12D shows a top view of a seal forming structure for a patient interface according to an example of the present technology.

Figure 12E:
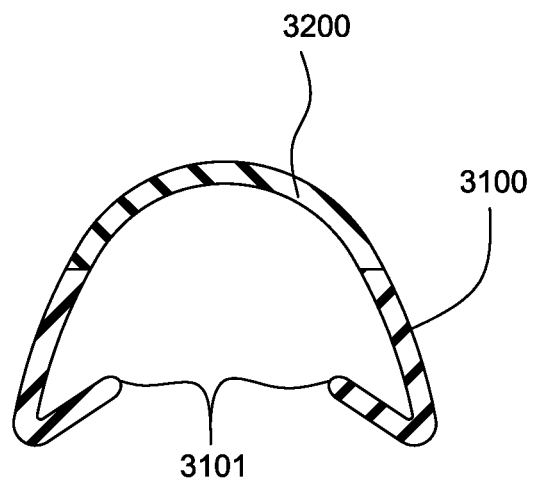

FIG. 12E shows a cross-sectional view of a seal forming structure for a patient interface according to an example of the present technology.

Figure 13A:
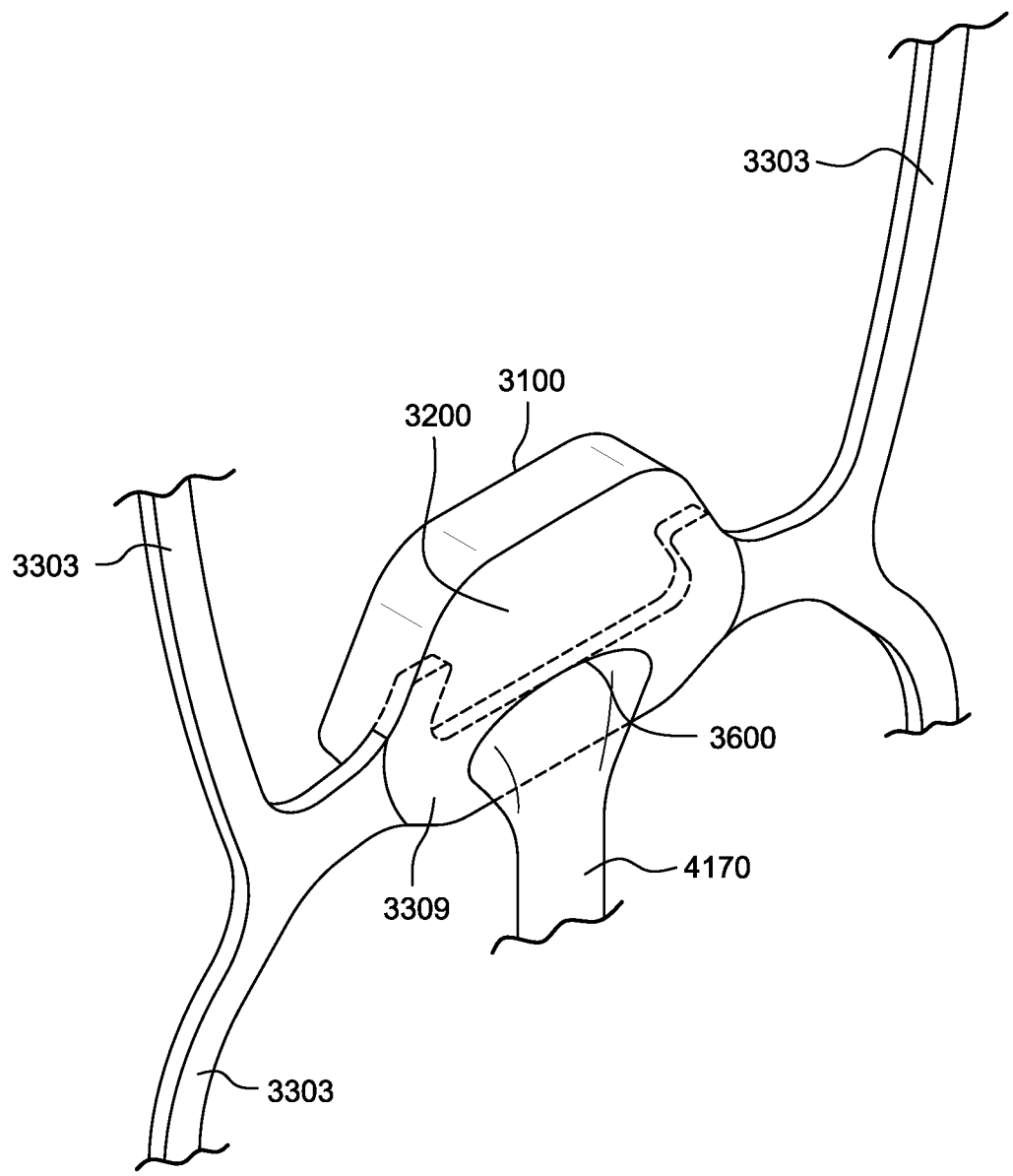

FIG. 13A shows a front perspective view of a patient interface according to an example of the present technology.

Figure 13B:
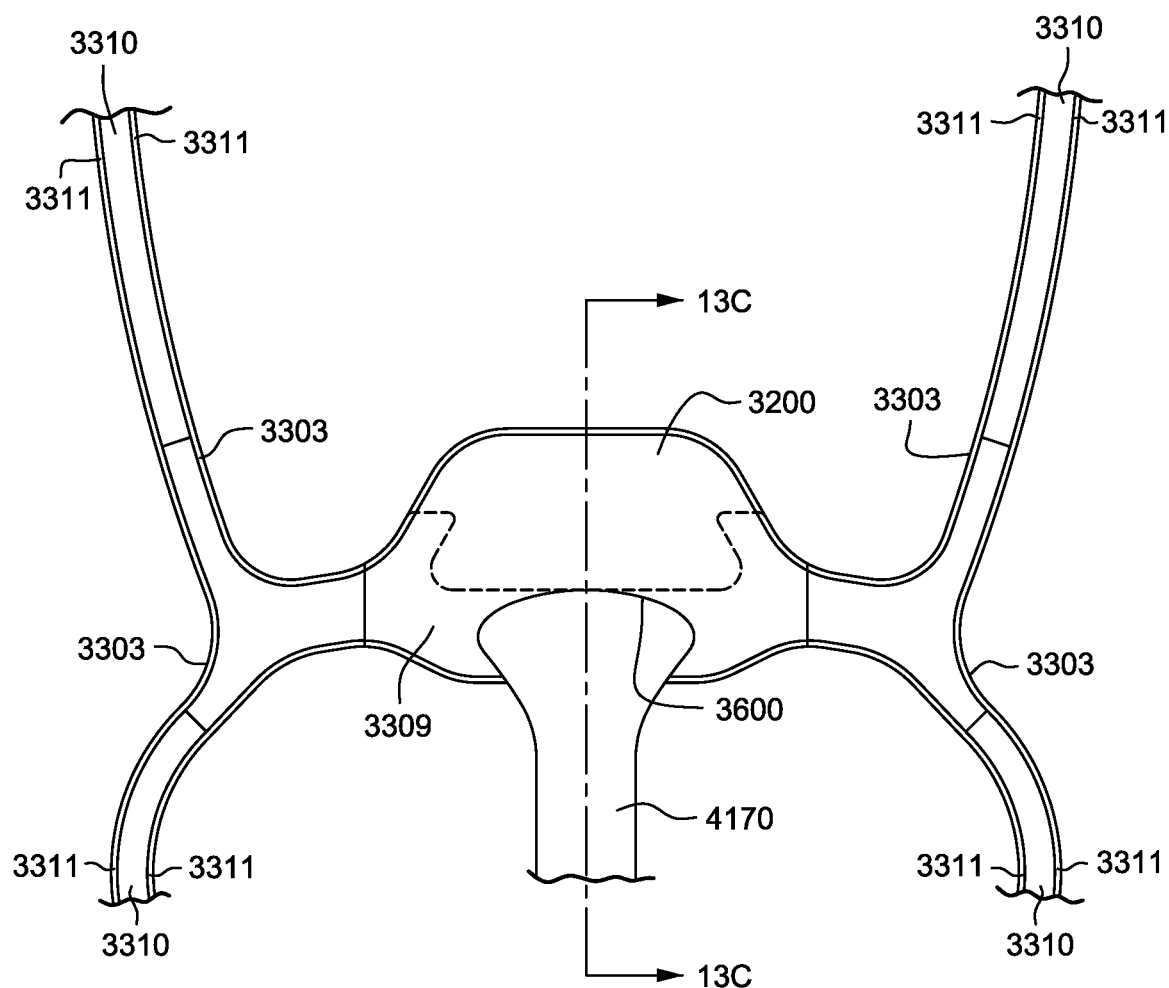

FIG. 13B shows a front view of a patient interface according to an example of the present technology.

Figure 13C:
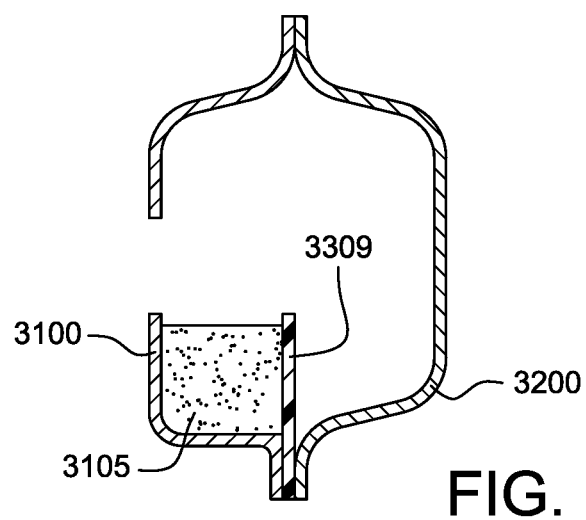

FIG. 13C shows a cross-sectional view of a plenum chamber and a seal forming structure of a patient interface according to an example of the present technology taken through line 13C-13C of FIG. 13B.

Figure 13D:
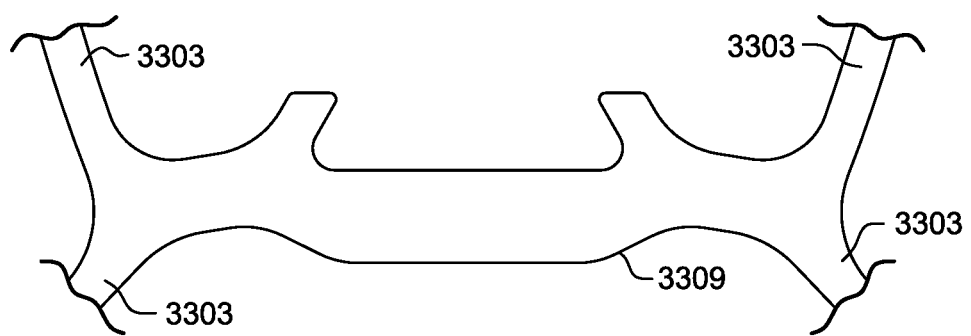

FIG. 13D shows a front view of a positioning and stabilising structure of a patient interface according to an example of the present technology.

Figure 14:
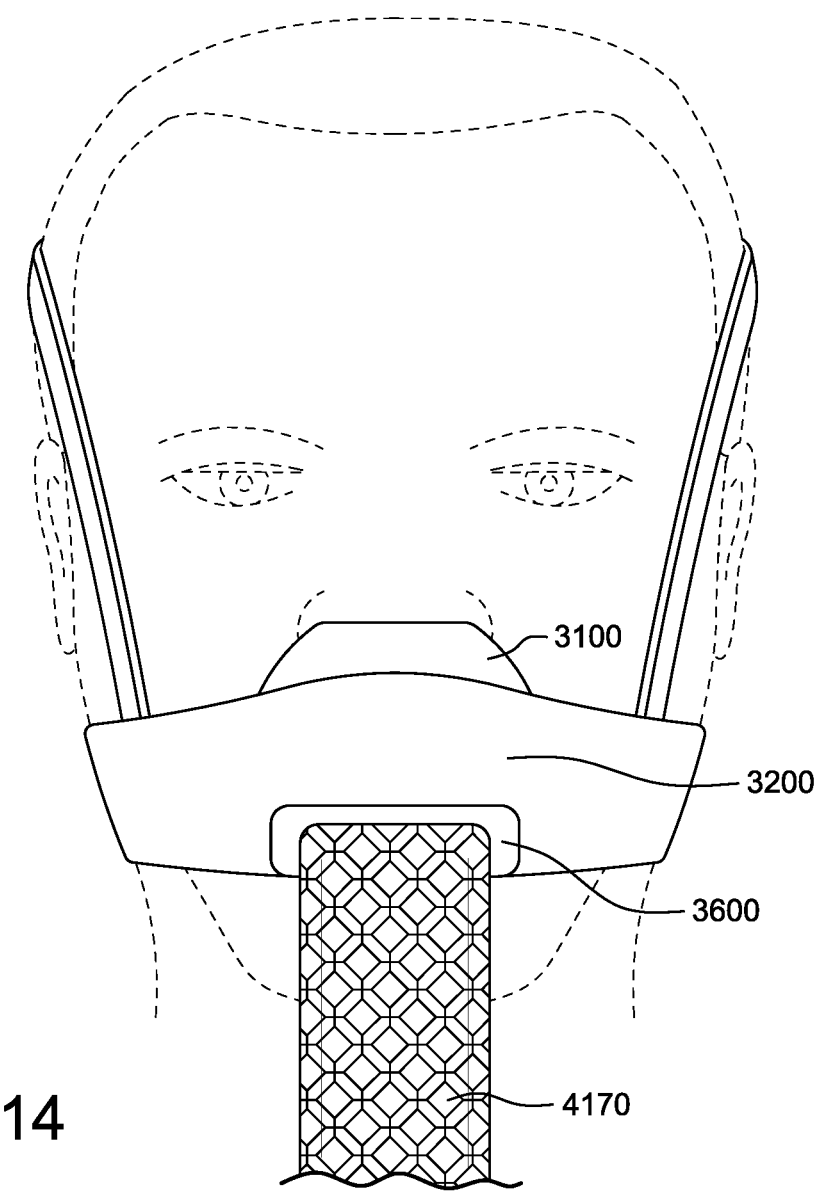

FIG. 14 shows a front view of a patient interface according to an example of the present technology.

Figure 15A:
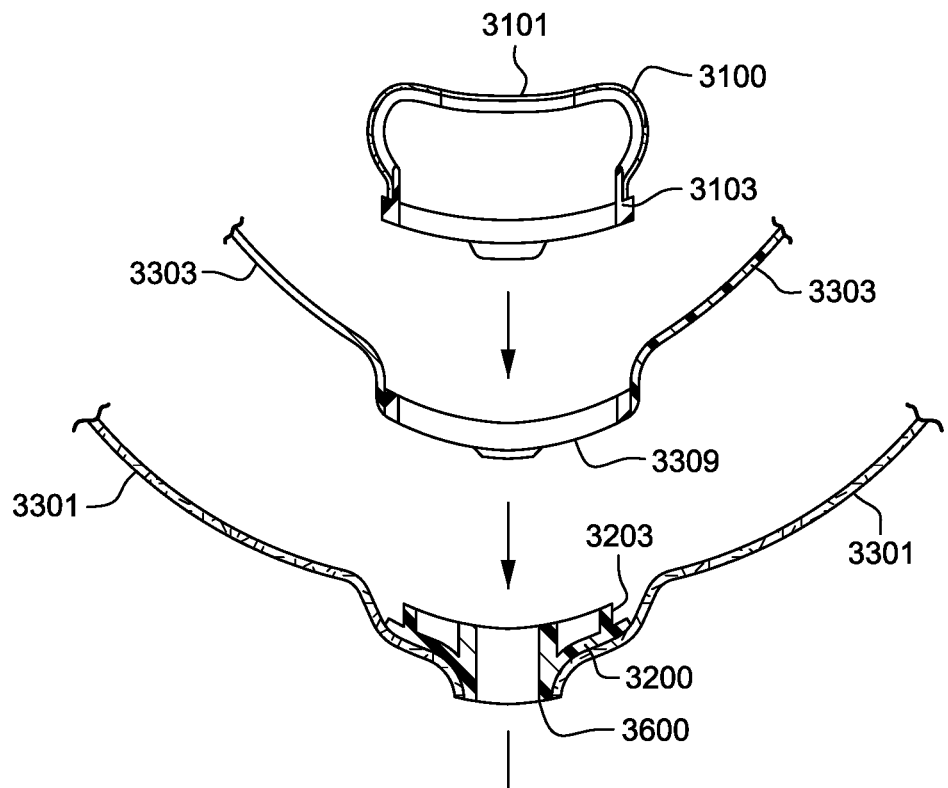

FIG. 15A shows an exploded view of a patient interface according to an example of the present technology.

Figure 15B:
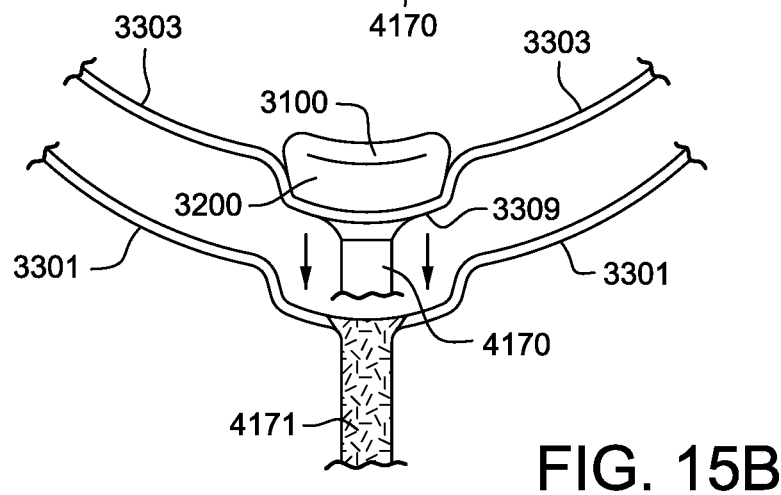

FIG. 15B shows a partially exploded view of a patient interface according to an example of the present technology.

Figure 16A:
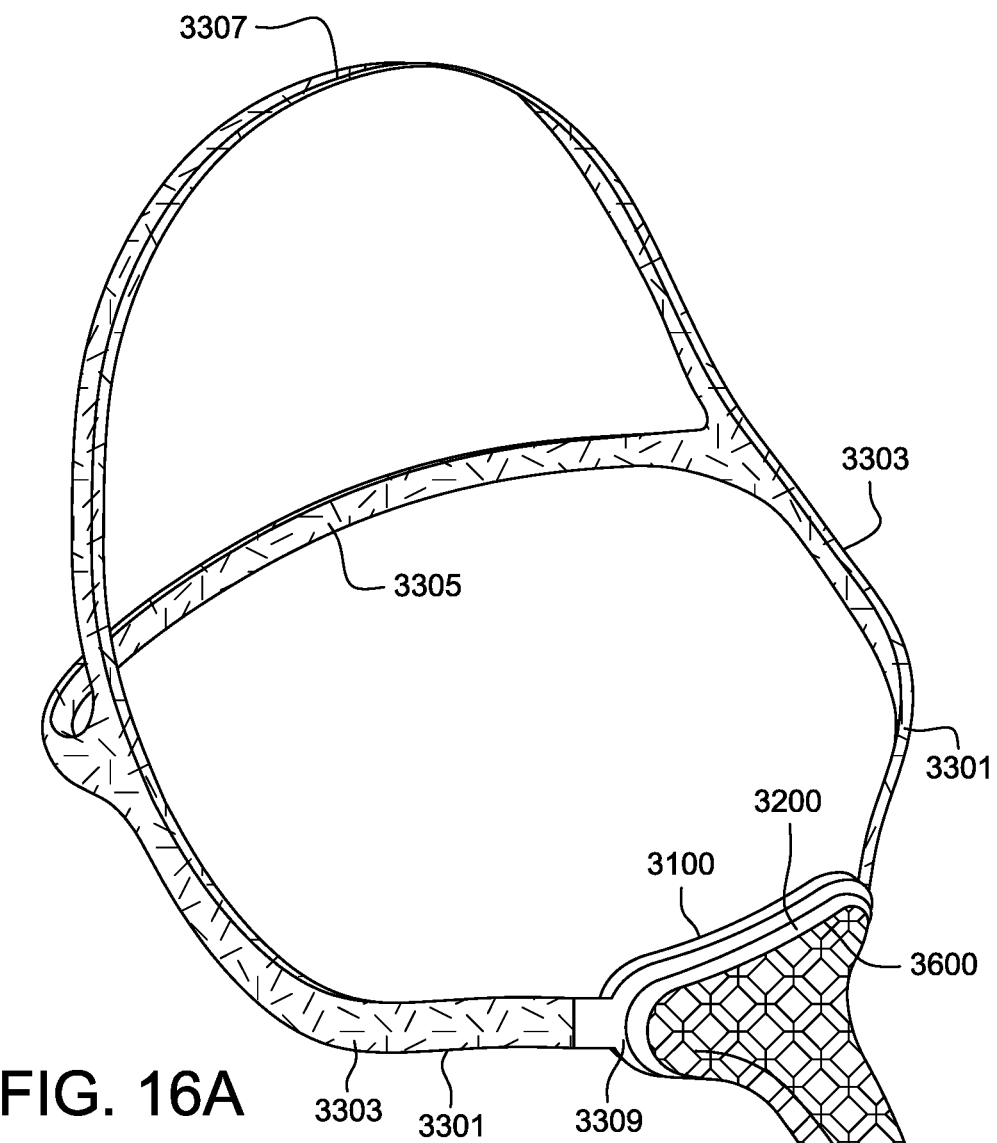

FIG. 16A shows a front perspective view of a patient interface according to an example of the present technology.

Figure 16B:
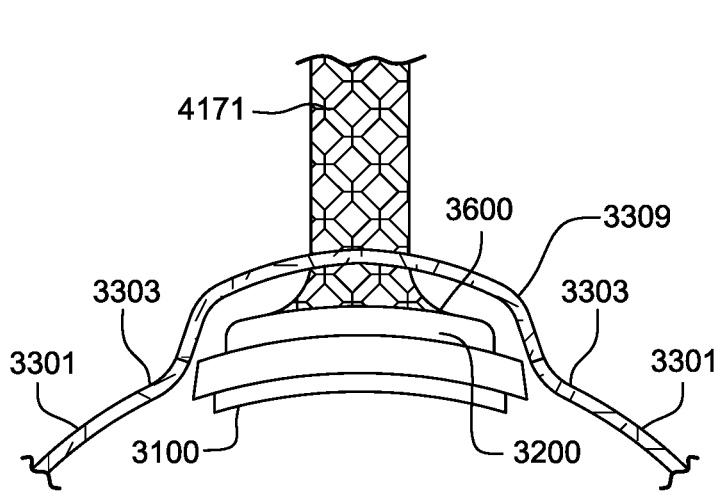

FIG. 16B shows a partially exploded top view of a patient interface according to an example of the present technology.

Figure 17A:
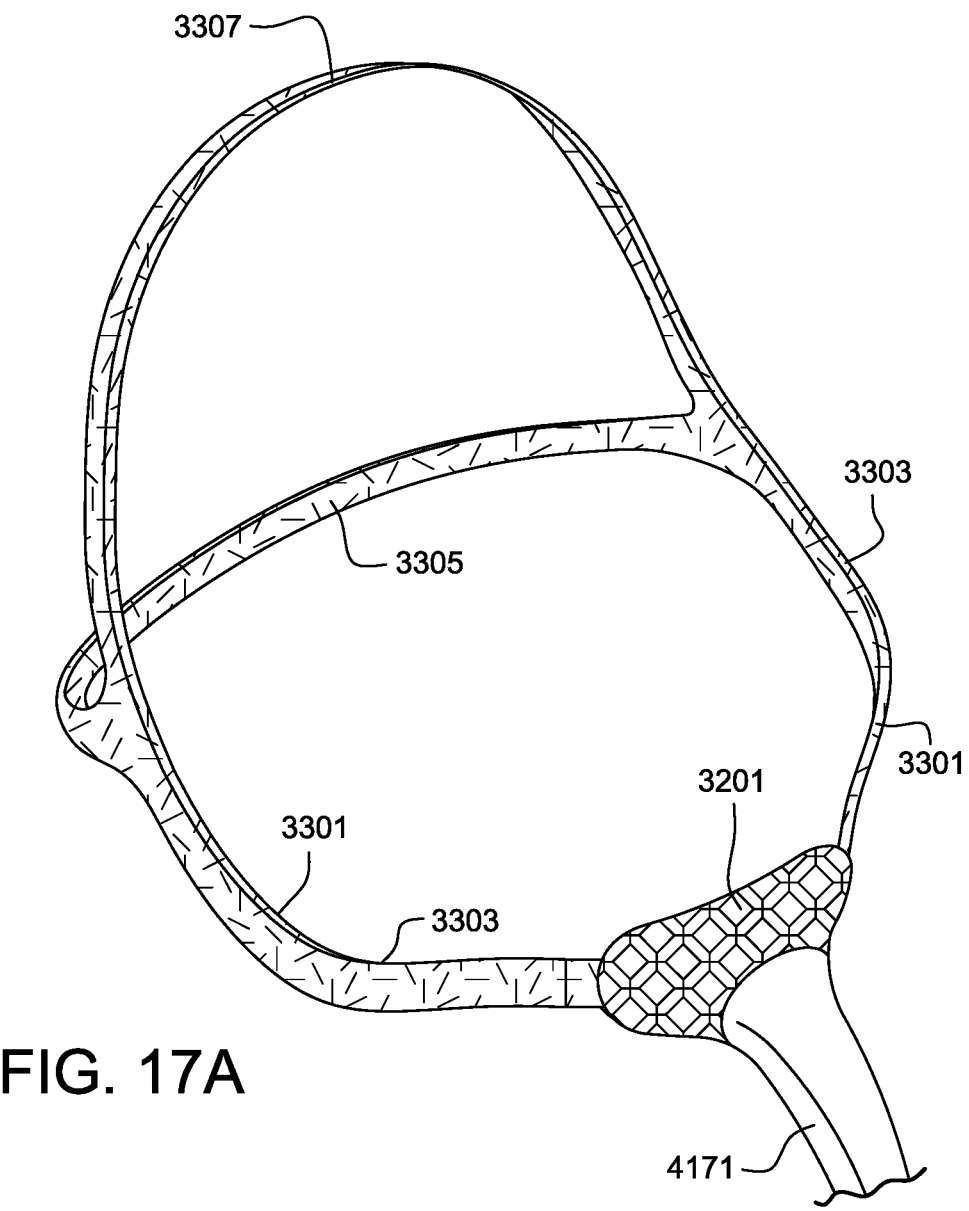

FIG. 17A shows a front perspective view of a patient interface according to an example of the present technology.

Figure 17B:
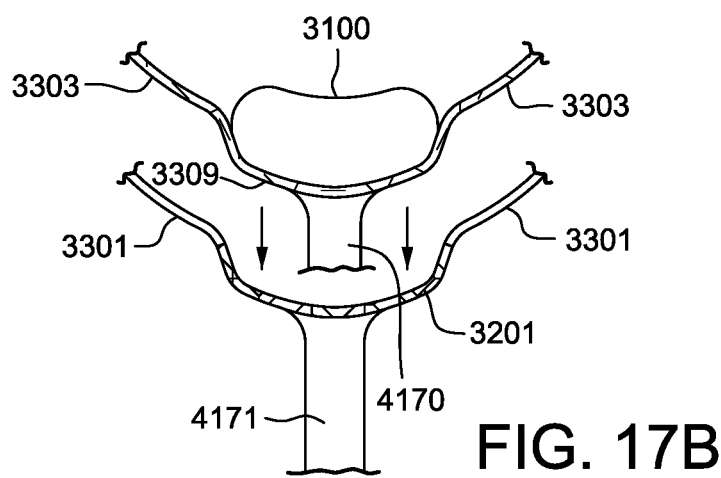

FIG. 17B shows a partially exploded top view of a patient interface according to an example of the present technology.

Figure 18:
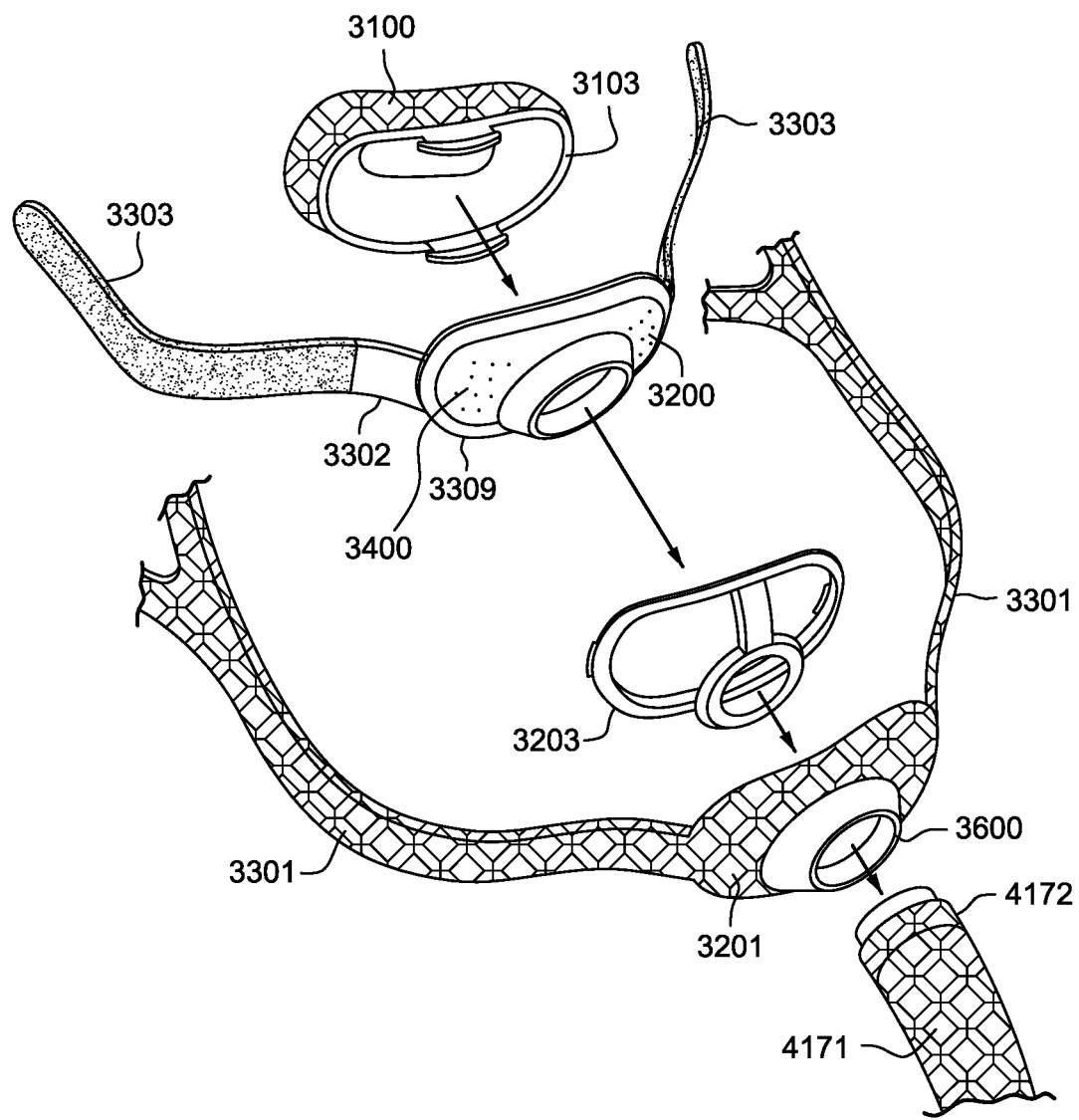

FIG. 18 shows an exploded front perspective view of a patient interface according to an example of the present technology.

Figure 19A:
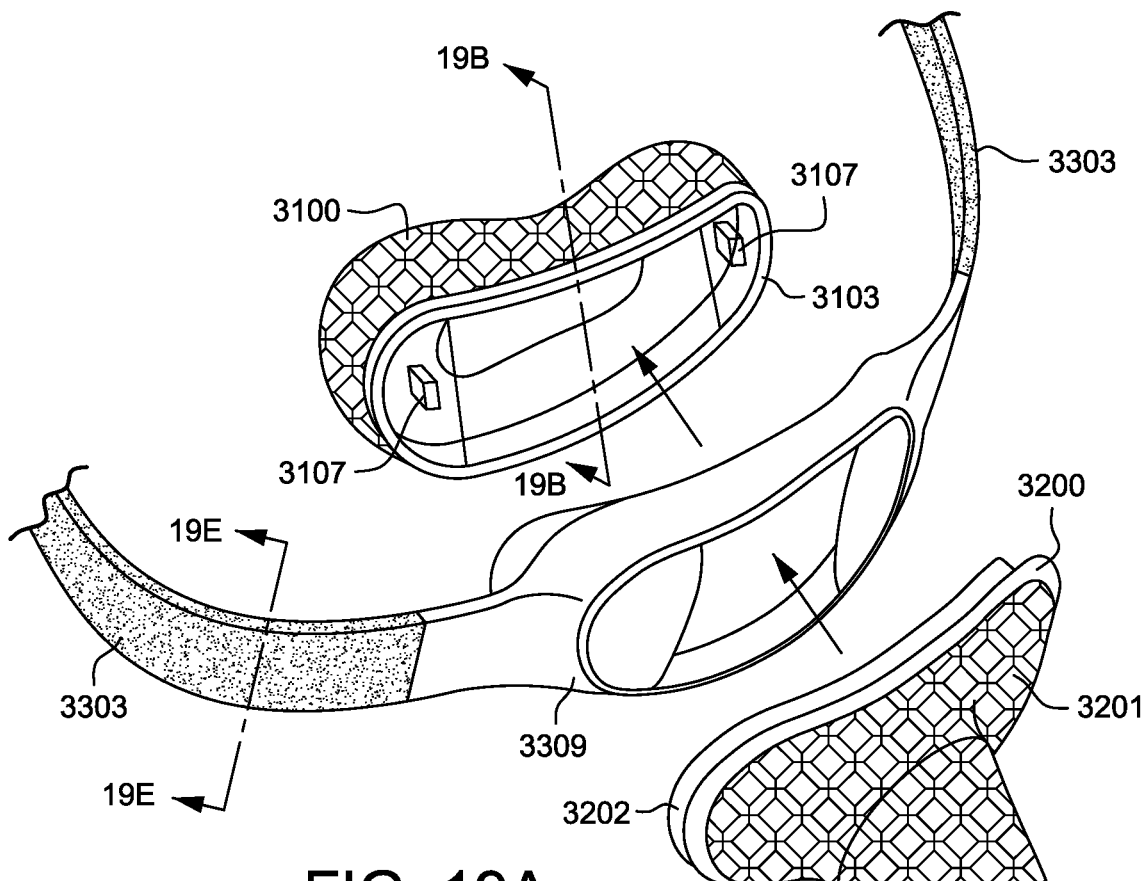

FIG. 19A shows an exploded front perspective view of a patient interface according to an example of the present technology.

Figure 19B:
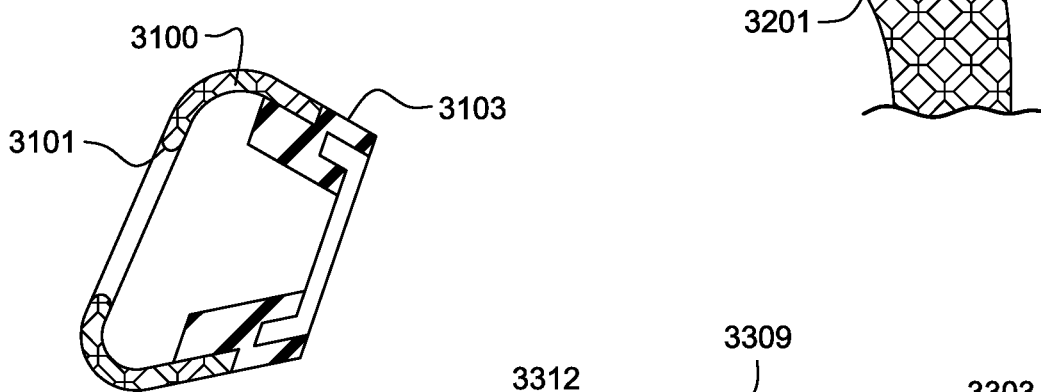

FIG. 19B shows a cross-sectional view of a seal forming structure and a plenum chamber of a patient interface according to an example of the present technology taken through line 19B-19B of FIG. 19A.

Figure 19C:
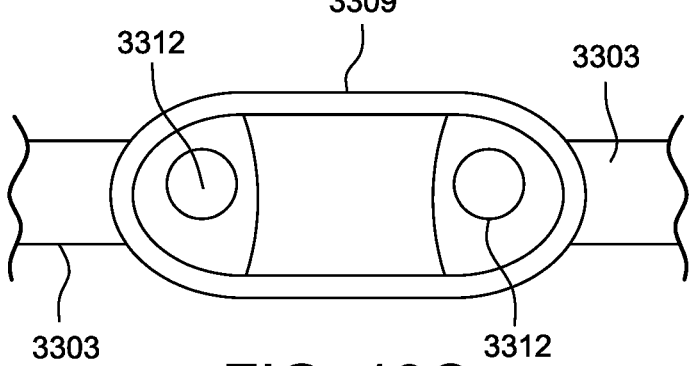

FIG. 19C shows a front view of a positioning and stabilising structure of a patient interface according to an example of the present technology.

Figure 19D:
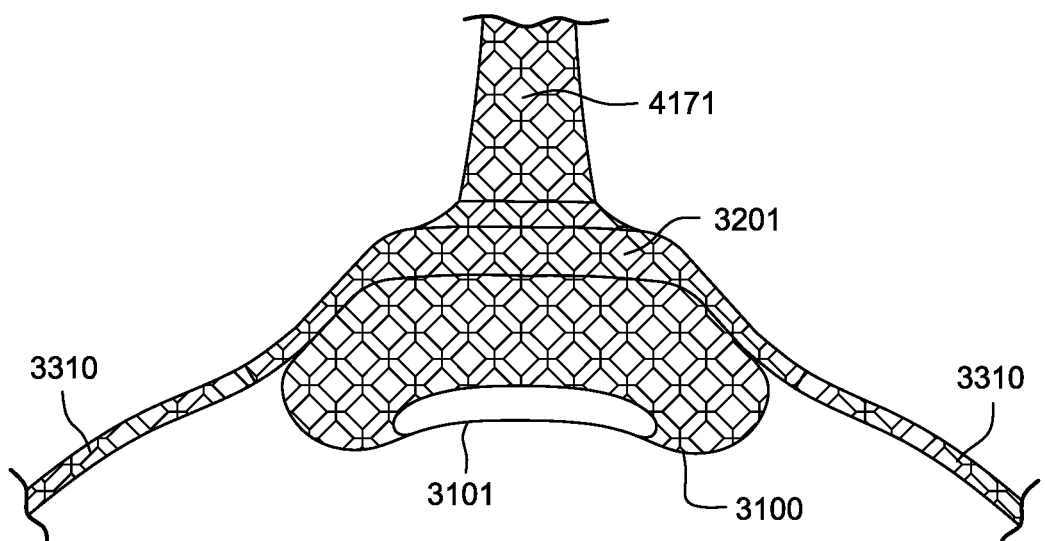

FIG. 19D shows a top view of a patient interface according to an example of the present technology.

Figure 19E:
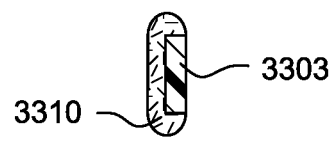

FIG. 19E shows a cross-sectional view of a positioning and stabilising structure of a patient interface according to an example of the present technology taken through line 19E-19E of FIG. 19A.

Figure 20A:
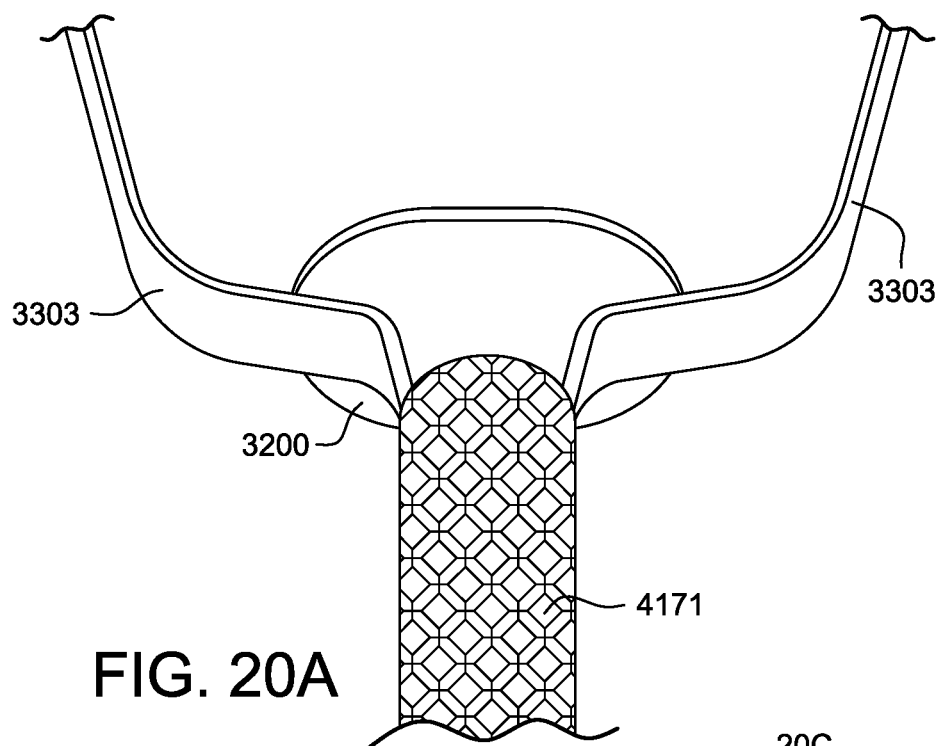

FIG. 20A shows a front view of a patient interface according to an example of the present technology.

Figure 20B:
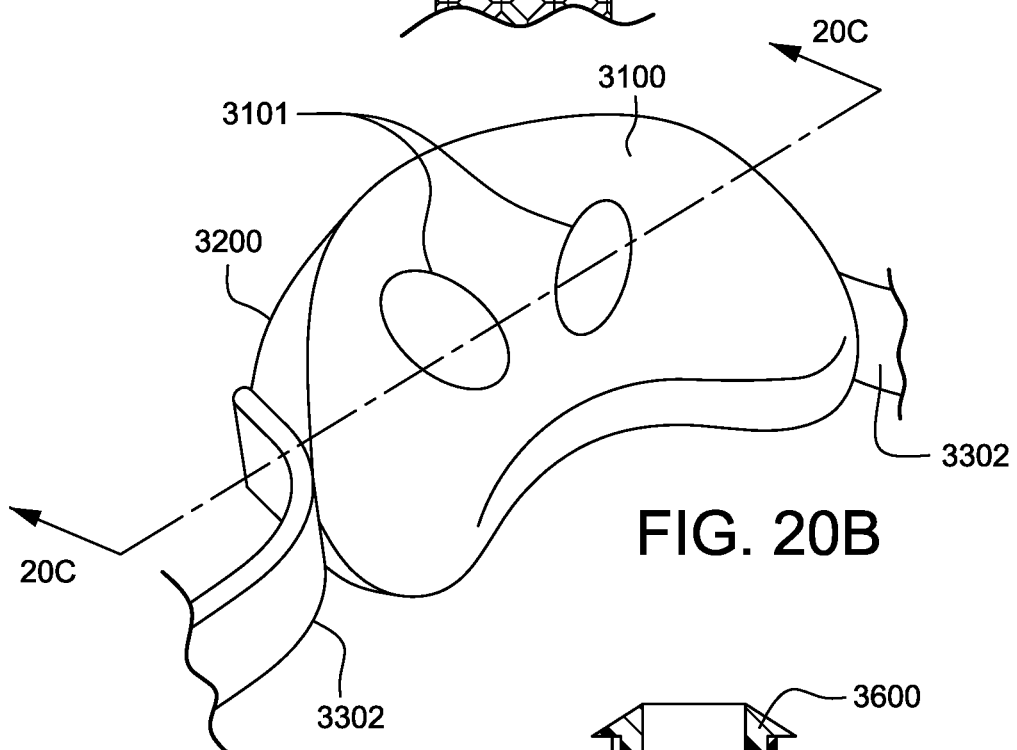

FIG. 20B shows a rear perspective view of a patient interface according to an example of the present technology.

Figure 20C:
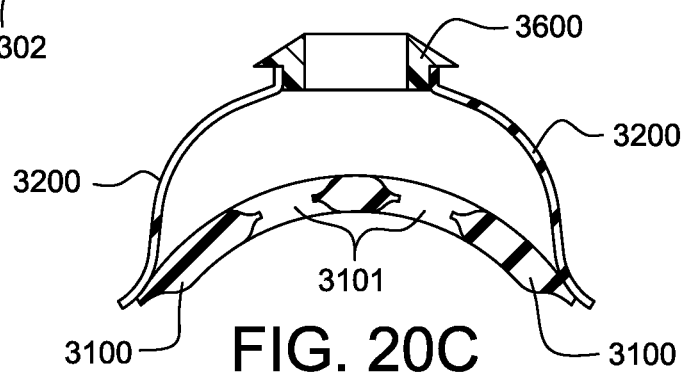

FIG. 20C shows a cross-sectional view of a plenum chamber and a seal forming structure of a patient interface according to an example of the present technology.

Figure 20D:
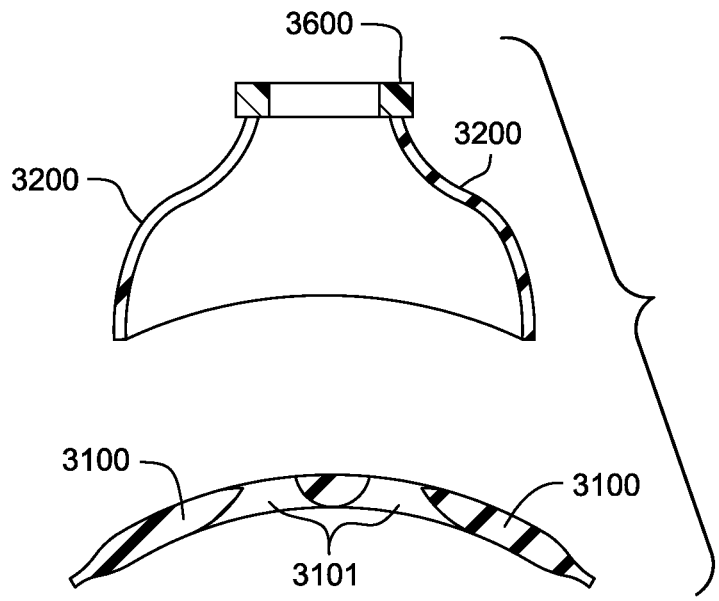

FIG. 20D shows an exploded view of a plenum chamber and seal-forming structure of a patient interface according to an example of the present technology.

Figure 20E:
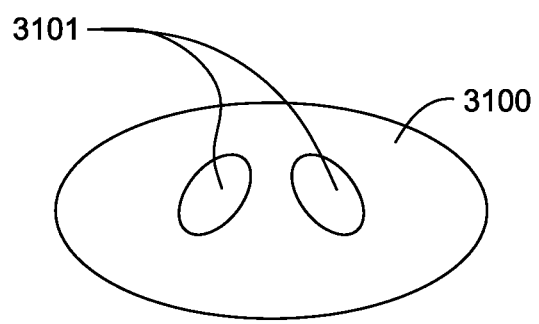

FIG. 20E shows a rear view of a seal forming structure of a patient interface according to an example of the present technology.

Figure 20F:
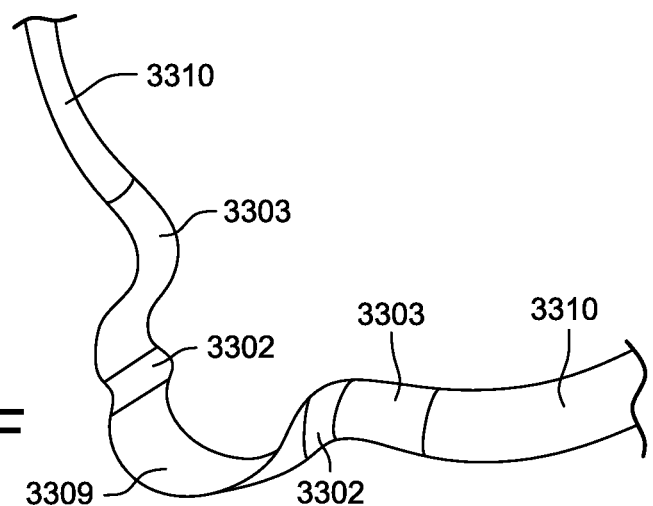

FIG. 20F shows a perspective view of a positioning and stabilising structure of a patient interface according to an example of the present technology.

Figure 21A:
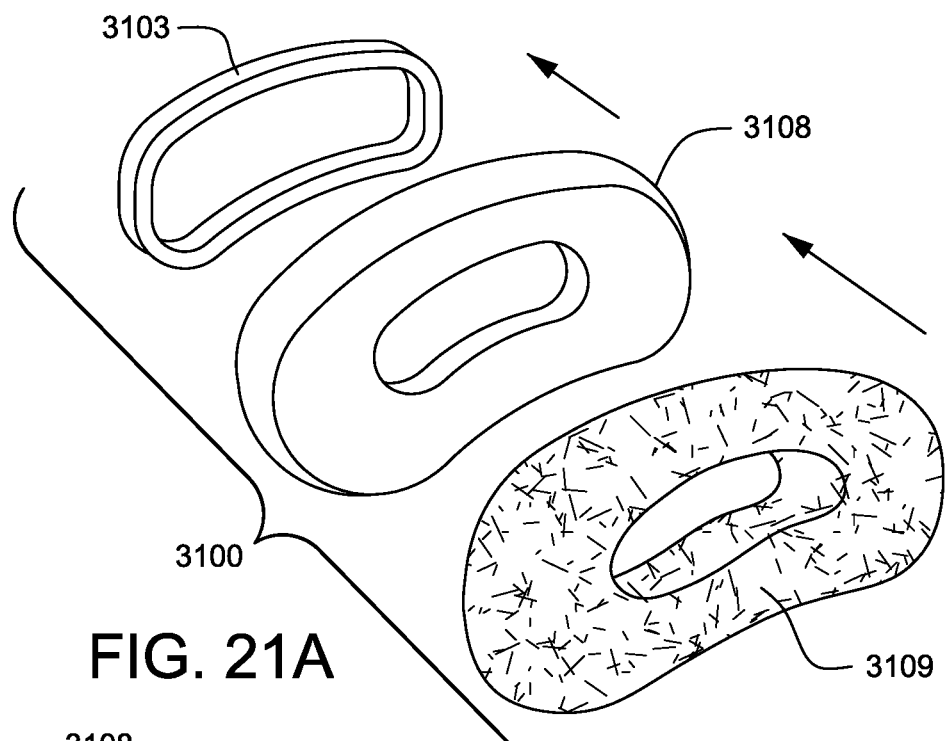

FIG. 21A shows an exploded view of a seal forming structure of a patient interface according to an example of the present technology.

Figure 21B:
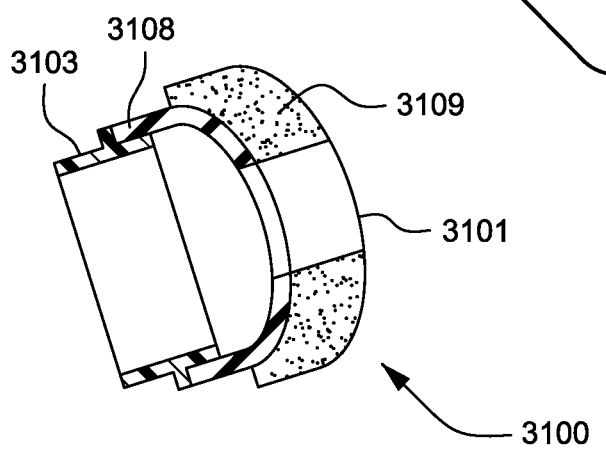

FIG. 21B shows a cross-sectional view of a seal forming structure of a patient interface according to an example of the present technology.

Figure 21C:
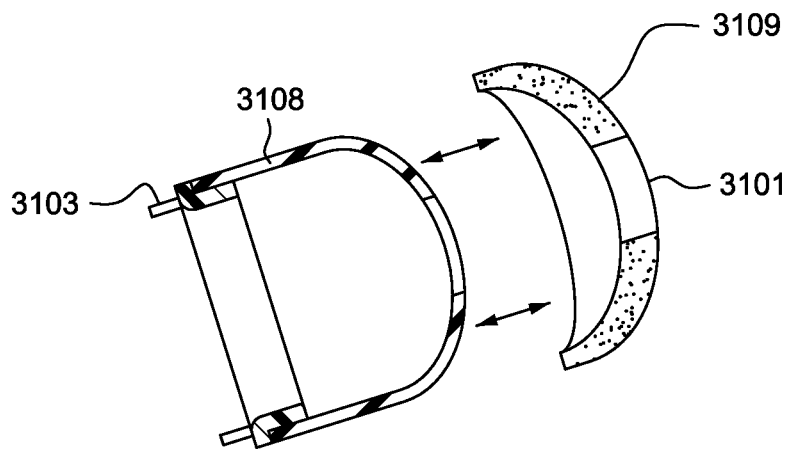

FIG. 21C shows a partially exploded cross-sectional view of a seal forming structure of a patient interface according to an example of the present technology.

Figure 22A:
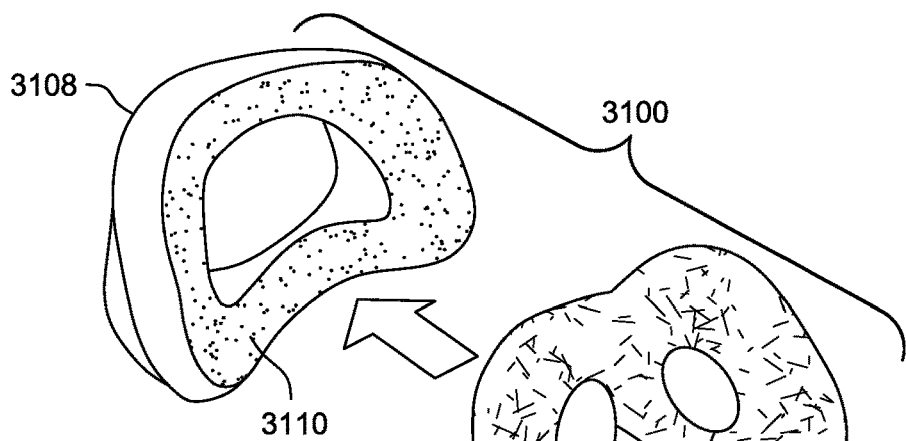

FIG. 22A shows an exploded rear view of a seal forming structure of a patient interface according to an example of the present technology.

Figure 22B:
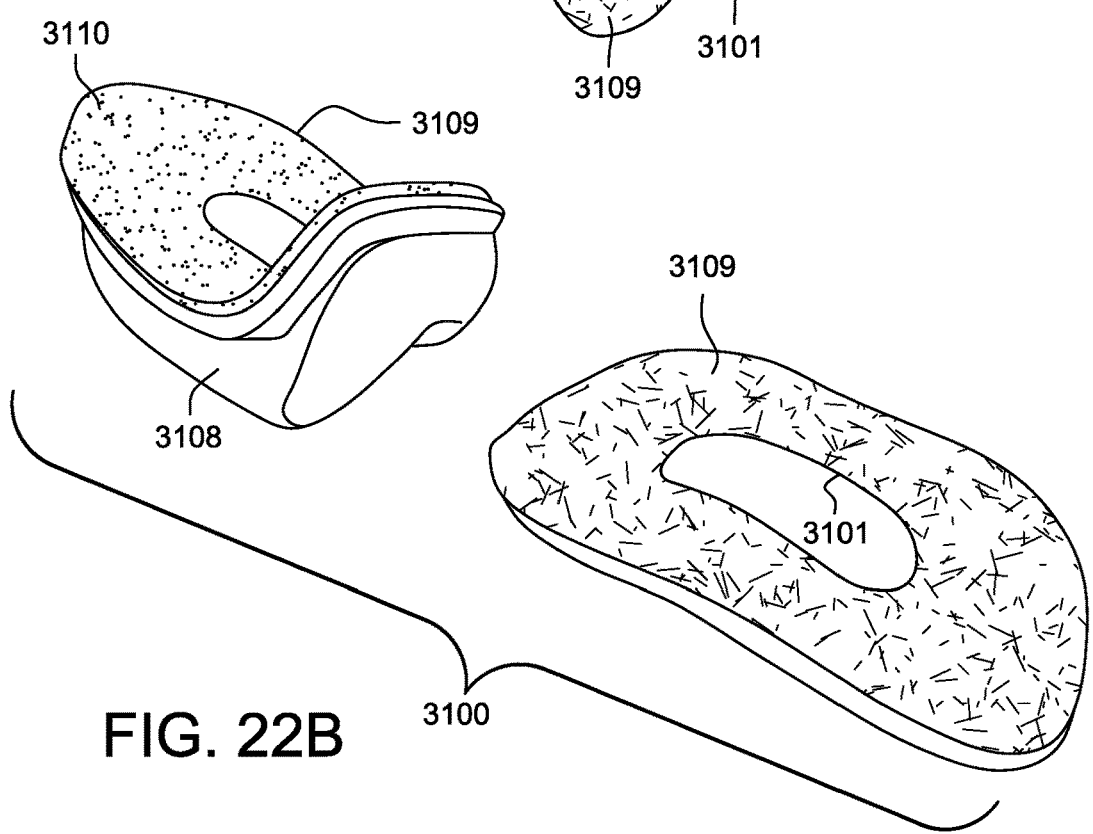

FIG. 22B shows an exploded top perspective view of a seal forming structure of a patient interface according to an example of the present technology.

Figure 22C:
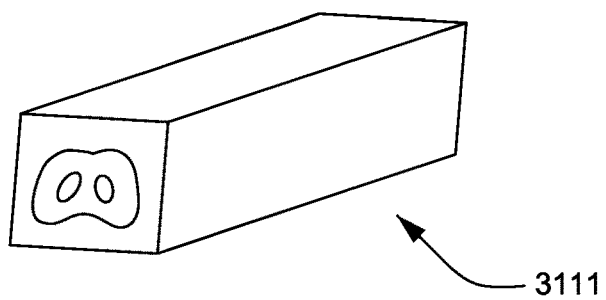

FIG. 22C shows a package of seal forming structure membranes of a patient interface according to an example of the present technology.

Figure 23:
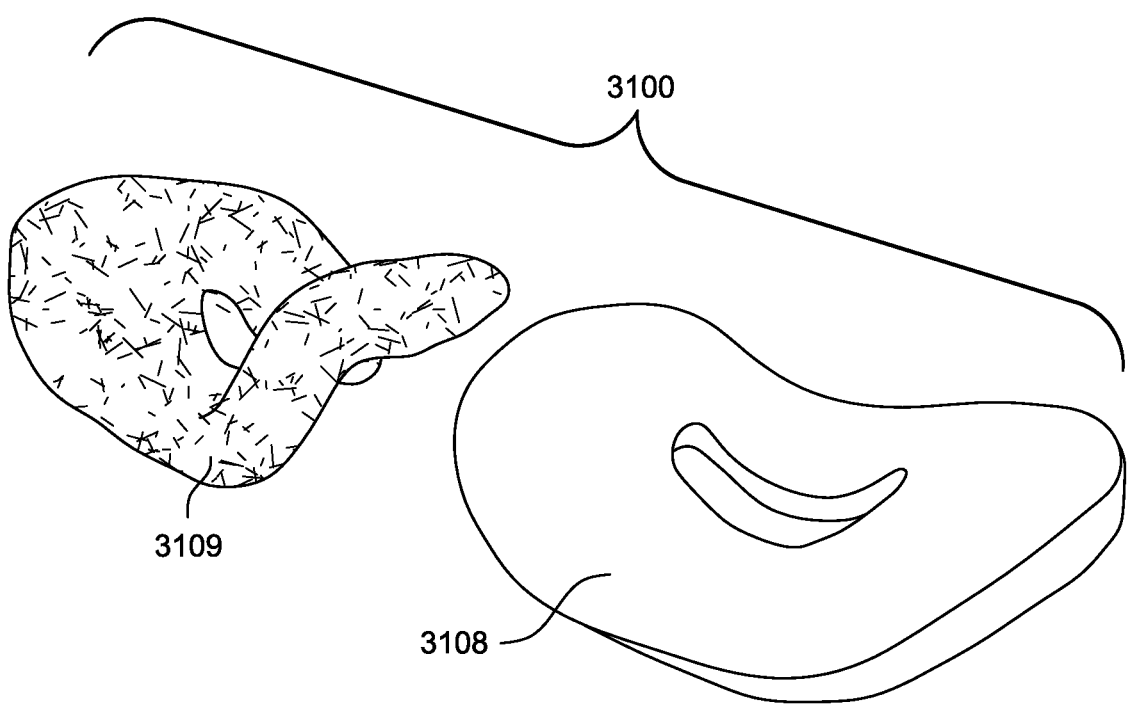

FIG. 23 shows an exploded view of a seal forming structure of a patient interface according to an example of the present technology.

Figure 24:
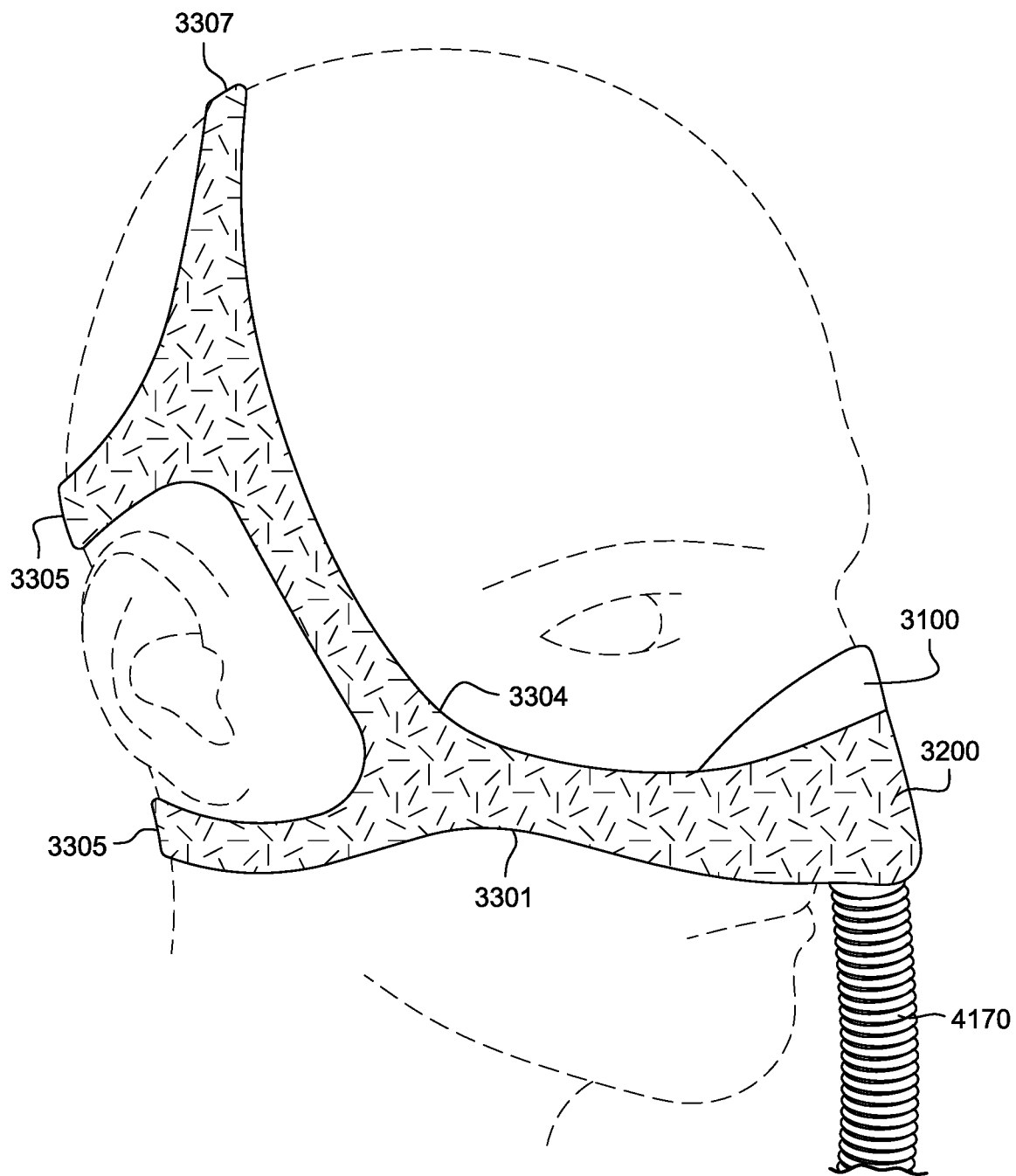

FIG. 24 shows a front perspective view of patient interface according to an example of the present technology worn by a patient.

Figure 25:
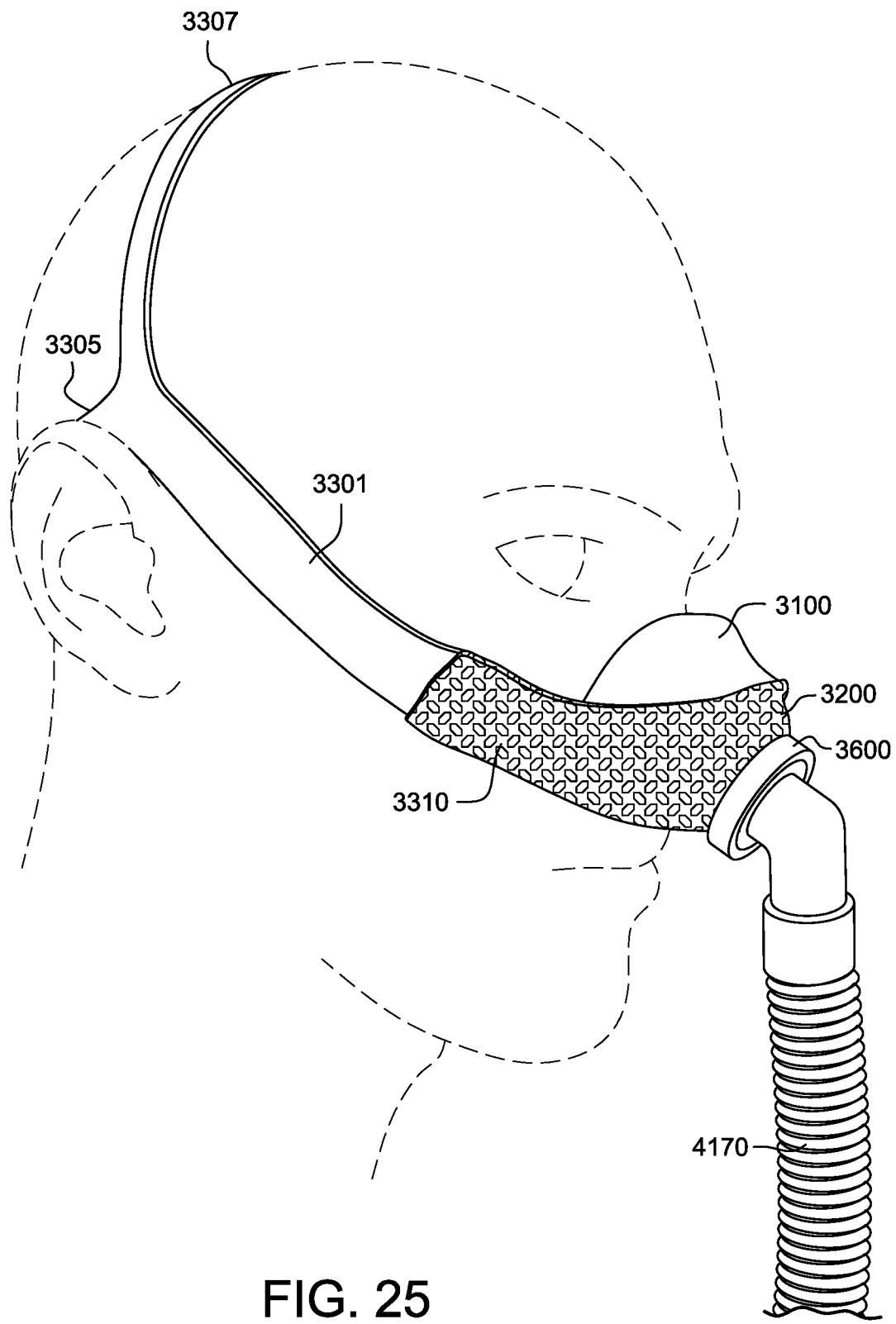

FIG. 25 shows a front perspective view of patient interface according to an example of the present technology worn by a patient.

Figure 26:
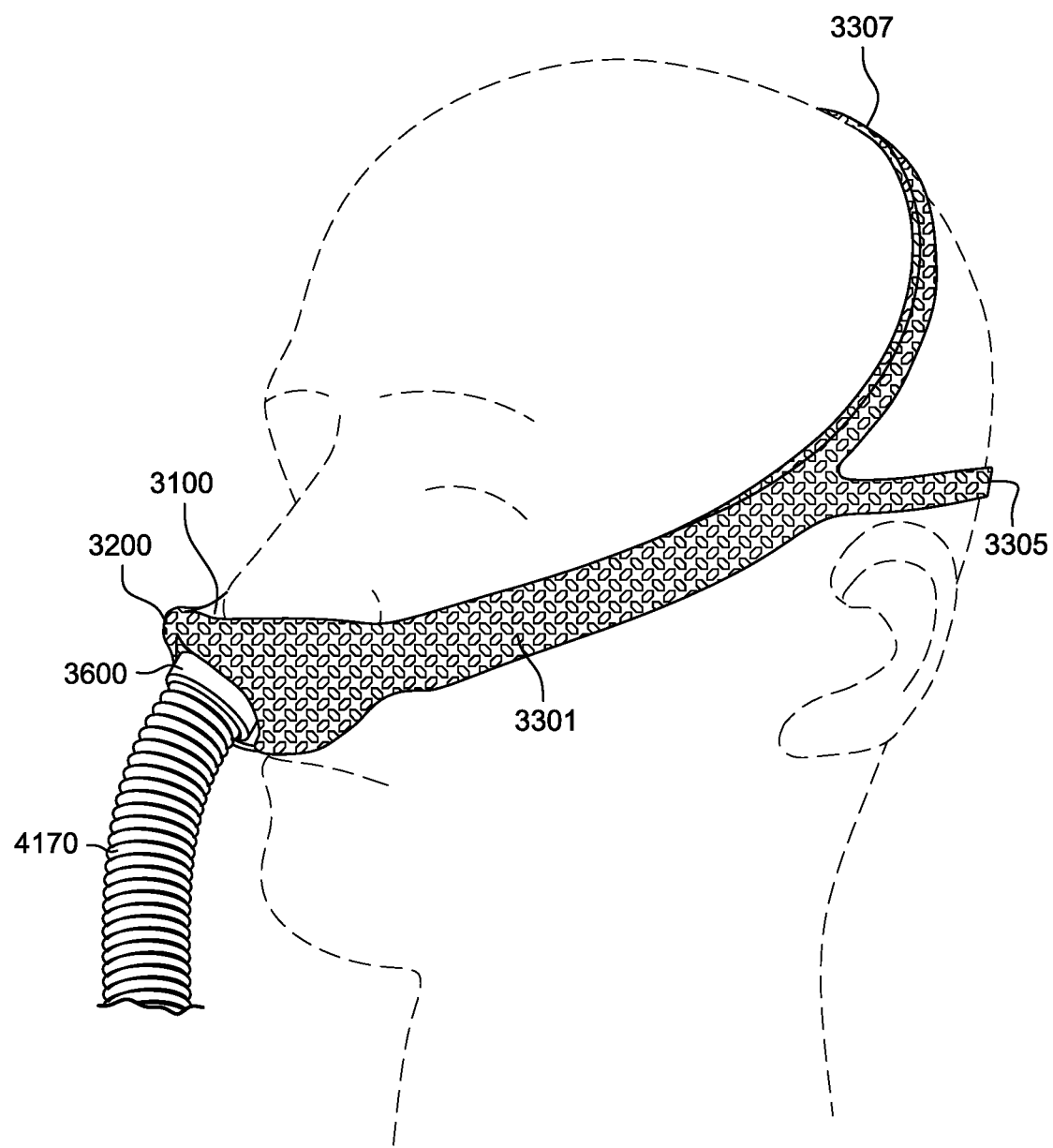

FIG. 26 shows a front perspective view of patient interface according to an example of the present technology worn by a patient.

Figure 27A:
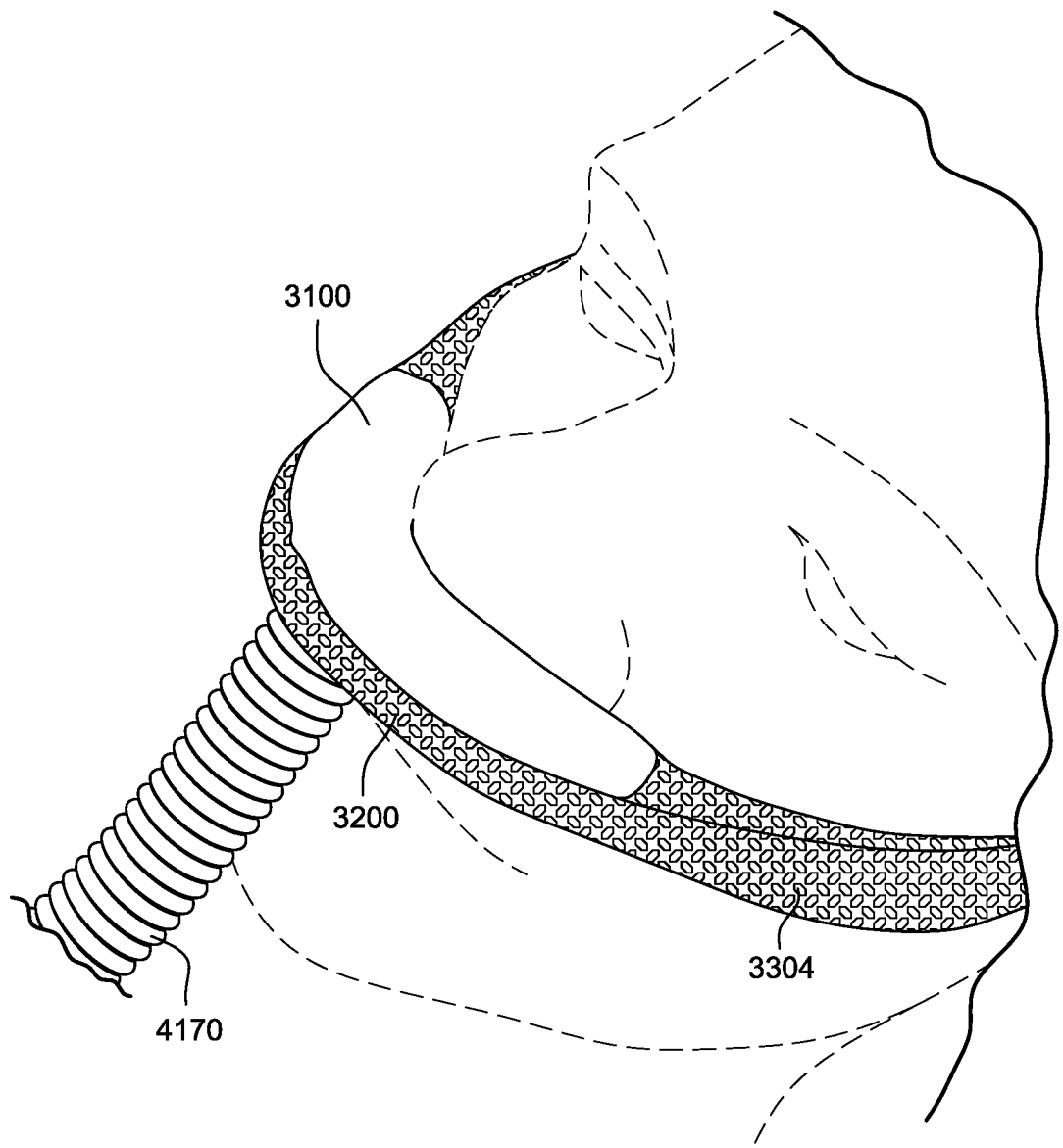

FIG. 27A shows a detailed front perspective view of patient interface according to an example of the present technology worn by a patient.

Figure 27B:
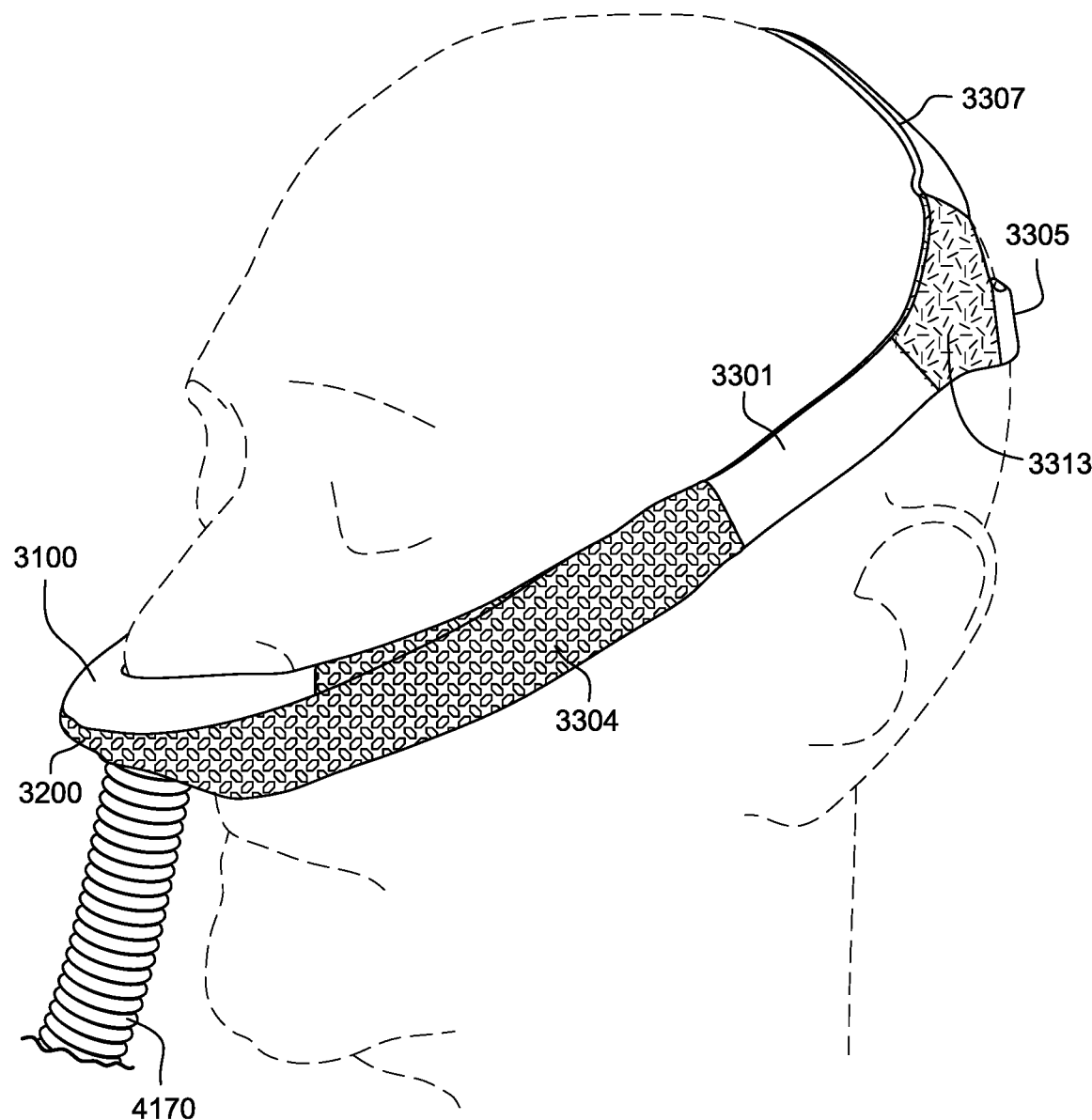

FIG. 27B shows a front perspective view of patient interface according to an example of the present technology worn by a patient.

Figure 27C:
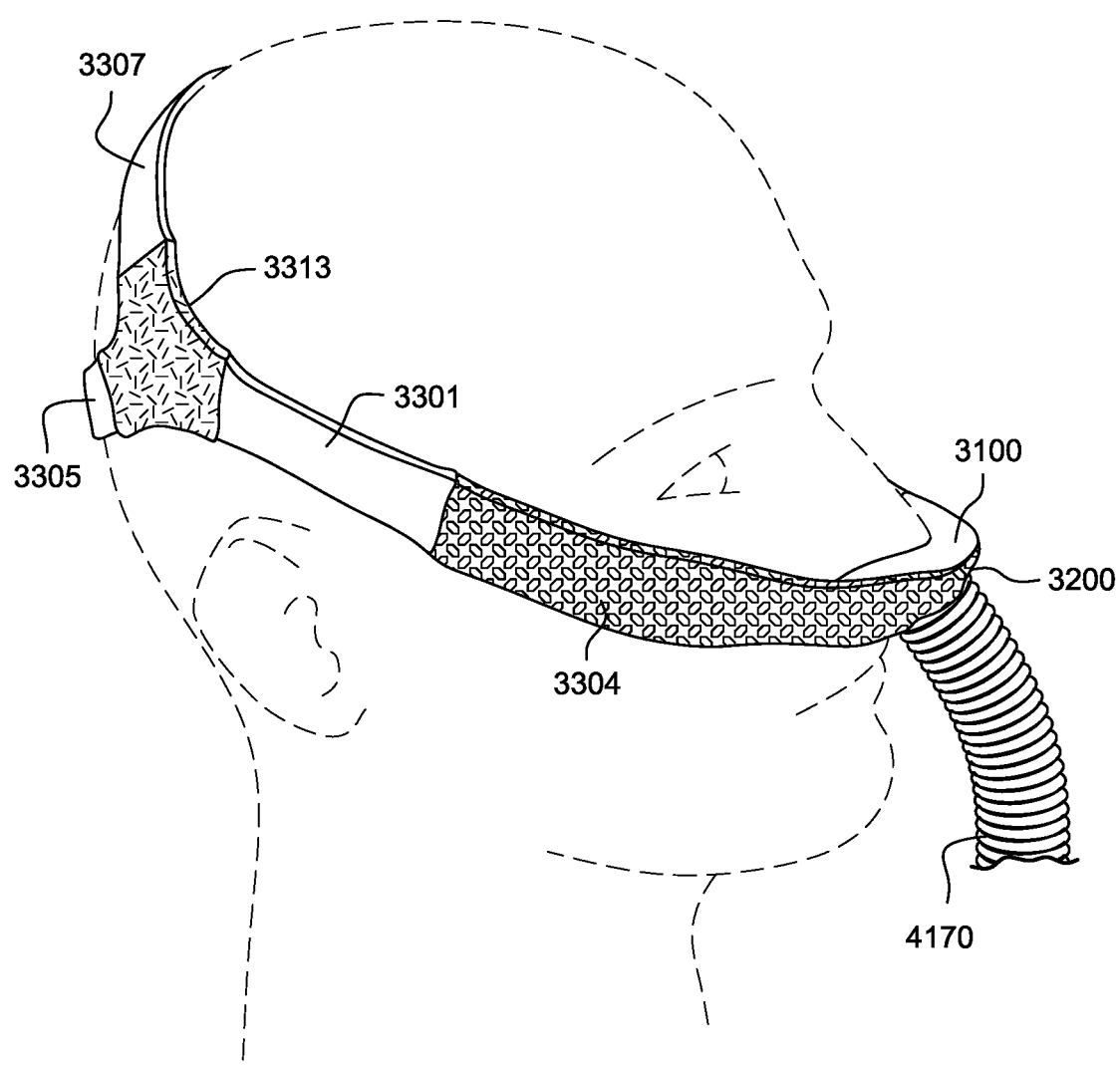

FIG. 27C shows another front perspective view of patient interface according to an example of the present technology worn by a patient.

Figure 28:
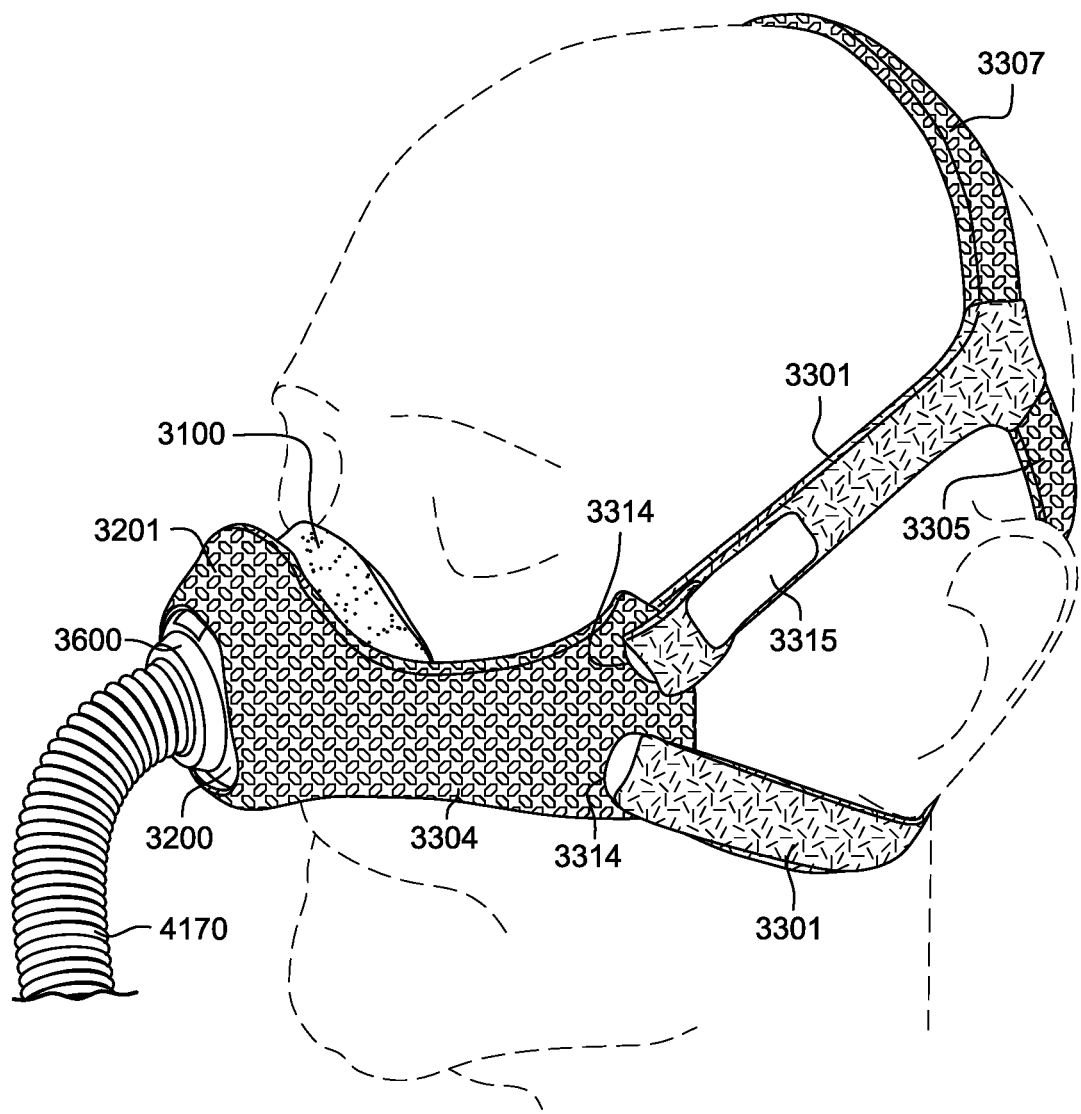

FIG. 28 shows a front perspective view of patient interface according to an example of the present technology worn by a patient.

Figure 29A:
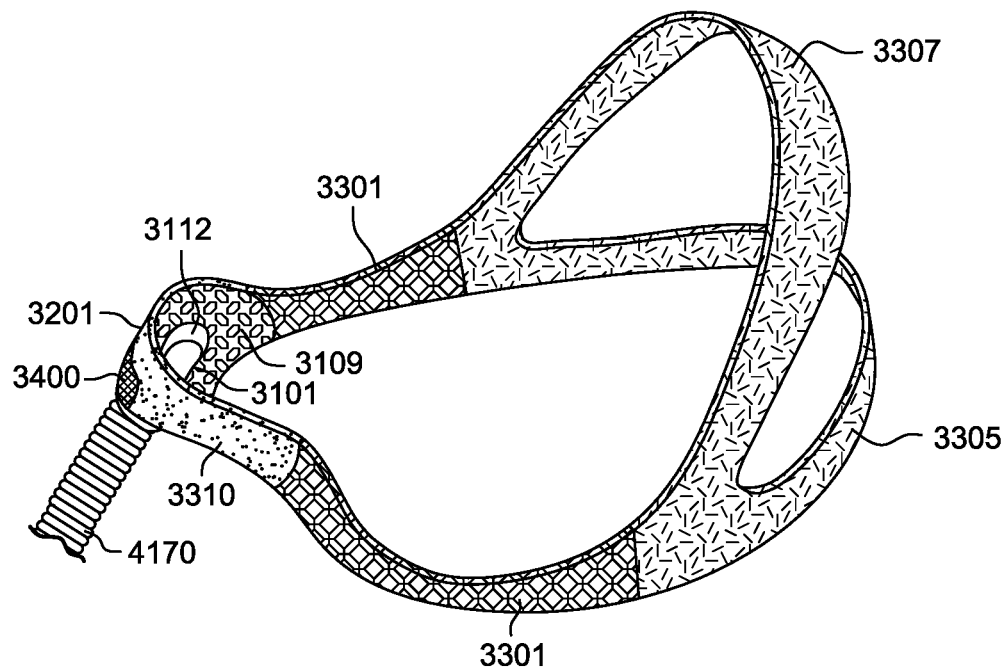

FIG. 29A shows a top perspective view of a patient interface according to an example of the present technology.

Figure 29B:
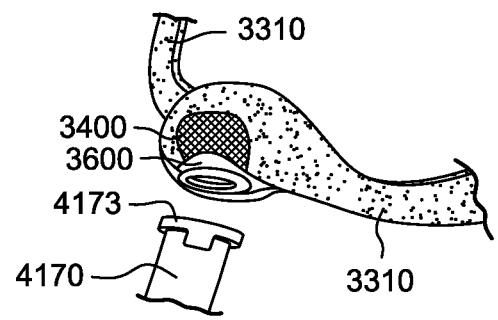

FIG. 29B shows an exploded view of an air circuit and a patient interface according to an example of the present technology.

Figure 29C:
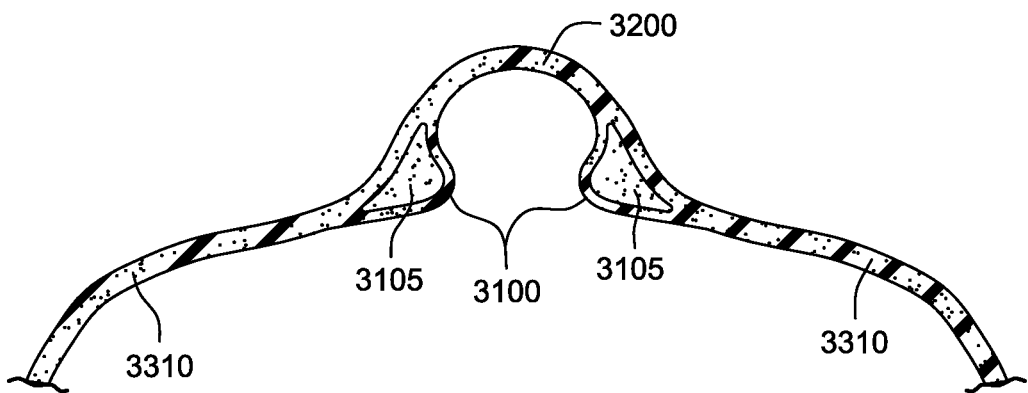

FIG. 29C shows a cross-sectional view of a patient interface according to an example of the present technology.

Figure 30:
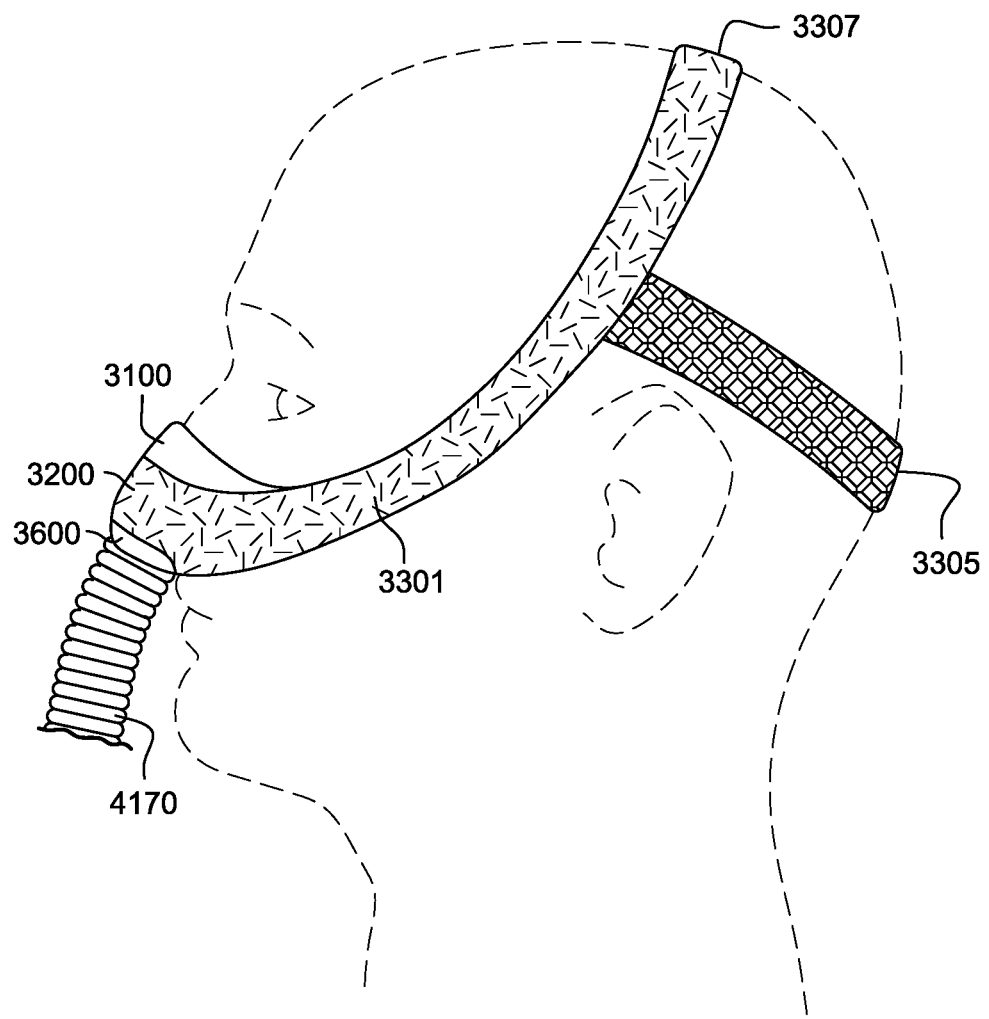

FIG. 30 shows a side view of a patient interface according to an example of the present technology worn by a patient.

Figure 31:
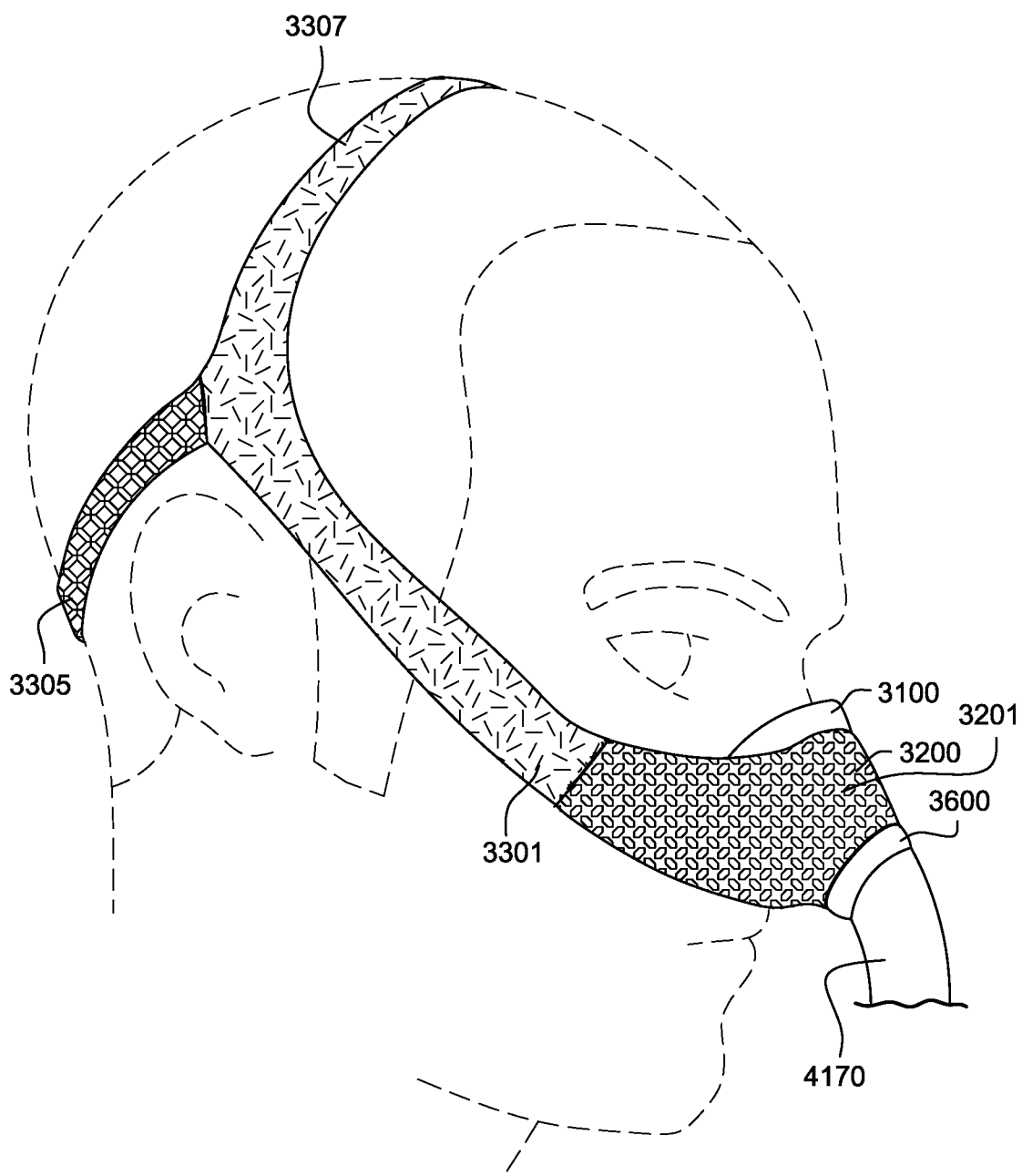

FIG. 31 shows a side view of a patient interface according to an example of the present technology worn by a patient.

FIG. 32A shows a front perspective view of a patient interface according to an example of the present technology worn by a patient.

FIG. 32B shows a rear view of a patient interface according to an example of the present technology.

FIG. 32C shows another rear view of a patient interface according to an example of the present technology.

FIG. 32D shows a front perspective view of a seal forming structure of a patient interface according to an example of the present technology against a patient's face.

FIG. 32E shows an exploded view of a seal forming structure of a patient interface according to an example of the present technology.

Figure 33A:
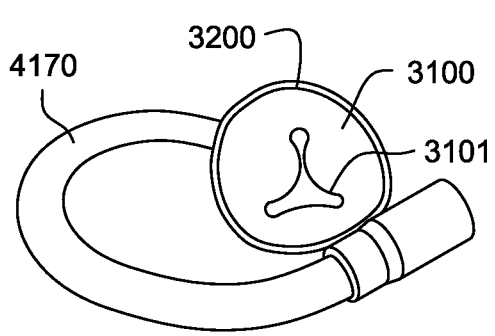

FIG. 33A shows a rear view of a patient interface according to an example of the present technology.

Figure 33B:
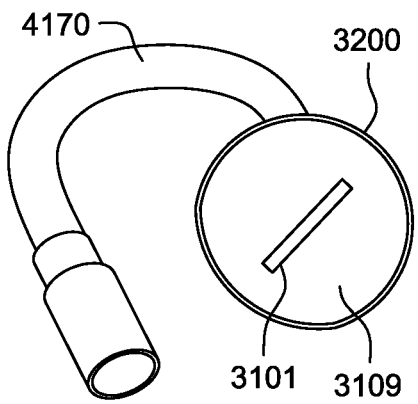

FIG. 33B shows a rear view of a patient interface according to another example of the present technology.

Figure 33C:
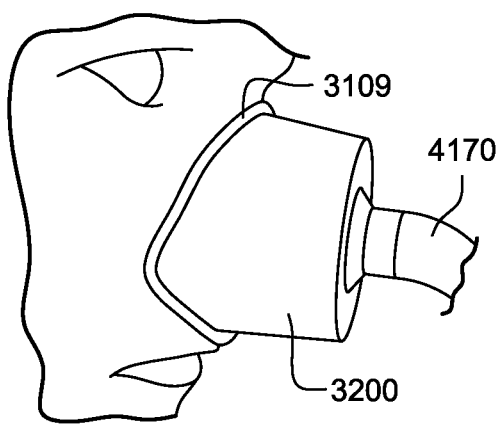

FIG. 33C shows a detailed side view of a patient interface according to an example of the present technology worn by a patient.

Figure 33D:
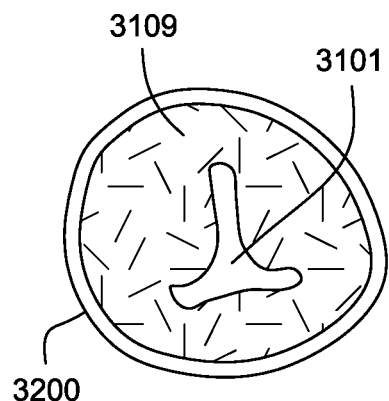

FIG. 33D shows a rear view of a seal forming structure and a plenum chamber of a patient interface according to an example of the present technology.

Figure 33E:
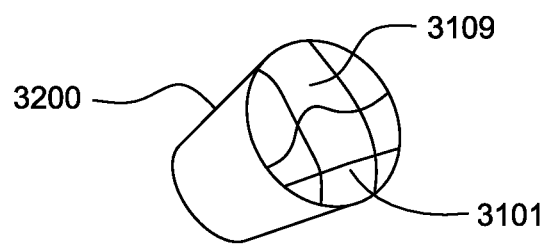

FIG. 33E shows a rear perspective view of a seal forming structure and a plenum chamber of a patient interface according to an example of the present technology.

Figure 34A:
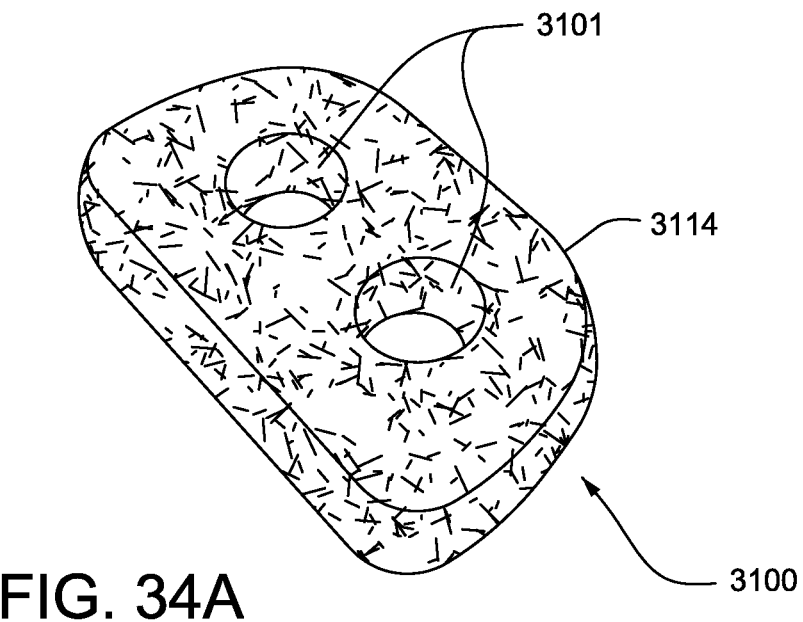

FIG. 34A shows a perspective view of a portion of a seal forming structure of a patient interface according to an example of the present technology.

Figure 34B:
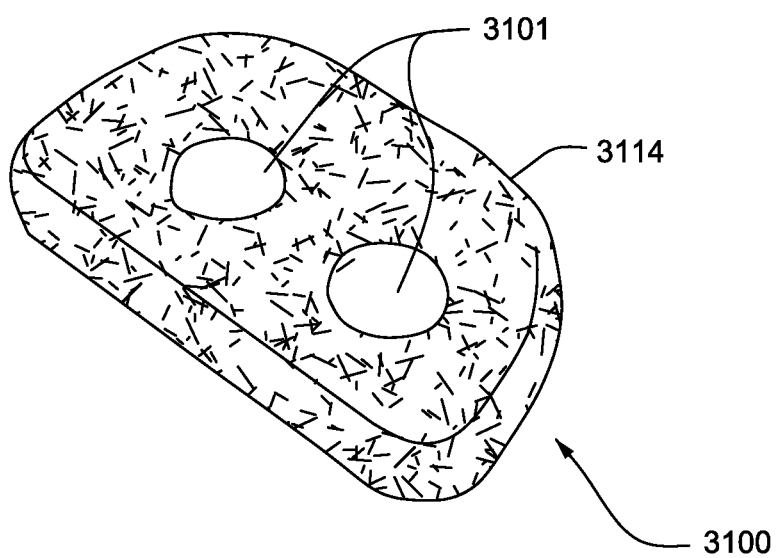

FIG. 34B shows a perspective view of a portion of a seal forming structure of a patient interface according to another example of the present technology.

Figure 35A:
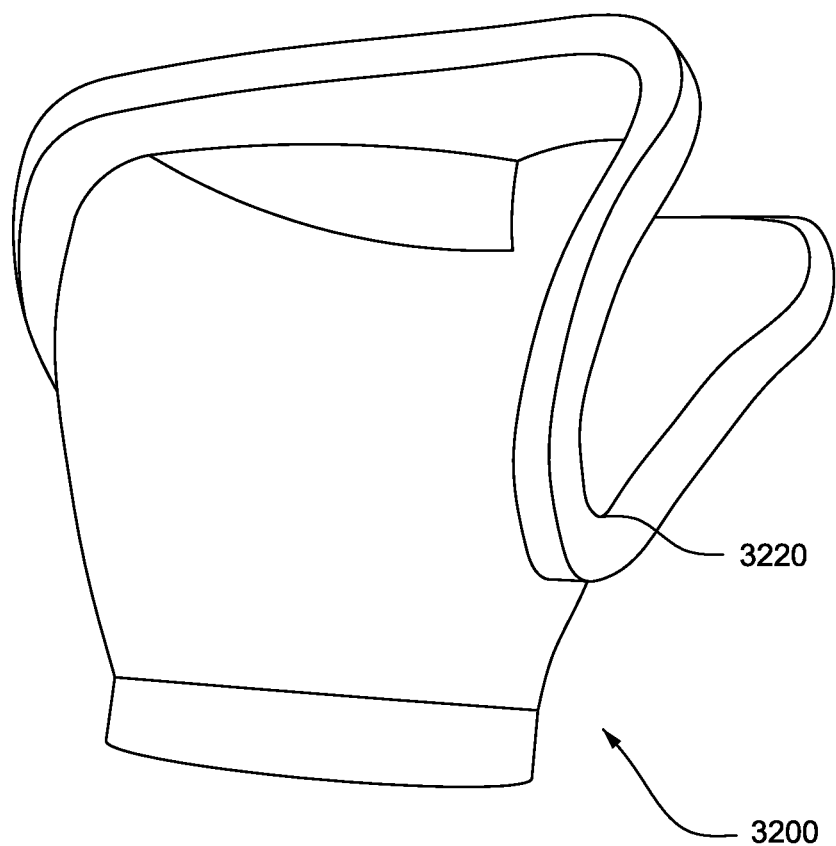

FIG. 35A shows a side view of a plenum chamber of a patient interface according to an example of the present technology.

Figure 35B:
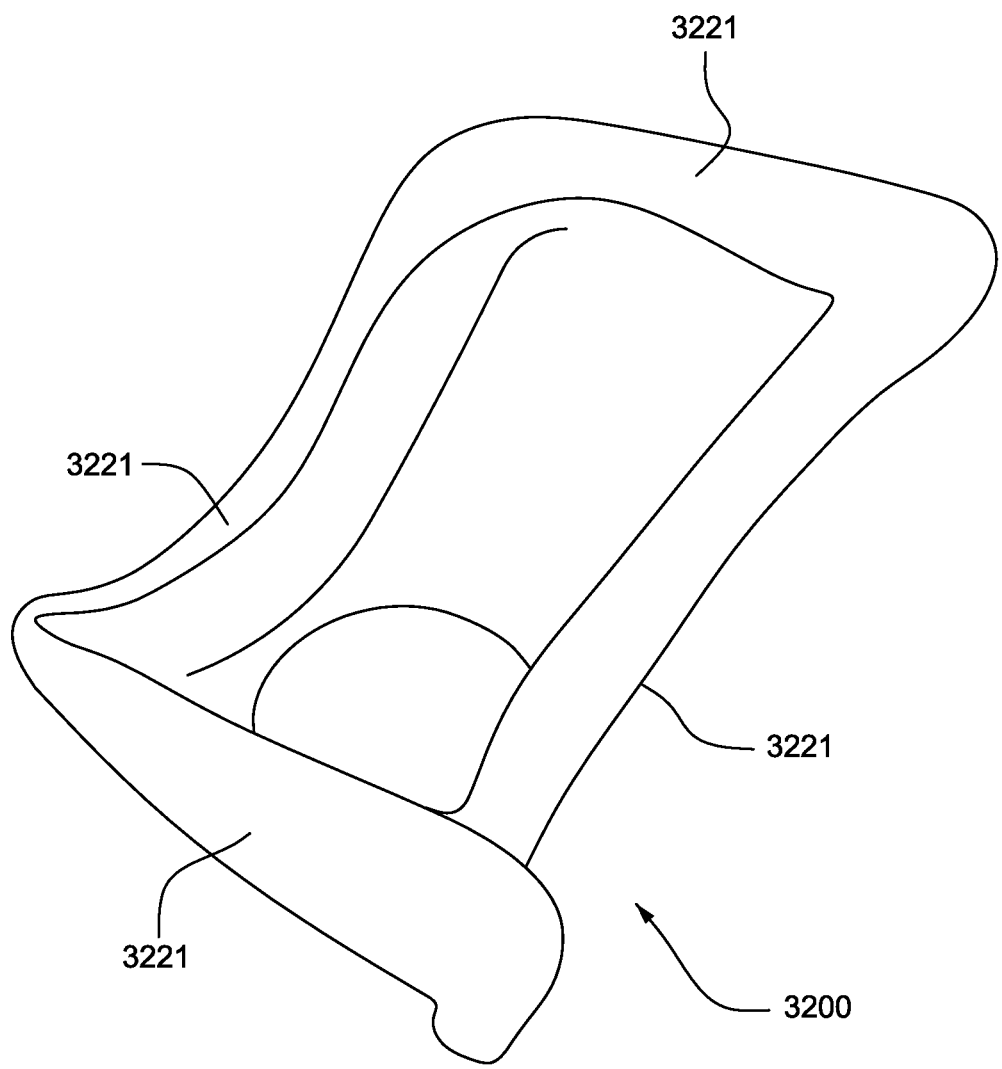

FIG. 35B shows a rear perspective view of a plenum chamber of a patient interface according to an example of the present technology.

Figure 35C:
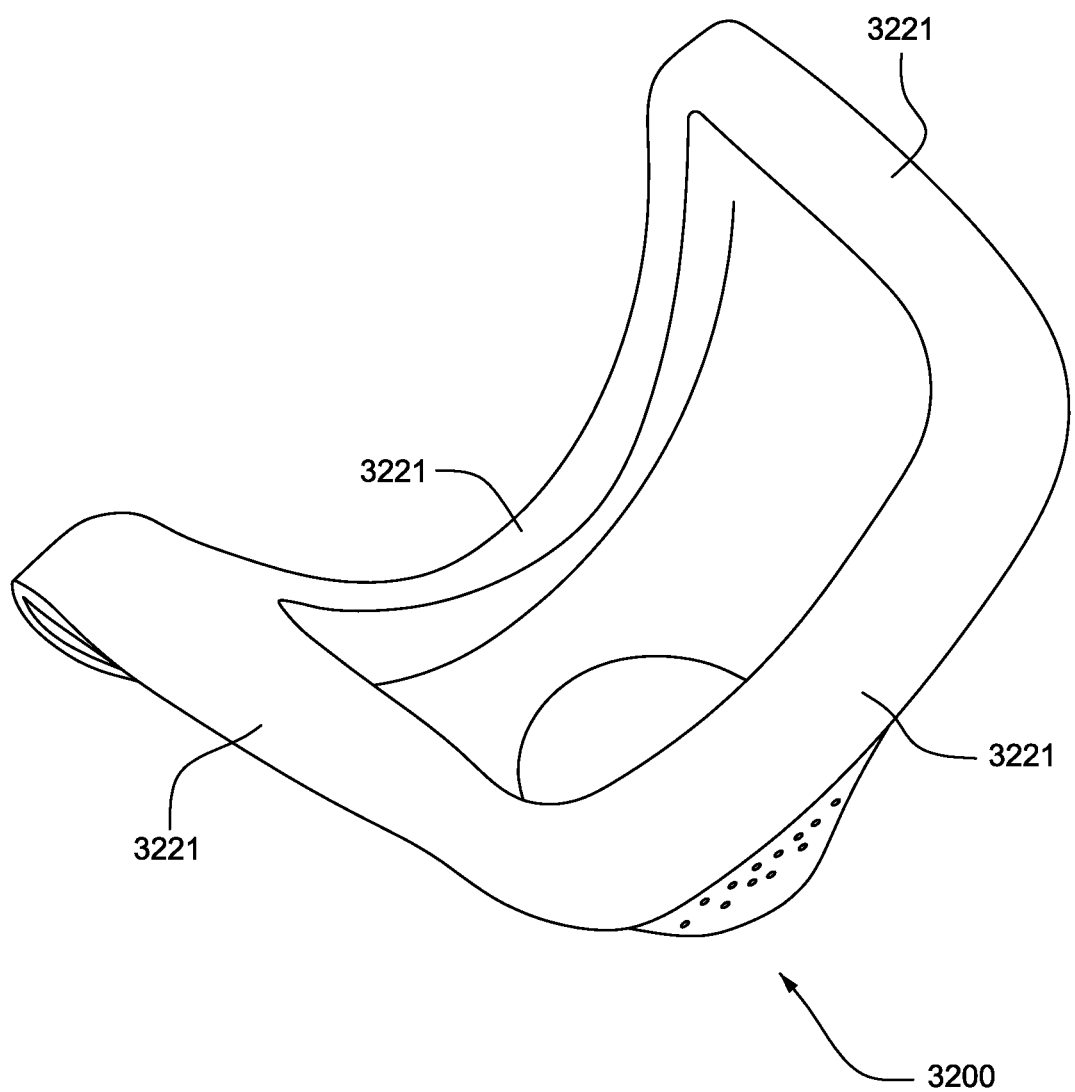

FIG. 35C shows a rear view of a plenum chamber of a patient interface according to an example of the present technology.

Figure 35D:
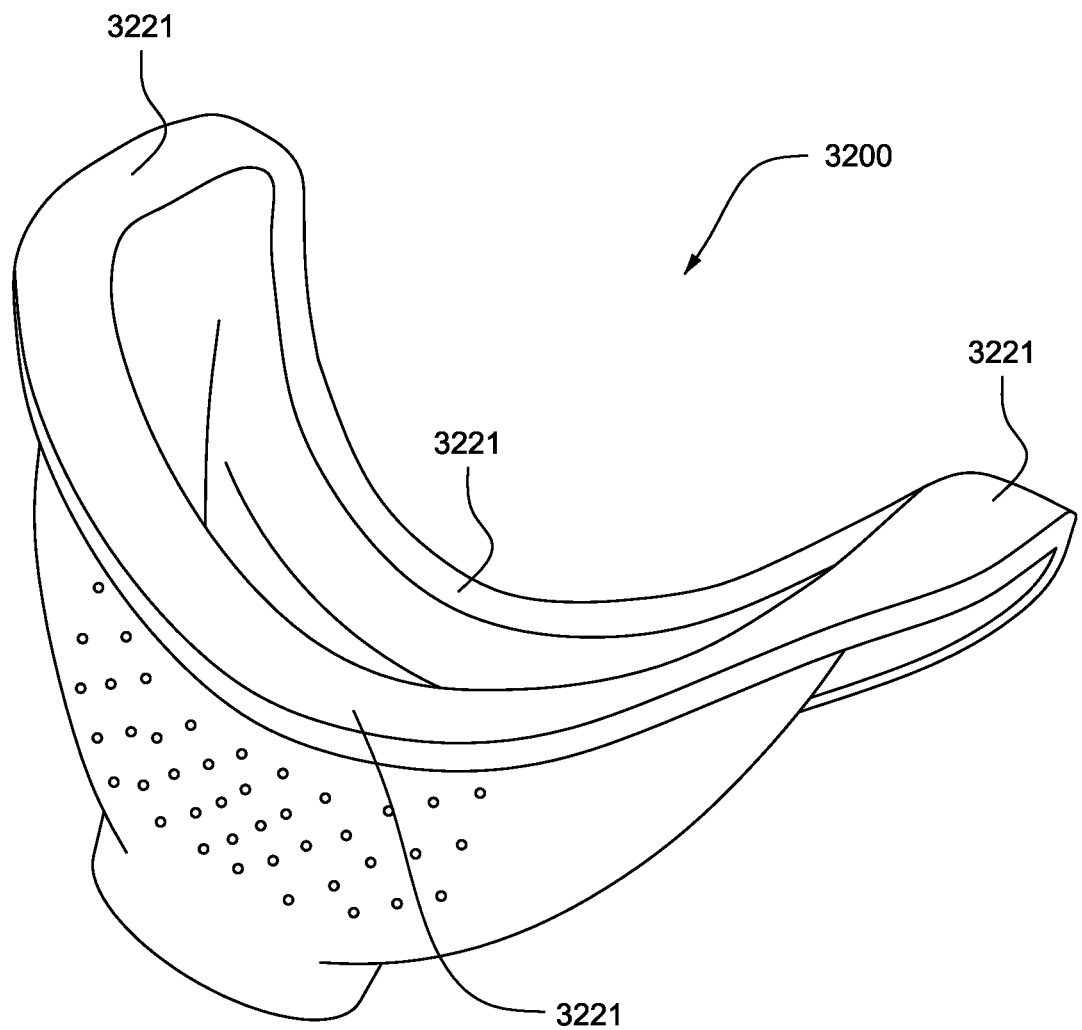

FIG. 35D shows a top view of a plenum chamber of a patient interface according to an example of the present technology.

Figure 36A:
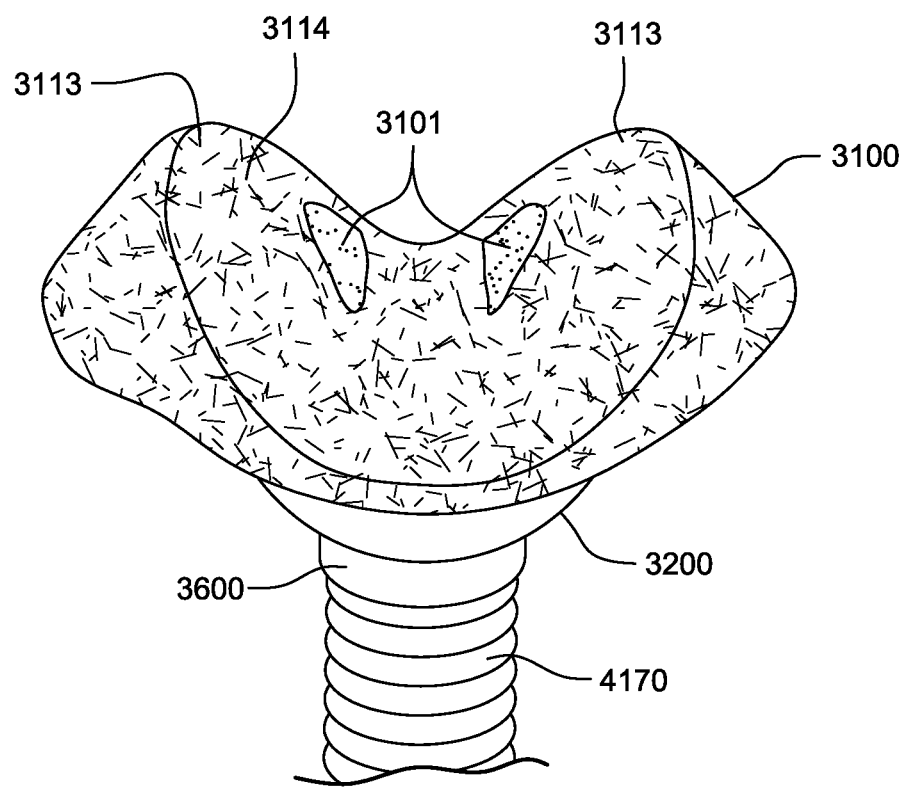

FIG. 36A shows a rear view of a patient interface according to an example of the present technology.

Figure 36B:
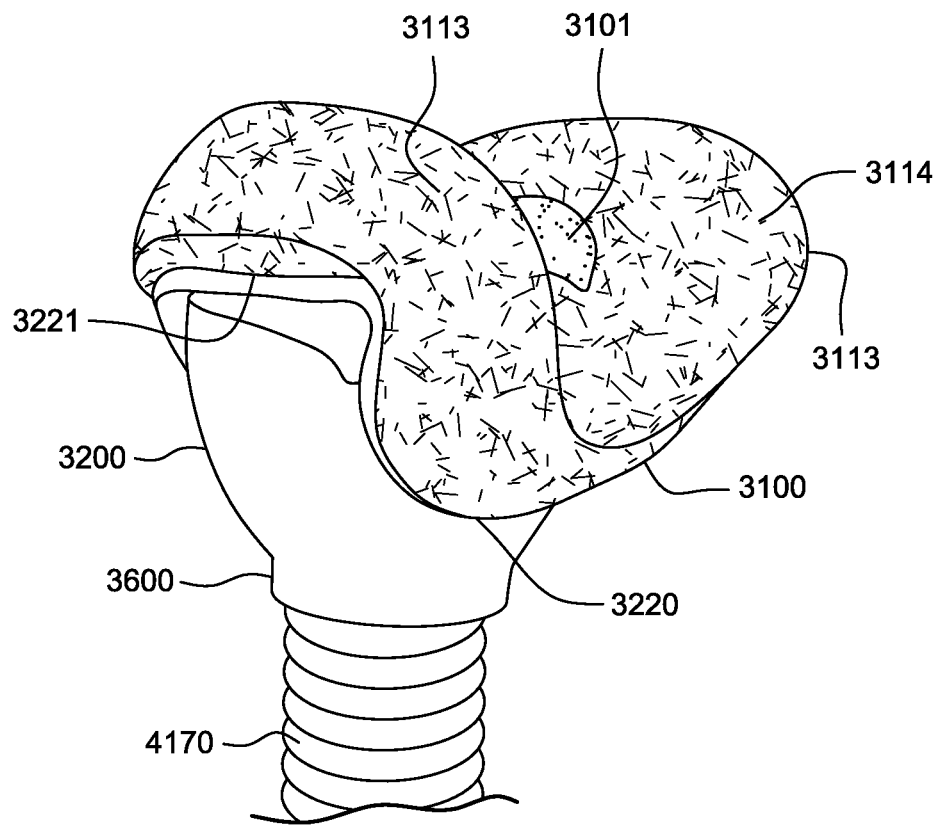

FIG. 36B shows a perspective view of a patient interface according to an example of the present technology.

Figure 36C:
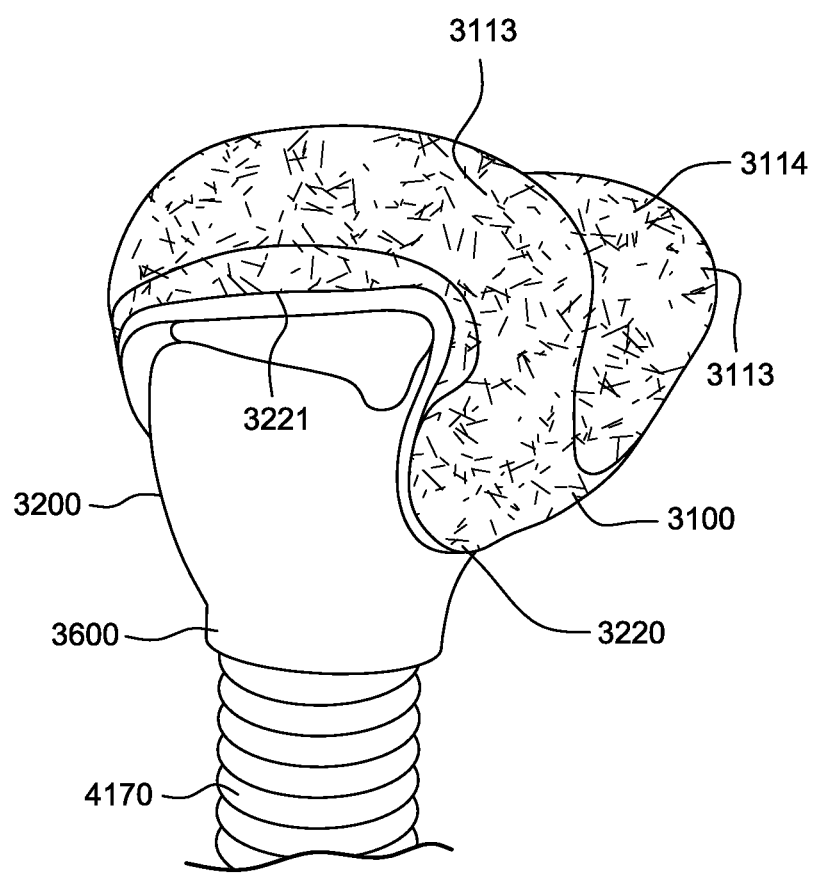

FIG. 36C shows a side view of a patient interface according to an example of the present technology.

Figure 36D:
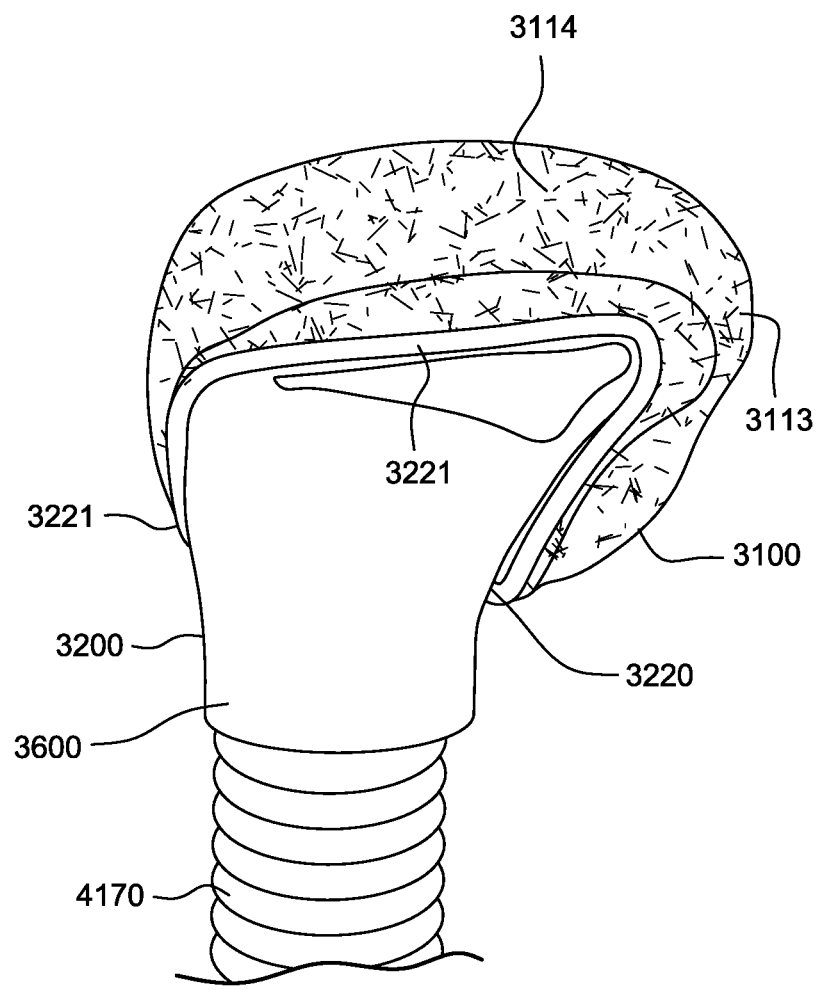

FIG. 36D shows another side view of a patient interface according to an example of the present technology.

Figure 36E:
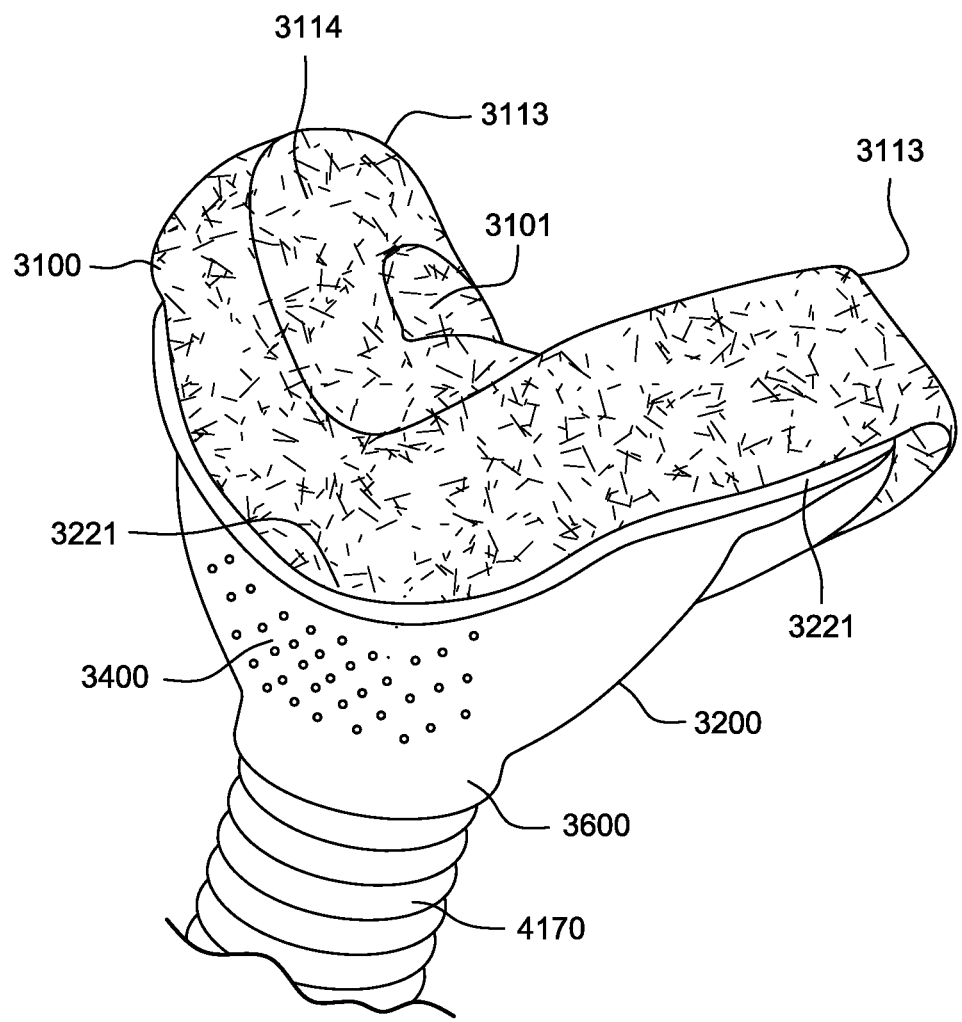

FIG. 36E shows a top perspective view of a patient interface according to an example of the present technology.

Figure 36F:
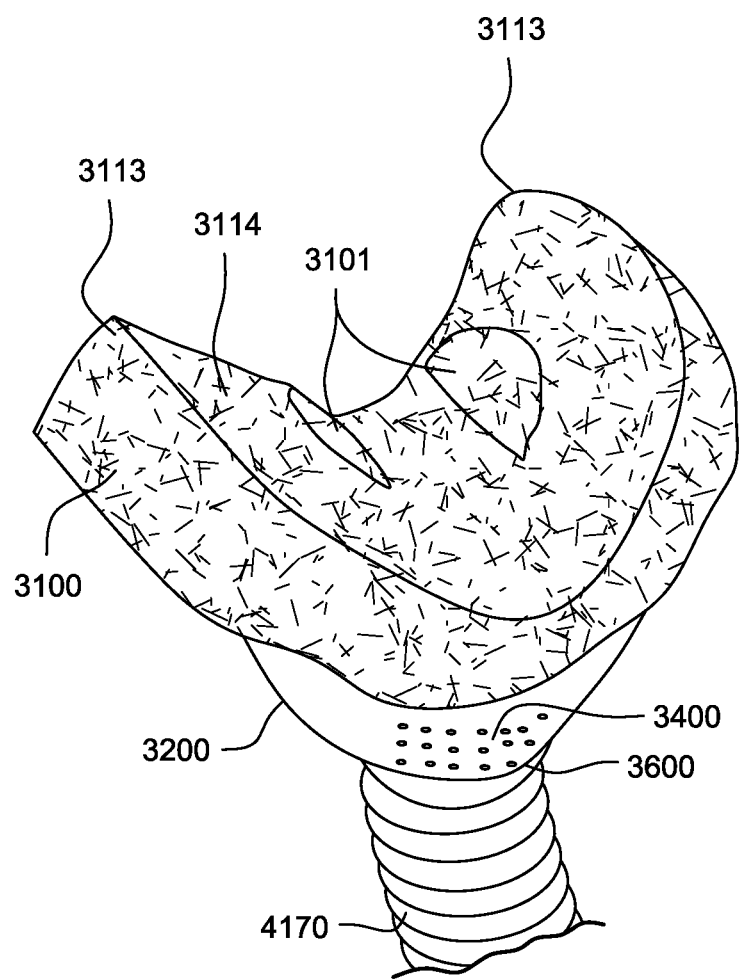

FIG. 36F shows another top perspective view of a patient interface according to an example of the present technology.

Figure 37A:
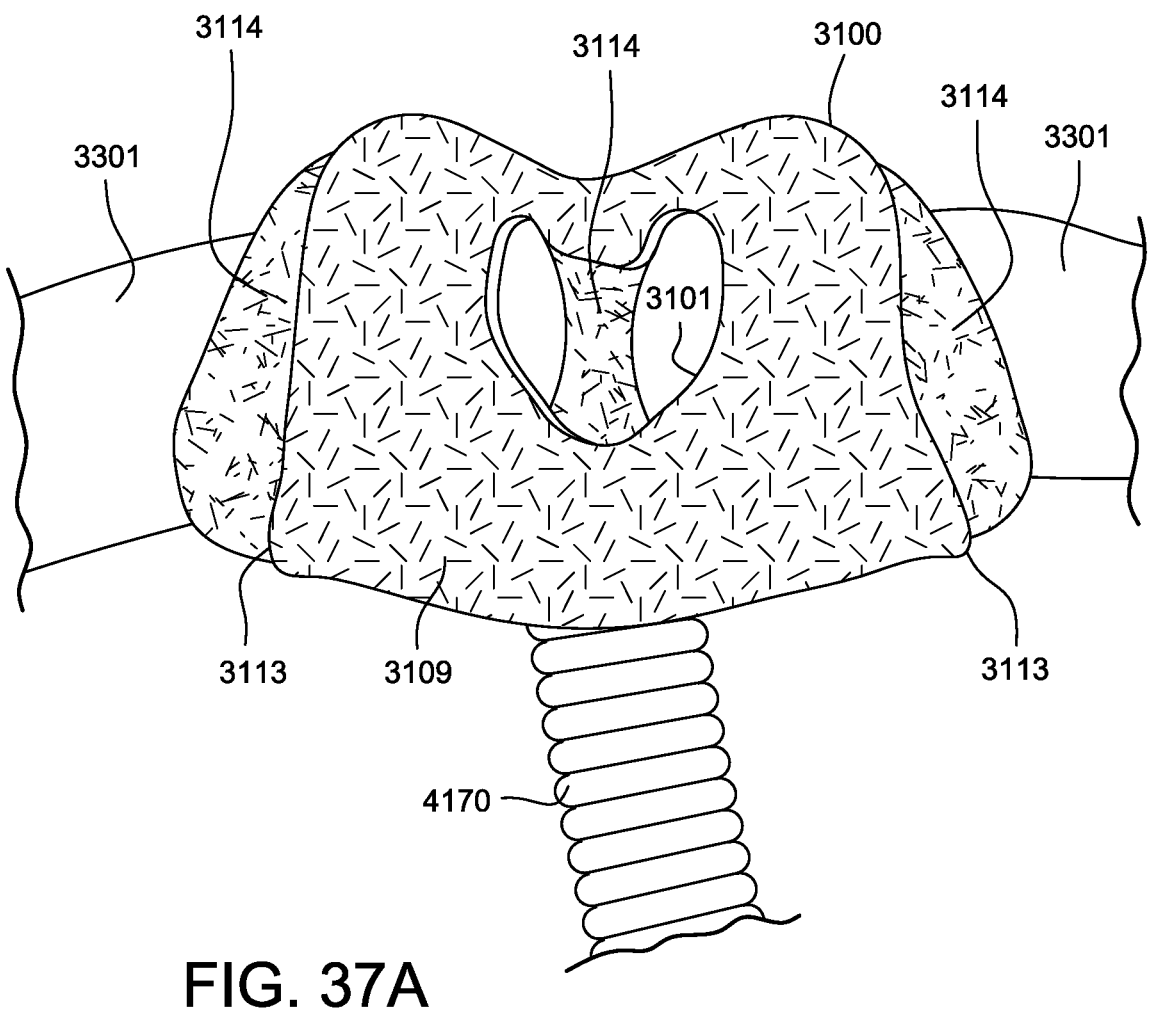

FIG. 37A shows a rear view of a patient interface according to an example of the present technology.

Figure 37B:
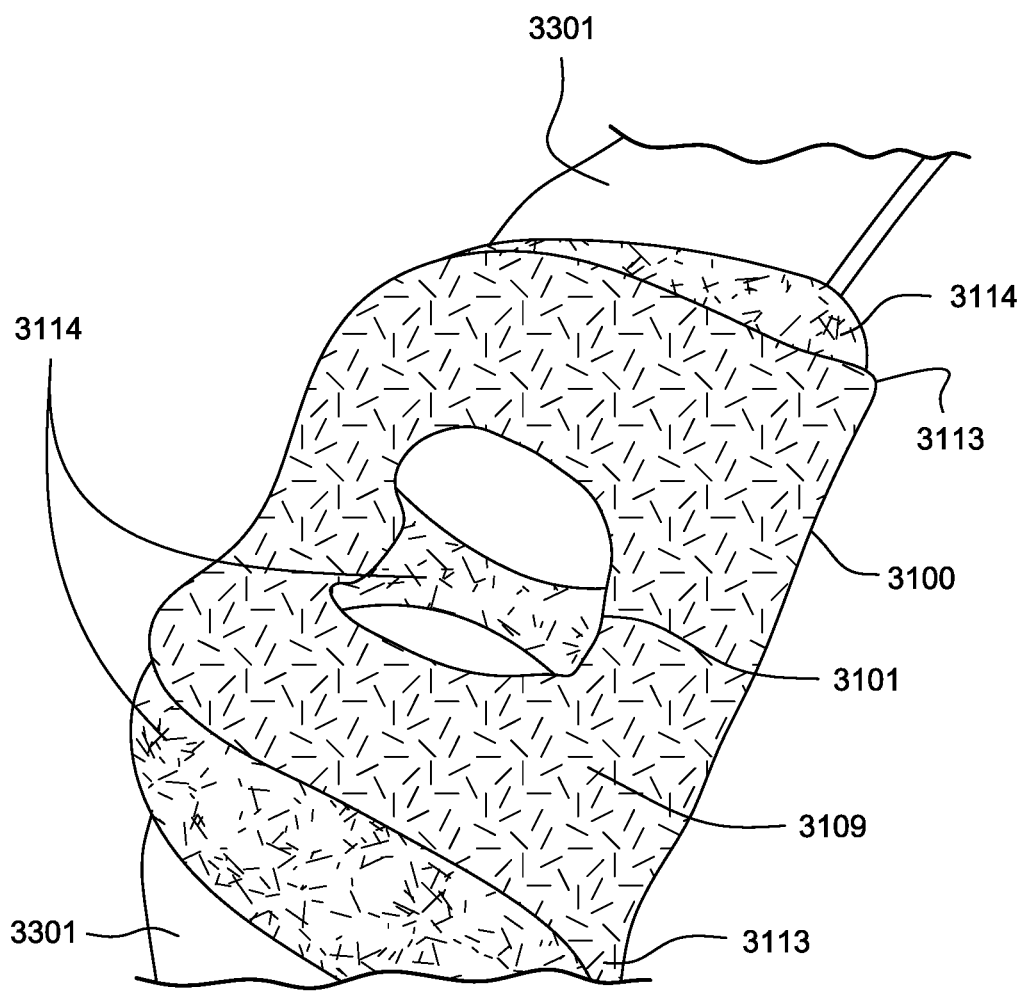

FIG. 37B shows a detailed rear perspective view of a patient interface according to an example of the present technology.

Figure 37C:
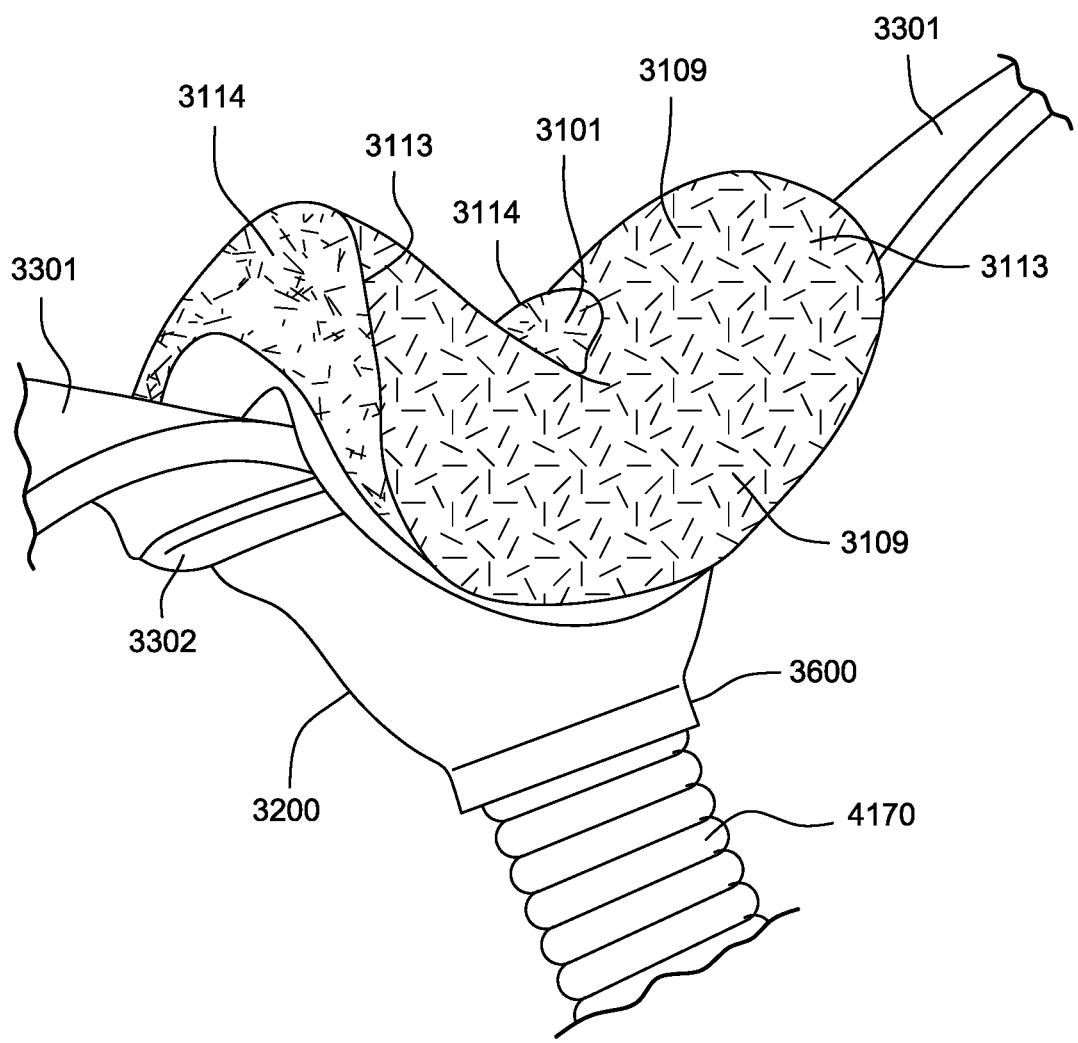

FIG. 37C shows a bottom perspective view of a patient interface according to an example of the present technology.

Figure 37D:
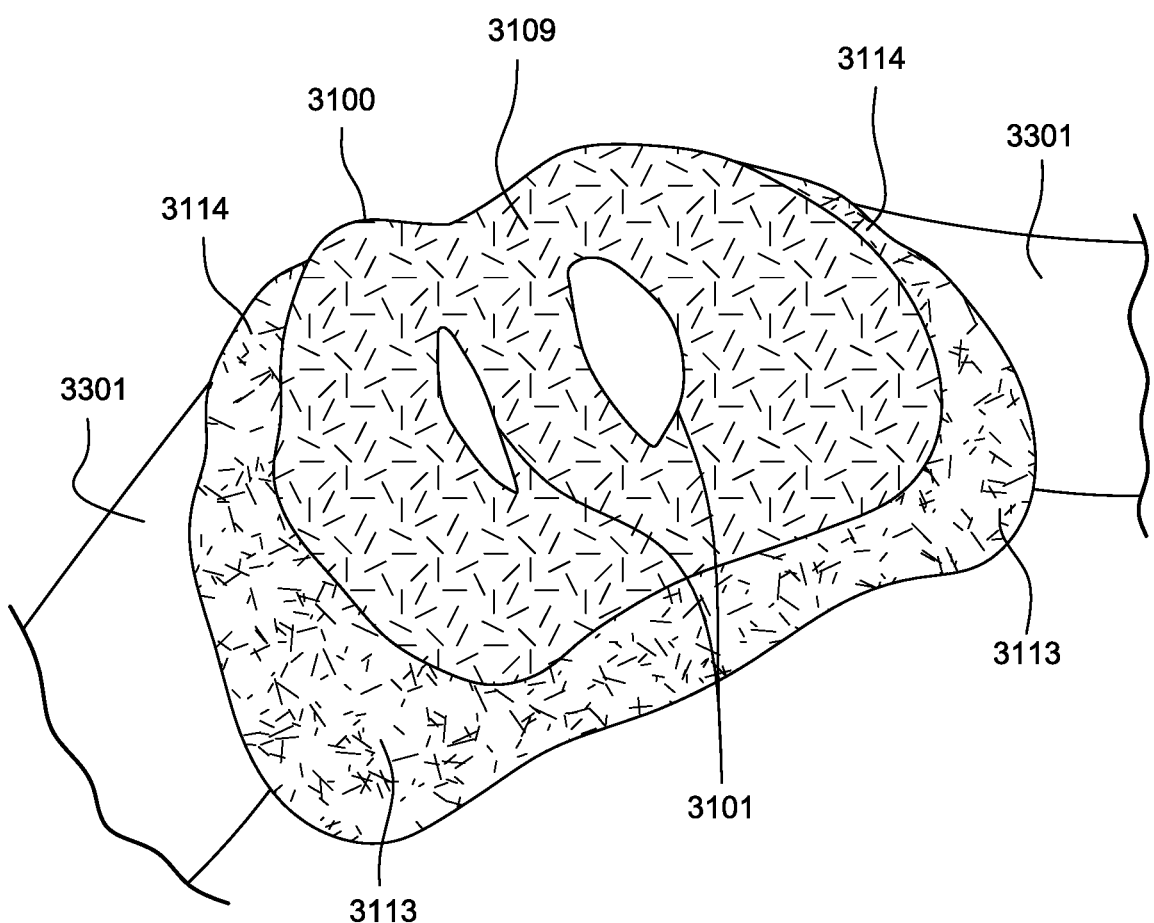

FIG. 37D shows another rear view of a patient interface according to an example of the present technology.

Figure 37E:
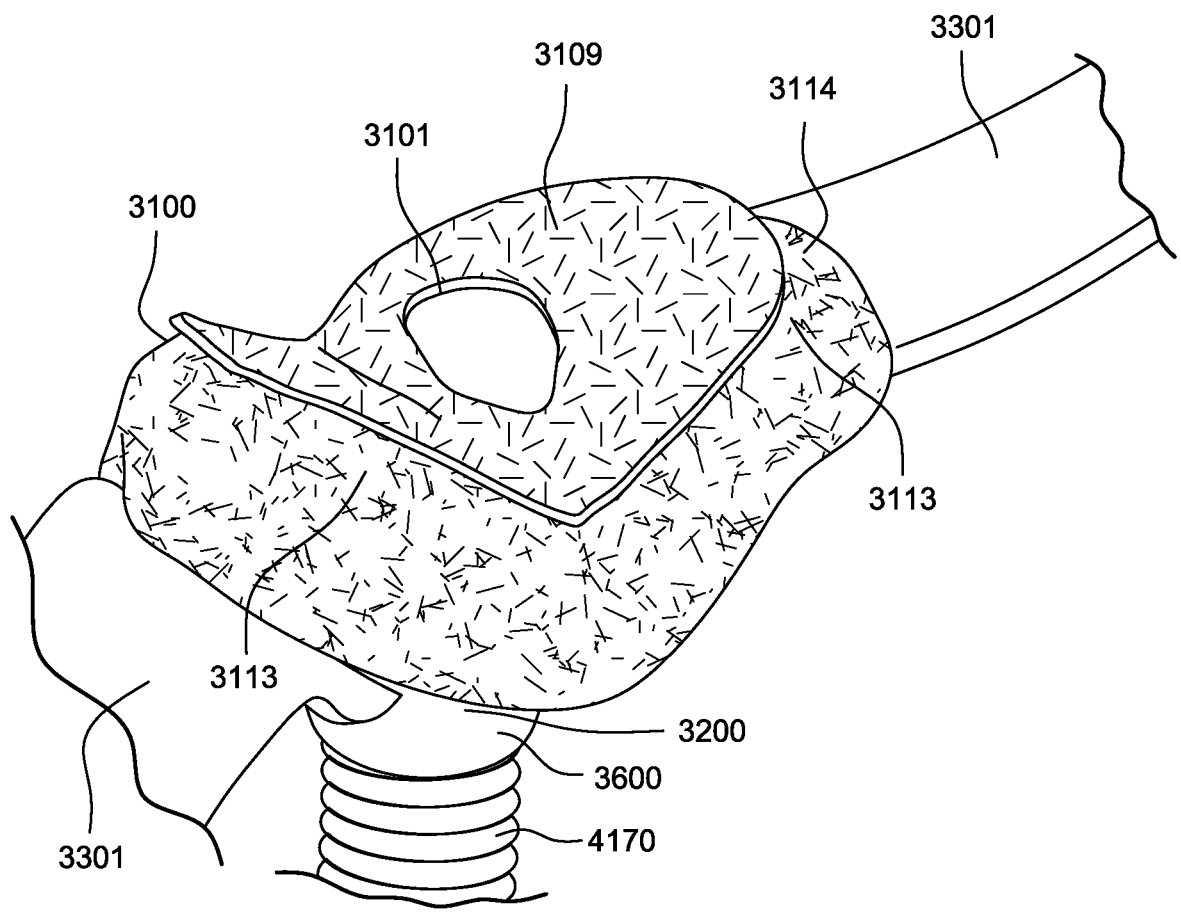

FIG. 37E shows a rear perspective view of a patient interface according to an example of the present technology.

Figure 37F:
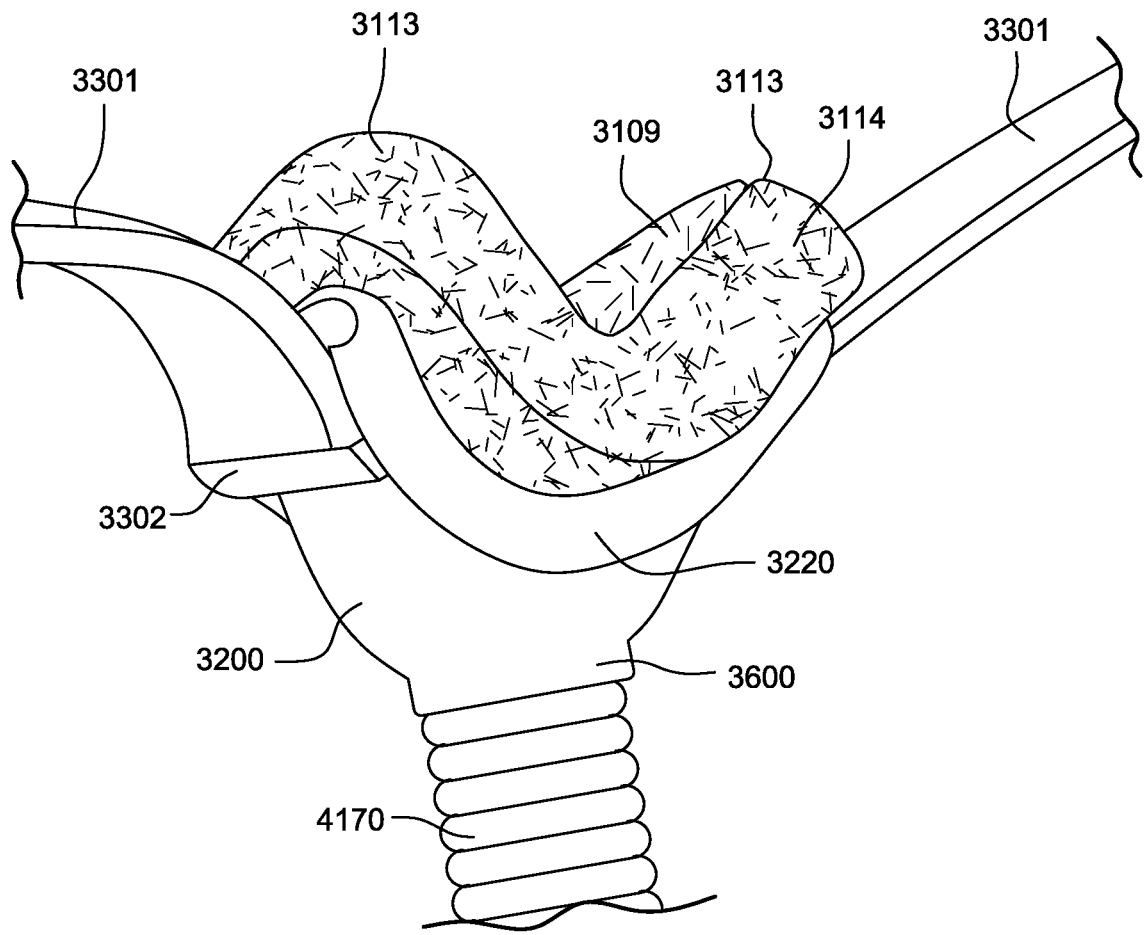

FIG. 37F shows another bottom perspective view of a patient interface according to an example of the present technology.

Figure 38A:
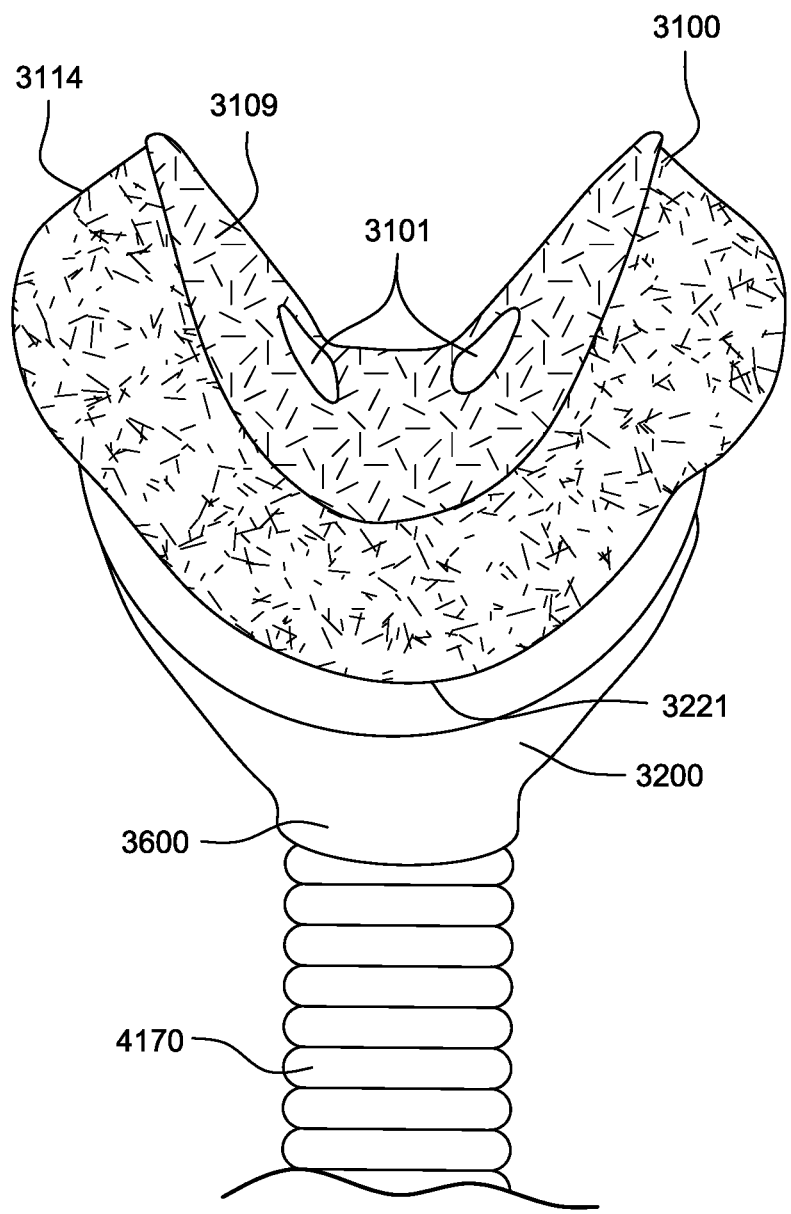

FIG. 38A shows a top view of a patient interface according to an example of the present technology.

Figure 38B:
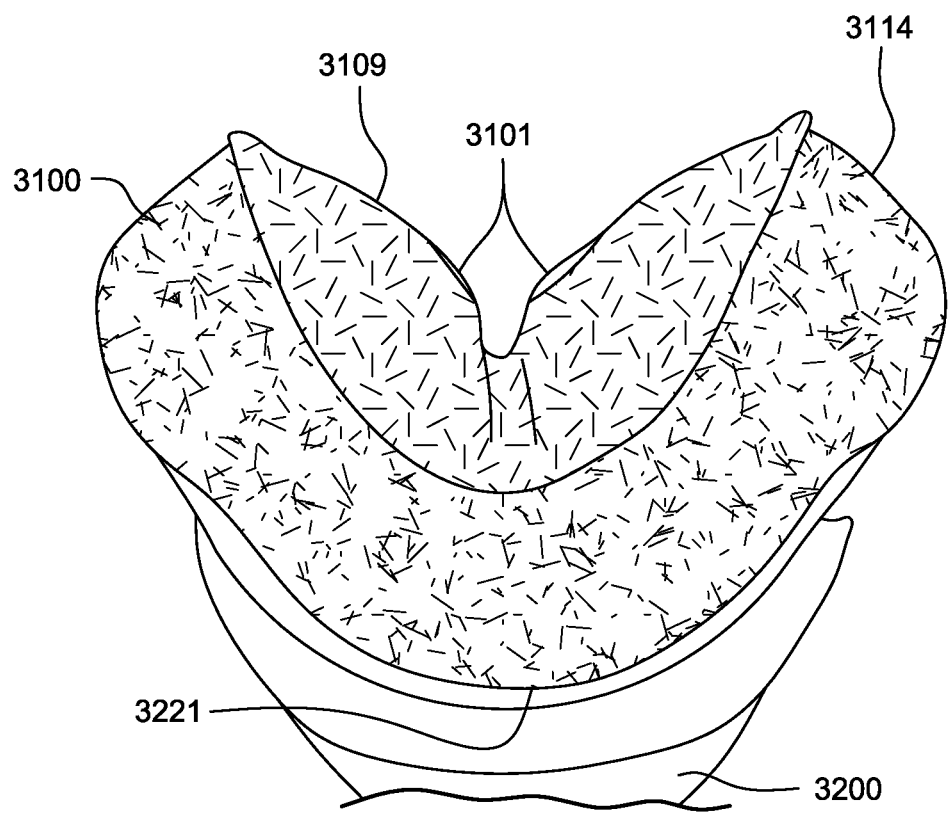

FIG. 38B shows a detailed top view of a patient interface according to an example of the present technology.

Figure 38C:
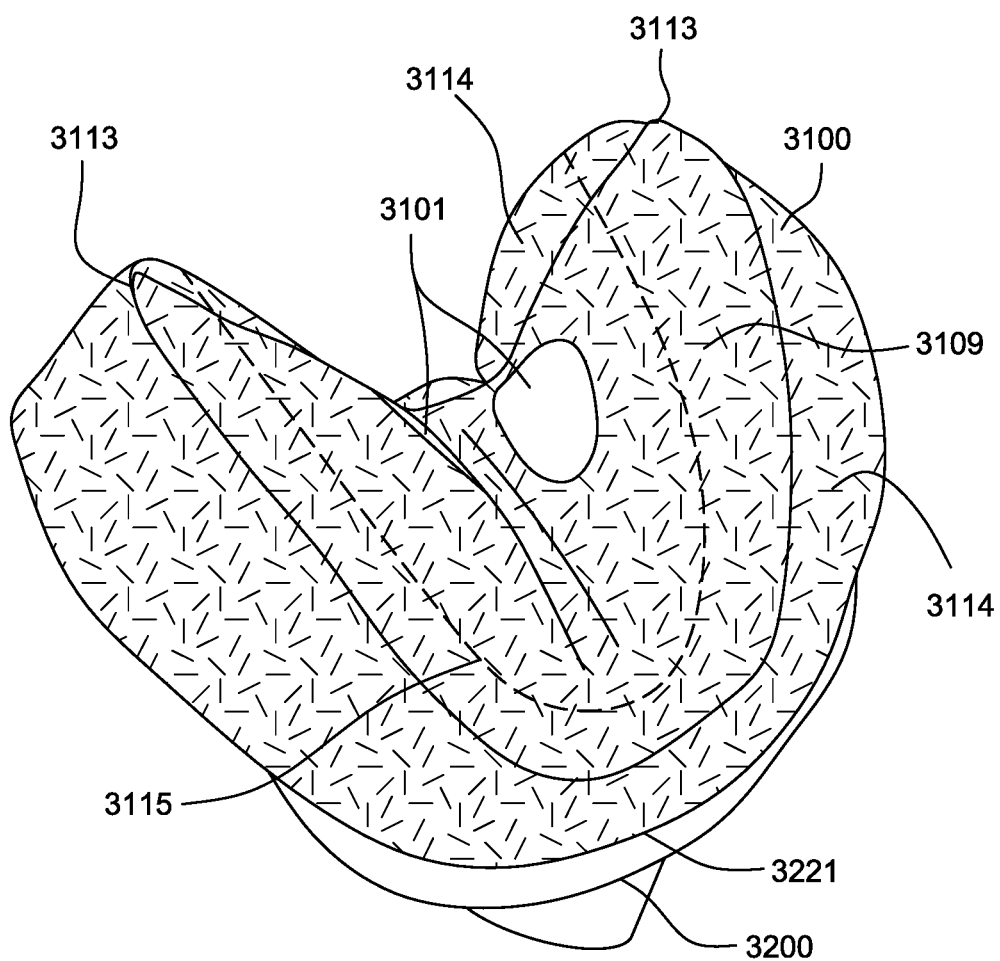

FIG. 38C shows a detailed perspective view of a patient interface according to an example of the present technology.

Figure 39A:
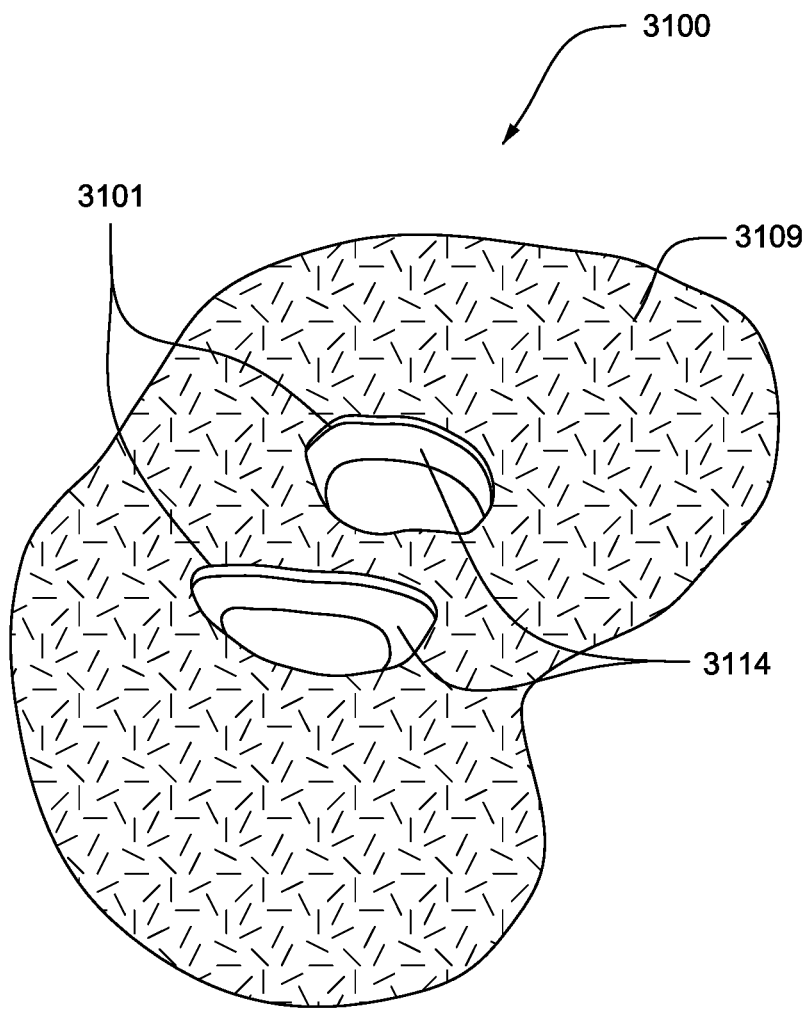

FIG. 39A shows a rear perspective view of a seal forming structure of a patient interface according to an example of the present technology.

Figure 39B:
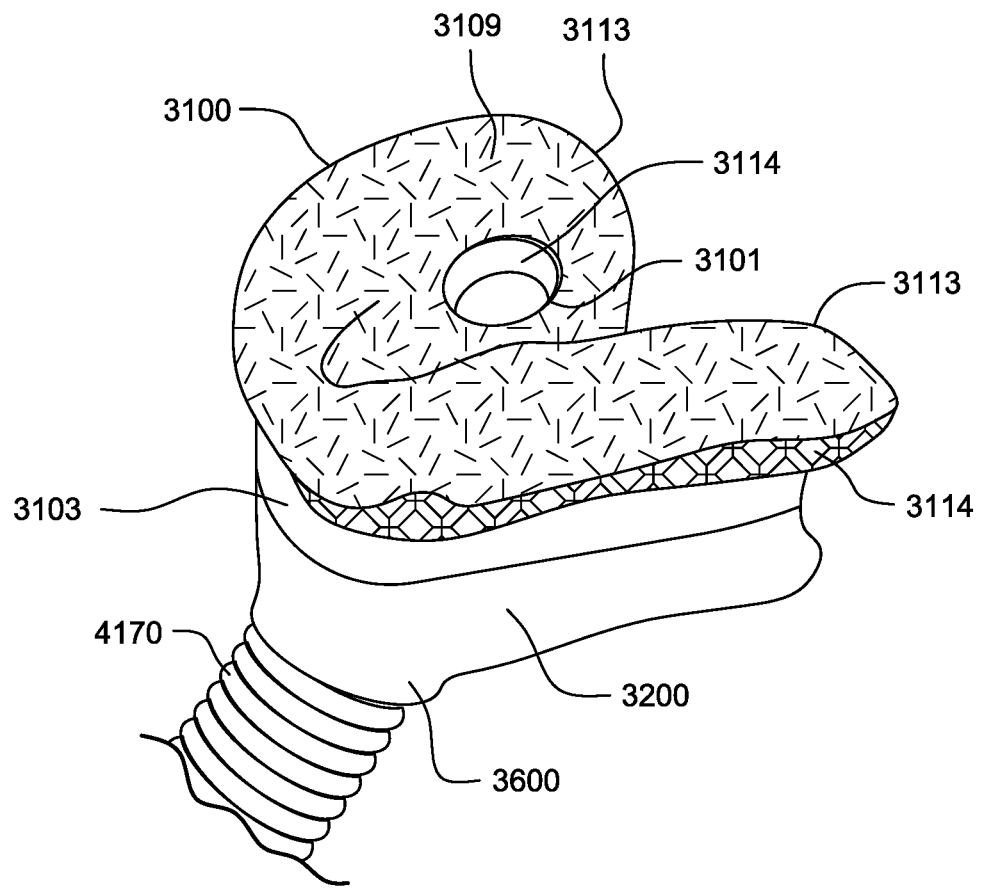

FIG. 39B shows another perspective view of a seal forming structure of a patient interface according to an example of the present technology.

Figure 39C:
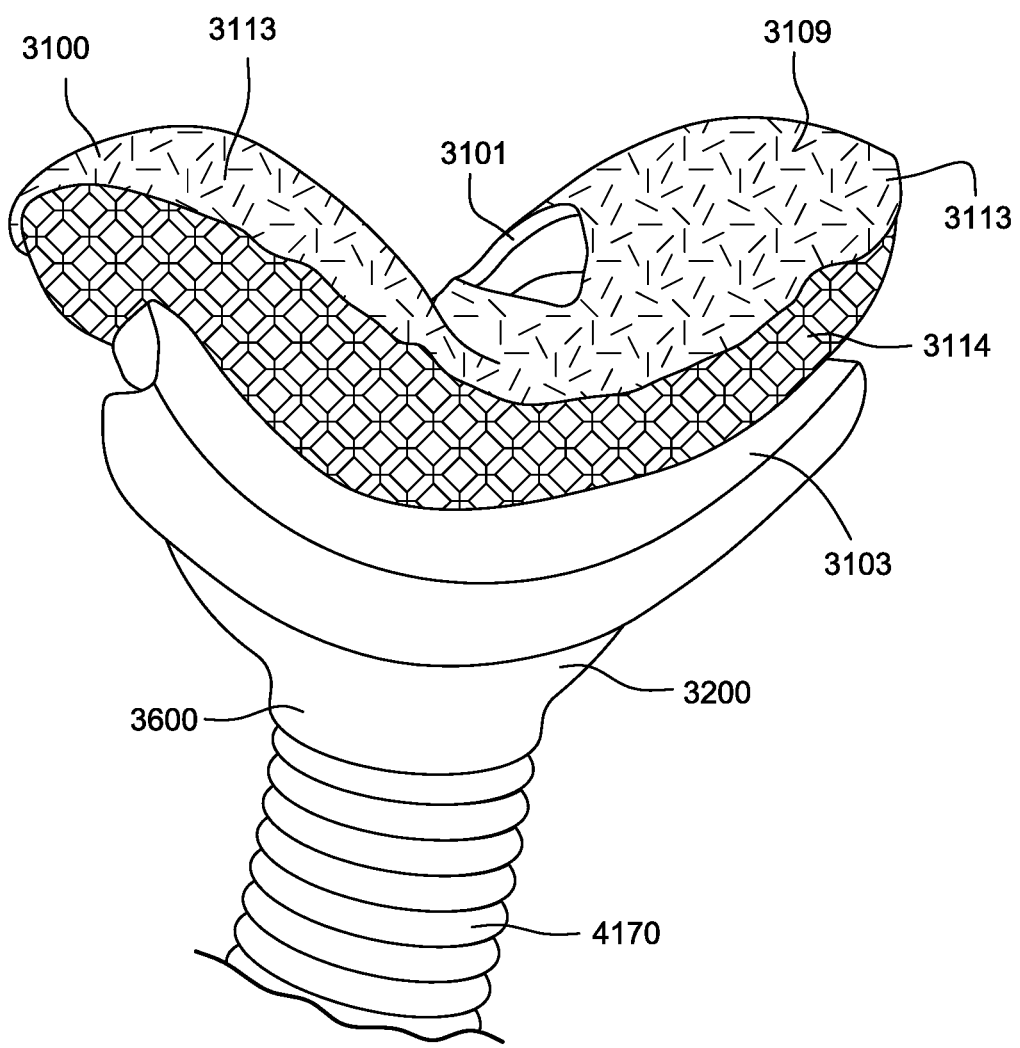

FIG. 39C shows a bottom view of a seal forming structure of a patient interface according to an example of the present technology.

Figure 40A:
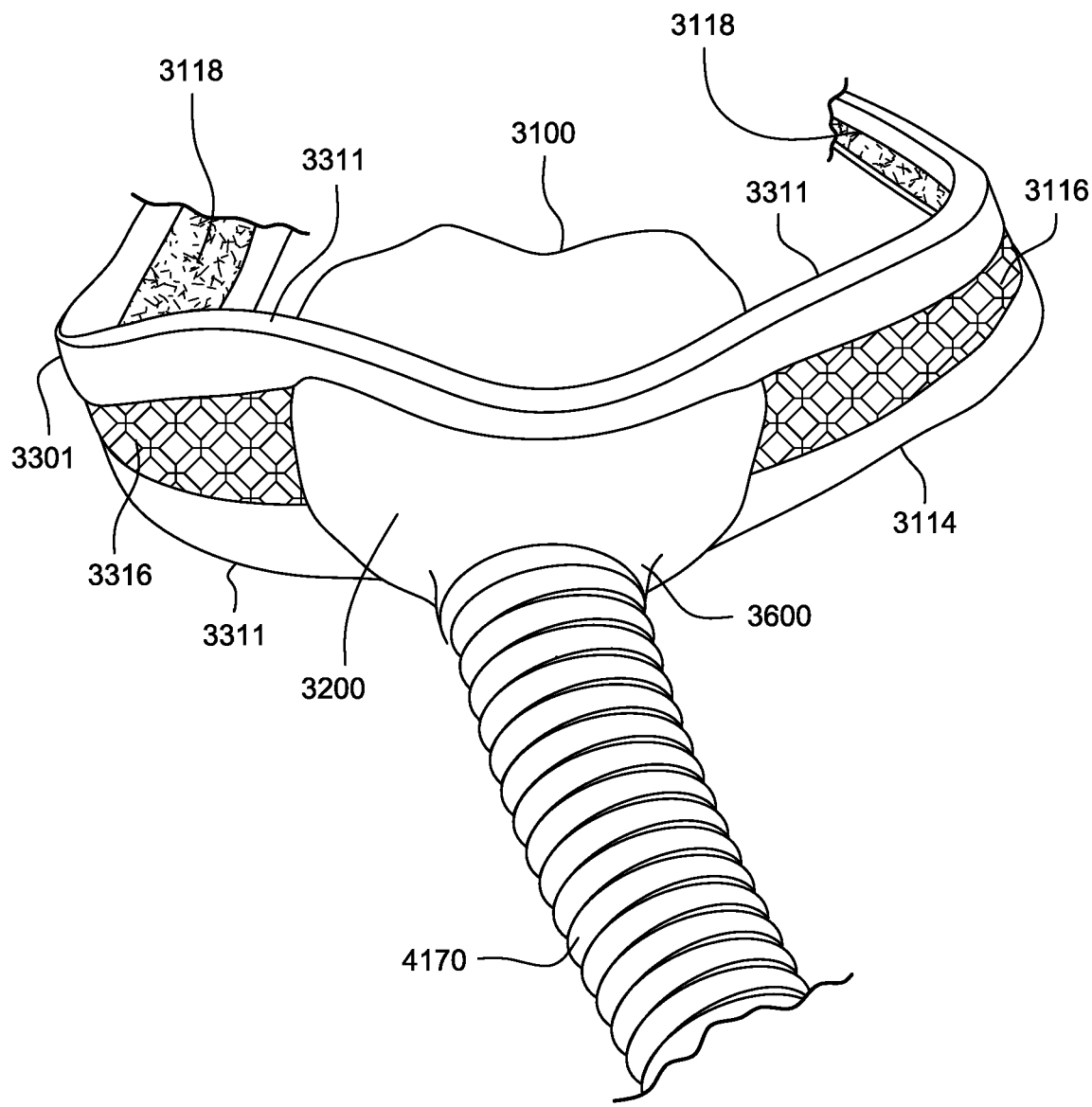

FIG. 40A shows a front view of a patient interface according to an example of the present technology.

Figure 40B:
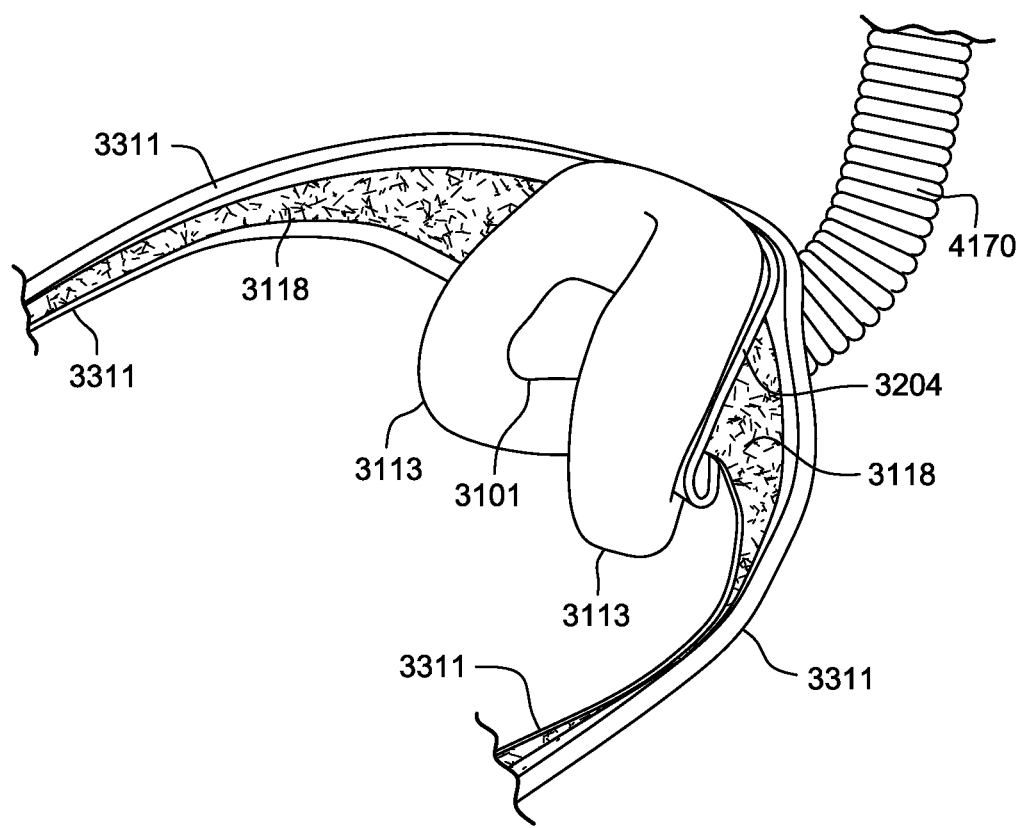

FIG. 40B shows a rear perspective view of a patient interface according to an example of the present technology.

Figure 40C:
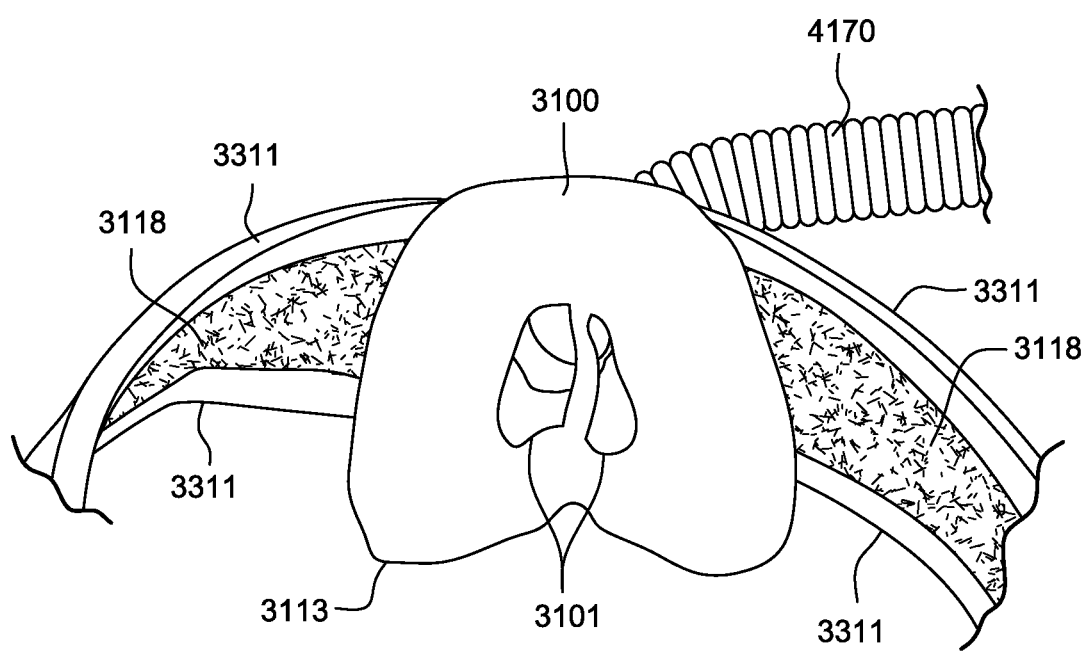

FIG. 40C shows a rear view of a patient interface according to an example of the present technology.

Figure 40D:
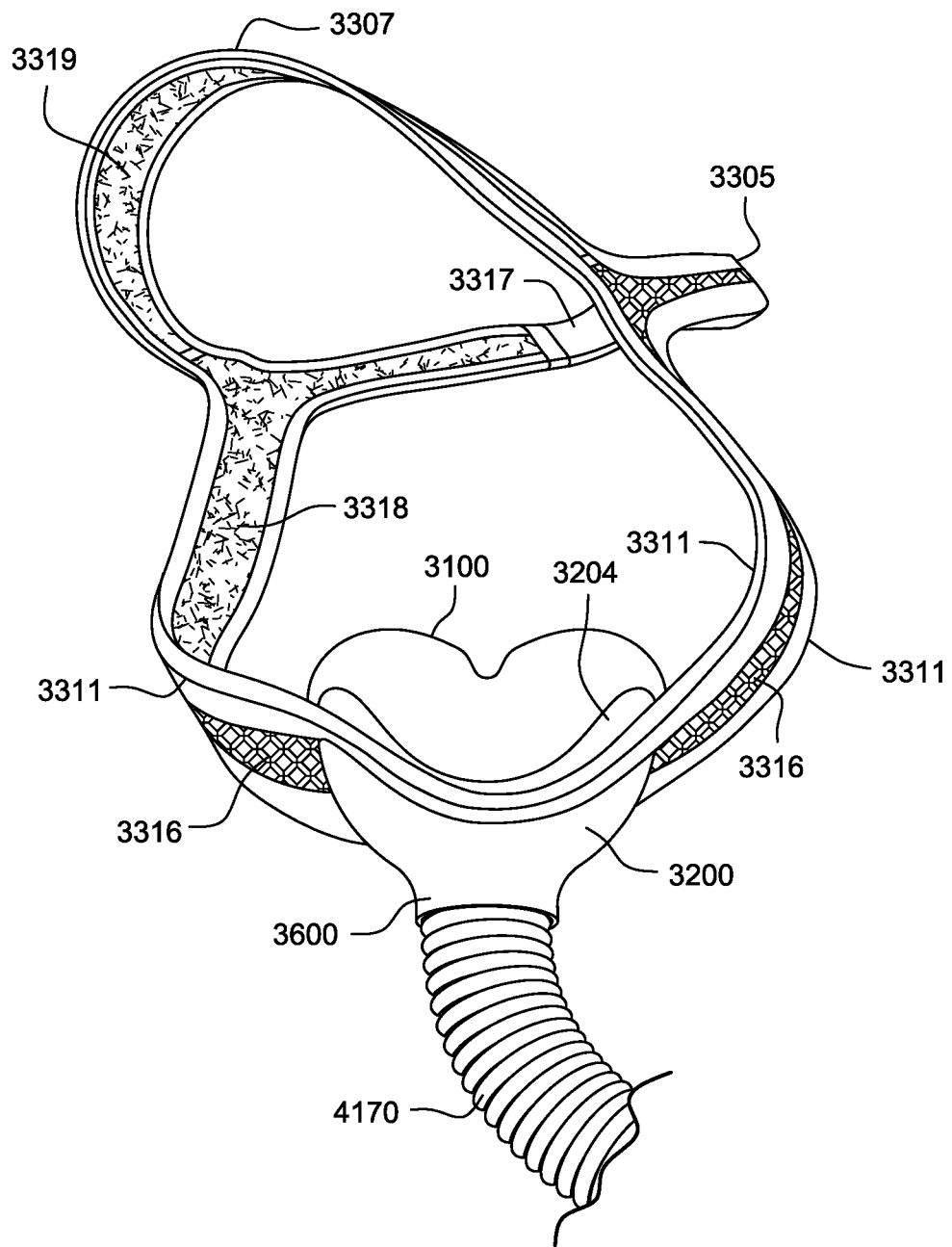

FIG. 40D shows a top view of a patient interface according to an example of the present technology.

Figure 41A:
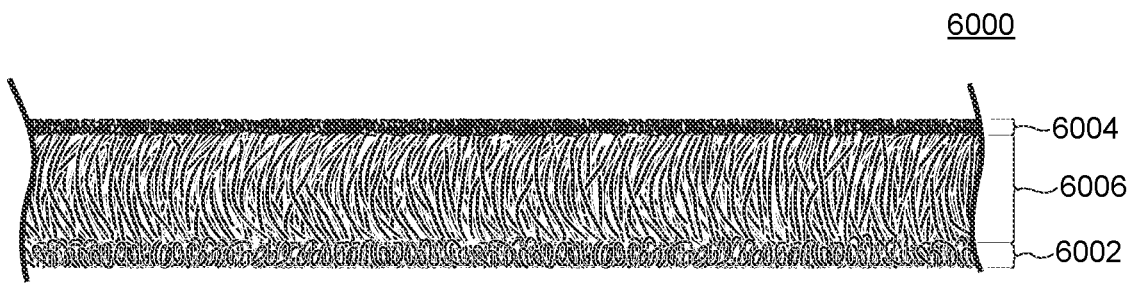

FIG. 41A shows a side or edge view of a first spacer fabric illustrating layers therein.

Figure 41B:
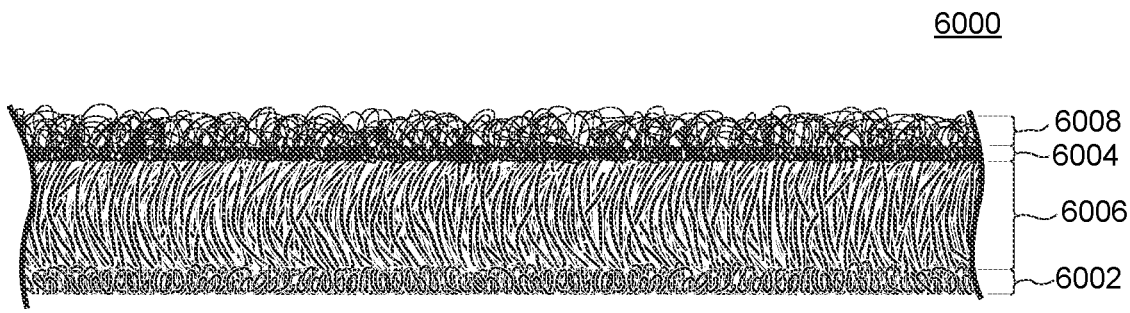

FIG. 41B shows a first side or edge view of a second spacer fabric illustrating layers therein.

Figure 42A:
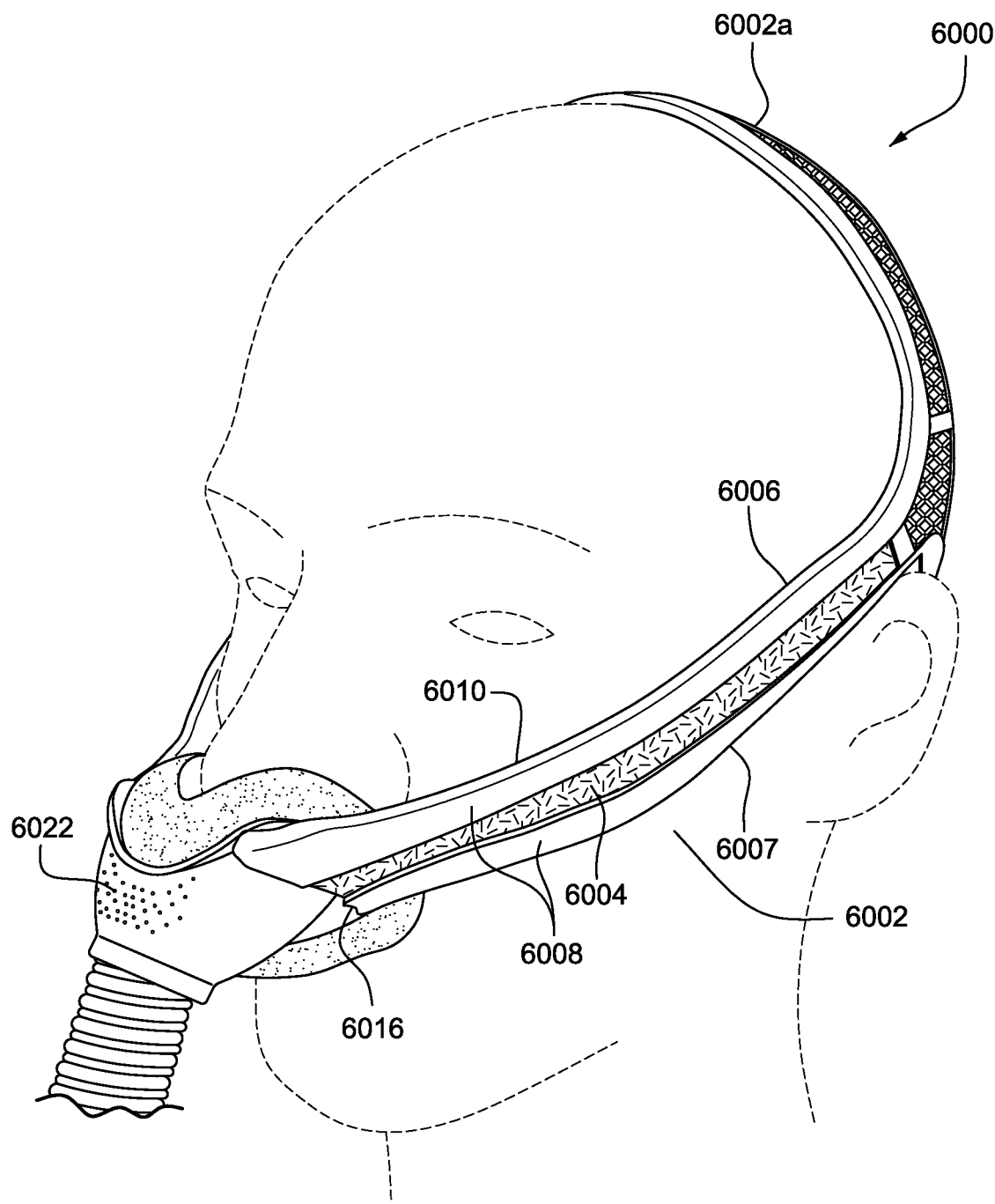

FIG. 42A shows a perspective view of headgear supporting a mask on a patient.

Figure 42B:
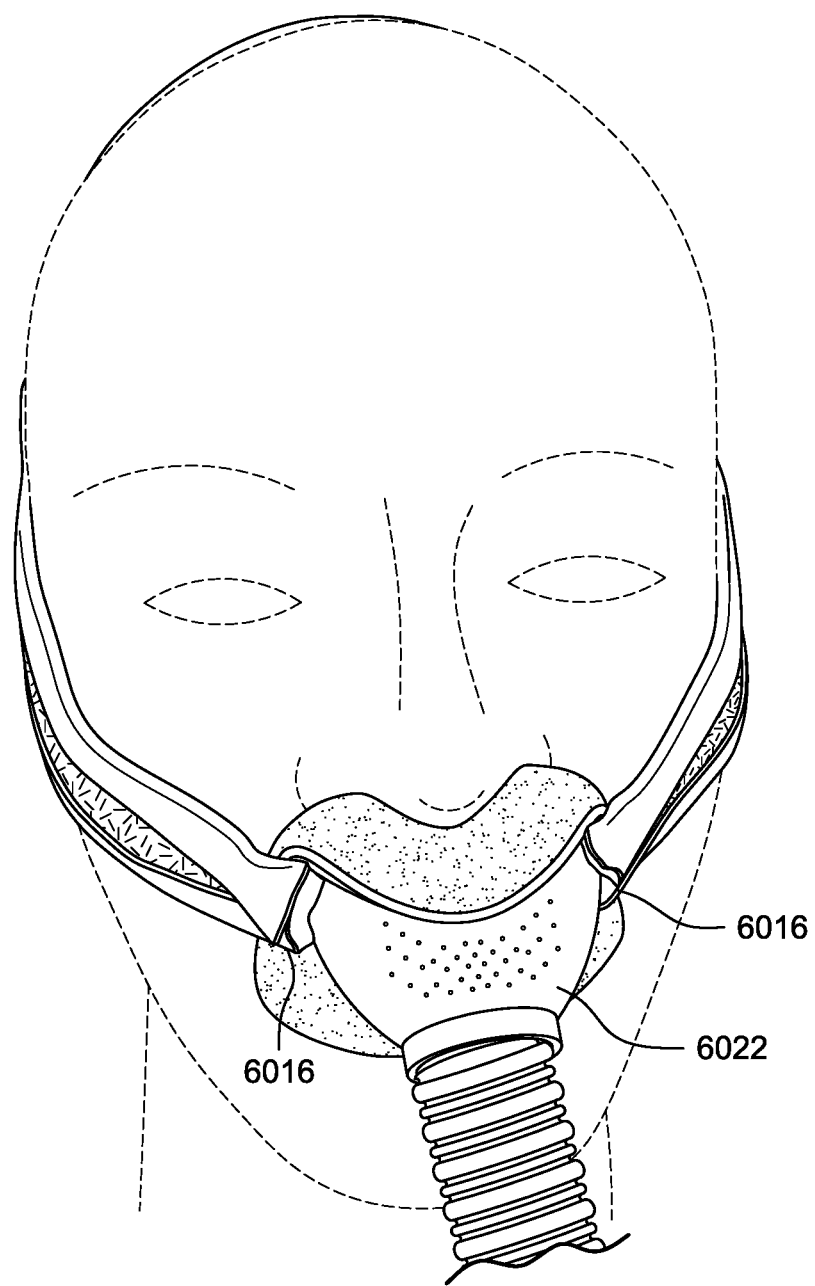

FIG. 42B shows a front view of headgear supporting a mask on a patient.

Figure 42C:
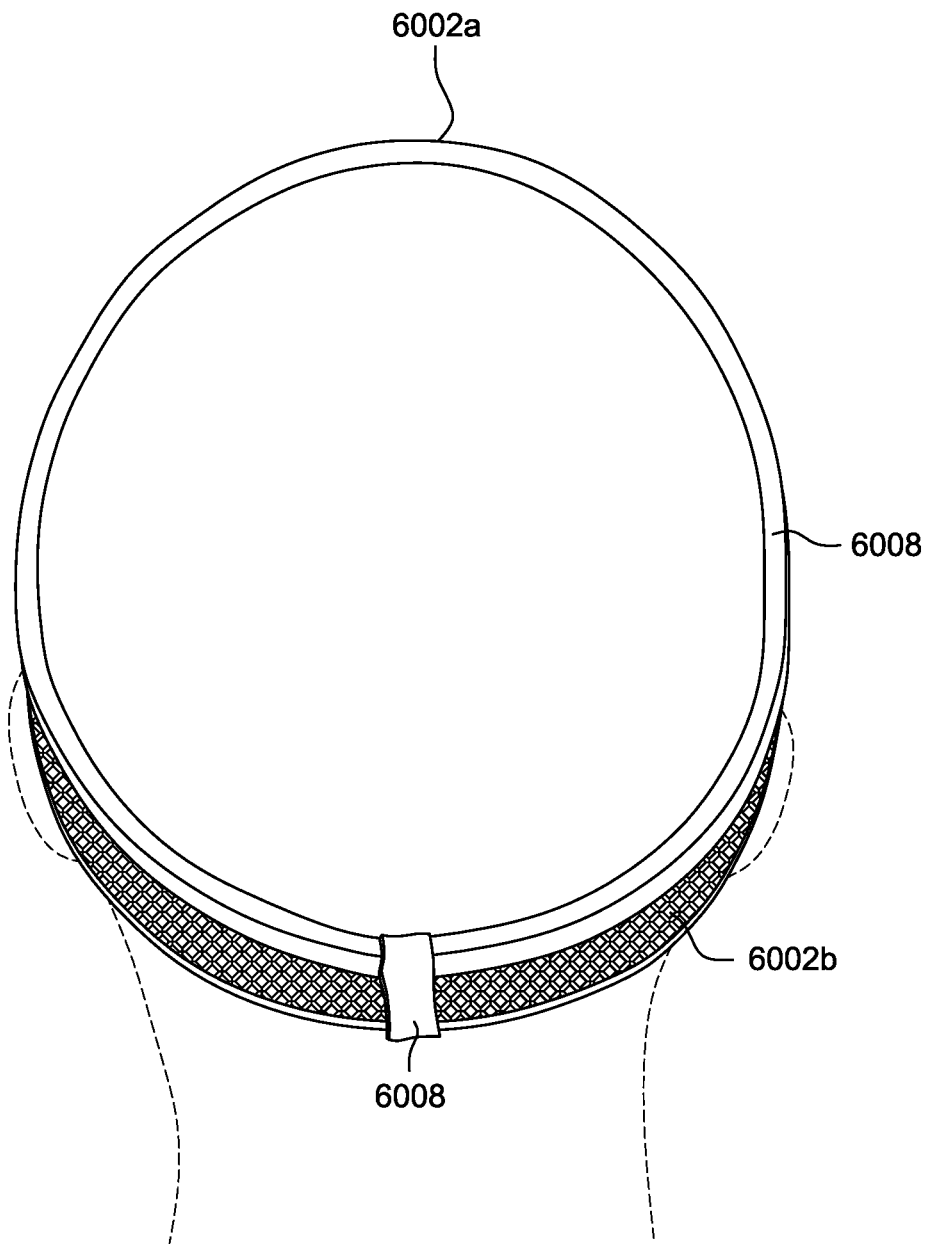

FIG. 42C shows a rear view of headgear supporting a mask on a patient.

Figure 42D:
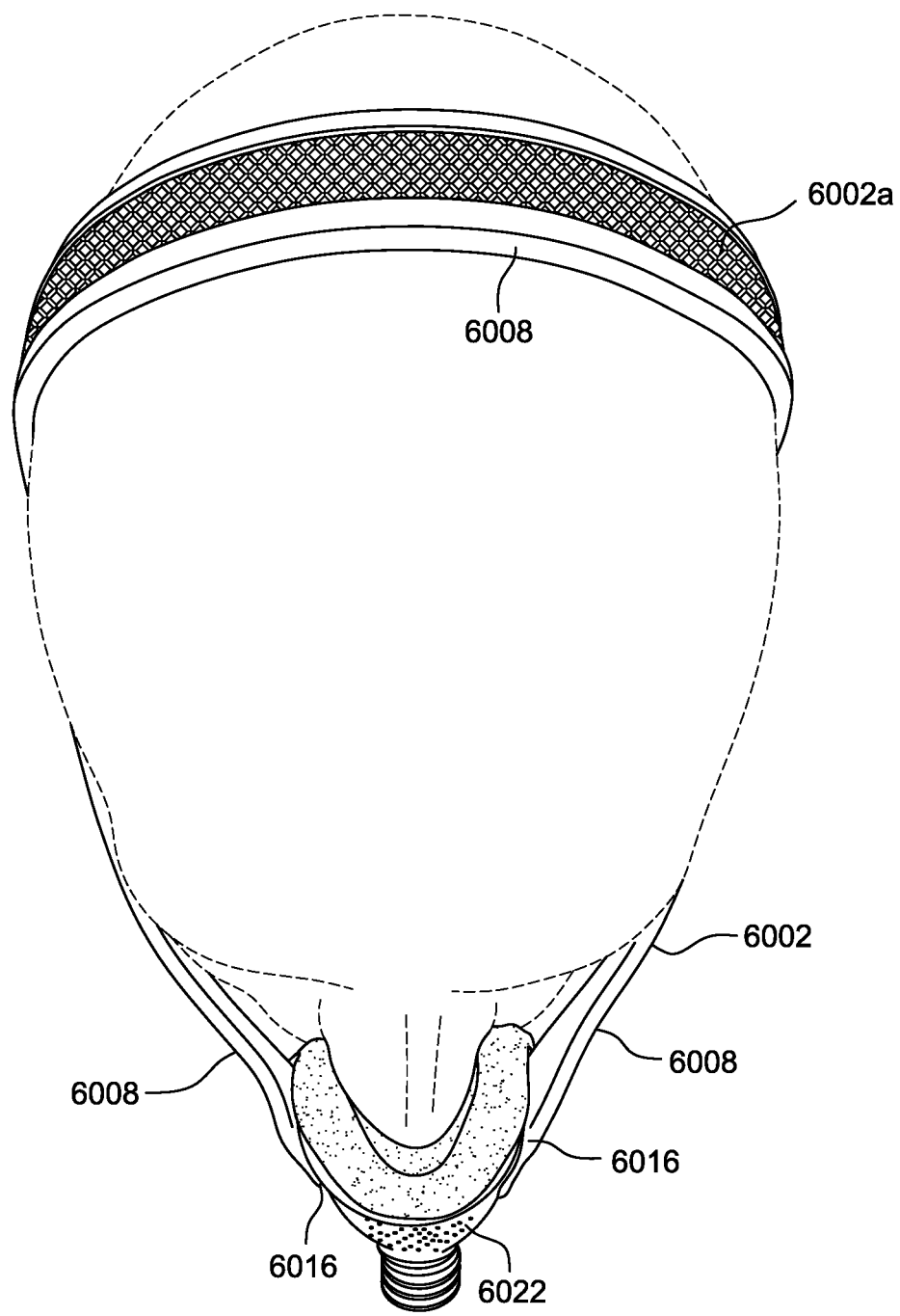

FIG. 42D shows a top view of headgear supporting a mask on a patient.

Figure 42E:
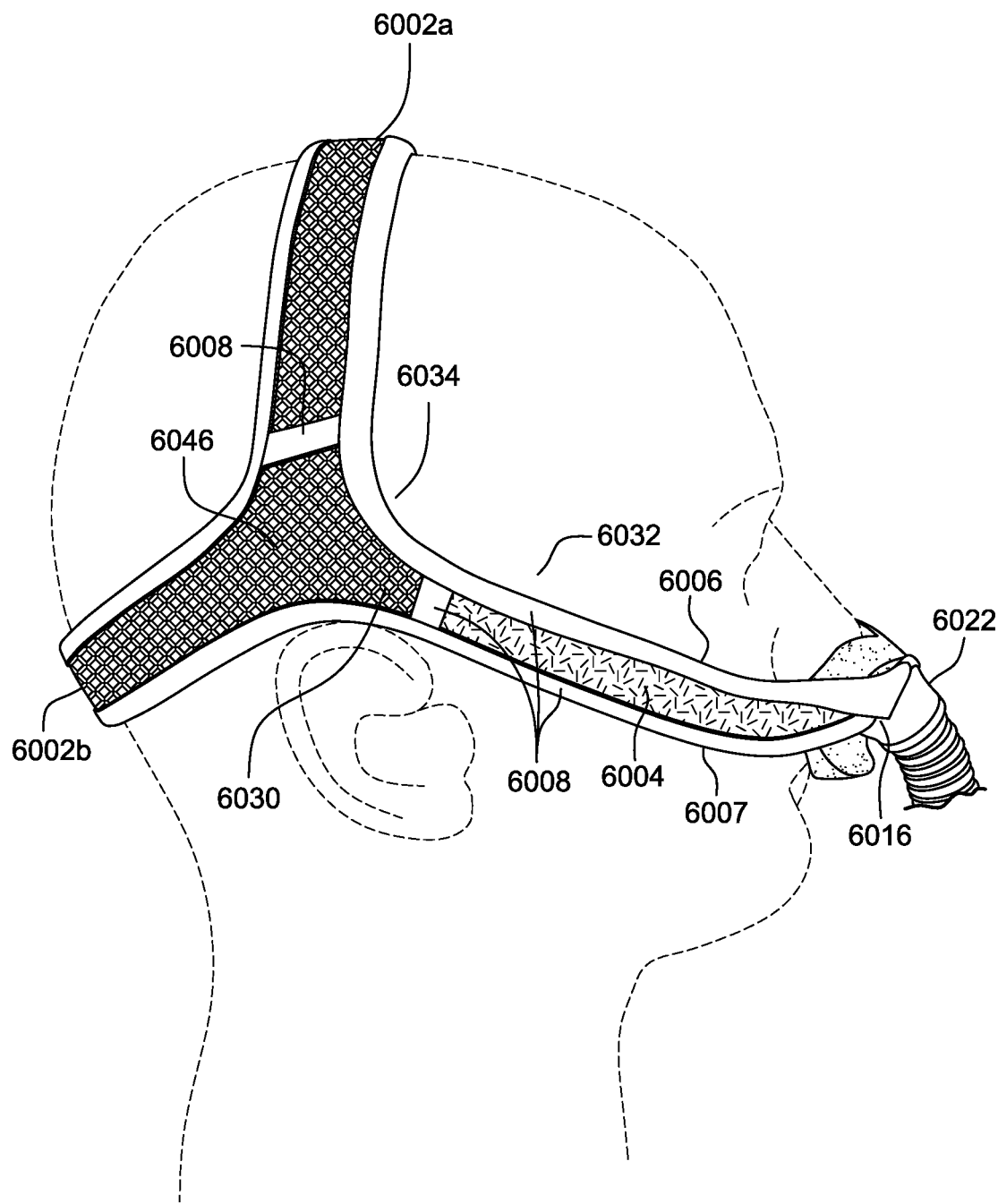

FIG. 42E shows a side view of headgear supporting a mask on a patient.

Figure 42F:
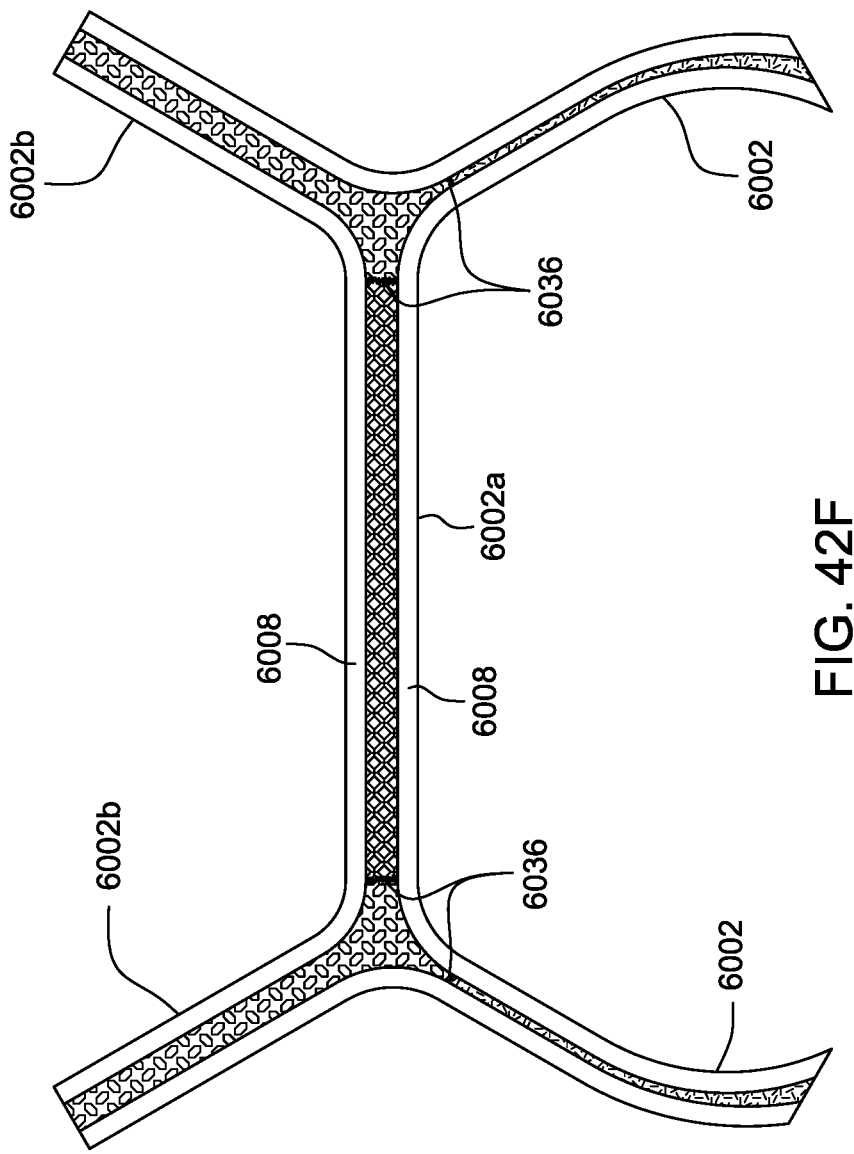

FIG. 42F shows headgear in a flat condition without a mask or connection to a mask.

Figure 42G:
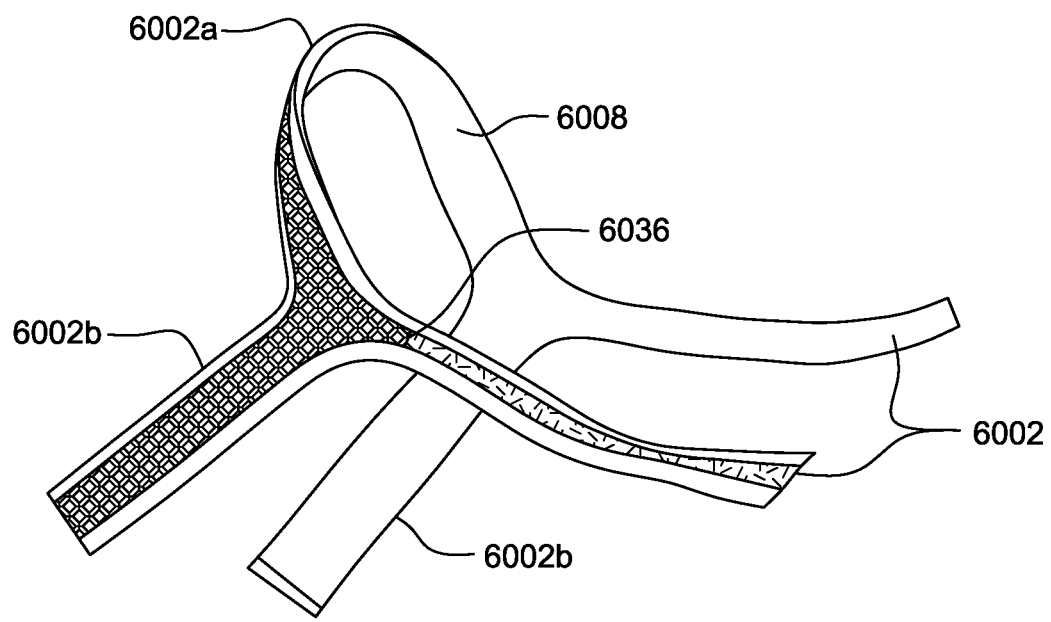

FIG. 42G shows the headgear of FIG. 42F in a folded condition.

Figure 42H:
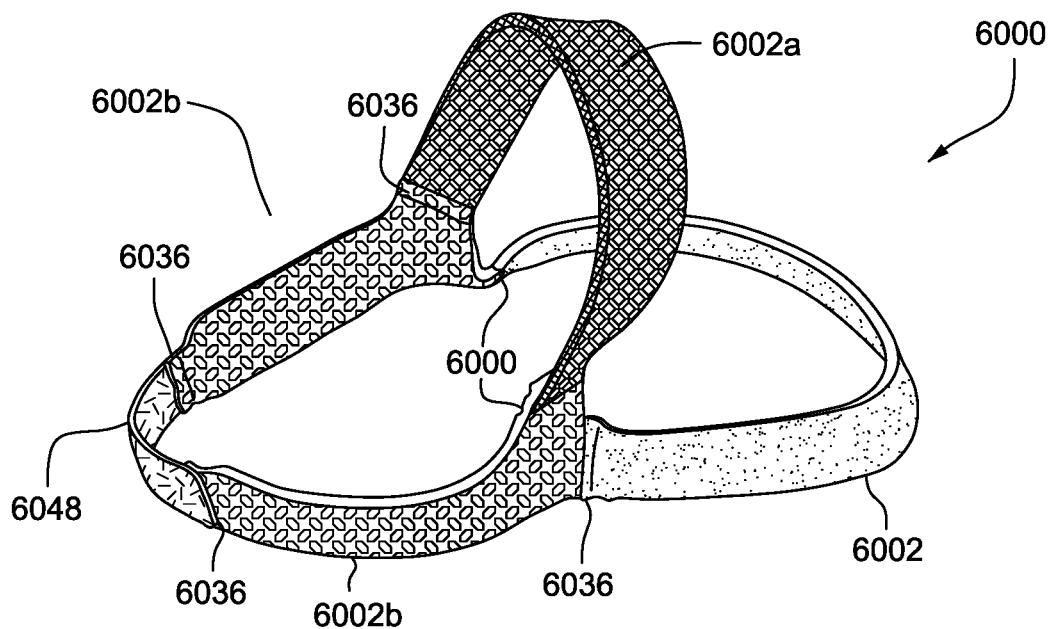

FIG. 42H shows headgear with structures omitted to view underlying structure.

Figure 42I:
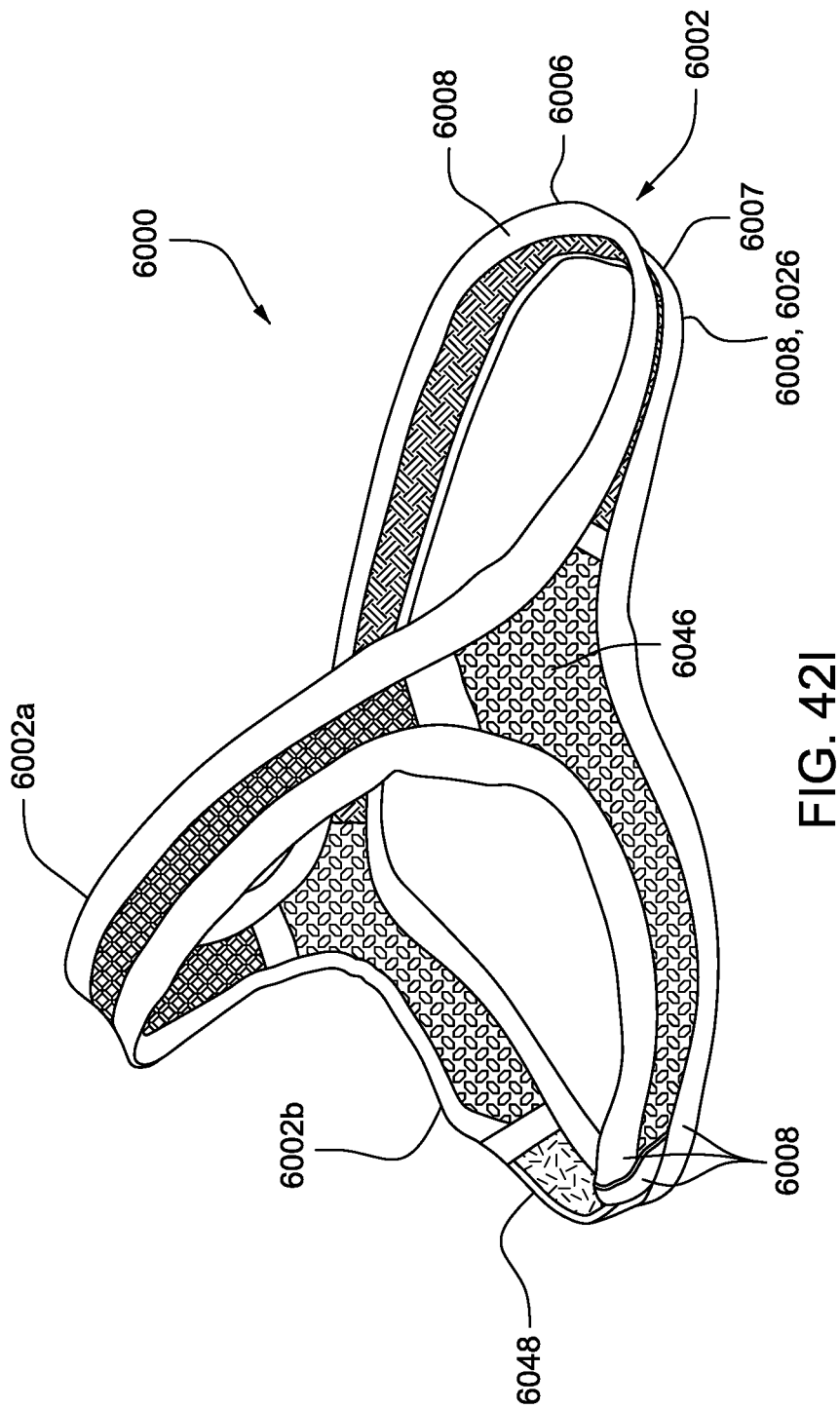

FIG. 42I shows headgear without a mask or connection to a mask.

Figure 42J:
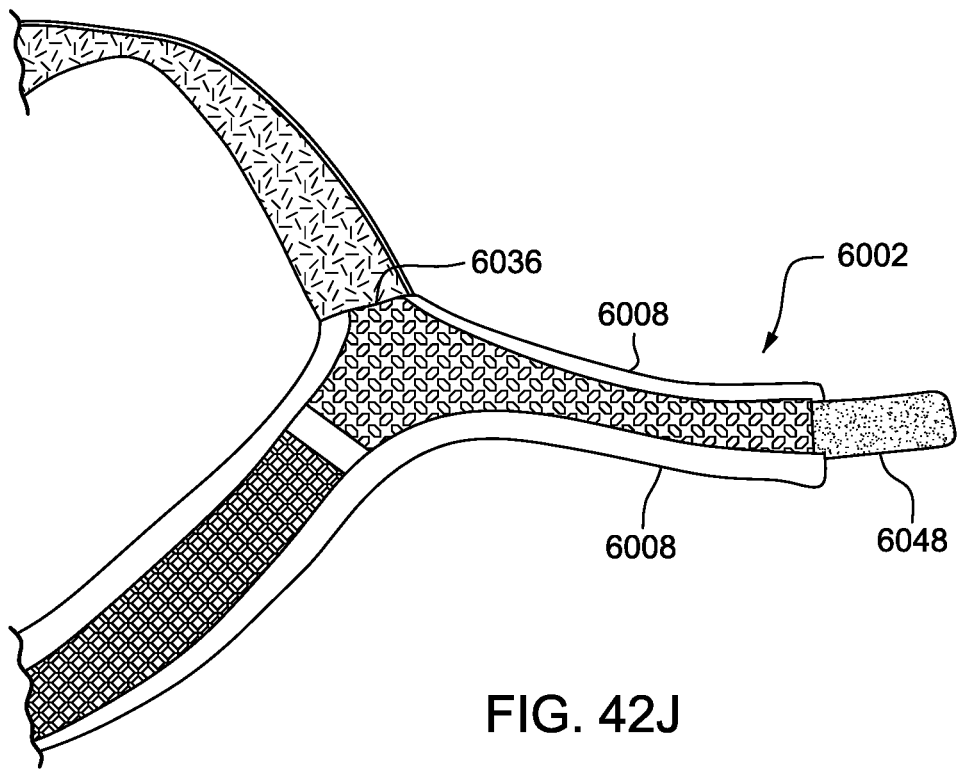

FIG. 42J shows a partial view of headgear where strap portions intersect.

Figure 42K:
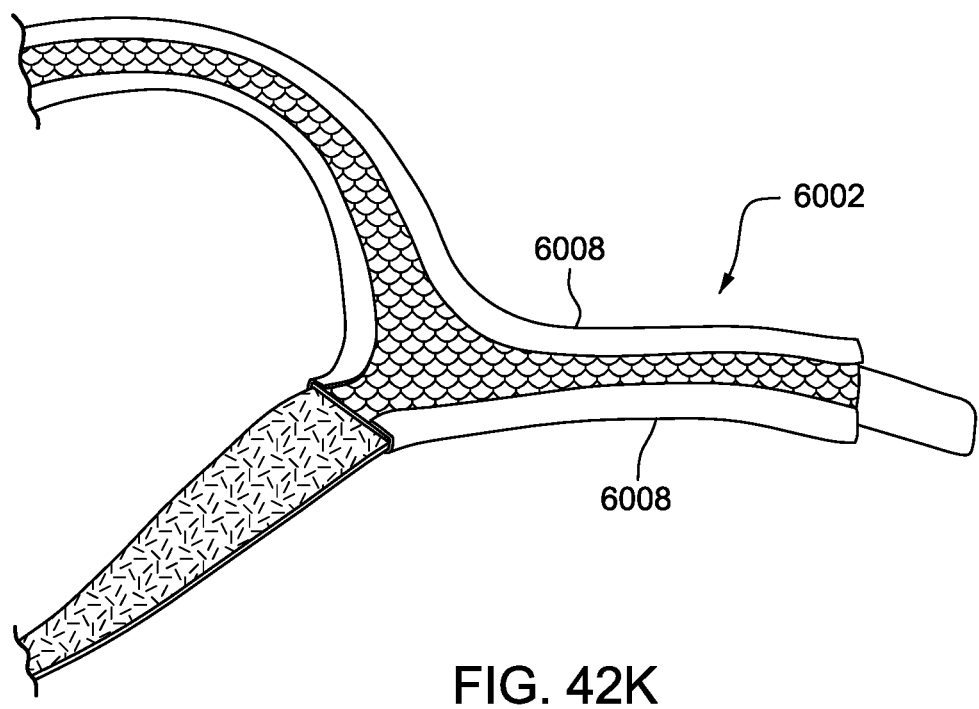

FIG. 42K shows the opposite side of the headgear illustrated in FIG. 42J.

Figure 42L:
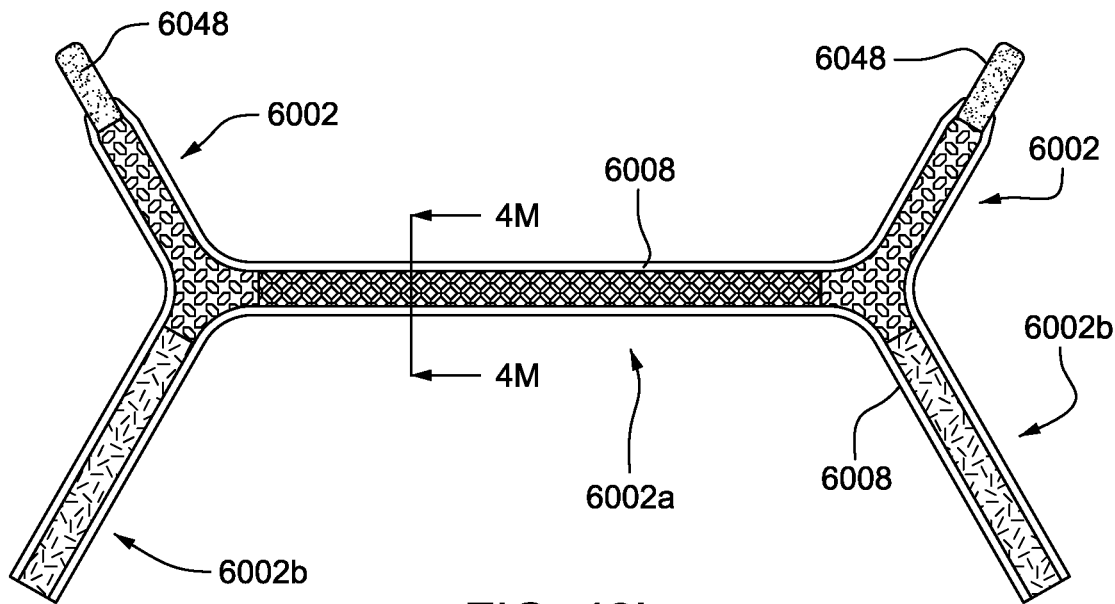

FIG. 42L shows partially completed headgear in a flat condition without a mask.

Figure 42M:
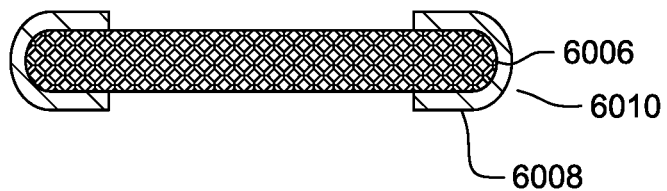

FIG. 42M shows a cross section taken through FIG. 42L.

Figure 42N:
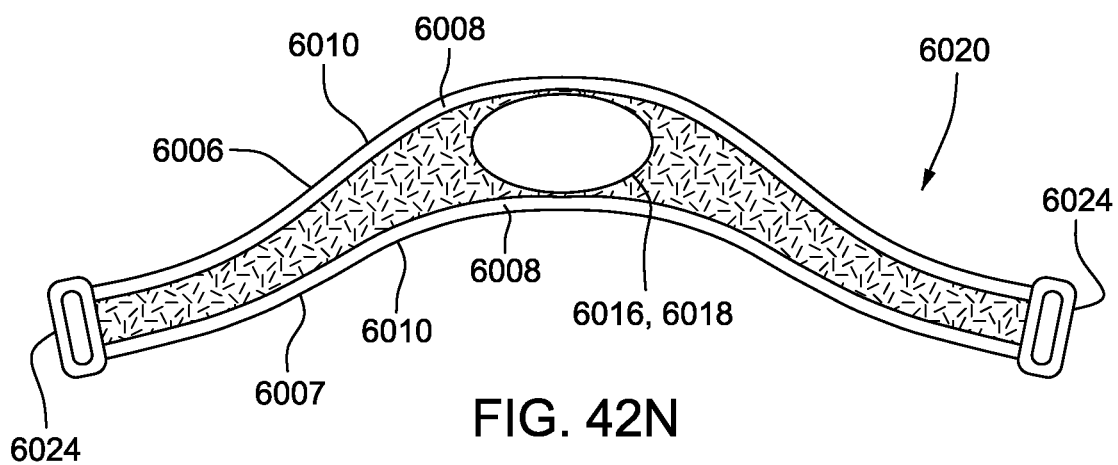

FIG. 42N shows a strap to retain a mask and attach to the headgear illustrated in FIG. 42L.

Figure 42O:
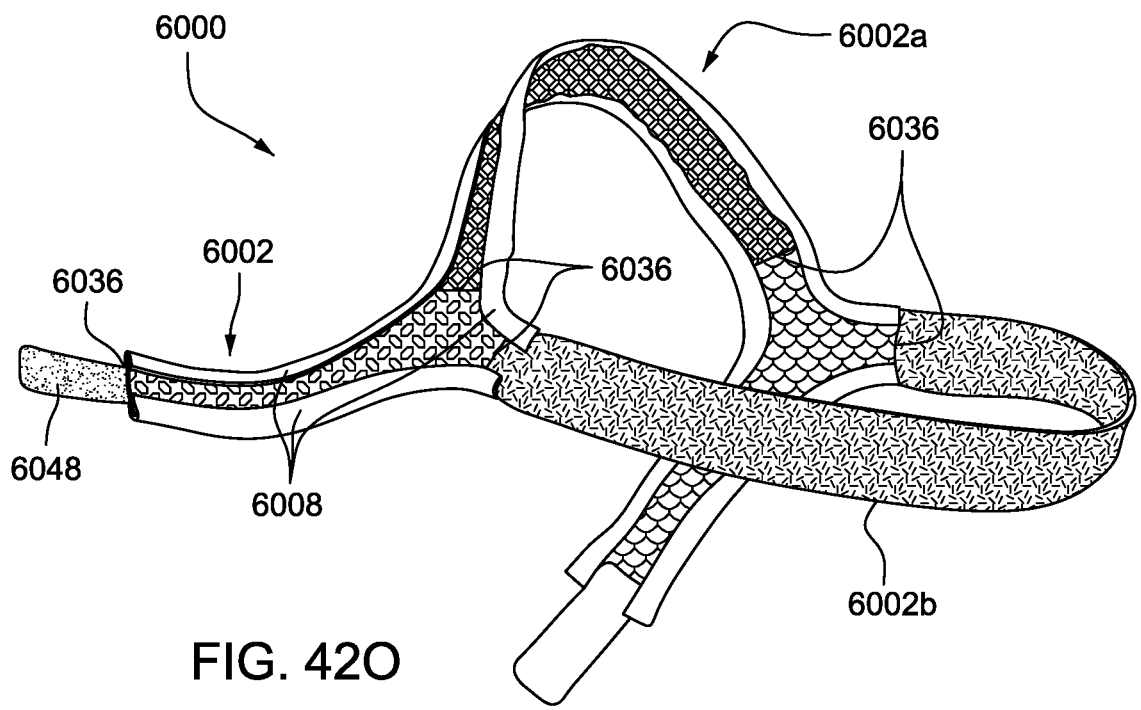

FIG. 42O shows headgear in an assembled condition but collapsed.

Figure 42P:
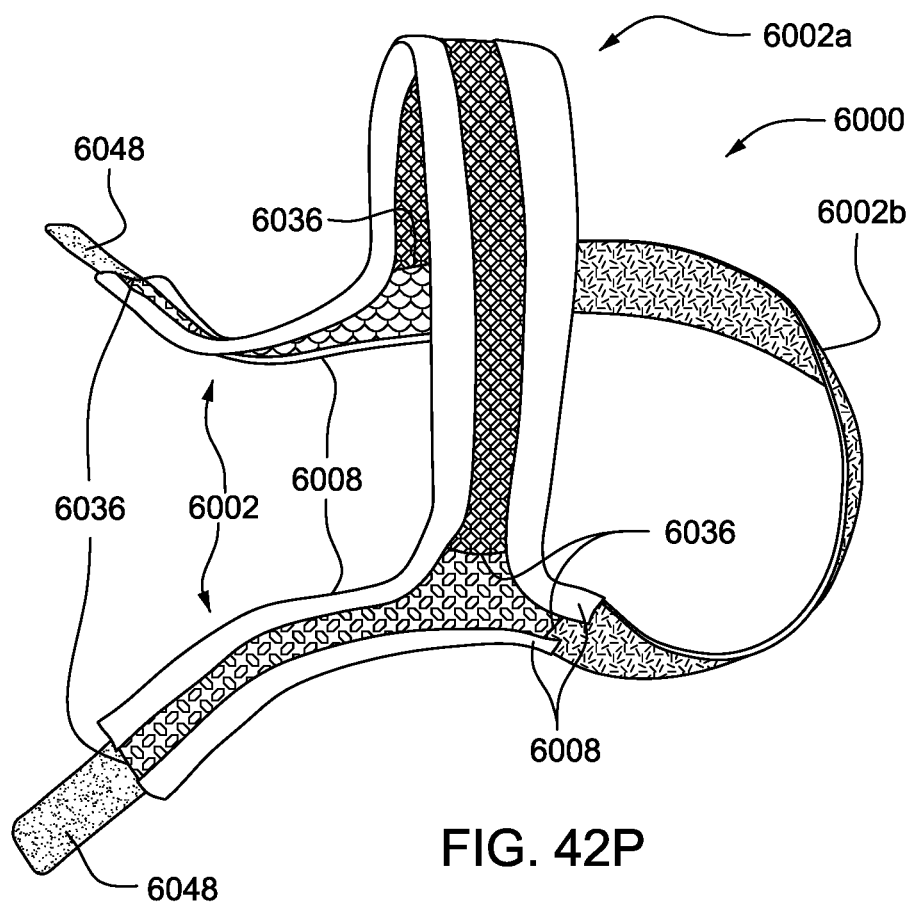

FIG. 42P shows headgear in an assembled condition.

Figure 42Q:
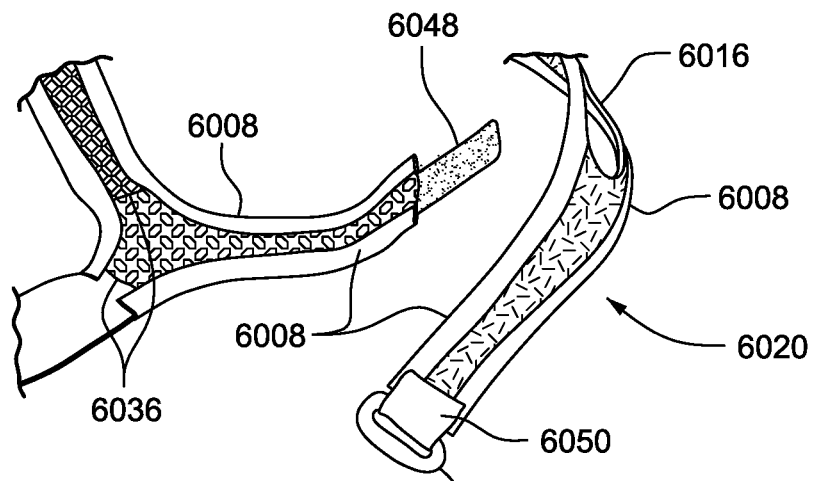

FIG. 42Q shows headgear with two strap portions disconnected from one another.

Figure 42R:
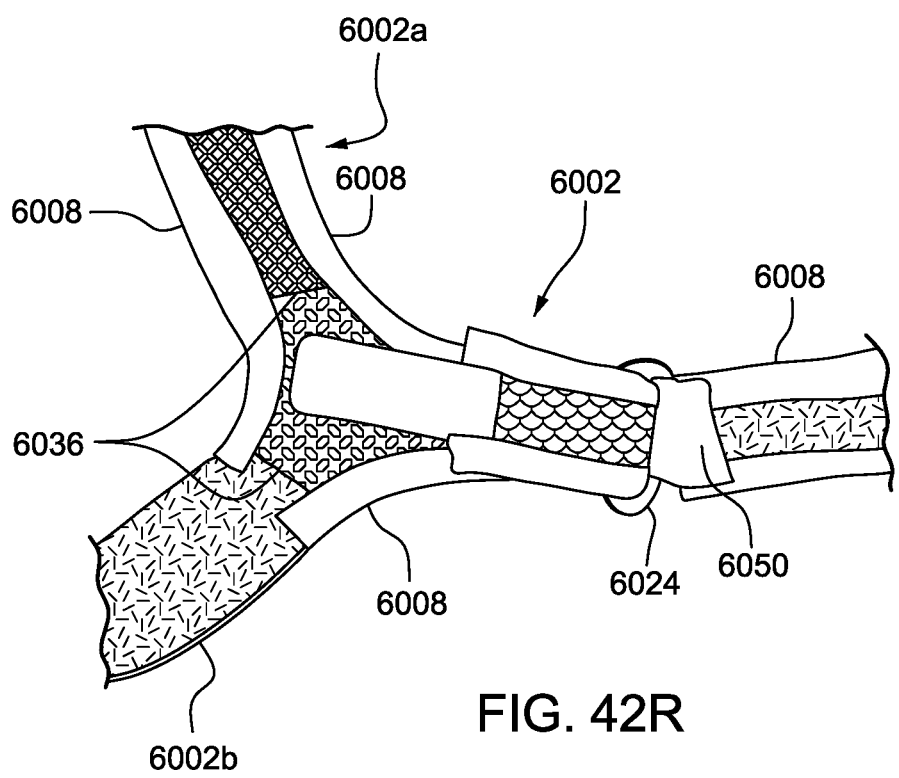

FIG. 42R shows the headgear of FIG. 42Q with the straps connected to one another.

Figure 42S:
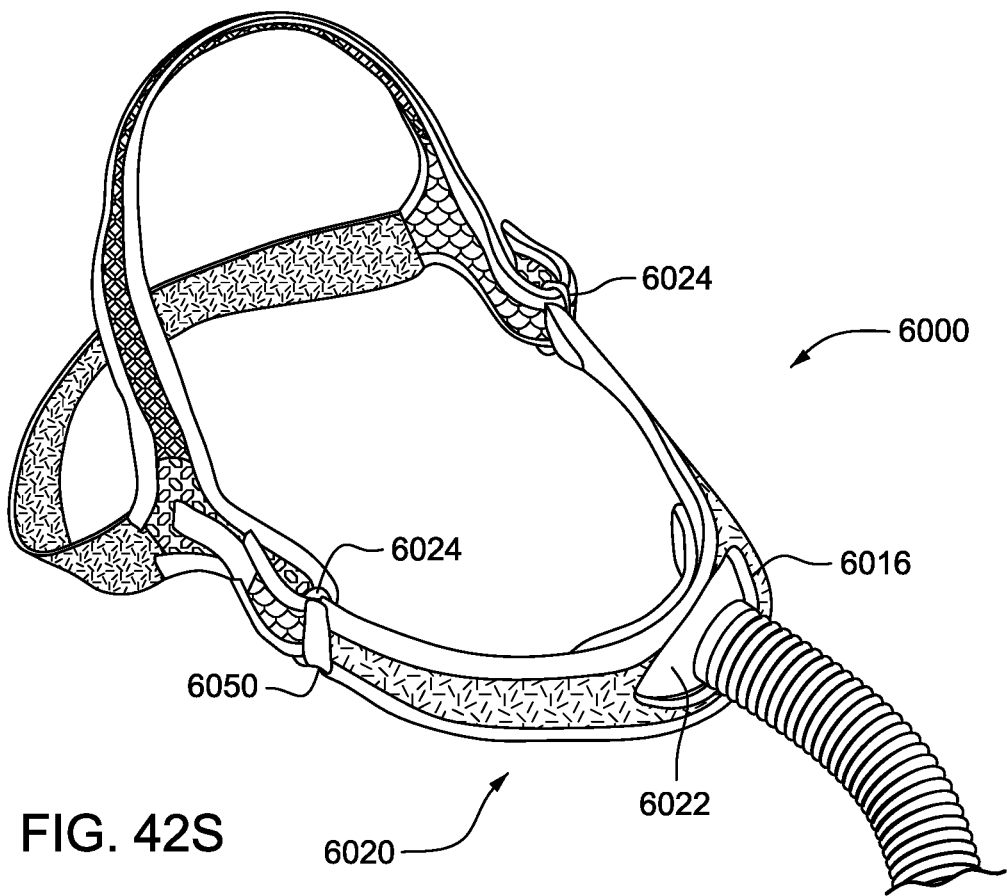

FIG. 42S shows the headgear of FIG. 42R with a mask.

Figure 42T:
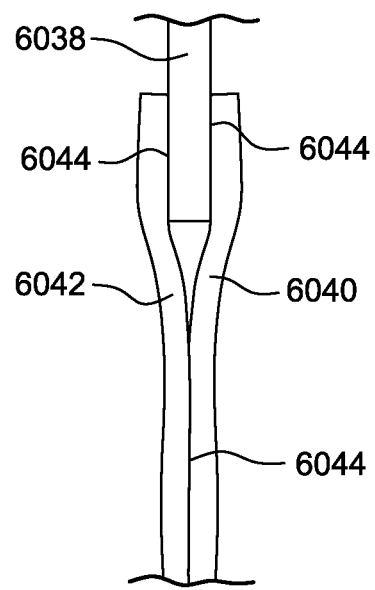

FIG. 42T shows a cross-section through a strap portion of headgear.

Figure 42U:
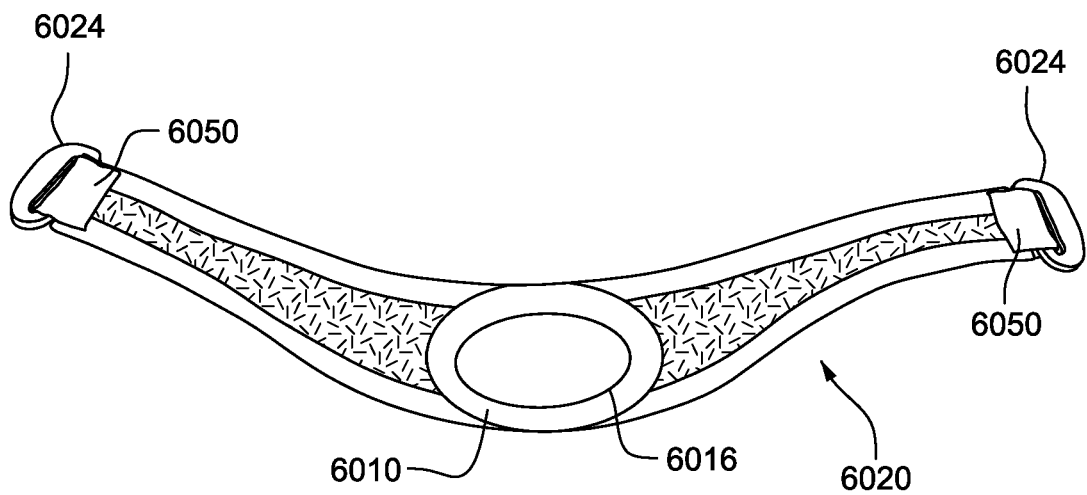

FIG. 42U shows a strap portion with an opening for a mask.

Figure 42V:
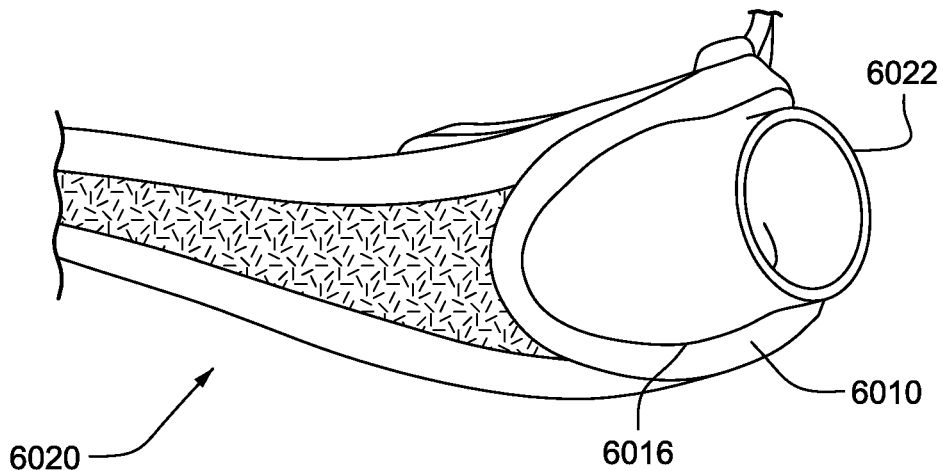

FIG. 42V shows the strap portion of FIG. 42U with a mask.

Figure 42W:
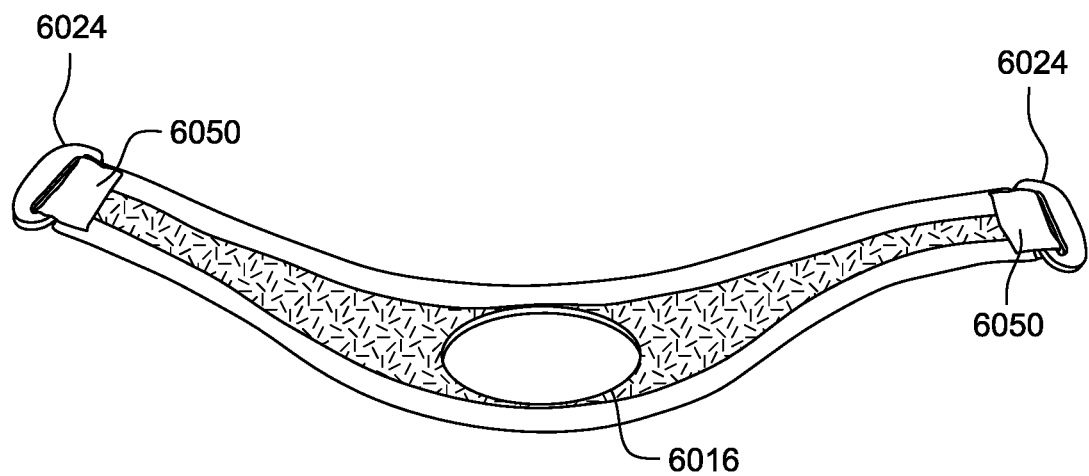

FIG. 42W shows a strap portion with an opening for a mask.

Figure 42X:
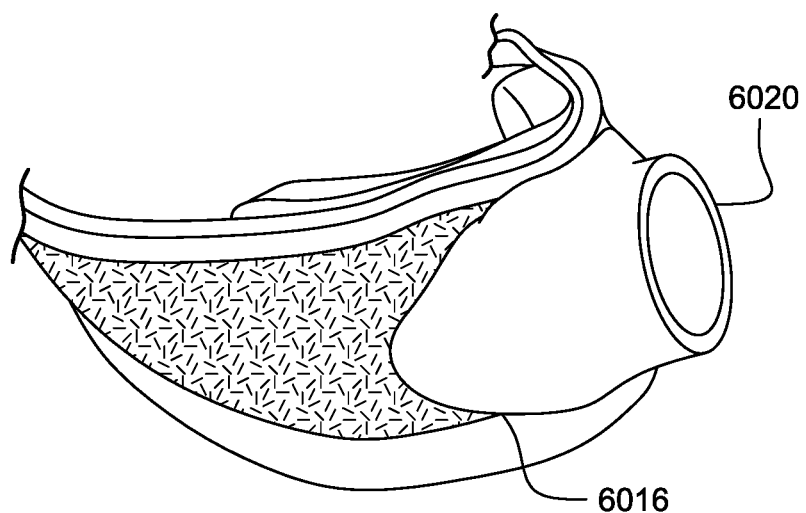

FIG. 42X shows the strap portion of FIG. 42W with a mask.

Figure 42Y:
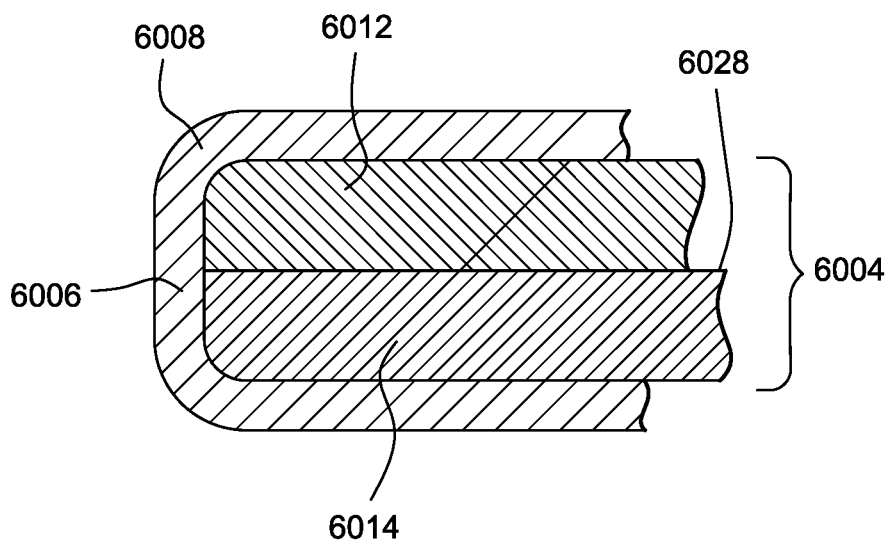

FIG. 42Y shows a partial cross-section through the edge of a strap portion.

Figure 43:
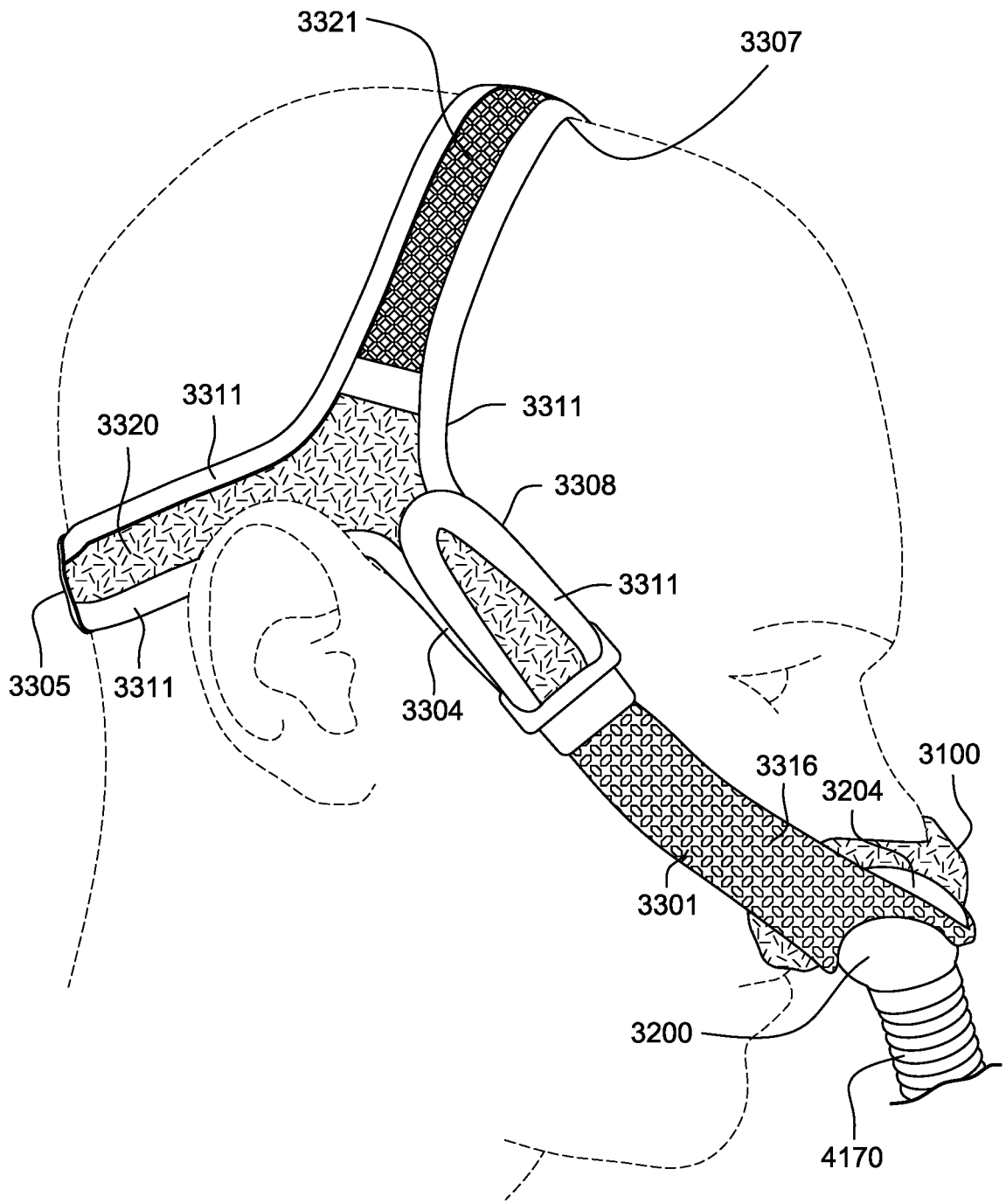

FIG. 43 shows a side view of a patient interface according to an example of the present technology worn by a patient.

Figure 44:
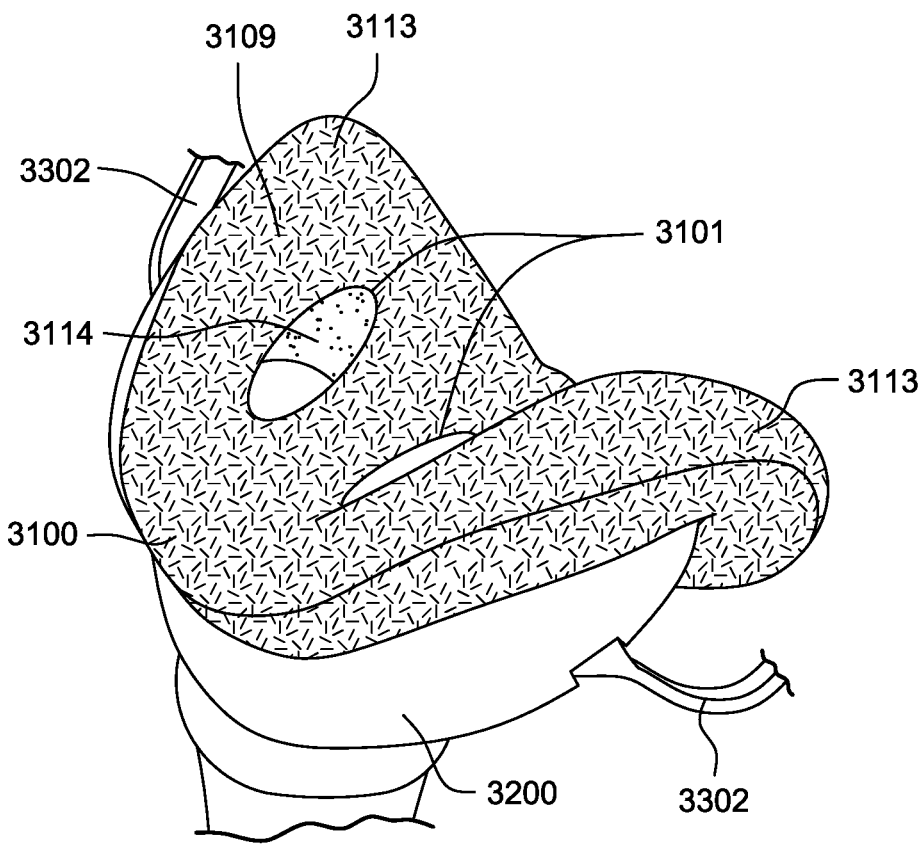

FIG. 44 shows a rear perspective view of a patient interface according to an example of the present technology.

Figure 45:
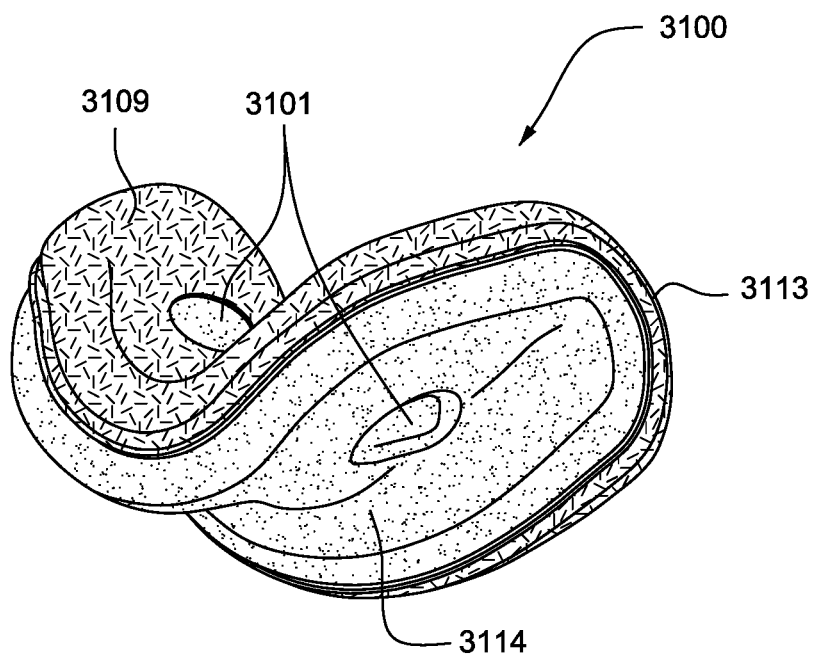

FIG. 45 shows a front perspective view of a seal forming structure of a patient interface according to an example of the present technology.

Figure 46:
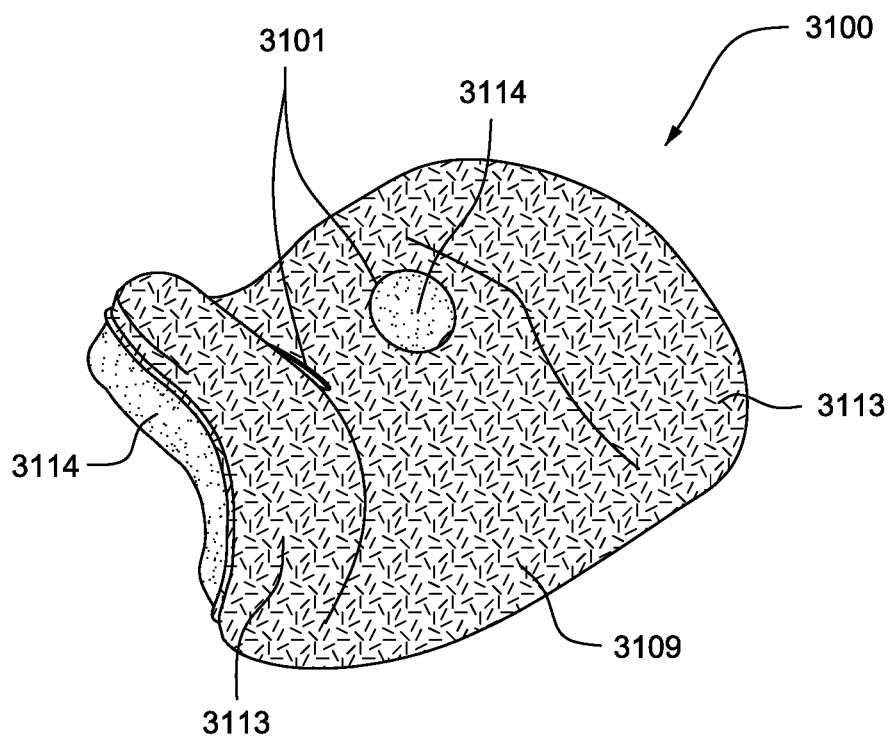

FIG. 46 shows a rear perspective view of a seal forming structure of a patient interface according to an example of the present technology.

Figure 47A:
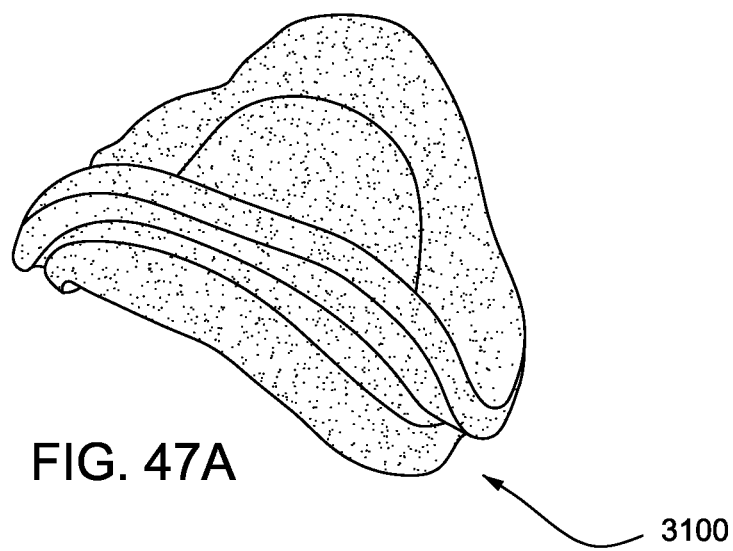

FIG. 47A shows a perspective view of a seal forming structure of a patient interface according to an example of the present technology at a first stage of production.

Figure 47B:
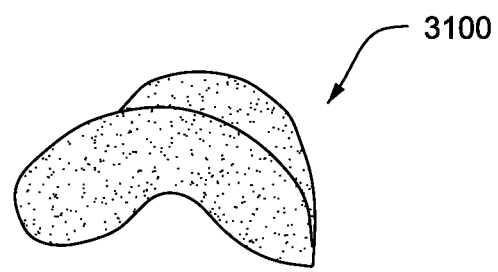

FIG. 47B shows a perspective view of a seal forming structure of a patient interface according to an example of the present technology at a second stage of production.

Figure 47C:
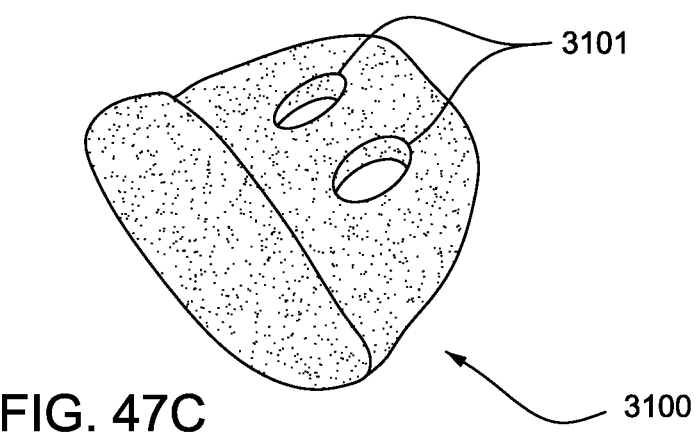

FIG. 47C shows a perspective view of a seal forming structure of a patient interface according to an example of the present technology at a completed stage of production.

Figure 48:
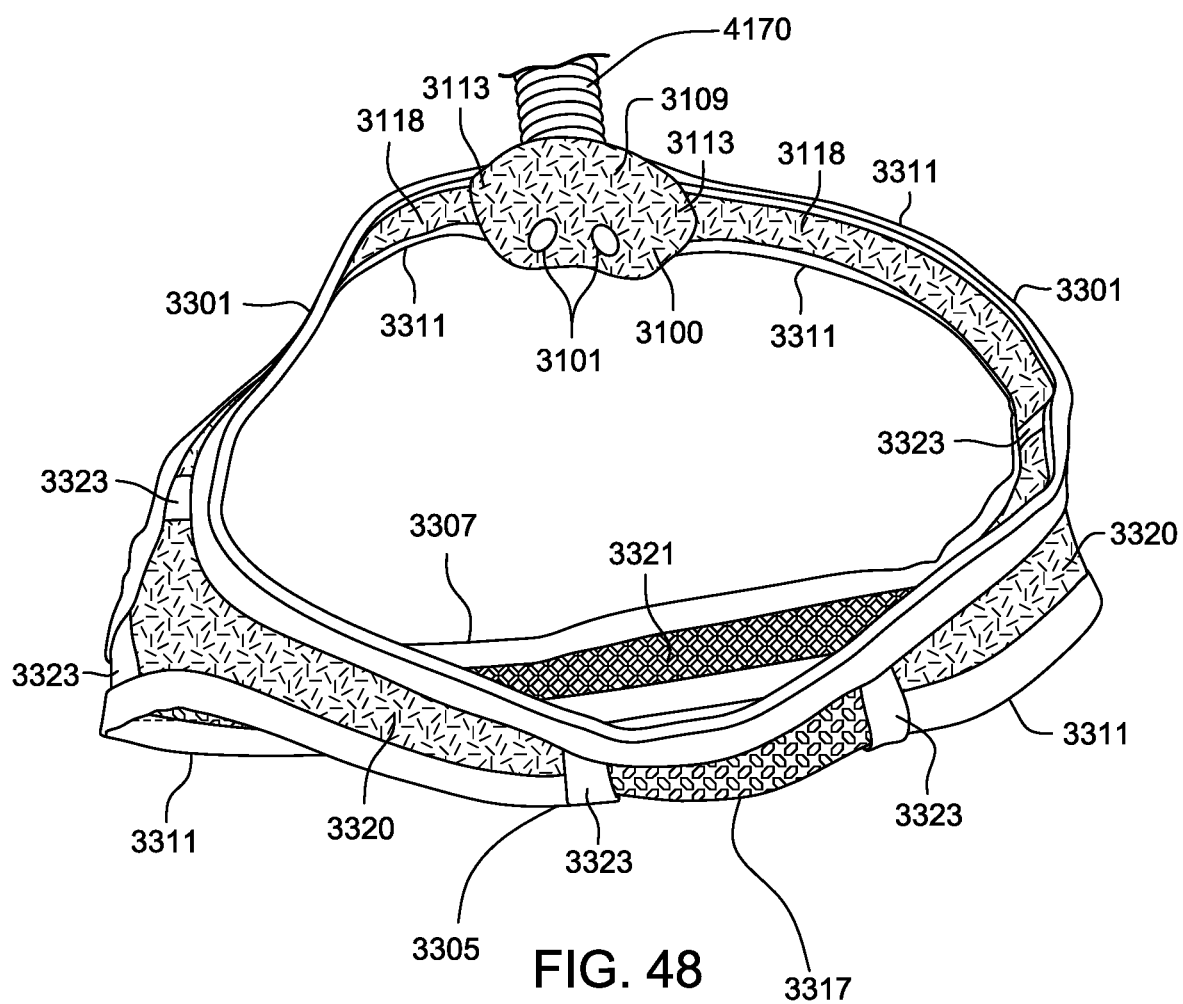

FIG. 48 shows a bottom rear view of a patient interface according to an example of the present technology.

Figure 49:
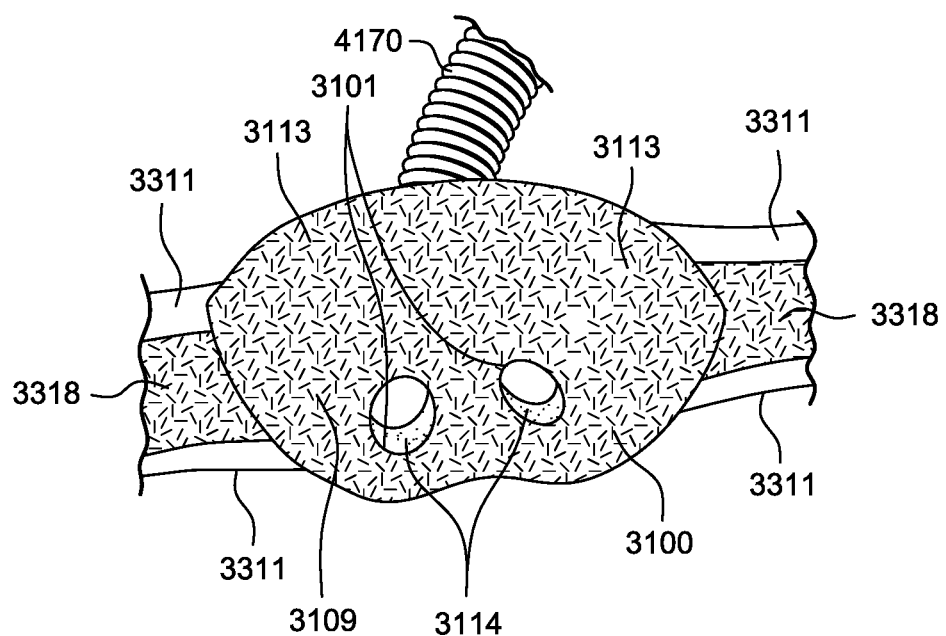

FIG. 49 shows a detailed rear view of a patient interface according to an example of the present technology.

Figure 50:
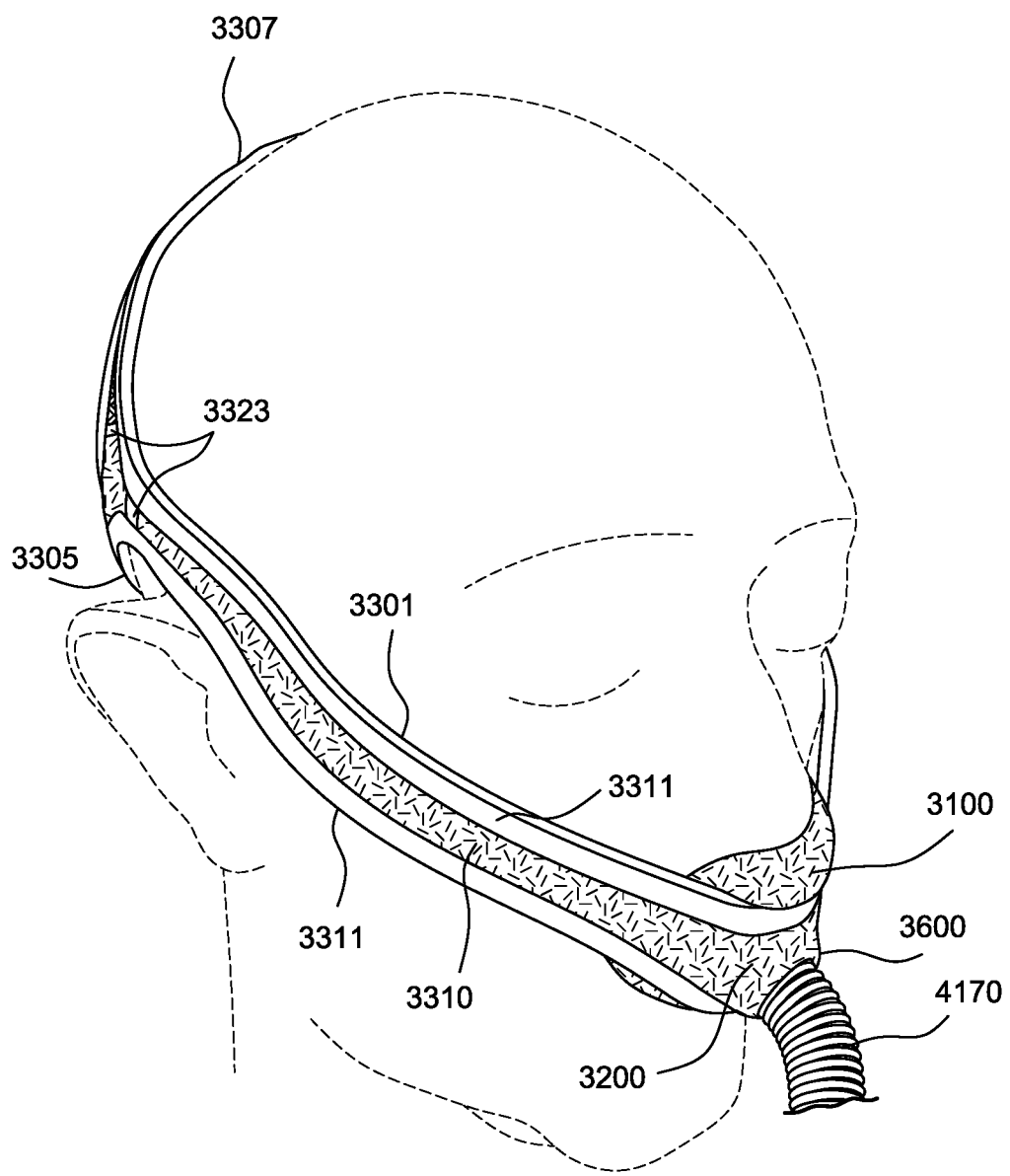

FIG. 50 shows a front perspective view of patient interface according to an example of the present technology worn by a patient.

Figure 51:
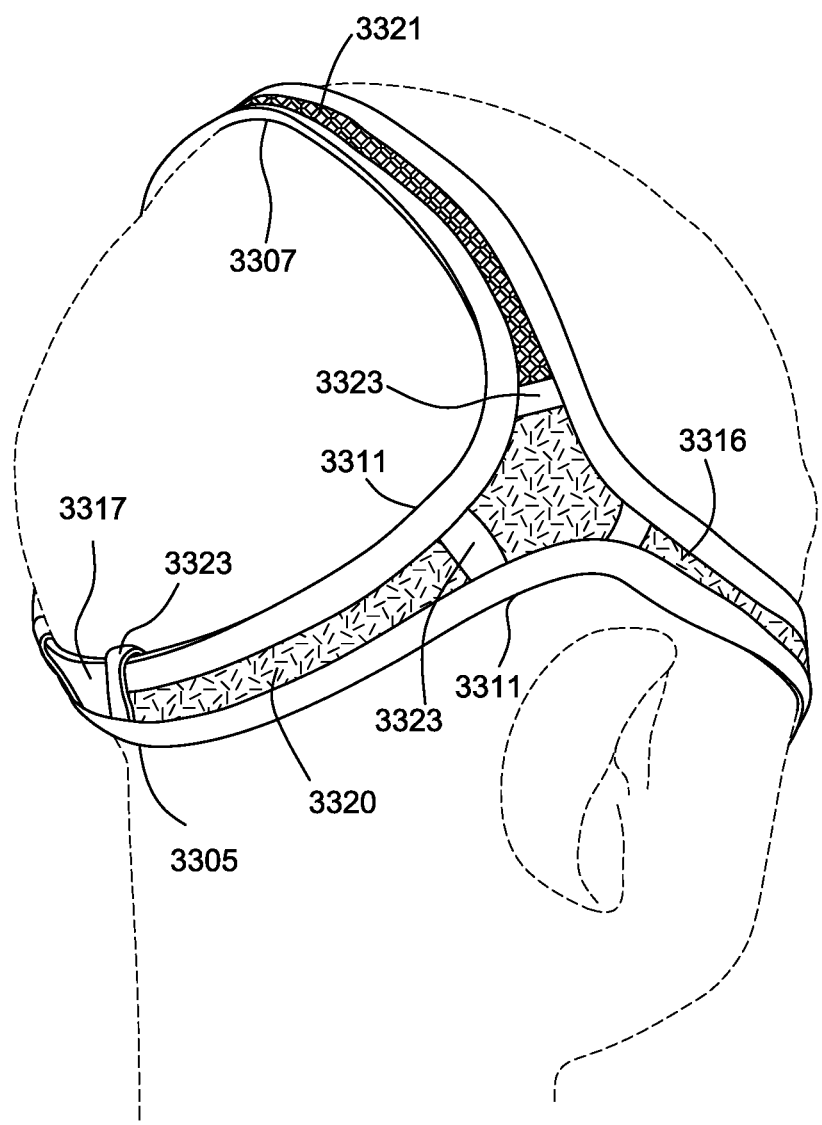

FIG. 51 shows a front perspective view of patient interface according to an example of the present technology worn by a patient.

Figure 52:
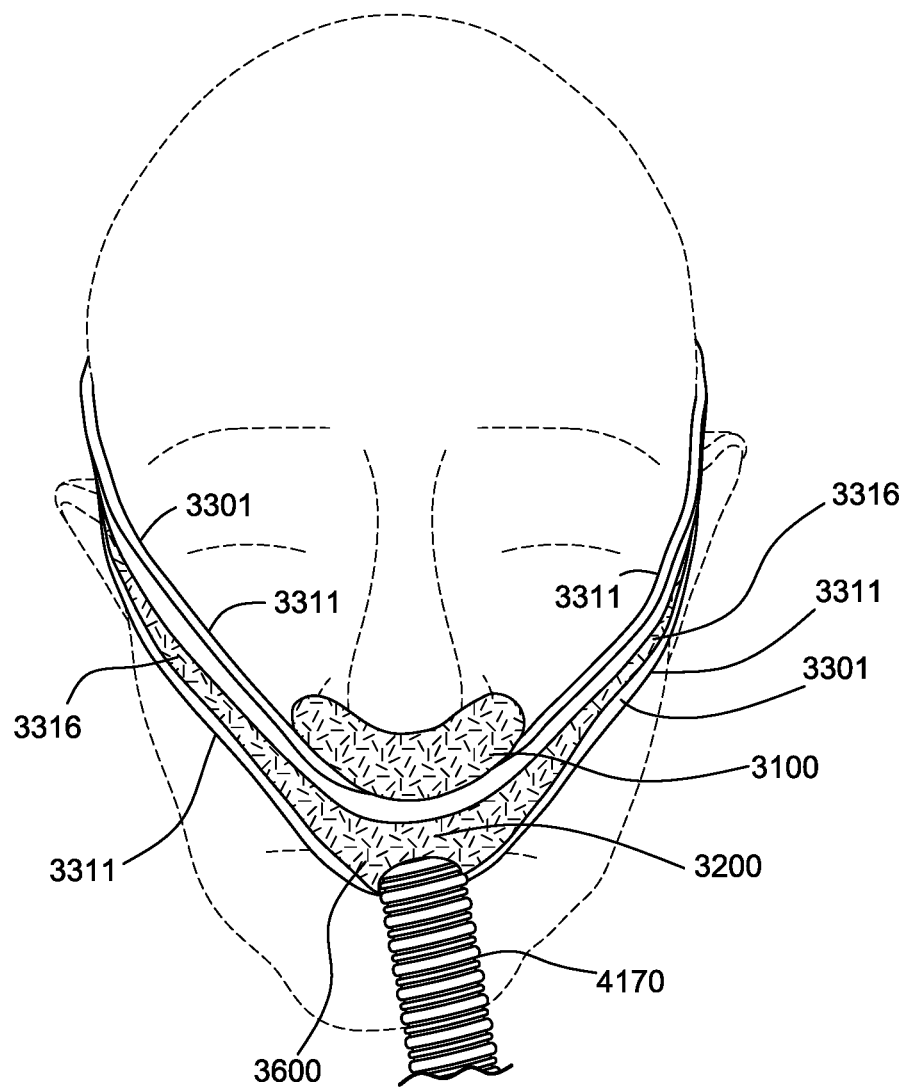

FIG. 52 shows a front view of patient interface according to an example of the present technology worn by a patient.

Figure 53:
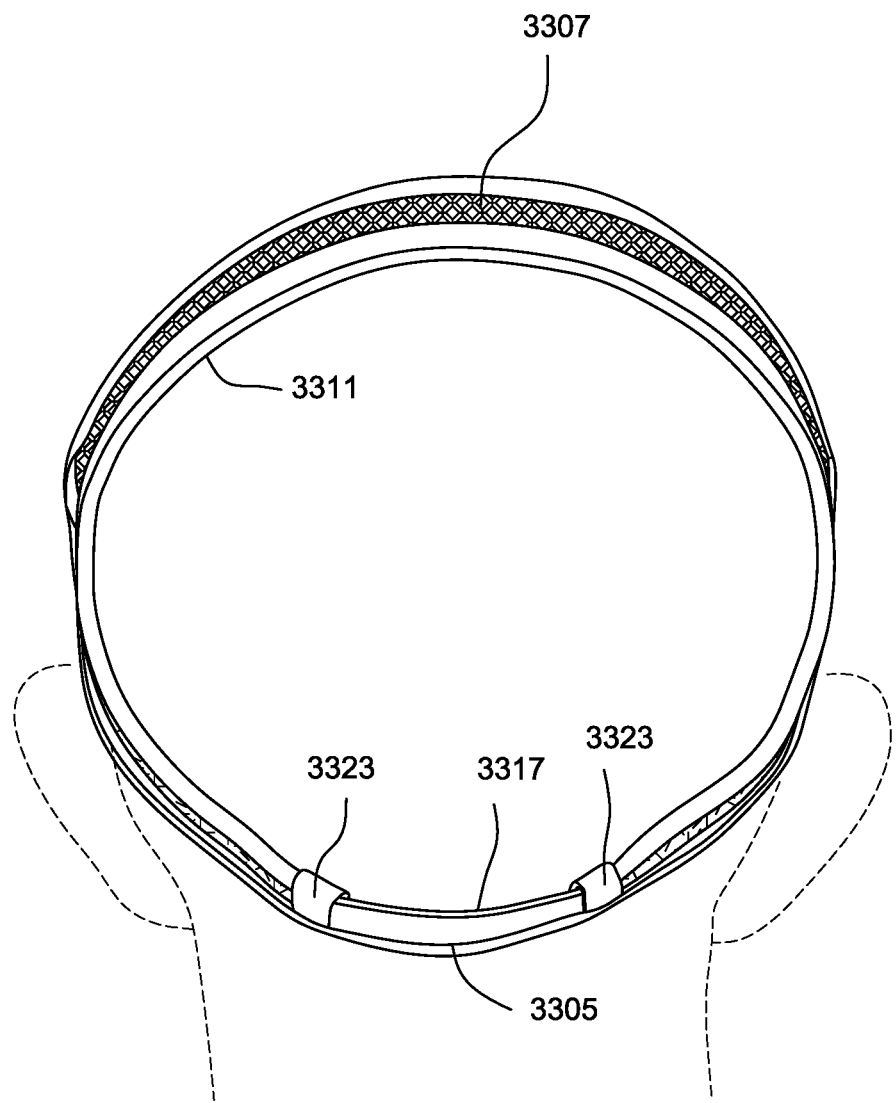

FIG. 53 shows a rear view of patient interface according to an example of the present technology worn by a patient.

Figure 54:
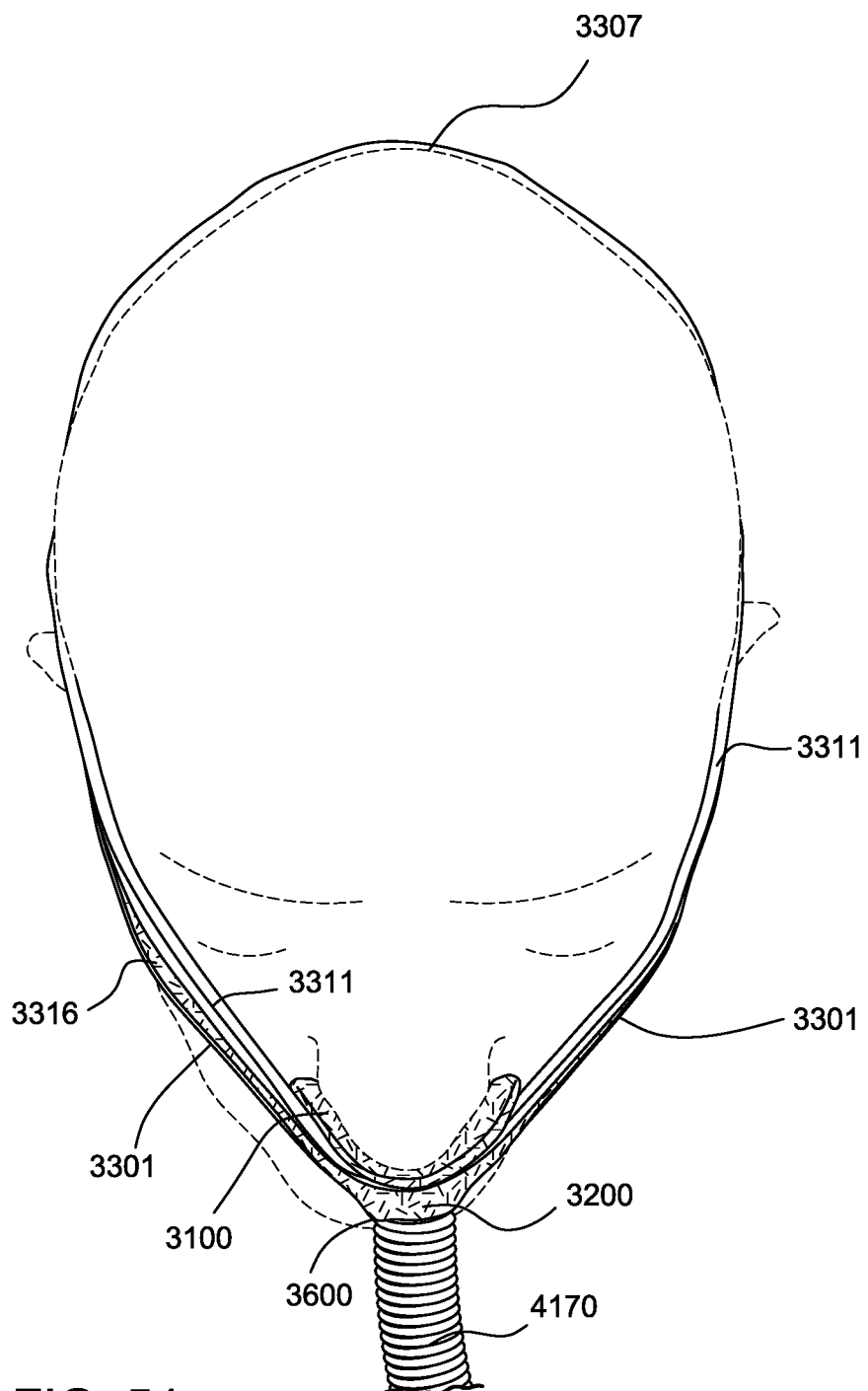

FIG. 54 shows a top front view of patient interface according to an example of the present technology worn by a patient.

Figure 55:
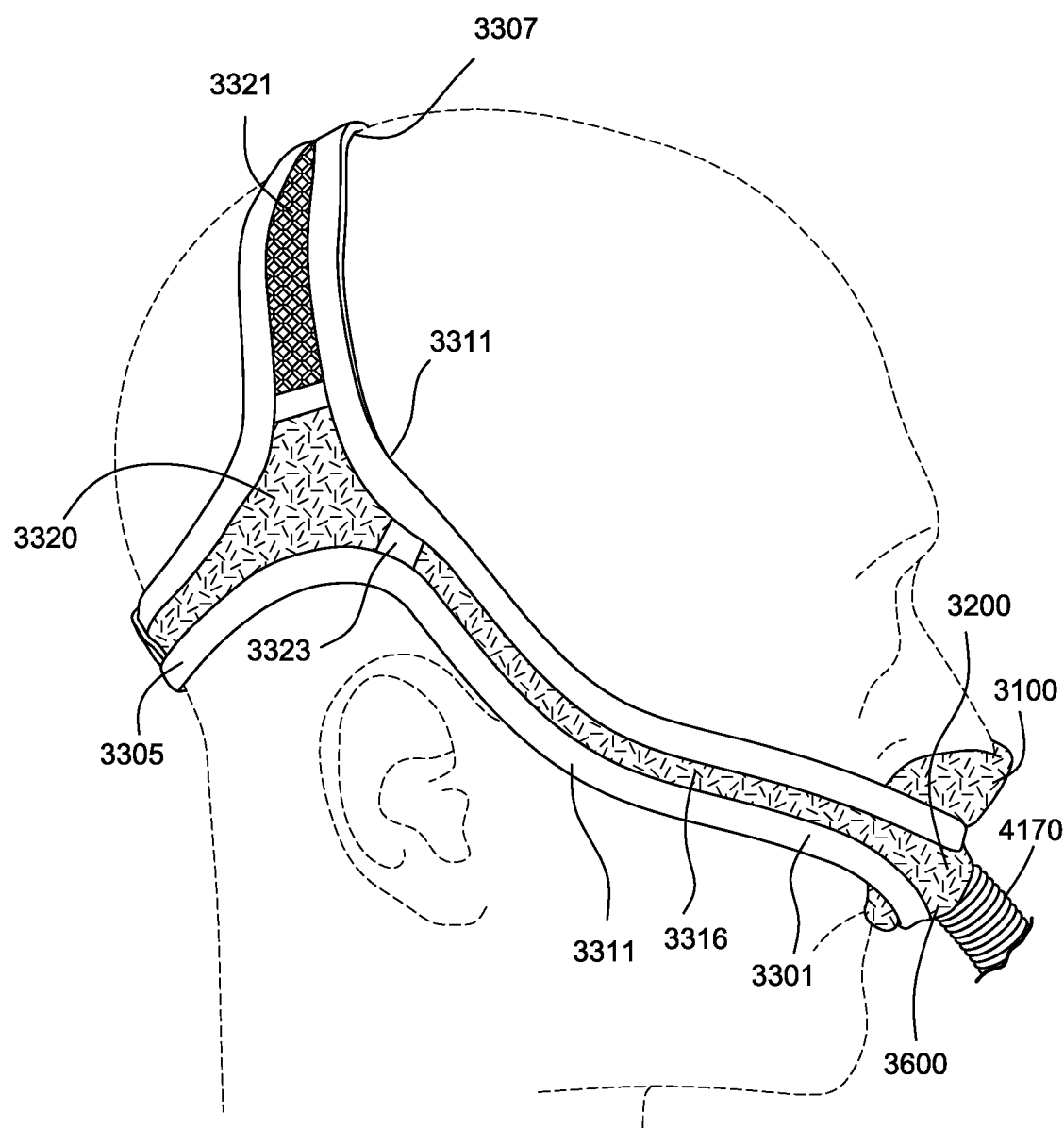

FIG. 55 shows a side view of patient interface according to an example of the present technology worn by a patient.

Figure 56:
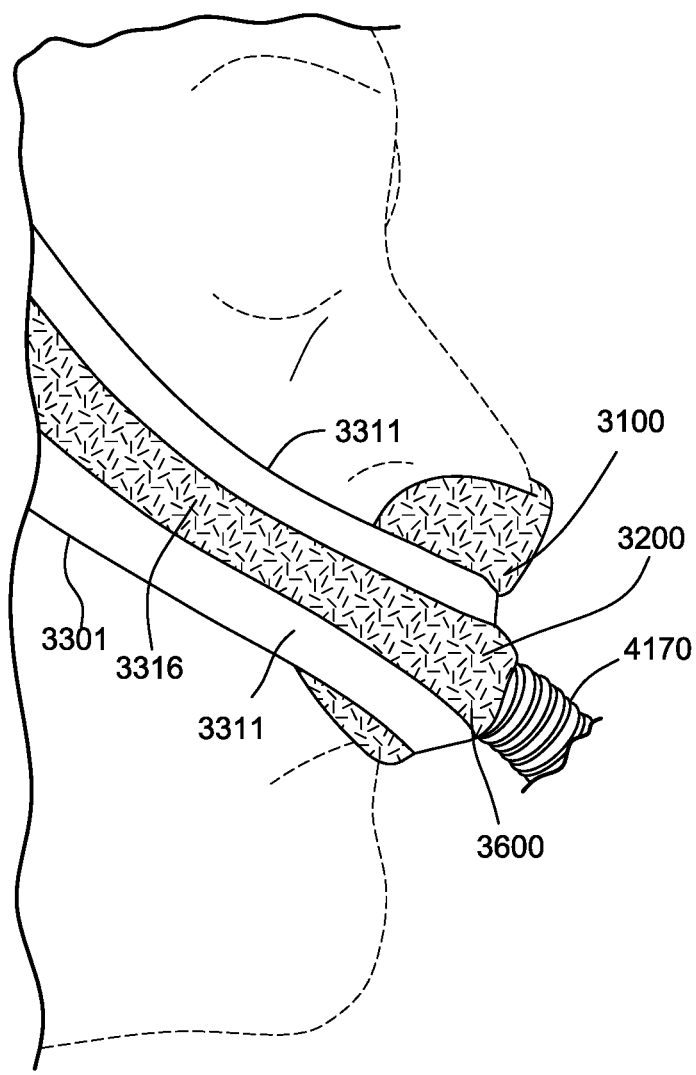

FIG. 56 shows a detailed side view of patient interface according to an example of the present technology worn by a patient.

Figure 57:
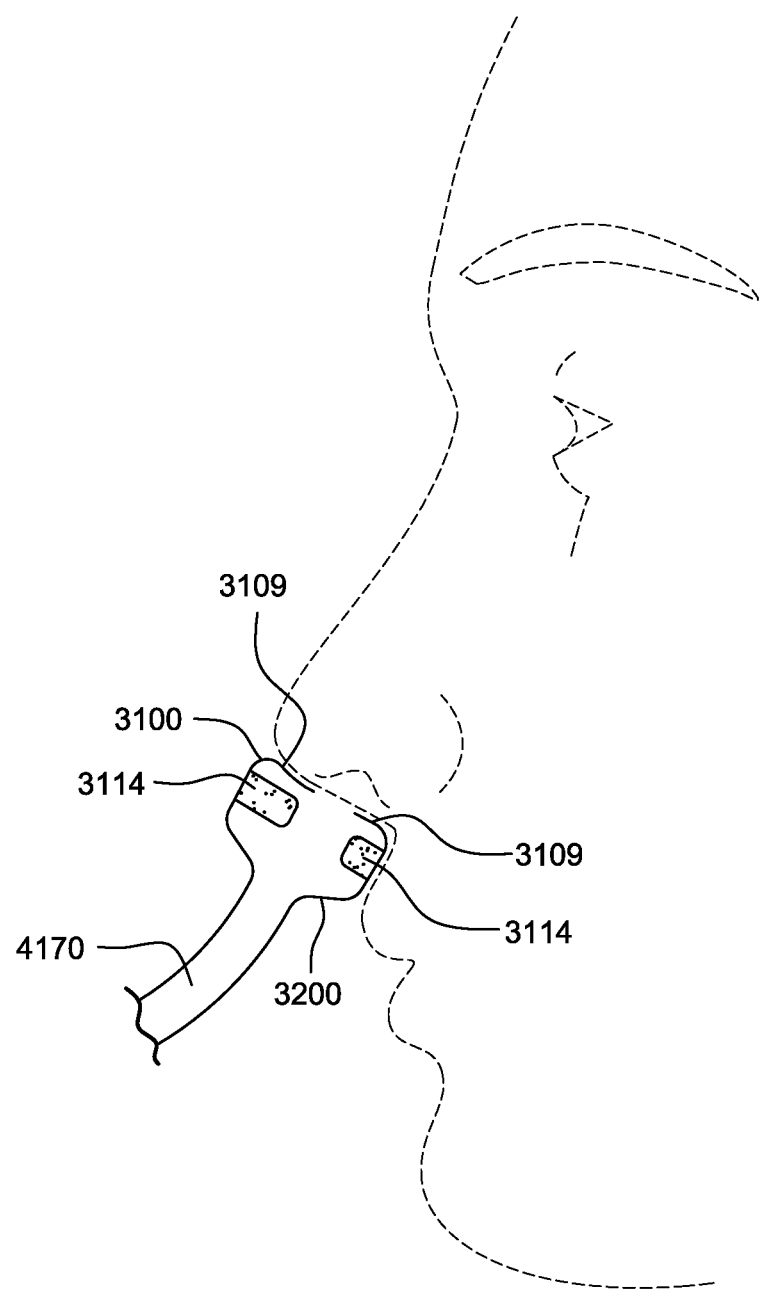

FIG. 57 depicts a cross-sectional view of a patient interface according to an example of the present technology worn by a patient.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

Accordingly to examples of the present technology, a patient interface 3000 may be provided with little or no rigid plastic components. This allows for a soft, light-weight and squeezable patient interface 3000 that is physically comfortable and appear/be perceived as comfortable. The patient interface 3000 may also be washable. The patient interface 3000 may be primarily made from foam material and textile material. For example, the frame, headgear and cushion of the patient interface 3000 may be made from foam material and/or textile material. The foam material may be covered by a textile material. Compressible foam covered with a textile material with air pressure assistance can improve seal and improve ease of setup.

Also, the shape and form of the patient interface 3000 may prevent it from protruding a large distance from the patient's face. In other words, the patient interface 3000 may have a shape closely corresponding to the anatomical shape of the patient's face and head.

The patient interface 3000 may be non-length adjustable but elastic, and made from a continuous unitary piece of material. The continuous unitary piece of material may be formed by 3D knitting or knit to shape manufacturing techniques.

Rigidised elements such as rigidiser arms 3303 may be integrated in the headgear (i.e., positioning and stabilising structure 3300), and covered by the foam material and/or textile material.

In another example, straps of the positioning and stabilising structure 3300 may be length adjustable.

The patient interface 3000 may form a seal around an inferior periphery of the patient's nose and at or near the tip of the patient's nose. This type of patient interface 3000 is sometimes referred to as a nasal cradle. The seal-forming structure 3100 is a foam member that is die cut such that there is a cut-out portion shaped to receive the lower parts of the patient's nose, and substantially exposes the tip of the patient's nose. Using a foam material allows it to conform to adjust around the patient's nose to obtain and maintain a seal when therapy is applied.

In another example, straps of the positioning and stabilising structure 3300 may connect to the mask frame or plenum chamber 3200 at two points. Two side straps 3301 bifurcate before the patient's ears at a bifurcation point. A crown strap 3307 and rear strap 3305 may join to the side straps 3301 at the bifurcation point. This provides stability for the patient interface 3000 when therapy is applied.

In another example, the seal-forming structure 3100 may be made from an air impermeable textile that has a predefined shaped to closely match the anatomical shape of the patient's nose. Two pressure actuated sealing portions of the seal-forming structure 3100 may seal against and around the tip of the patient's nose. The seal-forming structure 3100 can accommodate a large range of nose sizes.

In an alternative example, the seal-forming structure 3100 may be made from silicone, textile or foam.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone. Other materials may also be used for the seal-forming structure 3100, such as a textile or fabric material. The textile or fabric material may be made impermeable to air by occluding the spaces between the woven threads of the textile with a sealing material such a silicone. Rendering the textile air-impermeable may be accomplished by applying a sealing material (e.g., silicone) to the textile in a liquid or molten state such that the spaces between the woven threads of the textile are occluded when the sealing material hardens. It should be understood that the sealing material is applied in a sufficiently thin layer such that the textile material of the seal-forming structure 3100 retains the texture and tactile feel of textile.

In one form, the seal-forming structure 3100 comprises a sealing flange and a support flange. The sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In examples of the present technology that are described in greater detail below, the function of the support flange may be provided by a foam undercushion layer. The foam undercushion layer may be air permeable and may be covered by an air impermeable textile material that functions as the sealing flange.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

In certain forms of the present technology, a seal-forming structure 3100 is configured to correspond to a particular size of head and/or shape of face. For example one form of a seal-forming structure 3100 is suitable for a large sized head, but not a small sized head. In another example, a form of seal-forming structure 3100 is suitable for a small sized head, but not a large sized head.

5.3.1.1 Textile Seal Forming Structure

Examples of the present technology include a seal forming structure 3100 that is formed entirely of a textile material. These examples are depicted at FIGS. 6A to 6C and FIGS. 7A to 7G.

FIG. 6A shows an example of a seal forming structure 3100 formed from a textile material. The seal forming structure may have an opening 3101 through which the patient's airways may be provided with the supply of gas at positive pressure. The textile material of the seal forming structure may be impermeable to air such that when worn by a patient, as shown in FIG. 6B, the flow of gas at positive pressure supplied via the air circuit 4170 inflates the seal forming structure 3100 because the opening 3101 is sealed against the patient's face. The flexibility of the textile material and its ability to inflate under pressure allows the seal forming structure 3100 to form a seal against the patient's face. The seal forming structure 3100 of this example is also able to effectively provide a pneumatic seal for patients having a variety of face sizes and/or shapes. Additionally, the flexible nature of the seal formed by the exemplary textile seal forming structure 3100 allows the seal forming structure 3100 to maintain the seal while being subjected to movement of the patient or the patient interface 3000.

FIG. 6C depicts a variation of the seal forming structure 3100 of FIG. 6A in which a mesh structure 3102 is integrated into the seal forming structure 3100 at the opening 3101. The mesh structure 3102 may be a filtering material to filter undesirable particulate matter from the flow of pressurized gas before the gas reaches the patient's airways. The mesh structure 3102 may be a heat and moisture exchanging (HME) material that absorbs heat and moisture from gas exhaled by the patient, which is then absorbed by the flow of gas pressurized gas as it travels to the patient's airways during inhalation. The mesh structure 3102 may also be foam.

In the examples in FIGS. 6A to 6C, the positioning and stabilising structure 3300 may include side straps 3301. The side straps 3301 may also be made from a textile material. However, the textile material of the side straps 3301 may be a breathable (i.e., air permeable) material, because the side straps 3301 contact the patient's skin such that it would be desirable to reduce perspiration at the areas of contact by allowing air to flow through the straps. The positioning and stabilising structure 3300 may also include rigidiser arms, which are concealed by the side straps 3301 in these views, and the rigidiser arms may be attached to the plenum chamber by rigidiser arm connectors 3302. Accordingly, the textile material of the side straps 3301 may also be different in that it provides more cushioning from contact by the rigidiser arms against the patient's face.

The examples depicted in FIGS. 7A to 7G also depict various seal forming structures 3100 that may be formed from an air impermeable textile. FIGS. 7C to 7G depict cross-sectional views of exemplary seal forming structures 3100 with a clip 3103 that may be used to releasbly attach the seal forming structure 3100 to the plenum chamber 3200. The clip 3103 may be structured to engage the plenum chamber 3200 with at least one of a snap-fit, a press fit, and a friction fit. The clip 3103 may be permanently attached to the seal forming structure 3100 such that separation of these components would damage at least one of them. The clip 3103 may be made from a rigid plastic material, a thermoplastic elastomer (TPE), and/or silicone.

In FIG. 7C, the clip 3103 may be overmolded onto the textile material of the seal forming structure. Overmolding the clip 3103 to the seal forming structure 3100 may result in at least one of mechanical bond and a chemical bond to be formed therebetween.

In FIG. 7D, the clip 3103 may be secured to the seal forming structure 3100 via an intermediate clip connector 3104. The intermediate clip connector 3104 may be a silicone or thermoplastic elastomer component that is overmolded to the textile material of the seal forming structure 3100 similar to the clip 3103 in the example shown in FIG. 7C. The clip 3103 in FIG. 7D may be made from a rigid plastic material that is overmolded or otherwise permanently attached to the intermediate clip connector 3104. The including the intermediate clip connector 3104 may be beneficial when textile material of the seal forming structure 3100 and the material of the clip 3103 are difficult to join via overmolding. In other words, the silicone or TPE of the intermediate clip connector 3104 may readily join with the textile material of the seal forming structure 3100 and the material of the clip 3103 to provide an intermediate connection therebetween.

FIG. 7E depicts another example wherein the textile material of the seal forming structure 3100 is joined to the clip 3103 by welding. The welded connection at the interface of the clip 3103 may be formed, for example, by ultrasonic welding.

FIGS. 7F and 7G depict another example, which is similar to the example of FIG. 7E in that the clip 3103 and the seal forming structure 3100 are joined at their interface via welding. In this example, the seal forming structure 3100 is provided with the mesh structure 3102 at the opening 3101. The mesh structure 3102 may be a filtering material, an HME material, and/or a foam material.

Foam may also be used to provide support for the seal formed by the seal forming structure 3100, as shown in the example of FIGS. 10A to 10D. The seal forming structure 3100 may formed of a textile material that may be joined to the clip 3103 to secure the seal forming structure 3100 to the plenum chamber 3200. The seal forming structure 3100 may also include a foam interior 3105 that provides structural support to the textile material in use. The textile material of the seal forming structure 3100 and the foam interior 3105 may be joined by at least one of thermoforming, laminating, and welding.

Another example of the present technology includes a plenum chamber 3200 and a seal forming structure 3100 formed from two pieces of thermoformed textile that are then welded together. This example is depicted in FIGS. 1A to 11C. The seal forming structure 3100 may be provided with openings 3101 to seal with the nares and the mouth of the patient, as shown in FIG. 11C. The plenum chamber 3200 may also be molded as a thin-walled structure. Also, the plenum chamber 3200 may be attached to an air circuit 4170. Rigidiser arms 3303 may also be joined to the plenum chamber 3200 via rigidiser arm connectors 3302.

FIGS. 12A to 12E depict another example of a patient interface 3000 including wherein the seal forming structure 3100 and the plenum chamber 3200 are joined together. The seal forming structure 3100 may be one half that is formed from a textile or compressed foam material and the plenum chamber 3200 may be another half that is formed from a textile or compressed foam material. The seal forming structure 3100 and the plenum chamber 3200 are then connected at a joint 3106 by stitching and/or welding. The plenum chamber 3200 may also be formed with the connection port 3600 for attachment to the air circuit 4170 via welding or a magnetic clip. Additionally, the side straps 3301 may also be formed on the plenum chamber 3200, which may be connected to the cheek straps 3304 and the rear straps 3305 by a connector 3308 that may be stitched to the cheek strap 3304 and the rear strap 3305. Also, the connector 3308 may provide a hook and loop connection to the side straps 3301 wherein one of the connector 3308 and the side strap 3301 has hook material and the other has loop material.

Another variation of the present technology is depicted in FIGS. 13A to 13D. Here the patient interface 3000 may include a rigidiser arm frame 3309 that is sandwiched between the seal forming structure 3100 and the plenum chamber 3200 and then the three components are welded together. The seal forming structure 3100 may also include a foam interior 3105 to support the seal formed in use. Rigidiser arms 3303 may also extend from the rigidiser arm frame 3309 to provide support and direct the sealing force vectors of the positioning and stabilising structure 3300. The rigidiser arms 3303 and the rigidiser arm frame 3309 may be formed from one piece of flexible material such as TPE or silicone. To cushion the patient's face against the rigidiser arms 3303, a rigidiser arm cover 3310 made from textile may be welded to each rigidiser arm 3303. Also, the rigidiser arms 3303 may include edging 3311 to cushion the edge of the rigidiser arms 3303 against the patient's face. The edging 3311 may be a V-fold fabric, which is described below.

In another example of the present technology, the patient interface 3000 is provided with a seal forming structure 3100 having a cushion membrane layer 3109 that is made from textile. FIGS. 33A to 33C depict examples with a silicone cushion membrane layer 3109 and FIGS. 33D and 33E depict examples where the cushion membrane layer 3109 is made of a textile or fabric material that may be impermeable to air. This textile cushion membrane layer 3109 may provide benefits of being soft and comfortable to be worn against the patient's skin.

5.3.1.2 Seal Forming Structure with Foam Pads

In further examples of the present technology, seal forming structure 3100 may include foam pads or a foam layer. FIGS. 20A to 23 depict such examples.

In the example of FIGS. 20A to 20C, the seal forming structure 3100 may comprise a foam or a fabric laminate to form a seal with the patient's airways in use. The foam or fabric laminate may also be backed with TPE. Alternatively, the seal forming structure 3100 may be formed from a coated spacer fabric, as described below. The plenum chamber 3200 may be made from a polymer or TPE and may be welded to the seal forming structure 3100 at the interface. Additionally, the air circuit 4170 may be covered with a textile covering 4171 similar to other examples described below. Also, the positioning and stabilising structure 3300, including the rigidiser arm frame 3309 may be overmolded to the plenum chamber 3200.

FIGS. 21A to 21C depict other examples of the seal forming structure 3100 that may include foam. In these examples, the clip 3103 is formed from a rigid plastic material and a silicone cushion 3108 may be overmolded onto the clip 3103. The seal forming structure 3100 may also include a cushion membrane layer 3109 that may be made from textile or foam and may be glued onto the silicone cushion 3108. Alternatively, the cushion membrane layer 3109 may be made from a textile and the silicone cushion 3108 may be overmoulded onto the cushion membrane layer 3109. In another alternative, the cushion membrane layer 3109 may be made from textile and may be attached to the silicone cushion 3108 by a removable connection, e.g., using hook and loop material.

In the examples shown in FIGS. 22A to 22C, the silicone cushion 3108 may be provided with an adhesive portion 3110 to which the cushion membrane layer 3109 may be removably attached. Accordingly, it should be understood that the cushion membrane layer 3109 may be replaced. FIG. 22C depicts packaging 3111 in which a number of replacement cushion membrane layers 3109 may be packaged and sold to a patient for use. The foam of the cushion membrane layer 3109 may be flocked foam. In an alternative to using the adhesive portion 3110, the silicone cushion 3108 may be attached to the cushion membrane layer 3109 with another removable connection, e.g., using hook and loop material or an elastic liner.

FIG. 23 depicts another example similar to the example of FIGS. 22A to 22C, except that the cushion membrane layer 3109 may be made from 3D shaped foam to provide a better fit with the patient's face.

5.3.1.3 Foam Seal Forming Structure

Another exemplary patient interface 3000 of the present technology may include a seal forming structure 3100 made of foam. In the examples shown in FIGS. 32A to 32E, the seal forming structure 3100 may include a cushion membrane layer 3109 made of foam that forms a seal with the patient's airways. The cushion membrane layer 3109 made of foam may be able to better seal the face areas of the face characterized by shapes against which it may be difficult to form an effective seal, e.g., the region around the patient's ala. Also, foam is deformable, which may make the cushion membrane layer 3109 more comfortable. The deformable nature of foam may also facilitate easy set-up, i.e., the foam will readily to deform to fit the patient's face. Also, a cushion membrane layer 3109 of foam may obviate the need for hard plastic components. A foam cushion membrane layer 3109 may also be readily formed into the desired shape, as shown in FIG. 32E, in which the foam cushion membrane layer 3109 is compared with a seal forming structure 3100 of silicone.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

5.3.2.1 Textile and Foam Plenum Chamber

The plenum chamber 3200 of exemplary patient interfaces 3000 may also be made from textile, as well as foam, according to the present technology. FIGS. 9A to 9F depict such exemplary plenum chambers 3200.

In FIG. 9A, the plenum chamber 3200 may be formed from a textile outer layer 3210, a textile inner layer 3212, and a foam interior 3211. The textile outer layer 3210 and the textile inner layer 3212 may be joined to the foam interior 3211 by at least one of thermoforming, welding, and laminating. The plenum chamber 3200 may also include the side straps 3301 of the positioning and stabilising structure 3300 formed integrally therewith. It should also be understood that the side straps 3301 may be supplanted with rigidiser arms 3303. In FIG. 9A, the foam interior 3211 may be substantially the same thickness throughout.

FIG. 9B depicts another exemplary plenum chamber 3200 that is similar to the example of FIG. 9A, except that the thickness of the foam interior 3211 varies. Additionally, the foam interior 3211 may be the thickest in the middle portion between each end of the cross-section.

FIG. 9C depicts another exemplary plenum chamber 3200 that is similar to the example of FIG. 9A, except that the foam interior 3211 may have a rectangular profile that is completely surround by the textile outer layer 3210 and the textile inner layer 3212.

FIG. 9D depicts another exemplary plenum chamber 3200 that is similar to the example of FIG. 9A, except that a silicone overmold 3213 is provided at one end. The silicone overmold 3213 may form the connection port 3600, as shown in FIG. 9F, and/or provide a sealing function at the joint of the textile outer layer 3210 and the textile inner layer 3212.

FIGS. 9E and 9F also depict the seal forming structure 3100 that may be joined to the plenum chamber 3200.

5.3.3 Nasal Cradle Patient Interface Having Foam and Textile

An aspect of the present technology is directed to a patient interface 3000 in the form of a nasal cradle and comprising foam and textile materials. FIGS. 34A and 34B depict examples of a foam undercushion 3114. FIGS. 35A to 35D depict examples of the plenum chamber 3200. FIGS. 36A to 36F depict examples of the foam undercushion 3114 with the plenum chamber 3200. FIGS. 37A to 39C depict examples of the foam undercushion 3114 with a cushion membrane layer 3109, as well as the plenum chamber 3200. In these examples, there may a foam undercushion 3114 with a fabric membrane 3109 that may be pressure activated to seal with the patient's airways. The foam undercushion 3114 and the fabric or textile membrane 3109 may be operate in use similarly to a dual wall cushion. The air impermeable fabric (e.g. may be laminated on the side not touching the patient) of the membrane 3109 may contact the patient's face for comfort, and also because it inflates it can minimise or prevent leaks with difficult/complex anthropometric regions.

The textile/fabric material of the textile membrane 3109 may be coated with polyurethane (PU) to make it air impermeable by occluding any gaps between the woven/knitted textile fibres. The textile material may be cut to shape and then joined (e.g. via stitching) to the peripheral edge of the foam undercushion 3114. This anchors the textile membrane 3109 down to the foam undercushion 3114 or plenum chamber 3200, and may allow the textile seal to move relative to the foam undercushion 3114 and change its shape. Other materials could be used instead of PU to make the textile membrane 3109 air impermeable. An advantage of the present technology is that the strap tension of the positioning and stabilising structure 3300 does not have to be overly high to compress the seal forming structure 3100 into the patient's face to form a seal.

The foam geometry of the foam undercushion 3114 may be optimised and reduced as shown in FIG. 34A. In this example, the foam undercushion 3114 may be die cut. The foam undercushion 3114 may have a constant 12 mm thickness. Thicker and thinner foam undercushions 3114 could also be used. The thickness may not be uniform and can vary in thickness. FIG. 34B shows a compression cut foam undercushion 3114. Compression cut is an alternative manuufacturing method. The round tapered openings 3101 on the compression cut example in FIG. 34B produces less distorted nasal openings once the foam has been assembled (i.e., 3-Dimensionally formed) onto or pressed/deformed against the plenum chamber 3200.

The plenum chamber 3200 geometry shown in FIGS. 35A to 35D supports the foam undercushion 3114 and shapes it into a 3-dimensional shape. The plenum chamber 3200 holds the foam undercushion 3114 in a predetermined "cradle" shape to match the shape of the underside of the patient's nose. Details of the cradle shape enable the foam undercushion 3114 to compress differently at certain locations around the underside of the nose, which may help to establish a pneumatic seal and be comfortable around the underside of the nose. The plenum chamber 3200 in FIGS. 35A to 35D (without an air circuit 4170 attached) depicts how the foam undercushion 3114 may be 3-dimensionally shaped.

The rear wall 3220 that sits 90 degrees from the rear upper support surface 3221 enables the foam undercushion 3114 to wrap sharply from the septum sealing areas to the top lip sealing areas. Upper support surfaces 3221 may increase foam contact, which may ensure that no uncomfortable cradle details protrude into the foam undercushion 3114 causing discomfort to the user. The 3-dimensional structure of the foam undercushion 3114 may be created by these upper support surfaces 3221. The geometry of the plenum chamber 3200 may shape the foam undercushion 3114 into a tapered saddle shape (i.e., narrow front to wider back).

FIGS. 36A to 36F show the form of the foam undercushion 3114 once it has been assembled (e.g., glued) onto the plenum chamber 3200 with an air circuit 4170 attached. The V-shaped foam undercushion 3114 may seal along the alar angle of the nose. Prominent foam corners or alar sealing regions 3113, allow the foam undercushion 3114 to compress into the corners of the nose. Foam wraps around the rear lower corner of the plenum chamber 3200, i.e., at the rear wall 3220, in order to provide a compressed foam seal at both the septum and the top lip. FIG. 36D shows the structure of the support that the plenum chamber 3200 provides to produce a seal at the corners of the nose. The foam may be adhered to the plenum chamber 3200 profile which may produce shape for the upper foam surface to match the underside of the nose. The resultant shape of the foam undercushion 3114 may compress the foam at different rates under the nose to achieve seal and comfort.

An example of the present technology that may improve the seal of the nasal cradle patient interface 3000 includes an airtight/air impermeable textile membrane 3109 that may be added to the top surface of the foam undercushion 3114. This textile membrane 3109 is intended to function similarly to a conventional silicone membrane found on a dual wall cushion made of silicone.

It is envisaged in one example that the textile membrane 3109 inflates during therapy and sealingly engages with the underside of the nose. The inflation enables the seal to adjust dynamically to patient's face. Any movements of the nose away from the foam undercushion's 3114 upper surface, which may otherwise result in leak, may instead allow a seal to be maintained through the combination of the flexible airtight membrane 3109 and the treatment pressure causing the textile membrane 3109 to dynamically inflate. The seal may remain dynamic within a certain range of movement. In other words, the textile membrane may only be able to inflate to a certain extent. A leak may occur if the nose moves beyond the textile membrane's 3109 inflation range.

FIG. 37A depicts the inflating membrane 3109 with an airtight textile material. In FIG. 37B, the inflating membrane 3109 may be joined to the foam undercushion 3114 only around the outer periphery, which allows the membrane 3109 to inflate to this point. The membrane 3109 may be free at the nasal opening 3101 in order to allow treatment pressure to enter between the foam undercushion 3114 and the textile membrane 3109. The treatment pressure may create the inflation of the membrane 3109 against the underside of the nose. The membrane 3109 in FIG. 37B may have a single opening 3101 which can reduce nasal air occlusion and be more efficient regarding membrane inflation. A single opening 3101 may produce more sealing robustness at the tip of the nose. FIG. 37C shows that the inflating membrane 3109 can extend around to seal the top of lip regions and the corner of the nose. The dual opening 3101 of the membrane 3109 shown in FIG. 37D for the nares may produce more sealing robustness at the sides of the nares. The example in FIG. 37D also contains an alternative inflating membrane shape in which the membrane 3109 remains on the top surface of the foam undercushion 3114 and away from the rear edge of the foam undercushion 3114 so that exposed foam can be used to seal at the corners of the nose. FIGS. 37E and 37F shows further views of the example depicted in FIG. 37D where the inflating membrane 3109 is only on the top surface of the foam undercushion 3114 such that the foam is exposed for sealing purposes at the corners of the nose and to seal the rear surface of the foam undercushion 3114 against the top lip region.

FIGS. 38A to 38C depict inflation of the membrane 3109 by pressurized gas in the plenum chamber 3200. In FIG. 38A, the textile membrane 3109 has been attached at its outer periphery to the foam undercushion 3114. In FIG. 38B, the textile membrane 3109 inflates away from the foam undercushion 3114. The inflation may be maximised towards the middle of the seal forming structure 3100. Less inflation may occur where the membrane 3109 is joined to the foam undercushion 3114. It should be understood that in use that the inflation of the membrane 3109 occurs as a result of the openings 3101 being sealed against the patient's nares, but for clarity the patient's nose is omitted to better depict inflation of the membrane 3109. The inflating membrane 3109 may specifically target the front and sides of the nares for more effective sealing at these regions. The membrane 3109 has been designed in this example such that these areas experience the most inflation. FIG. 38C shows that the foam of the foam undercushion 3114 is exposed to seal at the corners of the nose. The corners of the nose may be difficult to seal and therefore a compliant sealing mechanism can improve the effectiveness of the seal. A nasal profile outline 3115 is also shown to indicate where the outline of the patient's nose may generally lie in use. Thus, the patient's nares should align with the openings 3101 of the sealing membrane 3109. The area within the nasal profile outline 3115 may form a bearing surface for sealing.

FIGS. 39A to 39C depict another example of patient interface 3000 with an aesthetic and cleanable seal forming structure 3100 that includes a laminated foam undercushion 3114 (both sides laminated) and an airtight membrane 3109 that is attached to the laminated top surface of the foam undercushion 3114. The exemplary seal forming structure 3100 may behave similarly to the examples described above. An air-tight textile membrane 3109 is attached to a foam undercushion 3114 which has been laminated on both sides. The air-tight membrane 3109 shown on the surface of the foam undercushion 3114 may contact the patient's face in use. The air-tight membrane 3109 can inflate sufficiently and contains sufficient drape to achieve a comfortable and robust seal around the nares and at the corners of the nose. The seal forming structure 3100 may be overmoulded to a clip 3103 for assembly to the plenum chamber 3200. Alternatively, the seal forming structure 3100 may be glued to the clip 3103 for the purpose of being assembled to the plenum chamber 3200. FIG. 39C shows the laminated foam undercushion 3114 with the air-tight membrane 3109 on top surface of the seal forming structure 3100. The seal forming structure 3100 may be attached to the plenum chamber 3200 via a moulded on clip 3103 or may be glued to the plenum chamber 3200.

FIGS. 43 to 47C depict additional examples of patient interfaces 3000 according to the present technology that include the seal forming structure 3100 having a foam undercushion 3114 and a textile membrane 3109.

In FIG. 43, such a seal forming structure 3100 may be attached to the plenum chamber 3200 by the clip 3103 (not shown) and the seal forming structure receiver 3204. The positioning and stabilising structure 3300 may also have a crown strap 3307 made of a crown strap material 3321 that is less stretchable than the materials used for other straps. Also, the rear strap 3305 may be made from a rear strap material 3320 that is also different from other strap materials.

FIG. 44 shows, among other things, the seal forming structure 3100 that may be used with the patient interface 3000 of FIG. 43. Also, this exemplary seal forming structure 3100 may include the features the seal forming structures described above, e.g., a foam undercushion 3114 and a textile membrane 3109.

FIGS. 45 and 46 depict further examples of the seal forming structure 3100 according to the present technology. These examples may also include a foam undercushion 3114 and a textile membrane 3109. The textiles used maybe multi-directional elastic textiles.

FIGS. 47A to 47C depict an example of a seal forming structure 3100 according to the present technology at different stages of production. FIG. 47A depicts the seal forming structure 3100 after being thermoformed into an airtight laminated textile and foam structure. FIG. 47B shows the seal forming structure 3100 after being cut to shape to have soft edges and FIG. 47C shows the finished the seal forming structure 3100.

FIGS. 48 to 56 depict still further examples of the present technology with a patient interface 3000 having a seal forming structure 3100 that may include the features the seal forming structures described above, e.g., a foam undercushion 3114 and a textile membrane 3109. Also, the exemplary patient interface 3000 may include a positioning and stabilising structure 3300 having straps including the V-fold textile described below, as well as several straps comprised of different textile materials. Additionally, the positioning and stabilising structure 3300 may include transition portions 3323 that may also be comprised of the V-fold textile described below. The positioning and stabilising structure 3300 may also utilize a single layer of mesh or net-like fabric for one or more of the various straps that also includes the V-fold textile described below.

In another example, at least one shape holding member may be positioned between the seal forming structure 3100 and plenum chamber cover 3201. The shape holding member may be embedded or sandwiched within the plenum chamber cover 3201. The shape holding member may be a unitary structure with a predetermined shape or boning. The shape holding member maintains a predetermined shape of the plenum chamber cover 3201 when no force is applied to provide the patient interface 3000 with a more rigid or semi-rigid skeletal structure that holds the shape of the flexible textile membrane 3109. The shape holding member also assists with positioning and aligning the seal forming structure 3100 relative to the plenum chamber cover 3201. The shape holding member may be rigid or stiff (e.g. made from polypropylene), or semi-rigid (e.g. made from silicone). The shape holding member is more rigid than the seal forming structure 3100 and plenum chamber cover 3201.

It should also be understood that the exemplary patient interface 3000 may be constructed such that a seal is only formed against the underside of the patient's nose in use. In other words, the seal forming structure 3100, including the textile membrane 3109 and the foam undercushion 3114, may only extend beyond to below the bridge of the patient's nose or below the tip of the patient's nose. FIG. 57 depicts an exemplary patient interface 3000 in a cross-sectional view taken through the opening 3101 and showing that the seal forming structure 3100, including the textile membrane 3109 and the foam undercushion 3114, does not extend past the tip of the patient's nose. FIG. 57 also depicts how the textile membrane 3109 may separate from the foam undercushion 3114 when it is inflated by the pressurized air. As can be seen, the textile membrane 3109 is attached at its periphery to the foam undercushion 3114 with an airtight seal such that when the textile membrane 3109 engages with the underside of the patient's nose and the opening(s) 3101 align with the nares the pressurized air will inflate the air impermeable textile membrane 3109 and may cause it to separate from the foam undercushion 3114 except at the periphery when the textile membrane 3109 and the foam undercushion 3114 are joined.

5.3.4 Positioning and Stabilising Structure

The seal-forming structure 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example, the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilizing structure 3300 provides a retaining force configured to correspond to a particular size of head and/or shape of face. For example one form of positioning and stabilizing structure 3300 provides a retaining force suitable for a large sized head, but not a small sized head. In another example, a form of positioning and stabilizing structure 3300 provides a retaining force suitable for a small sized head, but not a large sized head.

5.3.4.1 Textile Positioning and Stabilising Structure

Similar to examples of the seal forming structure 3100 described above, the positioning and stabilising structure 3300 may be formed, at least in part, by one or more textile materials. In addition, patient interfaces 3000 including such textile positioning and stabilising structures 3300 may also include a seal forming structure 3100 that includes a textile material, as described above.

The example shown in FIG. 8A includes a positioning and stabilising structure 3300 comprised entirely of textile. The seal forming structure 3100 may be an air impermeable textile material, as well as the textile material of the plenum chamber 3200, because these components define the breathing chamber through which pressurized gas is provided to the patient's airways. The positioning and stabilising structure 3300 may include side straps 3301, cheek straps 3304, a rear strap 3305, and a crown strap 3307, all of which are made of textile. It should be noted that one or more of these straps may be made from a different textile material than the others. For example, the different straps may be made of materials that stretch more than others. In the example of FIG. 8A, the rear strap 3305 and the crown strap 3307 may be made from one piece of textile, e.g., jersey knit or combed cotton. The various straps and components of this exemplary patient interface 3000 may be joined by at least one of sewing, stitching, and welding.

FIG. 8B depicts another example of a patient interface 3000 having textile straps and components. In this example, the side straps 3301, the rear strap 3305, and the crown strap 3307 may be made of one piece of textile. The plenum chamber 3200 may also be formed from the textile material of the side straps 3301, the rear strap 3305, and the crown strap 3307. The cheek strap 3304 may be made from a different textile material. The seal forming structure 3100 may be made from yet another textile material. The positioning and stabilising structure 3300 may also include an ear liner 3306 on each side to cushion against the ears, if the positioning and stabilising structure 3300 is stretched against the patient's ears. All of these straps and components may be attached by at least one of sewing, stitching, and welding.

FIG. 8D depicts another example of a patient interface 3000 having textile straps and components. In this example, the side straps 3301, the cheek straps 3304, and the crown strap 3307 are made from the same textile material, while the rear strap 3305 and the ear liner 3306 are made from another textile material. The seal forming structure 3100 and the plenum chamber 3200 may be made from yet another textile material.

FIG. 24 depicts another example of the present technology where the patient interface 3000 includes positioning and stabilising structure 3300 made from a textile material. As shown, the side straps 3301, cheek straps 3304, rear straps 3305, and crown strap 3307 may be a single piece of textile material. Alternatively, each strap of the positioning and stabilising structure 3300 may be made from a different textile material to provide a fee, function, and/or stretch that corresponds to the portion of the patient's head with which it engages in use. Accordingly, such different strap materials may be coloured differently to indicate such differences. Although not shown in this view, the rear straps 3305 may be joined together at the rear of the patient's head. The plenum chamber 3200 may also be made from a textile material, which may be the same piece of textile material as the positioning and stabilising structure 3300. The seal forming structure 3100 may be made from another textile material that provides a soft feel against the patient's skin. The textile material of the seal forming structure 3100 may be thermoformed to provide a stable seal.

FIG. 25 depicts another example of a patient interface 3000 with a positioning and stabilising structure 3300 made from a textile material. This example shows that the side strap 3301, rear strap 3305, and crown strap 3307 are made from the same piece of textile material. The rigidiser arm covering 3310 may be made from a different textile material and may cover rigidiser arms 3303, which are not shown. The rigidiser arm covering 3310 may be joined to the side strap 3301 by a hook and loop connection, magnets, stitching, or welding. The rigidiser arm covering 3310 may be made from the same material as the plenum chamber 3200. The plenum chamber 3200 may be provided with a connection port 3600 to connect to the air circuit 4170. Also, the seal forming structure 3100 according to this example may be made from silicone. Alternatively, the seal forming structure 3100 may be made from an air impermeable textile material in accordance with other examples described above.

FIG. 26 depicts another example of the present technology where the patient interface 3000 includes a positioning and stabilising structure 3300 that is made from a textile material. In this example, the plenum chamber 3200, the side straps 3301, the rear strap 3305, and the crown strap 3307 are made from a single piece of textile material. The seal forming structure 3100 may also be formed from this single piece of textile material, from a different textile material, or from silicone. The connection port 3600 can also be seen extending from the plenum chamber 3200 and being connected to the air circuit 4170.

FIGS. 27A to 27C depict still further examples of patient interfaces 3000 including a positioning and stabilising structure 3300 formed from textile materials. The seal forming structure 3100 may be from one type of textile material that is air impermeable and provides comfortable contact with the patient's skin while maintaining a stable seal with the patient's airways. Alternatively, the seal forming structure 3100 may be made from a foam material that is air impermeable and provides comfortable contact with the patient's skin while maintaining a stable seal with the patient's airways. Also, the cheek straps 3304 and the plenum chamber 3200 may be made from another textile material. The side straps 3301 may be made from yet another type of textile material. The side straps 3301 are, in turn, connected to a joint 3313 that may also be made from a different textile material. Joined to the joint 3313 are the rear strap 3305 and the crown strap 3307, which may each be formed from different textile materials. The different textile materials of each portion of the positioning and stabilising structure 3300 may each be selected based on the portion of the patient's head with which it engages and its relative contribution to the function of maintaining the seal forming structure 3100 in sealing engagement with the patient's airways.

FIG. 28 depicts another example of the present technology in which the patient interface 3000 includes a positioning and stabilising structure 3300 made from textile materials. In this example, the plenum chamber cover 3201, which covers the plenum chamber 3200, may be made from the same piece of textile material as the cheek straps 3304. The plenum chamber 3200 may also be made from a textile material, a foam material, or a rigid plastic material and may be attached to the seal forming structure 3100, which may be made from a textile material, a foam material, or silicone. The cheek straps 3304 may have openings 3314 through which the side straps 3301 may be looped. The side straps 3301 may be made from yet another textile material and may each have hook and loop connector 3315. Accordingly, each side strap 3301 and its respective hook and loop connector 3315 may each have one of a hook material and a loop material to facilitate the hook and loop connection to secure the side straps 3301 to the cheek straps 3304 at the openings 3314. The rear strap 3305 and the crown strap 3307 may also be made from other textile materials. The different textile materials of each portion of the positioning and stabilising structure 3300 may each be selected based on the portion of the patient's head with which it engages and its relative contribution to the function of maintaining the seal forming structure 3100 in sealing engagement with the patient's airways.

FIGS. 29A to 29C depict another exemplary patient interface 3000 according to the present technology where the positioning and stabilising structure 3300 is made from textile materials. In this example, the rear strap 3305 and the crown strap 3307 may be from a type of textile material that has properties desirable for use in straps that cradle the rear of the patient's head in use. The properties of the textile material of the rear strap 3305 and the crown strap 3307 may include a semi-soft structure, relatively low stretch as compared to the side straps 3301, relatively thin, and breathable. The side straps 3301 may be joined to the rear strap 3305 and the crown strap 3307 and may be made from a textile material having different properties. The side straps 3301 may be made from a textile material that is relatively more stretchable as compared to the rear strap 3305 and the crown strap 3307, relatively thin, breathable, and sufficiently soft to be comfortable for direct skin contact. The plenum chamber cover 3201 and the rigidiser arm covering 3310 may be made from yet another textile material. The seal forming structure 3100 may include a cushion membrane layer 3109 that is made from an air impermeable and stretchable textile material. Cushioning for the cushion membrane layer 3109 may be provided by the spacer fabric cushioning 3112. The vent 3400 may also be made from a space fabric mesh. The air circuit 4170 may be joined to the patient interface 3000 with a tube clip 4173 at the connection port 3600, which may be an overmolded ring. FIG. 29C shows that the seal forming structure 3100 may have a foam interior 3105 that provides support for the seal formed by engagement with the patient's airways in use.

FIG. 30 depicts a further example of the present technology with a patient interface 3000 that has a positioning and stabilising structure 3300 made of textile materials. In this example, the side straps 3301 and the crown strap 3307 may be made from one piece of textile material and this piece of textile material may be produced such that the side straps 3301 and the crown strap 3307 have a curved shape in an unstretched state, i.e., when not worn by the patient. The rear strap 3305 may be attached to the textile material of the side straps 3301 and the crown strap 3307 and may be made of a different textile material. The textile of the rear strap 3305 may be more stretchable than the textile material of the side straps 3301 and the crown strap 3307. It also may be different in at least one of texture and color to allow the patient to readily distinguish the straps to ensure that the positioning and stabilising structure is properly oriented on the patient's head in use. The plenum chamber 3200 may also be made from the same piece of material as the side straps 3301 and the crown strap 3307.

FIG. 31 depicts another exemplary patient interface 3000 according to the present technology where the positioning and stabilising structure is made from textile materials. In this example, the rear strap 3305 is made from an elastic textile, e.g., printed elastic, and the side straps 3301 and the crown strap 3307 are made from the same piece of textile, e.g., an elastic, soft fabric, that is different from the textile of the rear strap 3305. The side straps 3301 may be joined to the plenum chamber cover 3201, which may be thermo-formed to approximate the shape of the patient's nose and made from a non-elastic, semi-soft TPE material. The plenum chamber cover 3201 may also be made from a neoprene material that is breathable, such as materials produced under the Breathe-O-Prene® trademark. The seal forming structure 3100 may be interchangeable, i.e., releasably attached to the plenum chamber 3200, and made from at least one of foam, textile, and silicone. This example may have the air circuit 4170 connected directly to the connection port 3600. Also, no decoupling structure 3500 may be provided. Alternatively, the air circuit 4170 may be glued to the plenum chamber cover 3201.

5.3.4.2 Spacer Fabric

In one form of the present technology, the positioning and stabilising structure 3300 may include portions, such a straps, formed from a spacer fabric 6000 as illustrated in FIGS. 41A and 41B. Except as noted below, the entire positioning and stabilising structure 3300 may be formed from spacer fabric 6000. Spacer fabric 6000 may also be used in combination with the laminate structure described above.

The spacer fabric 6000 includes a first fabric layer 6002, a second fabric layer 6004 and a central fabric layer 6006. These three layers may be warp/weft knitted together, for example, by a warp knitting Raschel machine, warp-knit spacer machine, or circular knitting machine. The spacer fabric 6000 is porous and/or open celled, which provides benefits such as allowing the spacer fabric 6000 to breath, to be easily washed and to be faster to dry. A porous structure may enable the strap 3500 be washed more thoroughly and faster, as dirt and other foreign contaminants can be washed out faster and more is washed out without as much agitation compared to a conventional flame laminated headgear strap with a comparable amount of foreign contaminants.

The first fabric layer 6002 may be hydrophilic. If, for example, a hydrophilic layer is against the patient's skin, the hydrophilic material may wick away moisture, which may also provide cooling or a cooling sensation. The second fabric layer 6004 may be hygroscopic. This may aid the wicking effect of a hydrophilic layer. Alternatively or in addition, portions of the first fabric layer 6002 may be omitted to expose the central fabric layer. This may be advantageous if increased airflow, faster drying and/or reduced weight is desirable.

The central fabric layer 6006 may be made from a single filament or multiple filaments, for example, a single yarn or multiple yarns. This may allow for the central fabric layer 6006 to be spacer yarn or pile fabric, either of which may aid in transporting heat and/or liquid away from the patient. As illustrated in FIGS. 41A and 41B, the fibres of the central fabric layer 6006 extend from the first fabric layer 6002 to the second fabric layer 6004. Alternatively, the fibres of the central fabric layer 6006 are transverse to both the first fabric layer 6002 and the second fabric layer 6004 between the boundaries of those layers and thus may be considered to be oriented in a column-like fashion. With this configuration, the central fabric layer 6006 spaces the first fabric layer 6002 from the second fabric layer 6004 and the three layers together in this fashion may also be referred to as a 3D spacer fabric.

The spacer fabric 6002 may be elastic along a length of a strap. For example, any of the various straps illustrated in FIG. 3A may be elastic along the length (e.g., longest) dimension and may be inelastic, or less elastic, along the width or thickness.

Use of spacer fabric 6000 may differentiate over known straps and/or positioning and stabilising structures through the omission of foam. When foam is compressed, for example, when a patient sleeps on their side and the head-gear is pressed against the patient's cheek, the foam does not compress beyond a certain point. In contrast, when compression force is applied to the spacer fabric 6000, the central fabric layer 6006 may collapse, which may result in the spacer fabric 6000 forming a very thin structure. This may improve comfort for the patient when they are sleeping on their side. Spacer fabric 6000 also separates compression strength from tensile strength in contrast to foam which have both strength properties linked to each other. The spacer fabric 6000 may further differentiate over straps in known positioning and stabilising structures in that the straps can be formed seamlessly. Thus the three-dimensional shape illustrated in FIG. 3A may be manufactured without the illustrated seams. Known positioning and stabilising structures may be flame laminated together, which could also result in a seam between the laminated layers but can be avoided using spacer fabric 6000. Flame lamination may also result in a structure that is subject to cracking when stretched, which can also be avoided using spacer fabric 6000. The positioning and stabilising structure 3300 may thus be fabricated without flame laminating and/or without glue laminating layers together.

Known positioning and stabilising structures may comprise a hollow strap which may receive the insertion of a rigidiser arm. A hollow strap without a rigidiser arm inserted may be prone to twisting and folding. If this occurs during therapy, it may be uncomfortable for the patient. A rigidiser may be inserted into the central fabric layer 6006, pushing fibres out of the way. Such a rigidiser may be used to provide a direction or vector in which the spacer fabric 6000 is intended to stretch in use. For example, it may be advantageous to have such a vector between the patient's eyes and ears. Alternatively, a rigidiser may be used to prevent stretching in a location of the positioning and stabilising structure 3300 where elasticity is not desirable or should be limited.

The first fabric layer 6002 may be smooth to the touch and/or have a soft appearance. This may be suitable for contact with a patient's skin. The first fabric layer 6002 may be a mesh.

The second fabric layer 6004 may be smooth to the touch and/or breathable. This may be suitable for a surface facing away from the patient because, for example, being breathable may allow entrained moisture (such as perspiration) to wick away from the patient and evaporate.

One or any combination of the first fabric layer 6002, the second fabric layer 6004, the third fabric layer 6008 (discussed below) and the central fabric layer 6006 may be fabricated by 3D knitting (i.e. three-dimensional knitting) or more specifically by warp knitting. Warp knitting is a method of knitting where the fibre, such as yarn, zigzags along the length of the fabric. In warp knitting a number of separate strands of fibre is equal to a number of stitches in a row and results in columns of knitting rather than a single row. By way of comparison, knitting across the width of fabric is called weft knitting.

Known types of warp knitting include Tricot, Milanese knit, Raschel knit, stitch-bonding and extended stitch bonding.

Stitch bonding includes layers of threads and fabric being joined together with a knitting thread. This creates a layered structure. The layered structure is created through a warp-knitting thread system that is fixed on the reverse side of the fabric with a sinker loop, and a weft thread layer. A needle with the warp thread passes through the material, which requires the warp and knitting threads to be moving both parallel and perpendicular to the vertical/warp direction. Stitch bonding is a method that can be used to warp/weft knit fabric together.

In extended stitch-bonding, a compound needle that pierces the piles is shifted laterally according to yarn guides. This can avoid residual stress and improve tensile and impact strength.

Stitch bonding or extended stitch bonding may be used to create all of the layers of spacer fabric together, e.g., the first fabric layer 6002, the second fabric layer 6004, the central fabric layer 6006 and the third fabric layer 6008 (discussed below). Any knitting type that can join layers together may be used.

The central fabric layer 6006 may be formed from or include yarn, e.g., a yarn layer. The yarn may include cotton yarn, polyester yarn or combinations thereof. The yarn may be fully cotton, partially cotton, fully polyester, partially polyester, nylon, silicone, elastane and/or polypropylene. The central fabric layer 6006 may include a predetermined number of yarns per square centimetre to provide a predetermined amount of elasticity and flexibility to the positioning and stabilising structure. The yarns making up the central fabric layer 6006 may have a predetermined thickness and/or predetermined height to provide a predetermined amount of elasticity and flexibility to the positioning and stabilising structure.

FIG. 41B differs from FIG. 41A in that a third fabric layer 6008 is illustrated. The third fabric layer 6008 may be an unbroken loop layer (UBL) or a mesh layer, which may be suitable for mating and/or fastening with a hook layer (e.g., hook material 3520) of a hook and loop fastener. By including an unbroken loop layer or a mesh layer as the third fabric layer 6008, the spacer fabric 6000 may integrally form the loop half of a hook and loop fastener. The loop material 3510 may be the third fabric layer 6008. The hook material 3520 may need to be attached to the spacer fabric 6000 and/or positioning and stabilising structure 3300 by suitable fastening methods such as stitching, gluing, etc.

The spacer fabric may range in thickness from 2.0-6.0 mm, range in compression strength from 5-25 kilopascals, and range in elongation from 0.1%-20% with a 10 Newtons force applied. For example, in one form (e.g., a thick, low-stretch spacer fabric), the spacer fabric 6000 may have a thickness of 4.0-6.0 mm, a compression strength of 15-25 kilopascals, and an elongation of 1%-5% with a 10 Newtons force applied. In another form (e.g., thick, high-stretch spacer fabric), the spacer fabric 6000 may have a thickness of 4.0-6.0 mm, a compression strength of 15-25 kilopascals, and an elongation of 10%-20% with a 10 Newtons force applied. In yet another form (e.g., thin, medium-stretch spacer fabric), the spacer fabric 6000 may have a thickness of 2.0-4.0 mm, a compression strength of 5-20 kilopascals, and an elongation of 6%-10% with a 10 Newtons force applied. In another form, the combination of the first fabric layer 6002, second fabric layer 6004 and central fabric layer 6006 together may have 10% to 15% elongation when a 10 Newtons force is applied. In yet another form, the combination of the first fabric layer 6002, second fabric layer 6004 and central fabric layer 6006 together may have 10% to 30% elongation when a 2 Newtons force is applied. Spacer fabric with little or no stretch (e.g., 0.1% with 10 Newtons force applied) may be suitable for portions of the positioning and stabilising structure where stretch may not be desirable, for example, a strap on the crown of a patient's head.

Any of the various thicknesses of the spacer fabric 6000 may include the third fabric layer 6008. For example, a spacer fabric 6000 with a thickness of 2.0-4.0 mm may include the third fabric layer 6008.

By fabricating the spacer fabric 6000 using the 3D knitting techniques described above, the spacer fabric 6000 may seamlessly transition between these properties. For example, the spacer fabric could transition from a 2.0 mm thickness to a 6.0 mm thickness without a seam. The change in thickness may also result in proportional changes in the compression strength and elongation.

The spacer fabric 6000 may also be separately fabricated and joined together, e.g., by stitching or gluing, to utilize different combinations of properties above. For example, a spacer fabric with 2.0-4.0 mm thickness and the third fabric layer 6008 (e.g., thin, medium-stretch spacer fabric) could be fastened to a spacer fabric with 4.0-6.0 mm thickness (e.g., thick, high-stretch spacer fabric) so that part of the positioning and stabilising structure 3300 has unbroken loops where medium elongation (e.g., 6%-10%) is desired and omits unbroken loops where relatively high elongation (e.g., 10%-20%) is desired.

Of course, any combination of the various types of spacer fabric 6000 may be joined, either using conventional connection techniques like stitching and gluing or using knitting techniques, so that the properties are controlled as desired based upon their relative location in the positioning and stabilising structure 3300. Thus different strap portions of the positioning and stabilising structure 3300 can be formed with a first fabric layer 6002, a second fabric layer 6004 and a central fabric layer 6006 while achieving differing structural properties (such as thickness, elongation and compression strength).

3D knitting may provide a more durable headgear. For example, 3D knitting processes may produce a material that will not run even if cut.

The edge of the spacer fabric 6000 may be closed while it is manufactured. A closed and rounded edge is comfortable for a patient as it may avoid red marks on the patient's skin.

The spacer fabric 6000 may result in a positioning and stabilising structure and/or strap that is more breathable and lighter than a comparable flame laminated structure. The ability to knit to shape (e.g., 3D knitting) can reduce cost because, for example, scrap is eliminated as comparted to materials that must be cut to shape from a sheet of material. The shape of the positioning and stabilising structure of FIG. 3A can be achieved so that the straps and open spaces are initially formed by the knit to shape process. The ability to knit to shape also allows for controlled change of properties as described above.

The spacer fabric 6000 may be easier to clean than other types of material used for a positioning and stabilising structure. A bioburden cleaning confidence test was performed per ISO 15883-5 (2005) on a strip of spacer fabric as disclosed herein and on a strip of Breath-O-Prene. The result of the test was that spacer fabric displayed superior cleaning characteristics versus the Breath-O-Prene.

5.3.4.3 V-Fold Textile

The headgear 6000 illustrated throughout FIGS. 42A-42Y includes various patterns in the illustrations. Due to the limitations of black and white line drawings, the patterns, unless noted explicitly herein, are intended to allow the reader to distinguish between materials that may be similar and materials that may be different. Except as explicitly set forth herein, the patterns should not be considered limiting.

FIGS. 42A-42E illustrate headgear 6000 that includes straps, such as strap 6002, made of a first flexible material 6004. The strap 6002 extends generally from the area of a patient's Otobasion superior or Temporal bone to a breathing mask 6022. Another strap 6002a extends from the area of the patient's Otobasion superior or Temporal bone on one side of the patient's head, over the Parietal bone to the area of the patient's Otobasion superior or Temporal bone on the other side of the patient's head. Another strap 6002b extends from the area of a patient's Otobasion superior or Temporal bone on one side of the patient's head, wraps around the Occipital bone and/or Trapezius m. to the other side of the patient's head in the area of the patient's Otobasion superior or Temporal bone. As illustrated in these figures, the straps 6002a, 6002b form a continuous structure that conforms to and cradles the back and top of the patient's head. The continuous structure may be shaped similarly to a circle or ellipse so that the patient's head protrudes at least partially through the circle or ellipse. Except as expressly noted herein, the straps 6002a, 6002b may have the same or substantially the same structure as the strap 6002. Thus for the sake of brevity, only the strap 6002 will generally be referenced hereinafter.

The strap 6002 includes an elongate edge 6006 with a second flexible material 6008 wrapped around the elongate edge 6006. The second flexible material 6008 may be an elastic material. Preferably the second flexible material 6008 has a higher degree of elasticity than the first flexible material 6004. For example, the second flexible material may be similar to, or have properties similar to, that used in elastic bands for clothing. Also, the straps 6002a, 6002b may have a higher degree of elasticity than the strap 6002. A second elongate edge 6007 is opposite the elongate edge 6006 and together they define a width of the strap 6002. The second elongate edge 6007 may be substantially identical to the elongate edge 6006. Indeed, all elongate edges of the present technology may be formed in a similar manner. Thus the remainder of the present disclosure will only separately discuss other elongate edges where they differ from the elongate edge 6006.

The strap 6002a may comprise a mesh spacer fabric where holes may be visible. This configuration may be more visually aesthetic and may cause a user to perceive the headgear as lighter. This configuration may also be more breathable. It may be preferable to avoid mesh spacer fabric for the straps (e.g. strap 6002 and 6002b), because there may be a risk that those straps could snag and/or hook on bed linen due to the open nature of mesh spacer fabric open nature. Using mesh spacer fabric on a crown strap (e.g., strap 6002a) may not experience this problem because the top of the head typically does not contact bed linen and/or a pillow when the patient is sleeping.

The second flexible material 6008 is wrapped around the elongate edge 6006 to form a V-shaped fold 6010. As discussed herein, a V-shaped fold is intended to describe the process for creating the fold, which may not necessarily reflect the final shape of the fold. For example, as illustrated in FIG. 42M, the V-shaped fold 6010 conforms to the underlying material, which has a rounded edge, and results in a configuration that may be closer to a U-shape when viewed in cross-section. If the underlying material is relatively thinner or has a pronounced edge, the final shape of the V-shaped fold may be closer to a V-shape than what is illustrated in FIG. 42M. The V-shaped fold 6010 may enable a continuous edge all around the headgear 6000 or a continuous edge in any sub-portion of the headgear 6000. The V-shaped fold 6010 may be very visually appealing, as well as being smooth to avoid snagging or bumps in certain spots compared to if the edging material is made of multiple sections.

The second flexible material 6008 may be applied with the V-shaped fold 6010 with the aid of a Macpi machine model number 335 32, which can be used to apply a strip of adhesive along the edge of fabric. Macpi machine model number 335 48 may be used to fold over and apply the second flexible material 6008. In this way, adhesive may fix the second flexible material 6008 to the strap 6002 with the V-shaped fold 6010 by applying adhesive on opposite surfaces of the strap 6002 near the elongate edge 6006 and affixing the second flexible material 6008.

The material used for the V-shaped fold 6010 may be supplied with or without a pre-laminated adhesive. If a pre-laminated adhesive is not used, the MACPI machine may be used to laminate adhesive on, where the process and/or material can be controlled to suit the particular strap material. In the same process, after the lamination, the second flexible material 6008 may be bonded to the strap material (e.g. spacer fabric or Breath-O-Prene®). Breath-O-Prene® strap portions may be connected together, for example, by ultrasonic welding, stitching or any other suitable means. Attaching spacer fabric strap portions together may be achieved, for example, using stitching.

The second flexible material 6008 may extend along and cover an entire width of the strap 6002. For example, in FIG. 42A, the side of the strap 6002 that faces the patient may be completely covered by the second flexible material 6008 such that the second flexible material 6008 extends to and is wrapped around the second elongate edge 6007 in substantially the same manner as the elongate edge 6006. Alternatively, as illustrated in FIG. 42I, the second flexible material 6008 may not extend across the width of the strap 6002 and thus the second flexible material 6008 may be two separate pieces. This configuration may allow for an alternative second flexible material 6026 in place of the second flexible material 6008 so that the alternative second flexible material 6026 may have different properties, if necessary or desirable. For example, the alternative second flexible material 6026 could be an elastic with different extensive properties than an elastic used for the second flexible material 6008. The configurations in FIGS. 42A and 42I share a common feature in that on at least one side of the strap 6002, the second flexible material does not extend across the entire width of the strap 6002.

As illustrated in FIG. 42Y, the first flexible material 6004 may be formed of layers of material. For example, the first flexible material may include a third flexible material 6012 and a fourth flexible material 6014 that are adhered together by stitching, a layer of adhesive, ultrasonic welding or any other suitable substance or process for adhering the layers together. An adhesive film 6028 is illustrated. Although only two layers are illustrated, any number of layers may be provided. For example, three, four, or more layers may be provided, where the number of layers may be determined, for example, based upon the combined characteristics of the individual layers. As illustrated, the second flexible material 6008 may be wrapped around the layers of material such that edges of the material, and thus the stacked nature of the materials, is covered. If the second flexible material 6008 is sufficiently opaque, the stacked nature may not be visible when viewed along the elongate edge 6006.

The first flexible material 6004 may be any flexible material such as foam or a woven material. The woven material may be spacer fabric or other types of fabric or textile. A spacer fabric can be defined as a textile having an upper ground structure or layer, a lower ground structure or layer, and a floating or traversing yarn woven between the upper ground structure and lower ground structure to form a matrix like textile. The upper ground structure and lower ground structure may be formed from a fabric. The upper ground structure may have different properties than the lower ground structure, for example they may have different stretch, stiffness, flexibility, hand feel, or other characteristics. The upper and lower ground structures may be substantially parallel to one another. Spacer fabrics may be formed by flat knitting. At least one side (i.e. upper or lower ground structure) may be formed from a fabric having yarn of, for example, about 30-100 denier, 20-300 denier, or 50-200 denier for a pleasant hand feel. U.S. Patent Application Publication Nos. 2014/0102456 and 2014/0158136, both of which are incorporated by in their entireties, discuss spacer fabrics and some potential uses with respect to headgear. The first flexible material 6004 may also be Breath-O-Prene®, which may be easier to ultrasonically cut or die cut than spacer material.

FIGS. 42M and 42Y illustrate the elongate edge 6006 as rounded. A rounded edge may be formed by way of ultrasonic cutting. Alternatively, the elongate edge 6006 could be formed by other methods such as die cutting, which may result in a less-rounded cut or even a perpendicular intersection between the adjacent surfaces.

As best viewed in FIG. 42E, the strap 6002 transitions from the first flexible material 6004 to another flexible material, which is illustrated as a mesh material 6030. However, any flexible material, such as fabric or foam or layers thereof, may be used. Thus a first flexible strap portion 6032 of the strap 6002 includes the first flexible material 6004 and a second flexible strap portion 6034 of the strap 6002 includes the mesh material 6030. Where the first flexible strap portion 6032 joins the second flexible strap portion 6034, the intersection 6036 is covered by the second flexible material 6008. The second flexible material extends along the first and second elongate edges 6006, 6007 as well as the intersection 6036 between strap portions. Thus a portion of the second flexible material 6008 extends along a short edge transverse to the elongate edge 6006 defined at the intersection 6036. The intersection 6036 is best viewed in FIG. 42H. A different material may also be used to cover the intersection 6036 if desired or the intersection may remain uncovered. See, e.g., FIG. 42J. At the intersection 6036, materials may be joined by any suitable and/or convenient method. Two examples are zig-zag sewing (a type of stitching) and ultrasonic welding. Another example of the way that materials may be joined together is discussed below with respect to FIG. 42T.

By including a first flexible strap portion 6032 and a second flexible strap portion 6034 made from different materials, the properties of the headgear 6000 may be controlled. For example, one portion may stretch relatively more than another. This may be beneficial based upon relative movement of anatomy near the different portions of the headgear 6000. In FIG. 42E, the first strap portion 6032 is adjacent the patient's jaw, which may move relative to the patient's skull whereas the second strap portion 6034 is located near a portion of the patient's skull that may not move. Thus the first strap portion 6032 may be allowed to stretch in use to accommodate patient movement. Also, different amounts of stretch may be useful when the patient puts on or takes off the headgear 6000. These and other aspects of the headgear 6000 may thus be optimized by using different flexible materials and joining them. One or both of the first flexible strap portion 6032 and the second flexible strap portion 6034 may be made from spacer fabric but with the properties thereof (such as the weave or fibre used) selected to provide a desired amount of elasticity such that the spacer fabrics are functionally different. Spacer fabric or other fabrics may be employed that provide elasticity or substantially no elasticity. Thus either strap portion could be elastic or substantially non-elastic.

FIG. 42F illustrates the headgear 6000 in a flat condition prior to being fully assembled. This illustrates that the headgear 6000 may be formed flat and that after assembly the headgear may fit to the complex shape of the patient's head. In FIG. 42F, the straps 6002b (top and bottom in the figure) may have their free ends connected together and the straps 6002 may have their free ends connected to a breathing mask 6022 to result in the configuration illustrated in FIGS. 42A-42E. With this configuration, various strap materials for different strap portions may be joined together. The second flexible material 6008 may be one continuous and/or uninterrupted piece (e.g., cut from a single sheet) and then applied to the patient-side (i.e., the bottom side or side not visible in FIG. 42F) of the headgear 6000 and then wrapped around the elongate edge 6002. An adhesive sheet may be used to attach the second flexible material 6008. The adhesive sheet could be cut from a single sheet of adhesive (similar to that described above for the flexible material 6008) or could be cut into different components. This option may be beneficial if, for example, different types of adhesive are better suited for different areas of the headgear. For example, different types of adhesive may be better suited for joining the second flexible material 6008 to the different strap materials. Different types of adhesive may be desirable in areas where the headgear is likely to experience different levels of stretching in use. Other types of adhesive, such as adhesive applied in liquid (e.g., brushed on or sprayed on adhesive) may also be desirable to achieve different adhesive or assembly requirements.

FIG. 42G illustrates the headgear of FIG. 42F but in a non-flat condition with part of the side facing the patient visible.

FIG. 42T illustrates one way in which strap portions may be joined together. A first layer 6038 of one strap portion may be inserted between a second layer 6040 and third layer 6042 of a second strap portion. The second layer 6040 and the third layer 6042 may be connected by a layer of adhesive 6044, or any other suitable joining process, that does not extend to the ends of the second layer 6040 and third layer 6042. The layer of adhesive 6044 may be the same as or different from the adhesive film 6028. The resulting strap structure is substantially Y-shaped when viewed along the elongate edge 6006. The first layer 6038 may then be inserted into the Y-shape and secured between the second layer 6040 and third layer 6042 with additional layers of the adhesive 6044, or any other suitable joining process. This type of joining technique may be applied where three legs come together to form a Y-shaped profile 6046 when viewed from the patient's side (e.g., when viewed from a width side of the strap) as illustrated, for example, in FIGS. 42E and 42I.

The second layer 6040 and third layer 6042 may advantageously have different properties. For example, one of the second layer 6040 and the third layer 6042 may be half of a hook and loop fastener, such has the loop half. The first layer 6038 may be the other half of a hook and loop fastener, such as the hook half. This configuration would allow the strap to have a configuration allowing the strap to connect to itself as illustrated, for example, in FIG. 42S.

FIGS. 42J and 42K illustrate how a construction with different layers may result in a patient-side (e.g., FIG. 42K) of headgear versus and exterior side (e.g., FIG. 42J) of headgear with distinct materials and/or material intersections. Not including any intersections with the second material 6008, the four patterns of FIG. 42J illustrate four different intersections whereas the three patterns of FIG. 42K illustrate only two intersections. The result may or may not be as visually distinct as illustrated in the figures, which will depend on the visual differences, if any, of the materials chosen.

FIGS. 42O and 42P are similar to FIGS. 42J and 42K in that different materials intersect and have different configurations on the patient side versus the outside. However, FIGS. 42O and 42P differ in that the same number of intersections are present on the patient side and the outside of the headgear even though different materials are used in portions of the patient side versus portions of the outside of the headgear. In these figures, the strap 6002b may be an elastic material.

Another benefit of a two-layered structure is that a side of a strap facing a patient may have different properties than a side facing away from a patient. For example, the side of a strap facing a patient may preferably have a soft touch or feel to avoid irritation. A flexible material may not have such properties while providing adequate structural integrity for use in headgear. Alternatively, if a flexible material has adequate structural integrity as well as appropriately soft touch and feel but the flexible material may not be well suited for connecting to the hooks of a hook and loop fastener (e.g., the surface does not include unbroken loops). If so, the loop half of the hook and loop fastener can be attached as an outside layer. Or a fabric that has unbroken loops can be applied.

FIG. 42L is similar to FIG. 42 except that the straps 6002 are substantially straight in the flat condition and may employ the two-layered structure discussed above. The straps 6002 may include hook material 6048 so that the strap can fold back and attach to the material adjacent to the hook material 6048.

FIGS. 42H and 42I illustrate two stages of assembly for headgear 6000. In FIG. 42H, various straps are attached together to form the basic shape of the headgear. The various straps and strap portions may be formed of different materials as indicated by the different patterns used in FIG. 42H. FIG. 42H differs from FIG. 42I most notably by the omission of the second flexible material 6008 and thus may illustrate an early stage of assembly versus FIG. 42, which illustrates the second flexible material 6008 in place along the various edges.

Two notable differences in the configuration of the headgear 6000 in FIGS. 42H and 42I should be highlighted. First, there is no connection illustrated for a breathing mask. A hole 6018 as illustrated, for example, in FIGS. 42N and 42U could be provided in strap 6002 but has been omitted for clarity of these figures. Second, an elastic strap 6048 is illustrated between and connecting the ends of the straps 6002b. Such an elastic strap 6048 may be included in any of the headgear illustrated in this disclosure. The elastic strap 6048 may provide benefits such as greater adjustability or level of comfort for patients of varying head size while providing only one size of headgear. And the elastic strap 6048 may allow for the omission of, or reduction of, other relatively complex adjusting arrangements such as buckles or other fasteners. Omission of such buckles or fasteners may be beneficial in areas of the headgear where straps do not need to be disassembled during normal use but adjustment may be required.

FIGS. 42A, 42B, 42D, 42E, 42N, 42Q, 42S and 42U-42X illustrate a connection 6016 for a breathing mask 6022. In FIGS. 42N, 42Q, 42S and 42U-42X, the connection 6016 is illustrated in the form of a hole 6018 through a strap 6020, where the hole 6018 may be sized to conform to an outer perimeter of a section of the breathing mask 6022 such that the breathing mask 6022 at least partially passes or protrudes through the strap 6020. The strap 6020 may be similar to the strap 6002 in that two elongate edges 6006, 6007 are provided where each may be covered with a V-shaped fold 6010 of the second flexible material 6008. Alternatively, the V-shaped fold 6010 may be made from a different material. The hole 6018 may be provided with a V-shaped fold 6010 (see, e.g., FIGS. 42U and 42V), or the V-shaped fold may be omitted (see, e.g., FIGS. 42N, 42Q, 42S, 42W and 42X). On opposed ends of the strap 6020, loops 6024 may be provided to allow another strap to pass there through. See, e.g., FIGS. 42Q-42S. The loops 6024 may be used in conjunction with a strap that can connect to itself as illustrated in FIG. 42S so that two different straps of the headgear 6000 can be connected together. This arrangement may allow a "set and forget" arrangement so the user does not have to adjust length after the initial set up. The user can don/doff the mask by simply sliding off and on as the headgear, preferably when the headgear is elastic.

The strap 6002 and the strap 6020 may have a width of 16 mm to 24 mm or any value in between. For example, the width may be about 20 mm. If the strap width is too narrow it will pierce the skin, i.e. leave marks. Also, if it is too narrow, the geometry may be more likely to allow the strap to crease, kink and/or fold over. A certain level of width may provide rigidity of the side strap via geometry. If the strap width is too wide, then there is likely to be more physical contact with the user's face which may be uncomfortable and increased width will increase weight.

The loops 6024 may be attached to the strap 6020 using loops of elastic material 6050. As an alternative to the hole 6018, a groove (not illustrated) may be provided on the breathing mask 6022 that is similar to the loops 6024. Another alternative to the hole 6018 is to provide half of a hook and loop fastener on the mask and the other half on the strap 6020 (not illustrated). For example, hooks could be provided on the breathing mask 6022 with loops provided on the strap 6020. Another alternative is to attach the strap 6020 to the breathing mask 6022 using adhesive.

A benefit of the loops 6024 is that the strap 6020, which may be referred to as side straps because there are strap portions on each side of a patient's face or head, may be length adjustable. Such side straps may require a higher force for certain mask types (such as a nasal cradle or nasal pillows mask), compared to a full face mask or nasal mask. The loops 6024 or a buckle may be provided at the distal end of the side strap proximal to but lower than the patient's temple. The location of the buckle preferably avoids bone and abuts against a fleshy part of the patient's face, in use, for comfort purposes in case the patient sleeps on their side. Also, this buckle location may enable the side strap to curve and closely follow the patient's cheeks, which may be sleeker and aesthetically pleasing. Preferably the buckle is not located too high as it gets too close to the eyes, which may be distracting and/or uncomfortable to the patient. Providing the loops 6024 or a buckle on the strap 6020 may be preferable to providing the loops 6024 or a buckle on the mating component because this arrangement may be more intuitive to a user.

Various effects may be optimized with the headgear-related technologies discussed above. For example, by altering the thickness of the second flexible material 6008 applied in the V-shaped fold 6010, and/or the thickness of adhesive used to adhere the second flexible material 6008 in the V-shaped fold 6010, the hand feel and stiffness can be optimized. For example, if the second flexible material 6008 and adhesive are relatively thin, a soft hand feel and flat seem may be achieved but the headgear may retain its overall shape relatively poorly. If the second flexible material 6008 and adhesive are relatively thick, the headgear may hold its shape well but be too hard to be comfortable.

FIGS. 40A to 40D depict further examples of the present technology where the patient interface 3000 may include any of the exemplary seal forming structures 3100 and plenum chambers 3200 described above that have foam and/or textile portions. Although not shown in these views, the seal forming structure 3100 may be provided with a clip 3103, as described above, and the clip 3103 may secure the seal forming structure 3100 to the plenum chamber 3200 at a seal forming structure receiver 3204 that is structured to cooperate with the clip 3103. These examples may also include a positioning and stabilising structure 3300 that includes the V-fold fabrics described above. These examples may include a side strap material 3316 that faces away from the patient's skin in use. Also, a side strap liner 3318 may be provided to cushion the side straps 3301 against the patient's skin. The side strap liner 3318 may be a breathable material and may have a soft texture that is comfortable to be worn against the patient's skin for an extended period of time. Similarly, the crown strap 3307 may include a crown strap liner 3319 that may be made of the same material as the side strap liner 3318. Likewise, the rear strap 3305 may also include the liner material used for the side strap liner 3318. The rear strap 3305 may also include an elastic portion 3317. The positioning and stabilising structure 3300 may also include V-fold fabric portions 3311, as shown in FIGS. 40A to 40D and in accordance with the description above.

5.3.5 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

5.3.8 Forehead Support

In one form, the patient interface 3000 includes a forehead support 3700.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RP device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with an aspect of the present technology is a conduit or a tube constructed and arranged to allow, in use, a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

The air circuit 4170 provided with the patient interfaces 3000 described herein may also include the features disclosed in U.S. Patent Application Publication No. 2015/0217074, published on Aug. 6, 2015.

5.4.1.6.1 Textile Air Circuit

According to examples of the present technology, the air circuit 4170 itself may be formed from a textile material or the air circuit 4170 may have a textile covering. These examples are depicted in FIGS. 14 to 19E.

In FIG. 14, the exemplary patient interface 3000 includes a seal forming structure 3100, a plenum chamber 3200, and a connection port 3600. The air circuit 4170 is shown connected to the connection port 3600. According to this example, the air circuit 4170 is made from an air impermeable textile material to provide a flow path to the patient interface 3000 for the flow of gas.

FIGS. 15A and 15B depict another example of the present technology, where the air circuit 4170 has a textile covering 4171 that is welded to the air circuit 4170 at a welded area 4172. This example also includes plenum chamber clip 3203 that forms the connection port 3600 to which the air circuit 4170 is attached. The plenum chamber 3200 may be formed from a rigid plastic material and may be welded to the textile side straps 3301. The rigidiser arms 3303 may be received in the textile side straps 3301 that may be structured as sleeves. The rigidiser arm frame 3309 also attaches to the plenum chamber clip 3203 and the clip 3103 of the seal forming structure 3100 may be attached to the rigidiser arm frame 3309.

FIGS. 16A and 16B depict another example of the present technology where the air circuit 4170 has a textile 4171. In a further variation, the textile covering 4171 may be extended over the plenum chamber 3200. The rigidiser arms 3303 may be provided with textile sleeves in the form of the side straps 3301. The rigidiser arms 3303 may also be attached to the plenum chamber 3200 via the rigidiser arm frame 3309.

FIGS. 17A and 17B depict another example of the present technology that is similar to the example of FIGS. 16A and 16B in that the air circuit 4170 has a textile covering 4171. In this example, the plenum chamber 3200 also has a textile plenum chamber cover 3201. The side straps 3301, rear strap 3305, and crown strap 3307 are all made from a textile material. Additionally, the side straps 3301 cover the rigidiser arms 3303.

FIG. 18 depicts another example of the present technology having an air circuit 4170 with a textile covering 4171 joined at a welded area. This example also includes a plenum chamber clip 3203 that may be welded to the plenum chamber cover 3201 that may be made from a textile material. According to this example, the plenum chamber cover 3201 may be air permeable to allow for venting. The side straps 3301 may also be formed from the same piece of textile material as the plenum chamber cover 3201. The rigidiser arm frame 3309 may be connected to the rigidiser arms 3303 by rigidiser arm connectors 3302 and the rigidiser arm frame 3309 may be connected to the plenum chamber clip 3203. The rigidiser arm frame 3309 may also include vents 3400. The rigidiser arm connectors 3302 may be overmolded silicone or TPE. The clip 3103 may also attach the seal forming structure 3100 to the plenum chamber 3200 by releasable attachment to the rigidiser arm frame 3309.

FIGS. 19A to 19E depict another example of a patient interface 3000 with an air circuit 4170 having a textile covering 4171. The seal forming structure 3100 may be formed from a textile material and may include a silicone clip 3103 with clip connectors 3107 to attach the seal forming structure to the rigidiser arm frame 3309. The rigidiser arm frame 3309 may be formed with the rigidiser arms 3303 and have a silicone overmold. Also, the rigidiser arm frame 3309 may have rigidiser arm frame connectors 3312 to receive connect to the clip connectors 3107 with magnets or a snap fit. The plenum chamber 3200 may also have a lip seal 3202 to form sealed breathing chamber when engaged with the rigidiser arm frame 3309 and the seal forming structure 3100.

In still further examples of the present technology, the air circuit 4170 having a textile covering 4171 may include the textile material being overmolded to a silicone portion of the plenum chamber 3200 at the connection port 3600. Alternatively, the textile covering 4171 may be glued to the plenum chamber 3200 at the connection port 3600. Alternatively, the textile covering 4171 may be joined to the plenum chamber 3200 at the connection port 3600 with a removable connection, e.g., using hook and loop material.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 Humidifier Mechanical Components

5.4.3.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.4.3.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.4.3.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.4.3.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.4.4 Humidifier Electrical & Thermal Components

The humidifier 5000 may comprise a number of electrical and/or thermal components such as those listed below.

5.4.4.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.4.4.1.1 Pressure Transducer

One or more pressure transducers 5212 may be provided to the humidifier 5000 in addition to, or instead of, a pressure sensor 4272 provided in the RPT device 4000.

5.4.4.1.2 Flow Rate Transducer

One or more flow rate transducers 5214 may be provided to the humidifier 5000 in addition to, or instead of, a flow rate sensor 4274 provided in the RPT device 4000.

5.4.4.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.4.4.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.4.4.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.4.4.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4170 and/or a heating element controller 5252 configured to control the temperature of a heating element 5240.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.5.1.2 Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratoryflow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi))=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator A ventilator that measures patient ventilation, has a target ventilation, and which adjusts the level of pressure support to bring the patient ventilation towards the target ventilation.

Spontaneous/Timed (SIT): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.5.4 Anatomy 5.5.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittalplane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.5.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. Thefrontalprocess of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. A typical human left ear comprises a left-hand helix, see FIG. 3P. A typical human right ear comprises a right-hand helix, see FIG. 3Q. FIG. 3R shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3O), or alternatively by a left-hand rule (FIG. 3N).

Osculating plane: The plane containing the unit tangent vector and the unit principal normal vector. See FIGS. 3N and 3O.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3R, since T2>T1, the magnitude of the torsion near the top coils of the helix of FIG. 3R is greater than the magnitude of the torsion of the bottom coils of the helix of FIG. 3R With reference to the right-hand rule of FIG. 3O, a space curve turning towards the direction of the right-hand binormal may be considered as having a right-hand positive torsion (e.g. a right-hand helix as shown in FIG. 3R). A space curve turning away from the direction of the right-hand binormal may be considered as having a right-hand negative torsion (e.g. a left-hand helix).

Equivalently, and with reference to a left-hand rule (see FIG. 3N), a space curve turning towards the direction of the left-hand binormal may be considered as having a left-hand positive torsion (e.g. a left-hand helix). Hence left-hand positive is equivalent to right-hand negative. See FIG. 3S.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by the plane curve 301D.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole. See for example the cushion of FIG. 3L and the example cross-section there through in FIG. 3M. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by surface 302D.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| | |
|---|---|
| patient | 1000 |
| bed partner | 1100 |
| patient interface | 3000 |
| seal - forming structure | 3100 |
| opening | 3101 |
| mesh structure | 3102 |
| clip | 3103 |
| intermediate clip connector | 3104 |
| foam interior | 3105 |
| joint | 3106 |
| clip connector | 3107 |
| silicone cushion | 3108 |
| textile membrane | 3109 |
| cushion membrane layer | 3109 |
| adhesive portion | 3110 |
| packaging | 3111 |
| spacer fabric cushioning | 3112 |
| alar sealing region | 3113 |
| foam undercushion | 3114 |
| nasal profile outline | 3115 |
| plenum chamber | 3200 |
| plenum chamber cover | 3201 |
| lip seal | 3202 |
| plenum chamber clip | 3203 |
| seal forming structure receiver | 3204 |
| textile outer layer | 3210 |
| foam interior | 3211 |
| textile inner layer | 3212 |
| silicone overmold | 3213 |
| rear wall | 3220 |
| upper support surface | 3221 |
| positioning and stabilising structure | 3300 |
| side strap | 3301 |
| rigidiser arm connector | 3302 |
| rigidiser arm | 3303 |
| cheek strap | 3304 |
| rear strap | 3305 |
| ear liner | 3306 |
| crown strap | 3307 |
| connector | 3308 |
| rigidiser arm frame | 3309 |

| | |
|---|---|
| rigidiser arm covering | 3310 |
| v - fold fabric portion | 3311 |
| rigidiser arm frame connector | 3312 |
| joint | 3313 |
| opening | 3314 |
| loop connector | 3315 |
| side strap material | 3316 |
| elastic portion | 3317 |
| side strap liner | 3318 |
| rear strap liner | 3319 |
| rear strap material | 3320 |
| crown strap material | 3321 |
| transition portion | 3323 |
| vent | 3400 |
| strap | 3500 |
| decoupling structure | 3500 |
| loop material | 3510 |
| hook material | 3520 |
| connection port | 3600 |
| forehead support | 3700 |
| rpt device | 4000 |
| external housing | 4010 |
| upper portion | 4012 |
| lower portion | 4014 |
| panel | 4015 |
| chassis | 4016 |
| handle | 4018 |
| pneumatic block | 4020 |
| mechanical and pneumatic components | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| textile covering | 4171 |
| welded area | 4172 |
| tube clip | 4173 |
| supplemental oxygen | 4180 |
| electrical component | 4200 |
| PCBA | 4202 |
| power supply | 4210 |
| input device | 4220 |
| central controller | 4230 |
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithm | 4300 |
| therapy control module | 4330 |
| humidifier | 5000 |
| humidifier outlet | 5004 |
| humidifier base | 5006 |
| reservoir | 5110 |
| humidifier reservoir | 5110 |
| water reservoir | 5110 |
| conductive portion | 5120 |
| humidifier reservoir dock | 5130 |
| locking lever | 5135 |
| water level indicator | 5150 |
| humidifier transducer | 5210 |
| humidifier transducers sensor | 5210 |
| air pressure sensor | 5212 |
| pressure transducer | 5212 |
| flow rate transducer | 5214 |
| air flow rate transducer | 5214 |
| temperature transducer | 5216 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| spacer fabric | 6000 |
| headgear | 6000 |
| strap | 6002 |
| first fabric layer | 6002 |
| elongate edge | 6002 |
| spacer fabric | 6002 |
| first flexible material | 6004 |
| second fabric layer | 6004 |
| central fabric layer | 6006 |
| elongate edge | 6006 |
| second elongate edge | 6006 |
| edge | 6006 |
| second elongate edge | 6007 |
| edge | 6007 |
| second flexible material | 6008 |
| third fabric layer | 6008 |
| flexible material | 6008 |
| second material | 6008 |
| v - shaped fold | 6010 |
| third flexible material | 6012 |
| fourth flexible material | 6014 |
| connection | 6016 |
| hole | 6018 |
| strap | 6020 |
| breathing mask | 6022 |
| loop | 6024 |
| alternative second flexible material | 6026 |
| adhesive film | 6028 |
| mesh material | 6030 |
| first flexible strap portion | 6032 |
| second flexible strap portion | 6034 |
| intersection | 6036 |
| first layer | 6038 |
| second layer | 6040 |
| third layer | 6042 |
| adhesive | 6044 |
| y - shaped profile | 6046 |
| elastic strap | 6048 |
| hook material | 6048 |
| elastic material | 6050 |
| strap | 6002a |
| strap | 6002b |

The invention claimed is:

1. A patient interface for sealed delivery of a flow of air at positive pressure with respect to ambient air pressure to an entrance to the airways of a patient including at least the nares of the patient, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing, said patient interface comprising:

a plenum chamber at least partially forming a breathing chamber pressurisable to a therapeutic pressure above ambient air pressure, said plenum chamber including a plenum chamber inlet sized and structured to receive a flow of air at the therapeutic pressure for breathing by a patient;

a seal-forming structure constructed and arranged to seal with a region of the patient's face surrounding an entrance to the patient's airways, said seal-forming structure having an opening formed therein such that the flow of air at said therapeutic pressure is delivered to at least an entrance to the patient's nares; and a vent comprising a plurality of holes constructed and arranged to allow for the washout of exhaled gases, wherein the plenum chamber comprises a textile outer layer, a textile inner layer and a foam inner layer disposed between the textile outer layer and the textile inner layer, the textile outer layer and the textile inner layer being respectively joined to opposing sides of the foam inner layer.

2. The patient interface of claim 1, wherein the textile outer layer and the textile inner layer are joined to the foam inner layer by thermoforming, welding and/or laminating.

3. The patient interface of claim 1, wherein a thickness of the foam inner layer varies across the plenum chamber.

4. The patient interface of claim 1, wherein, in a transverse cross-sectional view of the plenum chamber, the foam inner layer has a relatively larger thickness in a central portion of the plenum chamber and a relatively smaller thickness at lateral end portions of the plenum chamber.

5. The patient interface of claim 1, wherein the foam inner layer has a uniform thickness throughout the plenum chamber.

6. The patient interface of claim 1, wherein the foam inner layer has a rectangular profile in cross-section.

7. The patient interface of claim 1, wherein the textile outer layer and the textile inner layer together completely surround the foam inner layer.

8. The patient interface of claim 1, wherein the plenum chamber has a connection port formed around the plenum chamber inlet for connection with an air supply circuit.

9. The patient interface of claim 8, wherein an overmold forms the connection port, the overmold sealing at a joint between the textile outer layer and the textile inner layer.

10. The patient interface of claim 1, wherein the seal-forming structure includes a textile membrane arranged to form the seal with a region of the patient's face.

11. The patient interface of claim 10, wherein the textile membrane has an air impermeable material provided thereon.

12. The patient interface of claim 10, wherein the textile membrane is configured to inflate upon pressurization of the breathing chamber.

13. The patient interface of claim 1, wherein the seal-forming structure includes a foam undercushion layer.

14. The patient interface of claim 1, further comprising a positioning and stabilizing structure to maintain the seal-forming structure in sealing contact with the patient's face, the positioning and stabilizing structure including a pair of side straps configured to extend along respective sides of the patient's face in use.

15. The patient interface of claim 14, wherein the side straps are integrally formed with the plenum chamber.

16. The patient interface of claim 1, wherein the plenum chamber includes the vent.

17. The patient interface of claim 1, wherein the seal-forming structure is constructed and arranged to seal with an underside of the patient's nose.

18. The patient interface of claim 1, wherein:
the textile outer layer and the textile inner layer are joined to the foam inner layer by thermoforming, welding and/or laminating;
the textile outer layer and the textile inner layer together completely surround the foam inner layer;
the plenum chamber has a connection port formed around the plenum chamber inlet for connection with an air supply circuit;
the seal-forming structure includes a textile membrane arranged to form the seal with a region of the patient's face;
the textile membrane has an air impermeable material provided thereon; and
a positioning and stabilizing structure is configured to maintain the seal-forming structure in sealing contact with the patient's face, the positioning and stabilizing structure including a pair of side straps configured to extend along respective sides of the patient's face in use;
the plenum chamber includes the vent; and
the seal-forming structure is constructed and arranged to seal with an underside of the patient's nose.

19. The patient interface of claim 18, wherein a thickness of the foam inner layer varies across the plenum chamber.

20. The patient interface of claim 18, wherein the foam inner layer has a uniform thickness throughout the plenum chamber.

* * * * *